United States Patent
Nagase et al.

(10) Patent No.: US 6,777,410 B2
(45) Date of Patent: Aug. 17, 2004

(54) ISOINDOLE DERIVATIVES

(75) Inventors: Toshio Nagase, Tsukuba (JP);
Tomoharu Iino, Tsukuba (JP);
Yoshiyuki Sato, Tsukuba (JP);
Teruyuki Nishimura, Tsukuba (JP);
Jun-ichi Eiki, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/408,220

(22) Filed: Apr. 8, 2003

(65) Prior Publication Data

US 2004/0053923 A1 Mar. 18, 2004

Related U.S. Application Data

(62) Division of application No. 10/069,376, filed as application No. PCT/JP00/05723 on Aug. 25, 2000, now Pat. No. 6,608,098.

(30) Foreign Application Priority Data

Aug. 25, 1999 (JP) ............................. 11-239004

(51) Int. Cl.$^7$ .................. A61K 31/423; A61K 31/5377; C07D 263/52; C07D 413/12
(52) U.S. Cl. .................... 514/233.2; 514/338; 514/375; 544/137; 546/271.1; 548/216; 548/217; 548/224
(58) Field of Search ................. 548/216, 217, 548/224; 546/271.1; 544/137; 514/233.2, 338, 375

(56) References Cited

U.S. PATENT DOCUMENTS

| 3,507,863 A | 4/1970 | Houlihan |
| 3,928,597 A | 12/1975 | Rosen |
| 4,565,566 A | 1/1986 | Draber et al. |
| 4,701,208 A | 10/1987 | Los |
| 4,717,414 A | 1/1988 | Hunt |
| 4,721,522 A | 1/1988 | Durr et al. |
| 4,726,838 A | 2/1988 | Durr et al. |
| 4,741,767 A | 5/1988 | Obrecht |
| 4,743,296 A | 5/1988 | Durr et al. |
| 4,846,876 A | 7/1989 | Draber et al. |
| 4,997,947 A | 3/1991 | Szczepanski et al. |

FOREIGN PATENT DOCUMENTS

| EP | 0 195 745 A1 | 9/1986 |
| JP | A-63-295575 | 12/1988 |
| JP | 6-507388 | 3/1991 |

OTHER PUBLICATIONS

Freytag, Beilsteins Handbuch Der Organischen Chemie Vierte Auflage (1938), vol. 27, p. 341 {Chemische Berichte, 48, (1915), 651}.*
Pesticide Biochemistry and Physiology, (1993), vol. 46, No. 2, pp. 120–130.
Journal of The Chemical Society, Perkin Trans. 1, p. 1547–1551 (1979).
Riley, R.J.; Leeder, J.S., "In vitro analysis of metabolic predisposition to drug herpsensitivity" Clinical and Experimental Immunology (1995) 99(1), 1–6.

* cited by examiner

Primary Examiner—Laura L. Stockton
(74) Attorney, Agent, or Firm—Nixon & Vanderhye P.C.

(57) ABSTRACT

This invention relates to compounds represented by the general formula [I]

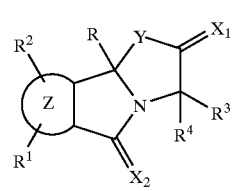

[I]

wherein, R represents an azido group, etc., $R^1$ and $R^2$ are the same or different and represent hydrogen atoms, etc., $R^3$ and $R^4$ are the same or different and represent hydrogen atoms, etc., $X_1$ represents an oxygen atom, etc., $X_2$ represents an oxygen atom, etc., Y represents an oxygen atom, etc., and Z represents a condensed aryl group, etc., or a pharmaceutically acceptable salt thereof, preparation processes thereof, and an agent for treating diabetes, a prophylactic agent for chronic complications of diabetes or a drug against obesity, containing, as an effective ingredient, the compound or the pharmaceutically acceptable salt thereof.

7 Claims, No Drawings

ISOINDOLE DERIVATIVES

This application is a division of application Ser. No. 10/069,376, filed Feb. 25, 2002, now U.S. Pat. No. 6,608,098 B1 which in turn is a §371 of PCT/JP00/05723 filed Aug. 25, 2000, the entire content of which is hereby incorporated by reference in this application.

TECHNICAL FIELD

Blood glucose levels in normal subjects are maintained at constant levels by insulin action. Diabetes mellitus is characterized by chronic hyperglycemia due to lost in the control of blood glucose level.

Basically, diabetes therapy aims to correct hyperglycemia, that is by decreasing blood glucose into normal level. Accordingly, the importance of therapeutic control on postprandial hyperglycemia without affecting fasting glucose level is getting a great deal of attention.

Currently, besides insulin injection, major drugs for diabetes treatment are classified into three: First group of drugs is called insulin secretagogues, and is represented by sulfonylureas. These drugs directly induce insulin secretion from pancreas. Insulin then reduces blood glucose level. Drugs from the second group are called insulin sensitizers, which were launched recently. These drugs do not directly stimulate insulin release but enhance glucose uptake in the peripheral tissues. The third group of drugs is called α-glucosidase inhibitors, which are able to prevent from rapid increase in postprandial glucose. These drug's action is to suppress the transient rise in glucose level occurring during meal by delaying digestion and absorption of dietary carbohydrate.

On the other hand, it is known that glucagon-like peptide-1 (hereinafter, referred to as GLP-1) is a hormone secreted from L-cells, which are endocrine cells existing in the intestinal epithelium of small intestine. GLP-1 lowers blood glucose level by inducing insulin secretion from β-cells existing in the pancreatic islet of Langerhans (Eur. J. Clin. Invest, volume 22, page 154, 1992). Importantly, it is reported that the effect of GLP-1 on insulin secretion is dependent on glucose, that is GLP-1 induces insulin secretion only when blood glucose level is high and does not induce it during normoglycemia (Lancet, volume 2, page 1300, 1987). GLP-1 also enhances insulin biosynthesis (Endocrinology, volume 130, page 159, 1992) and accelerates proliferation of β-cells (Diabetologia, volume 42, page 856, 1999). Therefore GLP-1 is not only stimulating insulin secretion but also is a very important hormone for the maintenance of pancreatic β-cells.

The efficacy of GLP-1 has been confirmed in patients with Type-II diabetes. The administration and maintaining high blood level of GLP-1 significantly reduces hyperglycemia (Diabetologia, volume 36, page 741, 1994 or ibid., volume 39, page 1546, 1996).

In addition, GLP-1 induces glucose utilization in peripheral tissues (Endocrinology, volume 135, page 2070, 1994 or Diabetologia, volume 37, page 1163, 1994). Intracerebroventricular injection of GLP-1 induces feeding behavior (Digestion, volume 54, page 360, 1993). It is also reported that GLP-1 reduced gastrointestinal motility (Dig. Dis. Sci., volume 43, page 1113, 1998).

Compounds closest to the compounds of the present invention in structure are described in U.S. Pat. No. 4,717,414 (hereinafter, referred to as Reference A) and J. Chem. Soc., Perkin Trans. 1, page 1547, 1979 (hereinafter, referred to as Reference B).

The compounds of Reference A have an imidazoisoindole-dione skeleton having an oxo group at the imidazo part condensing to the isoindole skeleton.

However, although the imidazoisoindole-dione skeleton is common to the compounds of the invention and the compounds of Reference A, the compounds of the invention have a functional group such as, for example, an aryl group at the substituent part at the 9-position on the skeleton and in that point are utterly different from the compounds of Reference A having a substituted alkyl group ($R^4C(Z)R^5$) such as, specifically for example, a nitromethyl group or a 1-nitro-1-ethylmethyl group, in structure. Further, the use in Reference A is herbicides and is utterly different from the invention in industrially applicable fields. Further, the preparation process in Reference A utilizes nucleophilic reaction of alkyl carbon anions, etc. onto dihydroimidazoisoindole-dione, etc., and is utterly different from the preparation process of the invention utilizing cyclization reaction.

Reference B discloses a compound having an oxazoloisoindole-dione skeleton which has an oxo group at the oxazolo part condensing to the isoindole skeleton.

However, Reference B mainly discloses novel preparation processes of isoindolobenzazepine derivatives, and merely discloses that, in the reaction step, only one compound having an oxazoloisoindole-dione skeleton is formed as a reaction by-product. The oxazoloisoindole-dione skeleton is common to the compounds of the invention and the compound of Reference B, but the compounds of the invention having a functional group such as, for example, an aryl group at the substituent part at the 9-position on the skeleton and in that point are utterly different from the compound of Reference B which is Compounds (1 1) having an α-bromobenzyl group as the substituent, in structure.

Further, Japanese Laid-open Patent Publication (Tokuhyo-hei) No. 507388/1994 (hereinafter, referred to as Reference C) and U.S. Pat. No. 3,507,863 (hereinafter, referred to as Reference D) disclose tricyclic heterocycles wherein a 6-membered ring, a 5-membered ring and a 5-membered ring are condensed.

Reference C discloses compounds having an oxazoloisoindole skeleton or an imidazoisoindole skeleton wherein the oxazolo part or the imidazo part is condensed to the isoindole skeleton, respectively.

However, although the oxazoloisoindole skeleton or the imidazoisoindole skeleton are common to the compounds of the invention and the compounds of Reference C, the compounds of the invention have a functional group such as, for example, an oxo group or a thioxo group at the the oxazolo part or the imidazo part condensed to the isoindole skeleton and in that point are utterly different from the compounds of Reference C not having the oxo group or the like, in structure. Further, the use in Reference C is antiviral drugs and is the same in the industrially applicable field, but is an use having no relation to the use in the invention.

Reference D discloses compounds having an oxazoloisoindole skeleton, an imidazoisoindole skeleton or a thiazoloisoindole skeleton wherein the oxazolo part, the imidazo part or the thiazolo part is condensed to the isoindole skeleton, respectively.

However, although the oxazoloisoindole skeleton, the imidazoisoindole skeleton and the thiazoloisoindole skeleton are common to the compounds of the invention and the compounds of Reference D, the compounds of the invention have a functional group such as, for example, an oxo group or a thioxo group at the the oxazolo part, the imidazo part or the thiazolo part condensed to the isoindole skeleton and in that point are utterly different from the compounds of Reference D not having the oxo group or the like, in structure. Further, the use in Reference D is antiinflammatories or anticonvulsants and the same in the industrially applicable field, but is an use having no relation to the use in the invention.

As background art disclosing an invention having relation to the use in the present invention, there can be mentioned U.S. Pat. No. 3,928,597 (hereinafter, referred to as Reference E). Reference E discloses an invention of a method of treating hyperglycemia comprising orally or parenterally administering a 2,3-dihydroimidazoisoindolol compound wherein a lower alkyl group is substituted at the imidazo part condensed to the isoindole skeleton, and an imidazolylphenyl phenyl ketone compound.

However, although the imidazoisoindolone skeleton is common to the compounds of the invention and the compounds of Reference E, the compounds of the invention have a functional group such as, for example, an oxo group or a thioxo group at the imidazo part condensed to the isoindole skeleton and in that point are utterly different from the compounds of Reference E not having the oxo group or the like, in structure. Moreover, the invention of Reference E is a use invention which was attained by administering both of the 2,3-dihydroimidazoisoindolol compound and the imidazolylphenyl phenyl ketone compound, each showing no antihyperglycemia effect solely, and is based on interaction between the two kinds of compounds, as described in Column 4 lines 39 to 45 of the specification, and is essentially different from the present invention in the subject of invention.

At present, drugs such as sulfonylureas, insulin sensitizers and α-glucosidase inhibitors are often used as anti-diabetic drugs. However, these drugs do not have satisfactory profiles. Indeed, sulfonylureas are difficult to use for correction of postprandial hyperglycemia due to slow onset and long duration of action. Moreover, sulfonylureas cause fasting hypoglycemia, which sometimes leads to fatal damage. Insulin sensitizers have side effects such as liver toxicity and edema. Therefore careful prescription of these drugs is necessary. As for α-glucosidase inhibitors, side effects such as flatulence and diarrhea come in to problema.

Therefore, it is necessary to develop much useful and safer anti-diabetic drugs which are able to regulate glucose level in a blood glucose-dependent manner.

DISCLOSURE OF INVENTION

The present inventors have made intense researches for creating drugs for treating diabetes, capable of controlling blood glucose levels depending on the blood glucose levels, prophylactic agents for chronic complications of diabetes, or drugs against obesity, found that the compounds of the general formula [I] attain high in vivo GLP-1 concentration in the blood, and completed the invention.

This invention relates to isoindole derivatives, processes for preparation thereof and uses thereof, and these inventions are not disclosed in literatures and novel.

Description is made on definitions of various symbols and terms described in the specification. Hereinafter, the terms "atom" and "group" are often omitted when being omitted is believed to be apparent, and for example, the term "(a) phenyl group(s)" is often abbreviated merely as "phenyl", and "(a) hydrogen atom(s)" is often abbreviated merely as "hydrogen".

As aryl groups, aryl groups having 6 to 15 carbon atoms are preferred, and for example, naphthyl, phenyl, etc. are mentioned, and among them phenyl, etc. are for example preferred.

As mono- to tricyclic $C_7$–$C_{15}$ aromatic carbocyclic groups, aromatic groups having 7 to 15 carbon atoms and having 1 to 3 cyclic groups are preferred, and there can for example be mentioned acenaphthylenyl, adamantyl, anthryl, indenyl, norbornyl, phenanthryl, etc. and preferred among them are for example anthryl, phenanthryl, etc.

As 5- or 6-membered heterocyclic groups, there can for example be mentioned isoxazolyl, isothiazolyl, imidazolyl, oxazolyl, oxadiazolyl, thiazolyl, thiadiazolyl, thienyl, triazinyl, triazolyl, pyridyl, pyrazinyl, pyrimidinyl, pyridazinyl, pyrazolyl, pyrrolyl, pyranyl, furyl, furazanyl, imidazolidinyl, imidazolinyl, tetrahydrofuranyl, pyrazolidinyl, pyrazolinyl, piperazinyl, piperidinyl, pyrrolidinyl, pyrrolinyl, morpholino, etc. (hereinafter. "isoxazolyl, . . . , morpholino" is referred to as a series of groups A), and preferred among them are for example thienyl. tetrahydrofuranyl, pyridyl, pyrazinyl, pyrimidinyl, furyl, morpholino, etc.

As mono- to tricyclic aromatic heterocyclic groups having per one ring 1 to 5 hetero atoms selected from the group consisting of nitrogen atoms, oxygen atoms and sulfur atoms, there can for example be mentioned acridinyl, isoquinolyl, isoindolyl, indazolyl, indolyl, indolizinyl, ethylenedioxyphenyl, carbazolyl, quinazolinyl, quinoxalinyl, quinolidinyl, quinolyl, cumaronyl, chromenyl, phenanthridinyl, phenanthrolinyl, dibenzofuranyl, dibenzothiophenyl, cinnolinyl, thionaphthenyl, naphthyridinyl, phenazinyl, phenoxazinyl, phenothiazinyl, phthalazinyl, pteridinyl, purinyl, benzimidazolyl, benzoxazolyl, benzothiazolyl, benzotriazolyl, benzofuranyl, methylenedioxyphenyl, etc. (hereinafter, "acridinyl, . . . , methylenedioxyphenyl" is referred to as a series of groups B), and preferred among them are for example ethylenedioxyphenyl, dibenzofuranyl, dibenzothiophenyl, methylenedioxyphenyl, etc.

Halogen atoms mean fluorine, chlorine, bromine and iodine, and preferred among them are fluorine, chlorine and iodine, and further preferred among them are fluorine and chlorine.

As cyclic saturated $C_3$–$C_9$ aliphatic groups, cyclic alkyl groups having 3 to 9 carbon atoms, etc. are preferred, and among them cyclic alkyl groups having 3 to 6 carbon atoms, etc. are preferred.

As the cyclic alkyl groups, there can for example be mentioned cyclopropyl, cyclobutyl, cyclopentyl, cyclohexyl, cycloheptyl, cyclooctyl, cyclononyl, etc., and preferred among them are for example cyclopropyl, cyclobutyl, cyclopentyl, cyclohexyl, etc.

As cyclic unsaturated $C_3$–$C_9$ aliphatic groups, cyclic alkenyl groups having 3 to 9 carbon atoms, etc. are preferred, and among them cyclic alkenyl groups having 3 to 6 carbon atoms, etc. are preferred.

As the cyclic alkenyl groups, there can for example be mentioned cyclopropenyl, cyclobutenyl, cyclopentenyl, cyclohexenyl, cycloheptenyl, cyclooctenyl, cyclononenyl, etc., and preferred among them are for example cyclopropenyl, cyclobutenyl, cyclopentenyl, cyclohexenyl, etc.

As aralkyl groups, aralkyl groups having 7 to 15 carbon atoms are preferred, and there can specifically be mentioned for example benzyl, α-methylbenzyl,. phenethyl, 3-phenylpropyl, 1-naphthylmethyl, 2-naphthylmethyl, α-methyl(1-naphthyl)methyl, α-methyl(2-naphthyl)methyl, α-ethyl(1-naphthyl)methyl, α-ethyl(2-naphthyl)methyl, diphenylmethyl, etc., and in particular preferred among them are benzyl, 1-naphthylmethyl, 2-naphthylmethyl, α-methylbenzyl, phenethyl, etc.

N-aralkylamino groups mean groups wherein an amino group is substituted with the above-mentioned aralkyl group, and there can specifically be mentioned for example N-benzylamino, N-(α-methylbenzyl)amino, N-phenethylamino, N-(3-phenylpropyl)amino, N-(1-naphthylmethyl)amino, N-(2-naphthylmethyl)amino, N-[α-methyl(1-naphthyl)methyl]amino, N-[α-methyl(2-naphthyl)methyl]amino, N-[α-ethyl(1-naphthyl)methyl]amino, N-[α-ethyl(2-naphthyl)methyl]amino, diphenylmethylamino, N-(dinaphthylmethyl)amino, etc., and preferred among them are N-benzylamino, N-(α-methylbenzyl)amino, N-phenethylamino, etc.

N,N-di-aralkylamino groups mean groups wherein an amino group is disubstituted with the above-mentioned aralkyl groups, and there can for example be mentioned N,N-dibenzylamino, N,N-di(α-methylbenzyl)amino, N,N-diphenethylamino, N,N-di(3-phenylpropyl)amino, N,N-di(1-naphthylmethyl)amino, N,N-di(2-naphthylmethyl)amino, N,N-di[α-methyl(1-naphthyl)methyl]amino, N,N-di[α-methyl(2-naphthyl)methyl]amino, N-benzyl-N-(α-methylbenzyl)amino, N-benzyl-N-phenethyl-amino, N-benzyl-N-(3-phenylpropyl)amino, etc., and preferred among them are N,N-dibenzylamino, N,N-di(α-methylbenzyl)amino, N,N-diphenethylamino, etc.

Aralkyloxy groups mean groups wherein an oxygen atom is substituted with the above-mentioned aralkyl group, and there can for example be mentioned benzyloxy, α-methylbenzyloxy, phenethyloxy, 3-phenylpropoxy, 1-naphthylmethoxy, 2-naphthylmethoxy, α-methyl(1-naphthyl)methoxy, α-methyl(2-naphthyl)methoxy, α-ethyl(1-naphthyl)methoxy, α-ethyl(2-naphthyl)methoxy, diphenylmethoxy, dinaphthylmethoxy, etc., and preferred among them are benzyloxy, α-methylbenzyloxy, phenethyloxy etc.

Aralkylcarbonyl groups mean groups wherein a carbonyl group is substituted with the above-mentioned aralkyl group, and there can for example be mentioned benzylcarbonyl, α-methylbenzylcarbonyl, phenethylcarbonyl, 3-phenylpropylcarbonyl, 1-naphthylmethylcarbonyl, 2-naphthylmethylcarbonyl, α-methyl(1-naphthyl)methylcarbonyl, α-methyl(2-naphthyl)methylcarbonyl, α-ethyl(1-naphthyl)methylcarbonyl, α-ethyl(2-naphthyl)methylcarbonyl, diphenylmethylcarbonyl, dinaphthylmethylcarbonyl, etc., and preferred among them are benzylcarbonyl, α-methylbenzylcarbonyl, phenethylcarbonyl, etc.

N-aralkylcarbamoyl groups mean groups wherein a carbamoyl group is substituted with the above-mentioned aralkyl group, and there can for example be mentioned N-benzylcarbamoyl, N-(α-methylbenzyl)carbamoyl, N-phenethylcarbamoyl, N-(3-phenylpropyl)carbamoyl, N-(1-naphthylmethyl)carbamoyl, N-(2-naphthylmethyl)carbamoyl, N-(α-methyl(1-naphthyl)methyl)carbamoyl, N-(α-methyl(2-naphthyl)methyl)carbamoyl, N-(α-ethyl(1-naphthyl)methyl)carbamoyl, N-(α-ethyl(2-naphthyl)methyl)carbamoyl, N-(diphenylmethyl)carbamoyl, N-(dinaphthyl-methyl)carbamoyl, etc., and preferred among them are N-benzylcarbamoyl, N-(α-methylbenzyl)carbamoyl, N-phenethylcarbamoyl, etc.

N-arylamino groups mean groups wherein an amino group is substituted with the above-mentioned aryl group, and there can for example be mentioned N-phenylamino, N-(1-naphthyl)amino, N-(2-naphthyl)amino, etc., and preferred among them are N-phenylamino, etc.

N,N-diarylamino groups mean groups wherein an amino group is disubstituted with the above-mentioned aryl groups, and there can for example be mentioned N,N-diphenylammino, N,N-di(1-naphthyl)amino, N,N-di(2-naphthyl)amino, N-phenyl-N-(1-naphthyl)amino, N-phenyl-N-(2-naphthyl)amino, N-(1-naphthyl)-N-(2-naphthyl) amino, etc., and preferred among them are N,N-diphenylammino, N,N-di(1-naphthyl)amino, N,N-di(2-naphthyl)amino, etc.

Aryloxy groups mean groups wherein an oxygen atom is substituted with the above-mentioned aryl group, and there can for example be mentioned phenoxy, naphthyloxy. etc., and preferred among them are phenoxy, etc.

Arylsulfonyl groups mean groups wherein a sulfonyl group is substituted with the above-mentioned aryl group, and there can for example be mentioned phenylsulfonyl, naphthylsulfonyl, etc., and preferred among them are phenylsulfonyl, etc.

Arylsulfonyloxy groups mean groups wherein an sulfonyloxy group is substituted with the above-mentioned aryl group, and there can for example be mentioned phenylsulfonyloxy, naphthylsulfonyloxy, etc., and preferred among them are phenylsulfonyloxy, etc.

N-arylsulfonylamino groups mean groups wherein an amino group is N-substituted with the above-mentioned arylsulfonyl group, and there can for example be mentioned N-phenylsulfonylamino, N-(1-naphthylsulfonyl)amino, N-(2-naphthylsulfonyl)amino, etc., and preferred among them are N-phenylsulfonylamino, N-(2-naphthylsulfonyl)amino, etc.

As N-arylsulfonylamino $C_1$–$C_{10}$ alkylamino groups, groups wherein an amino group is N-substituted with an alkyl group having 1 to 10 carbon atoms, having the above-mentioned arylsulfonylamino group are preferred, and there can for example be mentioned N-phenylsulfonylaminomethylamino, N-(1-phenylsulfonylaminoethyl)amino, N-(2-phenylsulfonylaminoethyl)amino, N-naphthylsulfonylaminomethylamino, N-(1-naphthylsulfonylaminoethyl)amino, N-(2-naphthylsulfonylaminoethyl)amino, etc., and preferred among them are N-phenylsulfonylaminomethylamino, N-(2-phenylsulfonylaminoethyl)amino, etc.

As N-arylsulfonylamino $C_1$–$C_{10}$ alkylcarbamoyl groups, groups wherein a carbamoyl group is N-substituted with an alkyl group having 1 to 10 carbon atoms, having the above-mentioned arylsulfonylamino group are preferred, and there can for example be mentioned N-phenylsulfonylaminomethylcarbamoyl, N-(1-phenylsulfonylaminoethyl)carbamoyl, N-(2-phenylsulfonylaminoethyl)carbamoyl, N-naphthylsulfonylaminomethylcarbamoyl, N-(1-naphthylsulfonylaminoethyl)-carbamoyl, N-(2-naphthylsulfonylaminoethyl)carbamoyl, etc., and preferred among them are N-phenylsulfonylaminomethylcarbamoyl, N-(2-phenylsulfonylaminoethyl)carbamoyl, N-(2-naphthylsulfonylaminoethyl)carbamoyl, etc.

As N-arylsulfonylamino $C_1$–$C_{10}$ alkoxylcarbonyl groups, groups wherein an alkoxycarbonyl group having 1 to 6 carbon atoms is substituted with the above-mentioned N-arylsulfonylamino group are preferred, and there can for example be mentioned N-phenylsulfonylaminomethoxycarbonyl, N-naphthylsulfonylamino-methoxycarbonyl, 1-(N-phenylsulfonylamino)ethoxycarbonyl, 2-(N-phenylsulfonyl-amino)ethoxycarbonyl, etc., and preferred among them are N-phenylsulfonyl-aminomethoxycarbonyl, N-naphthylsulfonylaminomethoxycarbonyl, etc.

Arylsulfamoyl groups mean groups wherein a sulfamoyl group is substituted with the above-mentioned aryl group, and there can for example be mentioned phenylsulfamoyl, naphthylsulfamoyl, etc., and preferred among them are phenylsulfamoyl, etc.

Arylsulfamoyloxy groups mean groups wherein a sulfamoyloxy group is substituted with the above-mentioned aryl group, and there can for example be mentioned phenylsulfamoyloxy, naphthylsulfamoyloxy, etc., and preferred among them are phenylsulfamoyloxy, etc.

As N-arylsulfamoyl $C_1$–$C_{10}$ alkylcarbamoyl groups, groups wherein an alkylcarbamoyl group having 1 to 10 carbon atoms is substituted with the above-mentioned arylsulfamoyl group are preferred, and there can for example be mentioned phenylsulfamoylmethylcarbamoyl, N-naphthylsulfamoylmethylcarbamoyl, etc., and preferred among them are N-naphthylsulfamoylmethylcarbamoyl, etc.

As arylsulfamoyl $C_1$–$C_6$ alkoxycarbonyl groups, groups wherein an alkoxylcarbonyl group having 1 to 6 carbon atoms is substituted with the above-mentioned arylsulfamoyl group are preferred, and there can for example be mentioned phenylsulfamoylmethoxycarbonyl, naphthylsulfamoylmethoxycarbonyl, etc., and preferred among them are phenylsulfamoylmethoxycarbonyl, etc.

N-arylcarbamoyl groups mean groups wherein a carbamoyl group is N-substituted with the above-mentioned aryl group, and there can for example be mentioned phenylcarbamoyl, naphthylcarbamoyl, and preferred among them are phenylcarbamoyl, etc.

As $C_2$–$C_6$ alkanoyl groups, groups wherein a carbonyl group is substituted with an alkyl group having 1 to 5 carbon atoms are preferred, and there can for example be mentioned acetyl, propionyl, butyryl, isobutyryl, valeryl, isovaleryl, pivaloyl, pentanoyl, etc., and preferred among them are acetyl, propionyl, pivaloyl, etc.

N—$C_2$–$C_6$ alkanoylamino groups mean groups wherein an amino group is substituted with the above-mentioned $C_2$–$C_6$ alkanoyl group, and there can for example be mentioned N-acetylamino, N-propionylamino, N-butyrylamino, N-isobutyrylamino, N-valerylamino, N-isovalerylamino, N-pivaloylamino, N-pentanoylamino, etc., and preferred among them are N-acetylamino, N-propionylamino, N-pivaloylamino, etc. N,N-di-$C_2$–$C_6$ alkanoylamino groups mean groups wherein an amino group is disubstituted with the above-mentioned $C_2$–$C_6$ alkanoyl groups, and there can for example be mentioned N,N-diacetylamino, N,N-dipropionylamino, N,N-dibutyrylamino, N,N-diisobutyrylamino, N,N-divalerylamino, N,N-diisovalerylamino, N,N-dipivaloylamino, N,N-dipentanoylamino, N-actyl-N-propionylamino, N-actyl-N-butyrylamino, N-actyl-N-pivaloylamino, etc., and preferred among them are N,N-diacetylamino, N,N-dipropionylamino, N,N-dibutyrylamino, N,N-dipivaloylamino, etc.

Aroyl groups mean groups wherein a carbonyl group is substituted with the above-mentioned aryl group, and there can for example be mentioned benzoyl, naphthylcarbonyl, etc., and preferred among them are benzoyl, etc.

Aroxy groups mean groups wherein an oxygen atom is substituted with the above-mentioned aroyl group, and there can for example be mentioned benzoyloxy, naphthylcarbonyloxy, etc., and preferred among them are benzoyloxy, etc.

N-aroylamino groups mean groups wherein an amino group is substituted with the above-mentioned aroyl group, and there can for example be mentioned N-benzoylamino, N-naphthylcarbonylamino, etc., and preferred among them are N-benzoylamino, etc.

As N-aroyl $C_1$–$C_{10}$ alkylamino groups, groups wherein an amino group is N-substituted with an alkyl group having 1 to 10 carbon atoms, having the above-mentioned aroyl group, are preferred, and there can for example be mentioned N-benzoylmethylamino, N-(1-benzoylethyl)amino, N-(2-benzoylethyl)amino, N-naphthylcarbonylamino, N-(1-naphthylcarbonylethyl)amino, N-(2-naphthylcarbonylethyl)amino, etc., and preferred among them are N-benzoylmethylamino, N-(2-benzoylethyl)amino, etc.

N-aroyl $C_1$–$C_{10}$ alkylcarbamoyl groups mean groups wherein a carbamoyl group is substituted with the above-mentioned N-aroyl $C_1$–$C_{10}$ alkyl group, and there can for example be mentioned N-benzoylmethylcarbamoyl, N-(1-benzoylethyl)carbamoyl, N-(2-benzoylethyl)carbamoyl, N-naphthylmethylcarbonylcarbamoyl, N-(1-naphthylcarbonylethyl)carbamoyl, N-(2-naphthylcarbonylethyl)carbamoyl, etc., and preferred among them are N-benzoylmethylcarbamoyl, N-(2-benzoylethyl)carbamoyl, etc.

N-(N-aroylamino) $C_1$–$C_{10}$ alkylcarbamoyl groups mean groups wherein a carbamoyl group is substituted with the above-mentioned N-aroylamino $C_1$–$C_{10}$ alkyl group, and there can for example be mentioned N-(N-benzoylaminomethyl)carbamoyl, N-(1-(N-benzoylamino)ethyl)carbamoyl, N-(2-(N-benzoyl)aminoethyl)carbamoyl, N-(N-naphthylcarbonylaminomethyl)carbamoyl, N-(1-(N-naphthylcarbonylamino)ethyl)-carbamoyl, N-(2-(N-naphthylcarbonylamino)ethyl)carbamoyl, etc., and preferred among them are N-(N-benzoylaminomethyl)carbamoyl, N-(2-(N-benzoylamino)ethyl)carbamoyl, etc.

N-aroylamino $C_1$–$C_{10}$ alkoxycarbonyl groups mean groups wherein an oxycarbonyl group is substituted with the above-mentioned N-aroylamino $C_1$–$C_{10}$ alkyl group, and there can for example be mentioned N-benzoylaminomethoxycarbonyl, 1-(N-benzoylamino)ethoxycarbonyl, 2-(N-benzoylamino)ethoxycarbonyl, N-naphthylcarbonylaminomethoxycarbonyl, 1-(N-naphthylcarbonylamino)ethoxycarbonyl, 2-(N-naphthylcarbonylamino)ethoxycarbonyl, etc., and preferred among them are N-benzoylaminomethoxycarbonyl, 2-(N-benzoylamino)ethoxycarbonyl, etc.

As N—$C_1$–$C_6$ alkylamino groups, groups wherein an amino group is N-substituted with an alkyl group having 1 to 6 carbon atoms are preferred, and there can for example be mentioned N-methylamino, N-ethylamino, N-propylamino, N-isopropylamino, N-butylamino, N-isobutylamino, N-sec-butylamino, N-tert-butylamino, N-pentylamino, N-neopentylamino, N-hexylamino, N-isohexylamino, etc., and preferred among them are N-methylamino, N-ethylamino, N-propylamino, N-isopropylamino, N-butylamino, N-isobutylamino, N-tert-butylamino, etc.

As N,N-di-$C_1$–$C_6$ alkylamino groups, groups wherein an amino group is N,N-disubstituted with alkyl groups having 1 to 6 carbon atoms are preferred, and there can for example be mentioned N,N-dimethylamino, N,N-diethylamino, N,N-dipropylamino, N,N-diisopropylamino, N,N-dibutylamino, N,N-di-tert-butylamino, N,N-dipentylamino, N,N-dihexylamino, N-ethyl-N-methylamino, N-methyl-N-propylamino, N-isopropyl-N-methylamino, N-tert-butyl-N-methylamino, N-ethyl-N-isopropylamino, etc., and preferred among them are N,N-dimethylamino, N,N-diethylamino, N,N-diisopropylamino, N,N-dibutylamino, N,N-di-tert-butylamino, N-ethyl-N-methylamino, N-methyl-N-propylamino, N-isopropyl-N-methylamino, N-ethyl-N-isopropylamino, etc.

As N—$C_1$–$C_{10}$ alkycarbamoyl groups, groups wherein a carbamoyl group is N-substituted with an alkyl group having 1 to 10 carbon atoms are preferred and there can for example be mentioned N-methylcarbamoyl, N-ethylcarbamoyl, N-propylcarbamoyl, N-isopropylcarbamoyl, N-butylcarbamoyl, N-isobutylcarbamoyl, N-sec-butylcarbamoyl, N-tert-butylcarbamoyl, N-pentylcarbamoyl, N-neopentyl-carbamoyl, N-hexylcarbamoyl, N-isohexylcarbamoyl, N-octylcarbamoyl, N-decylcarbamoyl, etc., and preferred among them are N-methylcarbamoyl, N-ethylcarbamoyl, N-propylcarbamoyl, N-isopropylcarbamoyl, N-isobutylcarbamoyl, N-sec-butylcarbamoyl, N-tert-butylcarbamoyl, N-octylcarbamoyl, N-decylcarbamoyl, etc.

As N,N-di-$C_1$–$C_{10}$ alkycarbamoyl groups, groups wherein a carbamoyl group is N,N-disubstituted with alkyl groups having 1 to 10 carbon atoms are preferred, and there can for example be mentioned N,N-dimethylcarbamoyl, N,N-diethylcarbamoyl, N,N-dipropylcarbamoyl, N,N-diisopropylcarbamoyl, N,N-dibutylcarbamoyl. N,N-di-tert-butylcarbamoyl, N,N-dipentylcarbamoyl, N,N-dihexylcarbamoyl, N-ethyl-N-methylcarbamoyl, N-isopropyl-N-methylcarbamoyl, N-tert-butyl-N-methylcarbamoyl, N-ethyl-N-isopropylcarbamoyl, etc., and preferred among them are N,N-dimethylcarbamoyl, N,N-diethylcarbamoyl, N,N-diisopropylcarbamoyl, N,N-dibutylcarbamoyl, N,N-di-tert-butylcarbamoyl, N-ethyl-N-methylcarbamoyl, N-isopropyl-N-methylcarbamoyl, N-ethyl-N-isopropylcarbamoyl, etc.

As N—$C_1$–$C_{10}$ alkythiocarbamoyl groups, groups wherein a thiocarbamoyl group is N-substituted with an alkyl group having 1 to 10 carbon atoms are preferred, and there can for example be mentioned N-methylthiocarbamoyl, N-ethylthiocarbamoyl, N-propylthiocarbamoyl, N-isopropylthiocarbamoyl, N-butylthiocarbamoyl, N-isobutylthiocarbamoyl, N-sec-butylthiocarbamoyl, N-tert-butylthiocarbamoyl, N-pentylthiocarbamoyl, N-neopentylthiocarbamoyl, N-hexylthiocarbamoyl, N-isohexylthiocarbamoyl, N-octylthiocarbamoyl, N-decylthiocarbamoyl, etc., and preferred among them are N-methylthiocarbamoyl, N-ethylthiocarbamoyl, N-propylthiocarbamoyl, N-isopropylthiocarbamoyl, N-isobutylthiocarbamoyl, N-sec-butylthiocarbamoyl, N-tert-butylthiocarbamoyl, N-octylthiocarbamoyl, N-decylthiocarbamoyl, etc.

As N,N-di-$C_1$–$C_{10}$ alkythiocarbamoyl groups, groups wherein a thiocarbamoyl group is N,N-disubstituted with alkyl groups having 1 to 10 carbon atoms are preferred, and there can for example be mentioned N,N-dimethylthiocarbamoyl, N,N-diethylthiocarbamoyl, N,N-dipropylthiocarbamoyl, N,N-diisopropylthiocarbamoyl, N,N-dibutylthiocarbamoyl, N,N-di-tert-butylthiocarbamoyl, N,N-dipentylthiocarbamoyl, N,N-dihexylthiocarbamoyl, N-ethyl-N-methylthiocarbamoyl, N-isopropyl-N-methylthiocarbamoyl, N-tert-butyl-N-methylthiocarbamoyl, N-ethyl-N-isopropylthiocarbamoyl, etc., and preferred among them are N,N-dimethylthiocarbamoyl, N,N-diethylthiocarbamoyl, N,N-diisopropylthiocarbamoyl, N,N-dibutylthiocarbamoyl, N,N-di-tert-butylthiocarbamoyl, N-ethyl-N-methylthiocarbamoyl, N-isopropyl-N-methylthiocarbamoyl, N-ethyl-N-isopropylthiocarbamoyl, etc.

As N-amino $C_1$–$C_{10}$ alkylcarbamoyl groups, groups wherein a carbamoyl group is N-substituted with an aminoalkyl group having 1 to 10 carbon atoms are preferred, and there can for example be mentioned N-aminomethylcarbamoyl, N-aminoethylcarbamoyl, N-aminopropylcarbamoyl, N-aminomethylethylcarbamoyl, N-aminobutylcarbamoyl, N-aminopropylcarbamoyl, N-aminopentylcarbamoyl, N-aminohexylcarbamoyl, etc., and preferred among them are N-aminomethylcarbamoyl, N-aminoethylcarbamoyl, N-aminopropylcarbamoyl, N-aminomethylethylcarbamoyl, etc.

As N—$C_1$–$C_6$ alkoxy $C_1$–$C_{10}$ alkylcarbamoyl groups, groups wherein an N—$C_1$–$C_{10}$ alkylcarbamoyl group is substituted with an alkoxy having 1 to 6 carbon atoms are preferred, and there can for example be mentioned N-methoxymethylcarbamoyl, N-methoxyethylcarbamoyl, N-methoxypropylcarbamoyl, N-methoxybutylcarbamoyl, N-ethoxypentylcarbamoyl, N-butoxyhexylcarbamoyl, etc., and preferred among them are N-methoxymethylcarbamoyl, N-methoxyethylcarbamoyl, N-methoxypropylcarbamoyl, N-methoxybutylcarbamoyl, etc.

As N—$C_1$–$C_6$ alkoxycarbonyl $C_1$–$C_{10}$ alkylcarbamoyl groups, groups wherein the above-mentioned N—$C_1$–$C_{10}$ alkylcarbamoyl group is substituted with an alkoxycarbonyl having 1 to 6 carbon atoms are preferred, and there can for example be mentioned N-methoxycarbonylmethylcarbamoyl, N-methoxycarbonylethylcarbamoyl, N-methoxycarbonylpropylcarbamoyl, N-methoxycarbonylbutylcarbamoyl, N-ethoxycarbonylpentylcarbamoyl, N-butoxycarbonylhexylcarbamoyl, N-tert-butoxycarbonylethylcarbamoyl, etc., and preferred among them are N-methoxycarbonylmethylcarbamoyl, N-methoxycarbonylethylcarbamoyl, N-methoxycarbonylpropylcarbamoyl, N-methoxycarbonylbutylcarbamoyl, N-tert-butoxycarbonylethylcarbamoyl, etc.

As amino $C_1$–$C_6$ alkoxycarbonyl groups, groups wherein a carbonyl group is substituted with an aminoalkoxy group having 1 to 6 carbon atoms are preferred, and there can for example be mentioned aminomethoxycarbonyl, aminoethoxycarbonyl, aminopropoxycarbonyl, 2-amino-2-methylpropoxycarbonyl, 2-aminomethylethoxycarbonyl, aminobutoxycarbonyl, 2-aminopropoxycarbonyl, aminopentyloxycarbonyl. aminohexyloxycarbonyl, etc., and preferred among them are aminomethoxycarbonyl, aminoethoxycarbonyl, aminopropoxycarbonyl, 2-aminomethylethoxycarbonyl, 2-amino-2-methylpropoxycarbonyl, etc.

As N—$C_1$–$C_6$ alkoxycarbonylamino $C_1$–$C_{10}$ alkylcarbamoyl groups, groups wherein the above-mentioned N—$C_1$–$C_{10}$ alkylcarbamoyl group is substituted with an alkoxycarbonylamino group having 1 to 6 carbon atoms are preferred, and there can for example be mentioned N-methoxycarbonylaminomethylcarbamoyl, N-methoxycarbonylaminoethylcarbamoyl, N-methoxycarbonylaminopropylcarbamoyl, N-methoxycarbonylaminobutylcarbamoyl, N-ethoxycarbonylaminopentylcarbamoyl, N-butoxycarbonylaminohexylcarbamoyl, N-tert-butoxycarbonylaminohexylcarbamoyl, etc., and preferred among them are N-methoxycarbonylaminomethylcarbamoyl, N-methoxycarbonylaminoethylcarbamoyl, N-methoxycarbonylaminopropylcarbamoyl, N-methoxycarbonylaminobutylcarbamoyl, N-tert-butoxycarbonylaminoethylcarbamoyl, etc.

As N—$C_1$–$C_6$ alkoxycarbonylamino $C_1$–$C_6$ alkoxycarbonyl groups, groups wherein a $C_1$–$C_6$ alkoxycarbonyl group is substituted with an N-alkoxycarbonylamino group having 1 to 6 carbon atoms are preferred, and there can for example be mentioned N-methoxycarbonylaminomethoxycarbonyl, N-methoxycarbonylaminoethoxycarbonyl, N-methoxycarbonylaminopropoxycarbonyl, N-methoxycarbonylaminobutoxycarbonyl, N-ethoxycarbonylaminopentyloxycarbonyl, N-butoxycarbonylaminohexyloxycarbonyl, N-tert-butoxycarbonylaminoethoxycarbonyl, etc., and preferred among them are N-methoxycarbonylaminomethoxycarbonyl, N-methoxycarbonylaminoethoxycarbonyl, N-methoxycarbonylaminopropoxycarbonyl, N-methoxycarbonylaminobutoxycarbonyl, N-tert-butoxycarbonylaminoethoxycarbonyl, etc.

As N—$C_2$–$C_6$ alkenylcarbamoyl groups, groups wherein a carbamoyl group is N-substituted with an alkenyl group having 2 to 6 carbon atoms are preferred, and there can for example be mentioned N-vinylcarbamoyl, N-allylcarbamoyl, N-(1-propenyl)carbamoyl, N-isopropenylcarbamoyl, N-(2-butenyl)carbamoyl, N-isobutenylcarbamoyl, N-(2-pentenyl)carbamoyl, N-(2-hexenyl)carbamoyl, N-(2-heptenyl)carbamoyl, N-(2-octenyl)carbamoyl, etc., and preferred among them are N-vinylcarbamoyl, N-allylcarbamoyl, N-(1-propenyl) carbamoyl, etc.

As N,N-di-$C_2$–$C_6$ alkenylcarbamoyl groups, groups wherein a carbamoyl group is N,N-disubstituted with alkenyl groups having 2 to 6 carbon atoms are preferred, and there can for example be mentioned N,N-divinylcarbamoyl, N,N-diallylcarbamoyl, N,N-di-(1-propenyl)carbamoyl, N,N-diisopropenylcarbamoyl, N-allyl-N-vinylcarbamoyl, N-allyl-N-isobutenylcarbamoyl, N-allyl-N-(2-pentenyl) carbamoyl, N-allyl-N-(2-hexenyl)carbamoyl, N-allyl-N-(2-heptenyl)carbamoyl, N-allyl-N-(2-octenyl)-carbamoyl, etc., and preferred among them are N-allyl-N-vinylcarbamoyl, N,N-diallylcarbamoyl, N-allyl-N-(1-propenyl)carbamoyl, etc.

As N—$C_1$–$C_6$ alkylsulfamoyl groups, groups wherein a sulfamoyl is N-substituted with an alkyl group having 1 to 6 carbon atoms are preferred, and there can for example be mentioned N-methylsulfamoyl, N-ethylsulfamoyl, N-propylsulfamoyl, N-isopropylsulfamoyl, N-butylsulfamoyl, N-isobutylsulfamoyl, N-sec-butylsulfamoyl, N-tert-butylsulfamoyl, N-pentylsulfamoyl, N-neopentylsulfamoyl, N-hexylsulfamoyl, N-isohexylsulfamoyl, etc., and preferred among them are N-methylsulfamoyl, N-ethylsulfamoyl, N-isopropylsulfamoyl, N-tert-butylsulfamoyl, etc.

As N,N-di-$C_1$–$C_6$ alkylsulfamoyl groups, groups wherein a sulfamoyl is N,N-disubstituted with alkyl groups having 1 to 6 carbon atoms are preferred, and there can for example be mentioned N,N-dimethylsulfamoyl, N,N-diethylsulfamoyl, N,N-dipropylsulfamoyl, N,N-diisopropylsulfamoyl, N,N-dibutylsulfamoyl, N,N-di-tert-butylsulfamoyl, N,N-dipentylsulfamoyl, N,N-dihexylsulfamoyl, N-ethyl-N-methylsulfamoyl, N-isopropyl-N-methylsulfamoyl, N-tert-butyl-N-methylsulfamoyl, N-ethyl-N-isopropylsulfamoyl, etc., and preferred among them are N,N-dimethylsulfamoyl, N,N-diethylsulfamoyl, N,N-diisopropylsulfamoyl, N,N-dibutylsulfamoyl, N,N-di-tert-butylsulfamoyl, N-ethyl-N-methylsulfamoyl, N-isopropyl-N-methylsulfamoyl, N-ethyl-N-isopropylsulfamoyl, etc.

As $C_1$–$C_6$ alkylsulfinyl groups, groups wherein a sulfinyl group is substituted with an alkyl group having 1 to 6 carbon atoms are preferred, and there can for example be mentioned methylsulfinyl, ethylsulfinyl, propylsulfinyl, isopropylsulfinyl, butylsulfinyl, isobutylsulfinyl, sec-butylsulfinyl, tert-butylsulfinyl, pentylsulfinyl, neopentylsulfinyl, hexylsulfinyl, isohexylsulfinyl, etc., and preferred among them are methylsulfinyl, ethylsulfinyl, propylsulfinyl, isopropylsulfinyl, butylsulfinyl, tert-butylsulfinyl, etc.

As $C_1$–$C_6$ alkylsulfonyl groups, groups wherein a sulfonyl group is substituted with an alkyl group having 1 to 6 carbon atoms are preferred, and there can for example be mentioned methylsulfonyl, ethylsulfonyl, propylsulfonyl, isopropylsulfonyl, butylsulfonyl, isobutylsulfonyl, sec-butylsulfonyl, tert-butylsulfonyl, pentylsulfonyl, neopentylsulfonyl, hexylsulfonyl, isohexylsulfonyl, etc., and preferred among them are methylsulfonyl, ethylsulfonyl, propylsulfonyl, butylsulfonyl, tert-butylsulfonyl, etc.

As $C_1$–$C_6$ alkylsulfonylamino groups, groups wherein an amino group is substituted with an alkylsulfonyl group having 1 to 6 carbon atoms are preferred, and there can for example be mentioned N-methylsulfonylamino, N-ethylsulfonylamino, N-propylsulfonylamino, N-isopropylsulfonylamino, N-butylsulfonylamino, N-isobutylsulfonylamino, N-sec-butylsulfonylamino, N-tert-butylsulfonylamino, N-pentylsulfonylamino, N-neopentylsulfonylamino, N-hexylsulfonylamino, N-isohexylsulfonylamino, etc., and preferred among them are N-methylsulfonylamino, N-ethylsulfonylamino, N-propylsulfonylamino, N-butylsulfonylamino, N-tert-butylsulfonylamino, etc.

As $C_1$–$C_6$ alkylthio groups, groups wherein a sulfur atom is substituted with an alkyl group having 1 to 6 carbon atoms are preferred, and there can for example be mentioned methylthio, ethylthio, propylthio, isopropylthio, butylthio, isobutylthio, sec-butylthio, tert-butylthio, pentylthio, neopentylthio, hexylthio, isohexylthio, etc., and preferred among them are methylthio, ethylthio, propylthio, isopropylthio. butylthio, tert-butylthio, etc.

As $C_1$–$C_6$ alkoxy groups, groups wherein an oxygen atom is substituted with an alkyl group having 1 to 6 carbon atoms are preferred, and there can for example be mentioned methoxy, ethoxy, propoxy, isopropoxy, butoxy, isobutoxy, sec-butoxy, tert-butoxy, pentyloxy, neopentyloxy, hexyloxy, isohexyloxy, etc., and preferred among them are methoxy, ethoxy, propoxy, isopropoxy, butoxy, isobutoxy, tert-butoxy, etc.

As $C_1$–$C_6$ alkoxycarbonyl groups, groups wherein a carbonyl group is substituted with an alkoxy group having 1 to 5 carbon atoms are preferred, and there can for example be mentioned methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyoxycarbonyl, neopentyoxycarbonyl, etc., and preferred among them are methoxycarbonyl, ethoxycarbonyl, propoxycarbonyl, isopropoxycarbonyl, butoxycarbonyl, tert-butoxycarbonyl, etc.

As N—$C_3$–$C_6$ cycloalkylamino groups, groups wherein an amino group is N-substituted with a cyclic alkyl group having 3 to 6 carbon atoms are preferred, and there can for example be mentioned N-cyclopropylamino, N-cyclobutylamino, N-cyclopentylamino, N-cyclohexylamino, etc., and preferred among them are N-cyclopropylamino, N-cyclopentylamino, N-cyclohexylamino, etc.

As N,N-di-$C_3$–$C_6$ cycloalkylamino groups, groups wherein an amino group is N,N-disubstituted with cyclic alkyl groups having 3 to 6 carbon atoms are preferred, and there can for example be mentioned N,N-dicyclopropylamino, N,N-dicyclobutylamino, N,N-dicyclopentylamino, N,N-dicyclohexylamino, N-cyclobutyl-N-cyclopropylamino, N-cyclopentyl-N-cyclopropylamino, N-cyclohexyl-N-cyclopropylamino, etc., and preferred among them are N,N-dicyclopropylamino, N,N-dicyclobutylamino, N,N-dicyclopentylamino, etc.

As $C_3$–$C_6$ cycloalkyloxy groups, groups wherein an oxygen atom is substituted with a cyclic alkyl group having 3 to 6 carbon atoms are preferred, and there can for example be mentioned cyclopropoxy, cyclobutoxy, cyclopentyloxy, cyclohexyloxy, etc., and preferred among them are cyclopropoxy, cyclopentyloxy, cyclohexyloxy etc.

As N—$C_3$–$C_6$ cycloalkycarbamoyl groups, groups wherein a carbamoyl group is N-substituted with a cyclic alkyl group having 3 to 6 carbon atoms are preferred, and there can for example be mentioned N-cyclopropylcarbamoyl, N-cyclobutylcarbamoyl, N-cyclopentylcarbamoyl, N-cyclohexylcarbamoyl, etc., and preferred among them are N-cyclopropylcarbamoyl, N-cyclopentylcarbamoyl, N-cyclohexylcarbamoyl. etc.

As N,N-di-$C_3$–$C_6$ cycloalkycarbamoyl groups, groups wherein a carbamoyl group is N,N-disubstituted with cyclic alkyl groups having 3 to 6 carbon atoms are preferred. and there can for example be mentioned N,N-dicyclopropylcarbamoyl, N,N-dicyclobutylcarbamoyl, N,N-dicyclopentylcarbamoyl, N,N-dicyclohexylcarbamoyl, N-cyclobutyl-N-cyclopropylcarbamoyl, N-cyclopentyl-N-cyclopropylcarbamoyl, N-cyclohexyl-N-cyclopropylcarbamoyl, etc., and preferred among them are N,N-dicyclopropylcarbamoyl, N,N-dicyclobutylcarbamoyl, N,N-dicyclopentylcarbamoyl, etc.

As saturated $C_1$–$C_9$ aliphatic groups, alkyl groups having 1 to 9 carbon atoms are preferred, and they may be straight-chain or branched. Among them straight-chain or branched alkyl groups having 1 to 6 carbon atoms are preferred.

As the alkyl groups, there can for example be mentioned methyl, ethyl, propyl, isopropyl, butyl, isobutyl, sec-butyl, tert-butyl, pentyl, neopentyl, hexyl, isohexyl, heptyl, octyl, nonyl, etc., and preferred among them are methyl, ethyl, propyl, isopropyl, isobutyl, sec-butyl, tert-butyl, etc.

As unsaturated $C_1$–$C_9$ aliphatic groups, alkenyl groups or alkynyl groups each having 1 to 9 carbon atoms are preferred, and they may be straight-chain or branched. Among them straight-chain or branched alkenyl groups or alkynyl groups each having 1 to 6 carbon atoms are preferred.

As the alkenyl groups, there can for example be mentioned vinyl, allyl, 1-propenyl, isopropenyl, 2-butenyl, isobutenyl, 2-pentenyl, 2-hexenyl, 2-heptenyl, 2-octenyl, etc., and preferred among them are vinyl, allyl, 1-propenyl, etc.

As the alkynyl groups, there can for example be mentioned ethynyl, 1-propynyl, 1-butynyl, 1-pentynyl, 1-hexynyl, 1-heptynyl, 1-octynyl, etc., and preferred among them are ethynyl, 1-propynyl, etc.

As 5- or 6-membered saturated carbocyclic groups, there can for example be mentioned cyclopentyl, cyclohexyl, etc., and preferred among them are cyclopentyl, etc.

As 5- or 6-membered unsaturated carbocyclic groups, there can for example be mentioned cyclopentenyl, cyclohexenyl, etc., and preferred among them are cyclopentenyl, etc.

As N—$C_1$–$C_{10}$ alkylcarbamoyl groups, N—$C_1$–$C_{10}$ alkylthiocarbamoyl groups, thiocarbonyl groups or carbonyl groups each substituted with a 5- or 6-membered heterocyclic group, N—$C_1$–$C_{10}$ alkylcarbamoyl groups, N—$C_1$–$C_{10}$ alkylthiocarbamoyl groups, thiocarbonyl groups or carbonyl groups each substituted with the above-mentioned heterocyclic group are preferred, and there can for example be mentioned N-isoxazolylalkylcarbamoyl such as N-isoxazolylmethylcarbamoyl, N-isothiazolylalkylcarbamoyl such as N-isothiazolylmethylcarbamoyl, N-imidazolylalkylcarbamoyl such as N-imidazolylmethylcarbamoyl, N-oxazolylalkylcarbamoyl such as N-oxazolylmethylcarbamoyl, N-oxadiazolylalkylcarbamoyl such as N-oxadiazolylmethylcarbamoyl, N-thiazolylalkylcarbamoyl such as N-thiazolylmethylcarbamoyl, N-thiadiazolylalkylcarbamoyl such as N-thiadiazolylmethylcarbamoyl, N-thienylalkylcarbamoyl such as N-thienylmethylcarbamoyl, N-triazinylalkylcarbamoyl such as N-triazinylmethylcarbamoyl, N-triazolylalkylcarbamoyl such as N-triazolylmethylcarbamoyl, N-pyridylalkylcarbamoyl such as N-pyridylmethylcarbamoyl, N-pyrazinylalkylcarbamoyl such as N-pyrazinylmethylcarbamoyl, N-pyrimidinylalkylcarbamoyl such as N-pyrimidinylmethylcarbamoyl, N-pyridazinylalkylcarbamoyl such as N-pyridazinylmethylcarbamoyl, N-pyrazolylalkylcarbamoyl such as N-pyrazolylmethylcarbamoyl, N-pyrrolylalkylcarbamoyl such as N-pyrrolylmethylcarbamoyl, N-pyranylalkylcarbamoyl such as N-pyranylmethylcarbamoyl, N-furylalkylcarbamoyl such as N-furylmethylcarbamoyl, N-furazanylalkylcarbamoyl such as N-furazanylmethylcarbamoyl, N-imidazolidinylalkylcarbamoyl such as N-imidazolidinylmethylcarbamoyl, N-imidazolinylalkylcarbamoyl such as N-imidazolinylmethylcarbamoyl, N-tetrahydrofuranylalkylcarbamoyl such as N-tetrahydrofuranylalkylcarbamoyl, N-pyrazolidinylalkylcarbamoyl such as N-pyrazolidinylmethylcarbamoyl, N-pyrazolinylalkylcarbamoyl such as N-pyrazolinylmethylcarbamoyl, N-piperazinylalkylcarbamoyl such as N-piperazinylmethylcarbamoyl, N-piperidinylalkylcarbamoyl such as N-piperidinylmethylcarbamoyl, N-pyrrolidinylalkylcarbamoyl such as N-pyrrolidinylmethylcarbamoyl, N-pyrrolinylalkylcarbamoyl such as N-pyrrolinylmethylcarbamoyl, N-morpholinoalkylcarbamoyl such as N-morpholinomethylcarbamoyl; for example, N-isoxazolylalkylthiocarbamoyl such as N-isoxazolylmethylthiocarbamoyl, N-isothiazolylalkylthiocarbamoyl such as N-isothiazolylmethylthiocarbamoyl, N-imidazolylalkylthiocarbamoyl such as N-imidazolylmethylthiocarbamoyl, N-oxazolylalkylthiocarbamoyl such as N-oxazolylmethylthiocarbamoyl, N-oxadiazolylalkylthiocarbamoyl such as N-oxadiazolylmethylthiocarbamoyl, N-thiazolylalkylthiocarbamoyl such as N-thiazolylmethylthiocarbamoyl N-thiadiazolylalkylthiocarbamoyl such as N-thiadiazolylmethylthiocarbamoyl, N-thienylalkylthiocarbamoyl such as N-thienylmethylthiocarbamoyl, N-triazinylalkylthiocarbamoyl such as N-triazinylmethylthiocarbamoyl, N-triazolylalkylthiocarbamoyl such as N-triazolylmethylthiocarbamoyl, N-pyridylalkylthiocarbamoyl such as N-pyridylmethylthiocarbamoyl, N-pyrazinylalkylthiocarbamoyl such as N-pyrazinylmethylthiocarbamoyl, N-pyrimidinylalkylthiocarbamoyl such as N-pyrimidinylmethylthio-carbamoyl, N-pyridazinylalkylthiocarbamoyl such as N-pyridazinylmethylthio-carbamoyl, N-pyrazolylalkylthiocarbamoyl such as N-pyrazolylmethylthiocarbamoyl, N-pyrrolylalkylthiocarbamoyl such as N-pyrrolylmethylthiocarbamoyl, N-pyranylalkylthiocarbamoyl such as N-pyranylmethylthiocarbamoyl, N-furylalkylthiocarbamoyl such as N-furylmethylthiocarbamoyl, N-furazanylalkylthiocarbamoyl such as N-furazanylmethylthiocarbamoyl, N-imidazolidinylalkylthiocarbamoyl such as N-imidazolidinylmethylthiocarbamoyl, N-imidazolinylalkylthiocarbamoyl such as N-imidazolinylmethylthiocarbamoyl, N-tetrahydrofuranylalkylthiocarbamoyl such as N-tetrahydrofuranylalkylthiocarbamoyl, N-pyrazolidinylalkylthiocarbamoyl such as N-pyrazolidinylmethylthiocarbamoyl. N-pyrazolinylalkylthiocarbamoyl such as N-pyrazolinylmethylthiocarbamoyl, N-piperazinylalkylthiocarbamoyl such as N-piperazinylmethylthiocarbamoyl, N-piperidinylalkylthiocarbamoyl such as N-piperidinylmethylthiocarbamoyl, N-pyrrolidinylalkylthiocarbamoyl such as N-pyrrolidinylmethylthiocarbamoyl, N-pyrrolinylalkylthiocarbamoyl such as N-pyrrolinylmethylthiocarbamoyl. N-morpholinoalkylthiocarbamoyl such as N-morpholinomethylthiocarbamoyl, etc.; for example, isoxazolylthiocarbonyl, isothiazolylthiocarbonyl, imidazolylthiocarbonyl, oxazolylthiocarbonyl, oxadiazolylthiocarbonyl, thiazolylthiocarbonyl, thiadiazolylthiocarbonyl, thienylthiocarbonyl, triazinylthiocarbonyl, triazolylthiocarbonyl, pyridylthiocarbonyl, pyrazinylthio-carbonyl, pyrimidinylthiocarbonyl, pyridazinylthiocarbonyl, pyrazolylthiocarbonyl, pyrrolylthiocarbonyl, pyranylthiocarbonyl, furylthiocarbonyl, furazanylthiocarbonyl, imidazolidinylthiocarbonyl, imidazolinylthiocarbonyl, tetrahydrofuranylthiocarbonyl, pyrazolidinylthiocarbonyl, pyrazolinylthiocarbonyl, piperazinylthiocarbonyl, piperidinylthiocarbonyl, pyrrolidinylthiocarbonyl, pyrrolinylthiocarbonyl, morpholinothiocarbonyl, etc.; for example, isoxazolylcarbonyl, isothiazolylcarbonyl, imidazolylcarbonyl, oxazolylcarbonyl, oxadiazolylcarbonyl, thiazolylcarbonyl, thiadiazolylcarbonyl, thienylcarbonyl, triazinylcarbonyl, triazolylcarbonyl, pyridylcarbonyl, pyrazylcarbonyl, pyrazinylcarbonyl, pyrimidinylcarbonyl, pyridazinylcarbonyl, pyrazolylcarbonyl, pyrrolylcarbonyl, pyranylcarbonyl, furylcarbonyl, furazanylcarbonyl, imidazolidinylcarbonyl, imidazolinylcarbonyl, tetrahydrofuranylcarbonyl, pyrazolidinylcarbonyl, pyrazolinylcarbonyl, pyranylcarbonyl, piperazinylcarbonyl, piperidinylcarbonyl, pyrrolidinylcarbonyl, pyrrolinylcarbonyl, morpholinocarbonyl, etc., and preferred among them are N—$C_1$–$C_{10}$ alkylcarbamoyl groups, N—$C_1$–$C_{10}$ alkylthiocarbamoyl groups, a thiocarbonyl group or a carbonyl group, etc. each substituted for example with thienyl, pyridyl, pyrazinyl, pyrimidinyl, furyl, tetrahydrofuranyl, morpholino or the like.

N—$C_1$–$C_{10}$ alkylcarbamoyl groups, N—$C_1$–$C_{10}$ alkylthiocarbamoyl groups, thiocarbonyl groups or carbonyl groups each substituted with a monocyclic to tricyclic aromatic heterocyclic group (excluding 5- or 6-membered heterocyclic groups) having per one ring 1 to 5 hetero atoms selected from the group consisting of a nitrogen atom, an oxygen atom and a sulfur atom mean N—$C_1$–$C_{10}$ alkylcarbamoyl groups, N—$C_1$–$C_{10}$ alkylthiocarbamoyl groups, thiocarbonyl groups or carbonyl groups each substituted with the above-mentioned aromatic heterocyclic group, and there can for example be mentioned N-acridinylalkylcarbamoyl such as N-acridinylmethylcarbamoyl, N-isoquinolylalkylcarbamoyl such as N-isoquinolylmethylcarbamoyl, N-isoindolylalkylcarbamoyl such as N-isoindolylmethylcarbamoyl, N-indazolylalkylcarbamoyl such as N-indazolylmethylcarbamoyl, N-indolylalkylcarbamoyl such as N-indolylmethylcarbamoyl, N-indolizinylalkylcarbamoyl such as N-indolizinylmethylcarbamoyl, N-ethylenedioxyphenylalkylcarbamoyl such as N-ethylenedioxyphenylmethylcarbamoyl, N-carbazolylalkylcarbamoyl such as N-carbazolylmethylcarbamoyl, N-quinazolinylalkylcarbamoyl such as N-quinazolinylmethylcarbamoyl, N-quinoxalinylalkylcarbamoyl such as N-quinoxalinylmethylcarbamoyl, N-quinolizinylalkylcarbamoyl such as N-quinolizinylmethylcarbamoyl, N-quinolylalkylcarbamoyl such as N-quinolylmethylcarbamoyl, N-cumaronylalkylcarbamoyl such as N-cumaronylmethylcarbamoyl, N-chromenylalkylcarbamoyl such as N-chromenylmethylcarbamoyl, N-phenanthridinylalkylcarbamoyl such as N-phenanthridinylmethylcarbamoyl, N-phenanthrolinylalkylcarbamoyl such as N-phenanthrolinylmethylcarbamoyl, N-dibenzofuranylalkylcarbamoyl such as N-dibenzofuranylmethylcarbamoyl, N-dibenzothiophenylalkylcarbamoyl such as N-dibenzothiophenylmethylcarbamoyl, N-cinnolinylalkylcarbamoyl such as N-cinnolinylmethylcarbamoyl, N-thionaphthenylalkylcarbamoyl such as N-thionaphthenylmethylcarbamoyl, N-naphthyridinylalkylcarbamoyl such as N-naphthyridinylmethylcarbamoyl, N-phenazinylalkylcarbamoyl such as N-phenazinylmethylcarbamoyl, N-phenoxazinylalkylcarbamoyl such as N-phenoxazinylmethylcarbamoyl, N-phenothiazinylalkylcarbamoyl such as N-phenothiazinylmethylcarbamoyl, N-phthalazinylalkylcarbamoyl such as N-phthalazinylmethylcarbamoyl, N-pteridinylalkylcarbamoyl such as N-pteridinylmethylcarbamoyl, N-purinylalkylcarbamoyl such as N-purinylmethylcarbamoyl, N-benzimidazolylalkylcarbamoyl such as N-benzimidazolylmethylcarbamoyl, N-benzoxazolylalkylcarbamoyl such as N-benzoxazolylmethylcarbamoyl, N-benzothiazolylalkylcarbamoyl such as N-benzothiazolylmethylcarbamoyl, N-benzotriazolylalkylcarbamoyl such as N-benzotriazolylmethylcarbamoyl, N-benzofuranylalkylcarbamoyl such as N-benzofuranylmethylcarbamoyl, N-methylenedioxyphenylalkylcarbamoyl such as N-methylenedioxyphenylmethylcarbamoyl, etc.; for example, N-acridinylalkylthiocarbamoyl such as N-acridinylmethylthiocarbamoyl, N-isoquinolylalkylthiocarbamoyl such as N-isoquinolylmethylthiocarbamoyl, N-isoindolylalkylthiocarbamoyl such as N-isoindolylmethylthiocarbamoyl, N-indazolylalkylthiocarbamoyl such as N-indazolylmethylthiocarbamoyl, N-indolylalkylthiocarbamoyl such as N-indolylmethylthiocarbamoyl, N-indolizinylalkylthiocarbamoyl such as N-indolizinylmethylthiocarbamoyl, N-ethylenedioxyphenylalkylthiocarbamoyl such as N-ethylenedioxyphenylmethylthiocarbamoyl, N-carbazolylalkylthiocarbamoyl such as N-carbazolylmethylthiocarbamoyl, N-quinazolinylalkylthiocarbamoyl such as N-quinazolinylmethylthiocarbamoyl, N-quinoxalinylalkylthiocarbamoyl such as N-quinoxalinylmethylthiocarbamoyl, N-quinolidinylalkylthiocarbamoyl such as N-quinolidinylmethylthiocarbamoyl, N-quinolylalkylthiocarbamoyl such as N-quinolylmethylthiocarbamoyl, N-cumaronylalkylthiocarbamoyl such as N-cumaronylmethylthiocarbamoyl, N-chromenylalkylthiocarbamoyl such as N-chromenylmethylthiocarbamoyl, N-phenanthridinylalkylthiocarbamoyl such as N-phenanthridinylmethylthiocarbamoyl, N-phenanthrolinylalkylthiocarbamoyl such as N-phenanthrolinylmethylthiocarbamoyl, N-dibenzofuranylalkylthiocarbamoyl such as N-dibenzofuranylmethylthiocarbamoyl, N-dibenzothiophenylalkylthiocarbamoyl such as N-dibenzothiophenylmethylthiocarbamoyl, N-cinnolinylalkylthiocarbamoyl such as N-cinnolinylmethylthiocarbamoyl, N-thionaphthenylalkylthiocarbamoyl such as N-thionaphthenylmethylthiocarbamoyl, N-naphthyridinylalkylthiocarbamoyl such as N-naphthyridinylmethylthiocarbamoyl, N-phenazinylalkylthiocarbamoyl such as N-phenazinylmethylthiocarbamoyl, N-phenoxazinylalkylthiocarbamoyl such as N-phenoxazinylmethylthiocarbamoyl, N-phenothiazinylalkylthiocarbamoyl such as N-phenothiazinylmethylthiocarbamoyl, N-phthalazinylalkylthiocarbamoyl such as N-phthalazinylmethylthiocarbamoyl, N-pteridinylalkylthiocarbamoyl such as N-pteridinylmethylthiocarbamoyl, N-purinylalkylthiocarbamoyl such as N-purinylmethylthiocarbamoyl, N-benzimidazolylalkylthiocarbamoyl such as N-benzimidazolylmethylthiocarbamoyl, N-benzoxazolylalkylthiocarbamoyl such as N-benzoxazolylmethylthiocarbamoyl N-benzothiazolylalkylthiocarbamoyl such as N-benzothiazolylmethylthiocarbamoyl, N-benzotriazolytalkylthiocarbamoyl such as N-benzotriazolylmethylthiocarbamoyl, N-benzofuranylalkylthiocarbamoyl such as N-benzofuranylmethylthiocarbamoyl, N-methylenedioxyphenylalkylthiocarbamoyl such as N-methylenedioxyphenylmethylthiocarbamoyl, etc.; for example, acridinylthiocarbonyl, isoquinolylthiocarbonyl, isoindolylthiocarbonyl, indazolylthiocarbonyl, indolylthiocarbonyl, indolizinylthiocarbonyl, ethylenedioxyphenylthiocarbonyl, carbazolylthiocarbonyl, quinazolinylthiocarbonyl, quinoxalinylthiocarbonyl, quinolizinylthiocarbonyl, quinolylthiocarbonyl, cumaronylthiocarbonyl, chromenylthiocarbonyl, phenanthridinylthiocarbonyl, phenanthrolinylthiocarbonyl, dibenzofuranylthiocarbonyl, dibenzothiphenylthiocarbonyl, cinnolinylthiocarbonyl, thionaphthenylthiocarbonyl, naphthyridinylthiocarbonyl, phenazinylthiocarbonyl, phenoxazinylthiocarbonyl, phenothiazinylthiocarbonyl, phthalazinylthiocarbonyl, pteridinylthiocarbonyl, purinylthiocarbonyl, benzimidazolylthiocarbonyl, benzoxazolylthiocarbonyl, benzothiazolylthiocarbonyl, benzotriazolylthiocarbonyl, benzofuranylthiocarbonyl, methylenedioxyphenylthiocarbonyl, etc.; for example, acridinylcarbonyl, isoquinolylcarbonyl, isoindolylcarbonyl, indazolylcarbonyl, indolylcarbonyl, indol izinylcarbonyl, ethylenedioxyphenylcarbonyl, carbazolylcarbonyl, quinazolinylcarbonyl, quinoxalinylcarbonyl, quinolizinylcarbonyl, quinolylcarbonyl, cumaronylcarbonyl, chromenylcarbonyl, phenanthridinylcarbonyl, phenanthrolinylcarbonyl, dibenzofuranylcarbonyl, dibenzothiphenylcarbonyl, cinnolinylcarbonyl, thionaphthenylcarbonyl, naphthyridinylcarbonyl, phenazinylcarbonyl, phenoxazinylcarbonyl, phenothiazinylcarbonyl, phthalazinylcarbonyl, pteridinylcarbonyl, purinylcarbonyl, benzimidazolylcarbonyl, benzoxazolylcarbonyl. benzothiazolylcarbonyl, benzotriazolylcarbonyl, benzofuranylcarbonyl. methylenedioxyphenylcarbonyl, etc., and preferred among them are N—$C_1$–$C_{10}$ alkylcarbamoyl groups, N—$C_1$–$C_{10}$ alkylthiocarbamoyl groups, thiocarbonyl groups and carbonyl groups each substituted for example with an ethylenedioxyphenyl group, a dibenzofuranyl group, a dibenzothiophenyl group, a methylenedioxyphenyl group or the like.

Condensed aryl groups mean groups wherein for example a phenyl group or a naphthyl group is bound to another ring to form a condensed benzene ring or a condensed naphthalene ring.

As di- or tricyclic saturated or unsaturated $C_6$–$C_{15}$ condensed carbocyclic groups, there can for example be mentioned acenaphthylenyl, adamantyl, anthryl, indanyl, indenyl, $C_6$–$C_8$ cycloalkanyl, $C_6$–$C_8$ cycloalkadienyl, $C_6$–$C_8$ cycloalkenyl, norbornyl, phenanthryl, fluorenyl, etc., and preferred among them are anthryl, $C_6$–$C_8$ cycloalkanyl, $C_6$–$C_8$ cycloalkadienyl, $C_6$–$C_8$ cycloalkenyl, etc.

As the $C_6$–$C_8$ cycloalkanyl groups, there can for example be mentioned cyclohexanyl, cycloheptanyl, cyclooctanyl, etc., and preferred among them are cyclohexanyl, etc.

As the $C_6$–$C_8$ cycloalkadienyl groups, there can for example be mentioned cyclohexadienyl, cycloheptadienyl, cyclooctadienyl, etc., and preferred among them are cyclohexadienyl, etc.

As the $C_6$–$C_8$ cycloalkenyl groups, there can for example be mentioned cyclohexenyl, cycloheptenyl, cyclooctenyl, etc., and preferred among them are cyclohexenyl, etc.

As 6-membered heterocyclic groups, or di- or tricyclic condensed aromatic heterocyclic groups having per one ring 1 to 5 hetero atoms selected from the group consisting of nitrogen atoms, oxygen atoms and surfur atoms, there can for example be mentioned isoquinolyl, isoindolyl, indazolyl, indolyl, indolizinyl, ethylenedioxyphenyl, quinazolinyl, quinoxalinyl, quinolizinyl, quinolyl, cumaronyl, chromenyl, thionaphthenyl, naphthyridinyl, pyridyl, pyrazinyl, pyrimidinyl, pyridazinyl, pyranyl, phthalazinyl, benzimidazolyl, benzoxazolyl, benzothiazolyl, benzotriazolyl, benzofuranyl, methylenedioxypheny, etc., and preferred among them are ethylenedioxypheny, pyridyl, pyrazinyl, pyrimidinyl, pyridazinyl, benzimidazolyl, benzoxazolyl, benzothiazolyl, benzotriazolyl, benzofuranyl, methylenedioxypheny, etc. Particularly preferred are ethylenedioxypheny, pyridyl, pyrazinyl, pyrimidinyl, pyridazinyl, methylenedioxypheny, etc.

R means, for example, an aryl group, a mono- to tricyclic $C_7$–$C_{15}$ aromatic carbocyclic group, a 5- or 6-membered heterocyclic group, or a mono- to tricyclic aromatic heterocyclic group having per one ring 1 to 5 hetero atoms selected from the group consisting of nitrogen atoms, oxygen atoms and sulfur atoms, etc.

Specifically, as the aryl groups, aryl groups having 6 to 15 carbon atoms are preferred, and there can for example be mentioned naphthyl, phenyl, etc., and preferred among them are pheny, etc.

As the mono- to tricyclic $C_7$–$C_{15}$ aromatic carbocyclic groups, aromatic groups having 7 to 15 carbon atoms and having 1 to 3 cyclic groups are preferred, and there can for example be mentioned acenaphthylenyl, adamantyl, anthryl, indenyl, norbornyl, phenanthryl, etc., and preferred among them are anthryl, phenanthryl, etc.

As the 5- or 6-membered heterocyclic groups, there can for example be mentioned the aforementioned series of groups A, etc., and preferred among them are thienyl, tetrahydrofuranyl, pyridyl, pyrazinyl, pyrimidinyl, furyl, morpholino, etc.

As the mono- to tricyclic aromatic heterocyclic groups having per one ring 1 to 5 hetero atoms selected from the group consisting of nitrogen atoms, oxygen atoms and surfur atoms, there can for example be mentioned the aforementioned series of groups B, etc., and preferred among them are ethylenedioxyphenyl, dibenzofuranyl, dibenzothiophenyl, methylenedioxyphenyl, etc.

In R, above all, aryl groups, etc. are preferred, and particularly phenyl, etc. are preferred. R can appropriately have 1 or more substituents.

As specific examples of the substituents, there can for example be mentioned
(1) substituents selected from the group consisting of azido, amino, carbamoyl, carbamoylamino, carbamoyloxy, carboxyl, cyano, sulfamoyl, sulfo, nitro, halogen, hydroxy, formyl, formylamino, cyclic saturated $C_3$–$C_9$ aliphatic groups, cyclic unsaturated $C_3$–$C_9$ aliphatic groups, aralkyl, N-aralkylamino, N,N-diaralkylamino, aralkyloxy, aralkylcarbonyl, N-aralkylcarbamoyl, aryl, N-arylamino, N,N-diarylamino, aryloxy, arylsulfonyl, arylsulfonyloxy, N-arylsulfonylamino, N-arylsulfonylamino $C_1$–$C_{10}$ alkylamino, N-arylsulfonylamino $C_1$–$C_{10}$ alkylcarbamoyl, N-arylsulfonylamino $C_1$–$C_6$ alkoxycarbonyl, arylsulfamoyl, arylsulfamoyloxy, N-arylsulfamoyl $C_1$–$C_{10}$ alkylcarbamoyl, arylsulfamoyl $C_1$–$C_6$ alkoxycarbonyl, N-arylcarbamoyl, aroyl, aroxy, N-(N-aroylamino) $C_1$–$C_{10}$ alkylcarbamoyl, N-aroylamino $C_1$–$C_{10}$ alkoxycarbonyl, $C_2$–$C_6$ alkanoyl, N—$C_2$–$C_6$ alkanoylamino, N,N-di-$C_2$–$C_6$ alkanoylamino, N—$C_1$–$C_6$ alkylamino, N,N-di-$C_1$–$C_6$ alkylamino, N—$C_1$–$C_{10}$ alkylcarbamoyl, N—$C_1$–$C_{10}$ alkylthiocarbamoyl, N,N-di-$C_1$–$C_{10}$ alkylcarbamoyl, N,N-di-$C_1$–$C_{10}$ alkylthiocarbamoyl, N—$C_2$–$C_6$ alkenylcarbamoyl, N,N-di-$C_2$–$C_6$ alkenylcarbamoyl, N-amino $C_1$–$C_{10}$ alkylcarbamoyl, N—$C_1$–$C_6$ alkoxy $C_1$–$C_{10}$ alkylcarbamoyl, N—$C_1$–$C_6$ alkoxycarbonyl $C_1$–$C_{10}$) alkylcarbamoyl, N—$C_1$–$C_6$ alkoxycarbonylamino $C_1$–$C_{10}$ alkylcarbamoyl, N—$C_1$–$C_6$ alkoxycarbonylamino $C_1$–$C_6$ alkoxycarbonyl, $C_1$–$C_6$ alkylthio, N—$C_1$–$C_6$ alkylsulfamoyl, N,N-di-$C_1$–$C_6$ alkylsulfamoyl, $C_1$–$C_6$ alkylsulfinyl, $C_1$–$C_6$ alkylsulfonyl, N—$C_1$–$C_6$ alkylsulfonylamino, $C_1$–$C_6$ alkoxy, $C_1$–$C_6$ alkoxycarbonyl, amino $C_1$–$C_6$ alkoxycarbonyl, N—$C_3$–$C_6$ cycloalkylamino, N,N-di-$C_3$–$C_6$ cycloalkylamino, $C_3$–$C_6$ cycloalkyloxy, N—$C_3$–$C_6$ cycloalkylcarbamoyl and N,N-di-$C_3$–$C_6$ cycloalkylcarbamoyl;
(2) 5- or 6-membered heterocyclic groups selected from the group consisting of the aforementioned series of groups A;
(3) monocyclic to tricyclic aromatic heterocyclic groups having per one ring 1 to 5 hetero atoms selected from the group consisting of nitrogen atoms, oxygen atoms and sulfur atoms, selected from the group consisting of the aforementioned series of groups B;
(4) substituents selected from the group consisting of N—$C_1$–$C_{10}$ alkylcarbamoyl groups, N—$C_1$–$C_{10}$ alkylthiocarbamoyl groups, thiocarbonyl groups and carbonyl groups each substituted with the heterocyclic group or the aromatic heterocyclic group; and
(5) substituents selected from the group consisting of straight-chain saturated $C_1$–$C_9$ aliphatic groups, straight-chain unsaturated $C_1$–$C_9$ aliphatic groups, branched saturated $C_1$–$C_9$ aliphatic groups, branched unsaturated $C_1$–$C_9$ aliphatic groups, $C_1$–$C_6$ alkoxy groups, $C_1$–$C_6$ alkylthio groups and N—$C_1$–$C_6$ alkylamino groups each of which may be substituted with the substituent,
(hereinafter, the above-mentioned groups (1) to (5) are referred to as a series of groups C).

Preferred among the substituents of R are, for example,
(1) substituents selected from the group consisting of amino, carbamoyl, carbamoylamino, carbamoyloxy, carboxyl, nitro, halogen, hydroxy, cyclic saturated $C_3$–$C_9$ aliphatic groups, cyclic unsaturated $C_3$–$C_9$ aliphatic groups, aralkyl, N-aralkylamino, aralkyloxy, aralkylcarbonyl, N-aralkylcarbamoyl, aryl, N-arylamino, aryloxy, arylsulfonyl, arylsulfonyloxy, N-arylsulfonylamino, N-arylsulfonylamino $C_1$–$C_{10}$ alkylamino, N-arylsulfonylamino $C_1$–$C_{10}$ alkylcarbamoyl, N-arylsulfonylamino $C_1$–$C_6$ alkoxycarbonyl, arylsulfamoyl, arylsulfamoyloxy, N-arylsulfamoyl $C_1$–$C_{10}$ alkylcarbamoyl, arylsulfamoyl $C_1$–$C_6$ alkoxycarbonyl, N-arylcarbamoyl, aroyl, aroxy, N-(N-aroylamino) $C_1$–$C_{10}$ alkylcarbamoyl, N-aroylamino $C_1$–$C_{10}$ alkoxycarbonyl, $C_2$–$C_6$ alkanoyl, N—$C_2$–$C_6$ alkanoylamino, N—$C_1$–$C_6$ alkylamino, N,N-di-$C_1$–$C_6$ alkylamino, N—$C_1$–$C_{10}$ alkylcarbamoyl, N—$C_1$–$C_{10}$ alkylthiocarbamoyl, N,N-di-$C_1$–$C_{10}$ alkylcarbamoyl, N,N-di-$C_1$–$C_{10}$ alkylthiocarbamoyl, N—$C_2$–$C_6$ alkenylcarbamoyl, N,N-di-$C_2$–$C_6$ alkenylcarbamoyl, N-amino $C_1$–$C_{10}$ alkylcarbamoyl, N—$C_1$–$C_6$ alkoxy $C_1$–$C_{10}$ alkylcarbamoyl, N—$C_1$–$C_6$ alkoxycarbamoyl $C_1$–$C_{10}$ alkylcarbamoyl, N—$C_1$–$C_6$ alkoxycarbonylamino $C_1$–$C_{10}$ alkylcarbamoyl, N—$C_1$–$C_6$ alkoxycarbonylamino $C_1$–$C_6$ alkoxycarbonyl, $C_1$–$C_6$ alkylthio, $C_1$–$C_6$ alkylsulfinyl, $C_1$–$C_6$ alkylsulfonyl, N—$C_1$–$C_6$ alkylsulfonylamino, $C_1$–$C_6$ alkoxy, $C_1$–$C_6$ alkoxycarbonyl, amino $C_1$–$C_6$ alkoxycarbonyl, N—$C_3$–$C_6$ cycloalkylamino, N,N-di-$C_3$–$C_6$ cycloalkylamino, $C_3$–$C_6$ cycloalkyloxy, N—$C_3$–$C_6$ cycloalkylcarbamoyl and N,N-di-C3–C6 cycloalkylcarbamoyl;

(2) 5- or 6-membered heterocyclic groups selected from the group consisting of isoxazolyl, isothiazolyl, imidazolyl, oxazolyl, oxadiazolyl, thiazolyl, thiadiazolyl, thienyl, triazolyl, pyridyl, pyrazinyl, pyrimidinyl, pyridazinyl, pyrazolyl, pyrrolyl, pyranyl, furyl, imidazolidinyl, imidazolinyl, tetrahydrofuranyl, pyrazolidinyl, pyrazolinyl, piperazinyl piperidinyl, pyrrolidinyl, pyrrolinyl and morpholino (hereinafter, "isoxazolyl, . . . and morpholino" is referred to as a series of groups A';

(3) monocyclic to tricyclic aromatic heterocyclic groups having per one ring 1 to 5 hetero atoms selected from the group consisting of nitrogen atoms, oxygen atoms and sulfur atoms, selected from the group consisting of isoquinolyl, isoindolyl, indazolyl, indolyl, ethylenedioxyphenyl, carbazolyl, quinazolinyl, quinoxalinyl, quinolidinyl, quinolyl, cumaronyl, chromenyl, phenanthridinyl, phenanthrolinyl, dibenzofuranyl, dibenzothiophenyl, cinnolinyl,thionaphthenyl, naphthyridinyl, phenazinyl, phenoxazinyl, benzimidazolyl, benzoxazolyl, benzothiazolyl, benzotriazolyl, benzofuranyl and methylenedioxyphenyl (hereinafter, "isoquinolyl, . . . and methylenedioxyphenyl" is referred to as a series of groups B');

(4) substituents selected from the group consisting of N—$C_1$–$C_{10}$ alkylcarbamoyl groups, N—$C_1$–$C_{10}$ alkylthiocarbamoyl groups, thiocarbonyl groups and carbonyl groups each substituted with the heterocyclic group or the aromatic heterocyclic group; and (5) substituents selected from the group consisting of straight-chain saturated $C_1$–$C_9$ aliphatic groups, straight-chain unsaturated $C_1$–$C_9$ aliphatic groups, branched saturated $C_1$–$C_9$ aliphatic groups, branched unsaturated $C_1$–$C_9$ aliphatic groups, $C_1$–$C_6$ alkoxy groups and $C_1$–$C_6$ alkylthio groups each of which may be substituted with the substituent, (hereinafter, the above-mentioned groups (1) to (5) are referred to as a series of groups C').

Particularly preferred among the substituents of R are, for example, (1) substituents selected from the group consisting of amino, carbamoyl, carboxyl, nitro, halogen, hydroxy, aralkylcarbonyl, N-aralkylcarbamoyl, aryl, aroyl, $C_2$–$C_6$ alkanoyl, N—$C_1$–$C_6$ alkylamino, N—$C_1$–$C_{10}$ alkylcarbamoyl, N—$C_1$–$C_{10}$ alkylthiocarbamoyl, N,N-di-$C_1$–$C_{10}$ alkylcarbamoyl, N,N-di-$C_1$–$C_{10}$ alkylthiocarbamoyl, N—$C_2$–$C_6$ alkenylcarbamoyl, N,N-di-$C_2$–$C_6$ alkenylcarbamoyl, N-amino $C_1$–$C_{10}$ alkylcarbamoyl, N—$C_1$–$C_6$ alkoxy $C_1$–$C_{10}$ alkylcarbamoyl, N—$C_1$–$C_6$ alkoxycarbonyl $C_1$–$C_{10}$ alkylcarbamoyl, $C_1$–$C_6$ alkoxy, amino $C_1$–$C_6$ alkoxycarbonyl, N—$C_3$–$C_6$ cycloalkylamino, N,N-di-$C_3$–$C_6$ cycloalkylamino, $C_3$–$C_6$ cycloalkyloxy, N—$C_3$–$C_6$ cycloalkylcarbamoyl and N,N-di-$C_3$–$C_6$ cycloalkylcarbamoyl;

(2) 5- or 6-membered heterocyclic groups selected from the group consisting of thienyl, pyridyl, pyrazinyl, pyrimidinyl, furyl, tetrahydrofuranyl and morpholino;

(3) monocyclic to tricyclic aromatic heterocyclic groups having per one ring 1 to 5 hetero atoms selected from the group consisting of nitrogen atoms, oxygen atoms and sulfur atoms, selected from the group consisting of ethylenedioxyphenyl, dibenzofuranyl, dibenzothiophenyl and methylenedioxyphenyl;

(4) substituents selected from the group consisting of N—$C_1$–$C_{10}$ alkylcarbamoyl groups, N—$C_1$–$C_{10}$ alkylthiocarbamoyl groups, thiocarbonyl groups and carbonyl groups each substituted with the heterocyclic group or the aromatic heterocyclic group; and (5) substituents selected from the group consisting of straight-chain saturated $C_1$–$C_9$ aliphatic groups, straight-chain unsaturated $C_1$–$C_9$ aliphatic groups, branched saturated $C_1$–$C_9$ aliphatic groups, branched unsaturated $C_1$–$C_9$ aliphatic groups and $C_1$–$C_6$ alkoxy groups each of which may be substituted with the substituent (hereinafter, the above-mentioned groups (1) to (5) referred to as a series of groups C").

Namely, preferred as R are, for example, (1) aryl groups; (2) mono- to tricyclic $C_7$–$C_{15}$ aromatic carbocyclic groups selected from the group consisting of adamantyl groups, anthryl groups, indenyl groups, norbornyl groups and phenanthryl groups; (3) 5- or 6-membered heterocyclic groups selected from the group consisting of the aforementioned series of groups A'; or (4) monocyclic to tricyclic aromatic heterocyclic groups having per one ring 1 to 5 hetero atoms selected from the group consisting of nitrogen atoms, oxygen atoms and sulfur atoms, selected from the group consisting of the aforementioned series of groups B', each of which groups (1) to (4) may have one or more substituents selected from the group consisting of the aforementioned series of groups C', and these preferred R groups are referred to as Ra.

Particularly preferred as R are, for example, (1) aryl groups; (2) mono- to tricyclic $C_7$–$C_{15}$ aromatic carbocyclic groups selected from the group consisting of anthryl groups and phenanthryl groups; (3) 5- or 6-membered heterocyclic groups selected from the group consisting of thienyl, pyridyl, pyrazinyl, pyrimidinyl, furyl, tetrahydrofuranyl and morpholino; or (4) monocyclic to tricyclic aromatic heterocyclic groups having per one ring 1 to 5 hetero atoms selected from the group consisting of nitrogen atoms, oxygen atoms and sulfur atoms, selected from the group consisting of ethylenedioxyphenyl, dibenzofuranyl, dibenzothiophenyl and methylenedioxyphenyl, each of which groups (1) to (4) may have one or more substituents selected from the group consisting of the aforementioned series of groups C", and these particularly preferred R groups are referred to as $R^b$.

$R^1$ and $R^2$ may be the same or different, and represent, for example, groups selected from the group consisting of hydrogen, azido, amino, carbamoyl, carbamoylamino, carbamoyloxy, carboxyl, cyano, sulfamoyl, sulfo, nitro, halogen, hydroxy, formyl, formylamino, cyclic saturated $C_3$–$C_9$ aliphatic groups, cyclic unsaturated $C_3$–$C_9$ aliphatic groups, aralkyl, N-aralkylamino, aralkyloxy, aralkylcarbonyl, aryl, N-arylamino, aryloxy, arylsulfonyl, N-arylsulfonylamino, N-arylsulfonylamino $C_1$–$C_{10}$ alkylamino, N-arylsulfonylamino $C_1$–$C_{10}$ alkylcarbamoyl, N-arylsulfonylamino $C_1$–$C_6$ alkoxycarbonyl, $C_2$–$C_6$ alkanoyl, N—$C_2$–$C_6$ alkanoylamino, aroyl, N-aroylamino, N-aroyl $C_1$–$C_{10}$ alkylamino, N-aroyl $C_1$–$C_{10}$ alkylcarbamoyl, N—$C_1$–$C_6$ alkylamino, N,N-di-$C_1$–$C_6$ alkylamino, N—$C_1$–$C_{10}$ alkylcarbamoyl, N,N-di-$C_1$–$C_{10}$ alkylcarbamoyl, N—$C_1$–$C_6$ alkylsulfamoyl, $C_1$–$C_6$ alkylsulfinyl, $C_1$–$C_6$ alkylsulfonyl, N—$C_1$–$C_6$ alkylsulfonylamino, $C_1$–$C_6$ alkylthio, $C_1$–$C_6$ alkoxy, $C_1$–$C_6$ alkoxycarbonyl, N—$C_3$–$C_6$ cycloalkylamino, $C_3$–$C_6$ cycloalkyloxy and N—$C_3$–$C_6$ cycloalkylcarbamoyl (hereinafter, "hydrogen, . . . and N—$C_3$–$C_6$ cycloalkylcarbamoyl" is referred to as a series of groups D); or straight-chain saturated $C_1$–$C_9$ aliphatic groups, straight-chain unsaturated $C_1$–$C_9$ aliphatic groups, branched saturated $C_1$–$C_9$ aliphatic groups or branched unsaturated $C_1$–$C_9$ aliphatic groups, N—$C_1$–$C_6$ alkylamino groups, $C_1$–$C_6$ alkylthio groups or $C_1$–$C_6$ alkoxy groups each of which may optionally be substituted with the above group.

Preferred as $R^1$ and $R^2$ are, for example, groups selected from the group consisting of hydrogen, amino, carboxyl, cyano, sulfamoyl, sulfo, nitro, halogen, hydroxy, formyl, cyclic saturated $C_3$–$C_9$ aliphatic groups, cyclic unsaturated $C_3$–$C_9$ aliphatic groups, aralkyl, aryl, N-arylamino, aryloxy, $C_2$–$C_6$ alkanoyl, N—$C_2$–$C_6$ alkanoylamino, aroyl, N—$C_1$–$C_6$ alkylamino, N,N-di-$C_1$–$C_6$ alkylamino, N—$C_1$–$C_{10}$ alkylcarbamoyl, N—$C_1$–$C_6$ alkylsulfamoyl, $C_1$–$C_6$ alkylsulfinyl, $C_1$–$C_6$ alkylsulfonyl, N—$C_1$–$C_6$ alkylsulfonylamino, $C_1$–$C_6$ alkoxy, $C_1$–$C_6$ alkoxycarbonyl, N—$C_3$–$C_6$ cycloalkylamino, $C_3$–$C_6$ cycloalkyloxy and N—$C_3$–$C_6$ cycloalkylcarbamoyl (hereinafter, "hydrogen, . . . and N—$C_3$–$C_6$ cycloalkylcarbamoyl" is referred to as a series of groups D'); or straight-chain saturated $C_1$–$C_9$ aliphatic groups, straight-chain unsaturated $C_1$–$C_9$ aliphatic groups, branched saturated $C_1$–$C_9$ aliphatic groups, branched unsaturated $C_1$–$C_9$ aliphatic groups or $C_1$–$C_6$ alkoxy groups each of which may optionally be substituted with the above group.

Particularly preferred as $R^1$ and $R^2$ are, for example, groups selected from the group consisting of hydrogen, amino, nitro, halogen, hydroxy, aryl, N-arylamino, N—$C_1$–$C_6$ alkylamino, N,N-di-$C_1$–$C_6$ alkylamino, N—$C_1$–$C_{10}$ alkylcarbamoyl, $C_1$–$C_6$ alkoxy, $C_1$–$C_6$ alkoxycarbonyl and N—$C_3$–$C_6$ cycloalkylamino; or straight-chain saturated $C_1$–$C_9$ aliphatic groups, straight-chain unsaturated $C_1$–$C_9$ aliphatic groups, branched saturated $C_1$–$C_9$ aliphatic groups, branched unsaturated $C_1$–$C_9$ aliphatic groups or $C_1$–$C_6$ alkoxy groups each of which may optionally be substituted with the above group.

$R^3$ and $R^4$ may be the same or different, and represent (1) for example, groups selected from the group consisting of hydrogen, azido, amidino, amino, carbamoyl, carbamoylamino, carbamoyloxy, carboxyl, guanidino, cyano, sulfamoyl, sulfo, nitro, halogen, hydroxy, formyl, formylamino, cyclic saturated $C_3$–$C_9$ aliphatic groups, cyclic unsaturated $C_3$–$C_9$ aliphatic groups, $C_2$–$C_6$ alkanoyl, N—$C_2$–$C_6$ alkanoylamino, N—$C_1$–$C_6$ alkylamino, N,N-di-$C_1$–$C_6$ alkylamino, N—$C_1$–$C_{10}$ alkylcarbamoyl, N,N-di-$C_1$–$C_{10}$ alkylcarbamoyl, $C_1$–$C_6$ alkylthio, N—$C_1$–$C_6$ alkylsulfamoyl, $C_1$–$C_6$ alkylsulfinyl, $C_1$–$C_6$ alkylsulfonyl, N—$C_1$–$C_6$ alkylsulfonylamino, $C_1$–$C_6$ alkoxy, $C_1$–$C_6$ alkoxycarbonyl, N—$C_3$–$C_6$ cycloalkylamino, $C_3$–$C_6$ cycloalkyloxy and N—$C_3$–$C_6$ cycloalkylcarbamoyl (hereinafter, "hydrogen, . . . and N—$C_3$–$C_6$ cycloalkylcarbamoyl" is referred to as a series of groups E), (2) for example, groups selected from the group consisting of straight-chain saturated $C_1$–$C_9$ aliphatic groups, straight-chain unsaturated $C_1$–$C_9$ aliphatic groups. branched saturated $C_1$–$C_9$ aliphatic groups and branched unsaturated $C_1$–$C_9$ aliphatic groups, each of which may optionally be substituted with the above-mentioned group, or (3) for example, aryl groups; monocyclic to tricyclic $C_7$–$C_{15}$ aromatic carbocyclic groups selected from the group consisting of acenaphthylenyl, adamantyl, anthryl, indenyl, norbornyl and phenanthryl; 5- or 6-membered heterocyclic groups selected from the group consisting of isoxazolyl, isothiazolyl, imidazolyl, oxazolyl, oxadiazolyl, thiazolyl, thiadiazolyl, thienyl, triazinyl, triazolyl, pyridyl, pyrazinyl, pyrimidinyl, pyridazinyl, pyrazolyl, pyrrolyl, pyranyl, furyl, furazanyl, imidazolidinyl, imidazolinyl, tetrahydrofuranyl, pyrazolidinyl, pyrazolinyl, piperazinyl, piperidinyl, pyrrolidinyl, pyrrolinyl and morpholino; monocyclic to tricyclic aromatic heterocyclic groups having per one ring 1 to 5 hetero atoms selected from the group consisting of nitrogen atoms, oxygen atoms and sulfur atoms, selected from the group consisting of the aforementioned series of groups B; or straight-chain saturated $C_1$–$C_9$ aliphatic groups, straight-chain unsaturated $C_1$–$C_9$ aliphatic groups, branched saturated $C_1$–$C_9$ aliphatic groups or branched unsaturated $C_1$–$C_9$ aliphatic groups, each of which groups may be substituted with the aryl group, the aromatic carbocyclic group, the heterocyclic group or the aromatic heterocyclic group, or (4) $R^3$ and $R^4$ combine together to form a straight-chain saturated $C_1$–$C_9$ aliphatic group, a straight-chain unsaturated $C_1$–$C_9$ aliphatic group, a branched saturated $C_1$–$C_9$ aliphatic group, a branched unsaturated $C_1$–$C_9$ aliphatic group, a 5- or 6-membered saturated carbocyclic group or a 5- or 6-membered unsaturated carbocyclic group.

When embodiments of $R^3$ and $R^4$ are specifically described, as preferred groups in (1), there can for example be mentioned groups selected from the group consisting of hydrogen, azido, amidino, amino, carbamoyl, carbamoylamino, carbamoyloxy, carboxyl, guanidino, cyano, sulfamoyl, sulfo, nitro, halogen, hydroxy, formyl, formylamino, cyclic saturated $C_3$–$C_9$ aliphatic groups, cyclic unsaturated $C_3$–$C_9$ aliphatic groups, $C_2$–$C_6$ alkanoyl, N—$C_1$–$C_6$ alkylamino, N—$C_1$–$C_{10}$ alkylcarbamoyl, $C_1$–$C_6$ alkylthio, N—$C_1$–$C_6$ alkylsulfamoyl, $C_1$–$C_6$ alkylsulfinyl, $C_1$–$C_6$ alkylsulfonyl, N—$C_1$–$C_6$ alkylsulfonylamino, $C_1$–$C_6$ alkoxy, $C_1$–$C_6$ alkoxycarbonyl and N—$C_3$–$C_6$ cycloalkylamino (hereinafter, "hydrogen, . . . and N—$C_3$–$C_6$ cycloalkylamino" is referred to as a series of groups E'), and particularly preferred among them are for example hydrogen, azido, amidino, amino, carbamoyl, carboxyl, guanidino, cyano, sulfamoyl, sulfo, nitro, halogen, hydroxy, formyl, cyclic saturated $C_3$–$C_9$ aliphatic groups, cyclic unsaturated $C_3$–$C_9$ aliphatic groups, N—$C_1$–$C_6$ alkylamino, N—$C_1$–$C_{10}$ alkylcarbamoyl, $C_1$–$C_6$ alkylthio, $C_1$–$C_6$ alkoxy and $C_1$–$C_6$ alkoxycarbonyl (hereinafter, "hydrogen, . . . and $C_1$–$C_6$ alkoxycarbonyl" is referred to as a series of groups E"), As preferred groups in (2), there can for example be mentioned groups selected from the group consisting of straight-chain saturated $C_1$–$C_9$ aliphatic groups, straight-chain unsaturated $C_1$–$C_9$ aliphatic groups, branched saturated $C_1$–$C_9$ aliphatic groups and branched unsaturated $C_1$–$C_9$ aliphatic groups, each of which groups may be substituted with the group referred to in the immediately above (1), namely a group selected from the group consisting of the above-mentioned series of groups E', especially the above-mentioned series of groups E".

As preferred groups in (3), there can for example be mentioned aryl groups; mono- to tricyclic $C_7$–$C_{15}$ aromatic carbocyclic groups selected from the group consisting of adamantyl, anthryl, indenyl, norbornyl and phenanthryl; 5- or 6-membered heterocyclic groups selected from the group consisting of the aforementioned series of groups A'; monocyclic to tricyclic aromatic heterocyclic groups having per one ring 1 to 5 hetero atoms selected from the group consisting of nitrogen atoms, oxygen atoms and sulfur atoms, selected from the group consisting of the aforementioned series of groups B'; and straight-chain saturated $C_1$–$C_9$ aliphatic groups, straight-chain unsaturated $C_1$–$C_9$ aliphatic groups, branched saturated $C_1$–$C_9$ aliphatic groups or branched unsaturated $C_1$–$C_9$ aliphatic groups, each of which may be substituted with the aryl group, the aromatic carbocyclic group, the heterocyclic group or the aromatic heterocyclic group.

Particularly preferred as the groups in (3) are for example aryl groups; mono- to tricyclic $C_7$–$C_{15}$ aromatic carbocyclic groups selected from the group consisting of anthryl and phenanthryl; 5- or 6-membered heterocyclic groups selected from the group consisting of thienyl, pyridyl, pyrazinyl, pyrimidinyl, furyl, tetrahydrofuranyl and morpholino; monocyclic to tricyclic aromatic heterocyclic groups having per one ring 1 to 5 hetero atoms selected from the group consisting of nitrogen atoms, oxygen atoms and sulfur atoms, selected from the group consisting of ethylenedioxyphenyl, dibenzofuranyl, dibenzothiophenyl and methylenedioxyphenyl; and straight-chain saturated $C_1$–$C_9$ aliphatic groups, straight-chain unsaturated $C_1$–$C_9$ aliphatic groups, branched saturated $C_1$–$C_9$ aliphatic groups or branched unsaturated $C_1$–$C_9$ aliphatic groups, each of which may be substituted with the aryl group, the aromatic carbocyclic group, the heterocyclic group or the aromatic heterocyclic group.

In (3), the aryl groups; the mono- to tricyclic $C_7$–$C_{15}$ aromatic carbocyclic groups; the 5- or 6-membered heterocyclic groups; the monocyclic to tricyclic aromatic heterocyclic groups having per one ring 1 to 5 hetero atoms selected from the group consisting of nitrogen atoms, oxygen atoms and sulfur atoms; and the straight-chain saturated $C_1$–$C_9$ aliphatic groups, straight-chain unsaturated $C_1$–$C_9$ aliphatic groups, branched saturated $C_1$–$C_9$ aliphatic groups or branched unsaturated $C_1$–$C_9$ aliphatic groups each of the groups being optionally substituted with the aryl group, the aromatic carbocyclic group, the heterocyclic group or the aromatic heterocyclic groups, may have one or more substituents. As the substituents, the same substituents as those which R may have can be mentioned.

As preferred embodiments in (4), there can be mentioned the case where $R^3$ and $R^4$ combine together to form a straight-chain saturated $C_1$–$C_9$ aliphatic group, a straight-chain unsaturated $C_1$–$C_9$ aliphatic group, a branched saturated $C_1$–$C_9$ aliphatic group, a branched unsaturated $C_1$–$C_9$ aliphatic group, a 5- or 6-membered saturated carbocyclic group, or a 5- or 6-membered unsaturated carbocyclic group, and preferred among them is the case where a straight-chain unsaturated $C_1$–$C_9$ aliphatic group or a 5- or 6-membered saturated carbocyclic group is formed.

Therefore, preferably, $R^3$ and $R^4$ are the same or different and represent (1a) groups selected from the group consisting of the aforementioned series of groups E', (2a) straight-chain saturated $C_1$–$C_9$ aliphatic groups, straight-chain unsaturated $C_1$–$C_9$ aliphatic groups, branched saturated $C_1$–$C_9$ aliphatic groups or branched unsaturated $C_1$–$C_9$ aliphatic groups, each of which groups may be substituted with the above group, or (3a) (3a-1) aryl groups; (3a-2) mono- to tricyclic $C_7$–$C_{15}$ aromatic carbocyclic group selected from the group consisting of adamantyl, anthryl, indenyl, norbornyl and phenanthryl; (3a-3) 5- or 6-membered heterocyclic groups selected from the group consisting of the aforementioned series of groups A'; (3a-4) monocyclic to tricyclic aromatic heterocyclic groups having per one ring 1 to 5 hetero atoms selected from the group consisting of nitrogen atoms, oxygen atoms and sulfur atoms, selected from the group consisting of the aforementioned series of groups B'; or (3a-5) straight-chain saturated $C_1$–$C_9$ aliphatic groups, straight-chain unsaturated $C_1$–$C_9$ aliphatic groups, branched saturated $C_1$–$C_9$ aliphatic groups or branched unsaturated $C_1$–$C_9$ aliphatic groups, each of which groups may be substituted with the above-mentioned aryl group, aromatic carbocyclic group, heterocyclic group or aromatic heterocyclic group;

each of the above-mentioned groups (3a-1) to (3a-5) being optionally substituted with one or more substituents selected from the group consisting of the aforementioned series of groups C', or (4a) $R^3$ and $R^4$ combine together to form a straight-chain saturated $C_1$–$C_9$ aliphatic group, a straight-chain unsaturated $C_1$–$C_9$ aliphatic group, a branched saturated $C_1$–$C_9$ aliphatic group or a branched unsaturated $C_1$–$C_9$ aliphatic group, a 5- or 6-membered saturated carbocyclic group, or a 5- or 6-membered unsaturated carbocyclic group, and these preferred $R^3$ and $R^4$ groups are referred to as $R^{3a}$ and $R^{4a}$.

Particularly preferably, $R^3$ and $R^4$ are the same or different, and represent (1b) groups selected from the group consisting of the aforementioned series of groups E'', (2b) groups selected from the group consisting of straight-chain saturated $C_1$–$C_9$ aliphatic groups, straight-chain unsaturated $C_1$–$C_9$ aliphatic groups, branched saturated $C_1$–$C_9$ aliphatic groups and branched unsaturated $C_1$–$C_9$ aliphatic groups, each of which groups may be substituted with the above-mentioned group, or (3b) (3b-1) aryl groups; (3b-2) mono- to tricyclic $C_7$–$C_{15}$ aromatic carbocyclic group selected from the group consisting of anthryl and phenanthryl; (3b-3) 5- or 6-membered heterocyclic groups selected from the group consisting of thienyl, pyridyl, pyrazinyl, pyrimidinyl, furyl, tetrahydrofuranyl and morpholino; (3b-4) monocyclic to tricyclic aromatic heterocyclic groups having per one ring 1 to 5 hetero atoms selected from the group consisting of nitrogen atoms, oxygen atoms and sulfur atoms, selected from the group consisting of ethylenedioxyphenyl, dibenzofuranyl, dibenzothiophenyl and methylenedioxyphenyl; or (3b-5) straight-chain saturated $C_1$–$C_9$ aliphatic groups, straight-chain unsaturated $C_1$–$C_9$ aliphatic groups, branched saturated $C_1$–$C_9$ aliphatic groups or branched unsaturated $C_1$–$C_9$ aliphatic groups, each of which groups may be substituted with the above-mentioned aryl group, aromatic carbocyclic group, heterocyclic group or aromatic heterocyclic group;

each of the above-mentioned groups (3b-1) to (3b-5) being optionally substituted with one or more substituents selected from the group consisting of the aforementioned series of groups C'', or (4b) $R^3$ and $R^4$ combine together to form a straight-chain unsaturated $C_1$–$C_9$ aliphatic group or a 5- or 6-membered saturated carbocyclic group, and these particularly preferred $R^3$ and $R^4$ groups are referred to as $R^{3b}$ and $R^{4b}$.

$X_1$ represents for example an oxygen atom, a sulfur atom or a group $NR^5$ (wherein $R^5$ represents a group selected from the group consisting of hydrogen, halogen, hydroxy, N—$C_1$–$C_6$ alkylsulfonylamino, $C_1$–$C_6$ alkoxy, $C_1$–$C_6$ alkoxycarbonyl, $C_2$–$C_6$ alkanoyl, carbamoyl and N—$C_1$–$C_{10}$ alkylcarbamoyl; or a straight-chain saturated $C_1$–$C_9$ aliphatic group, a straight-chain unsaturated $C_1$–$C_9$ aliphatic group, a branched saturated $C_1$–$C_9$ aliphatic group or a branched unsaturated $C_1$–$C_9$ aliphatic group, each of which groups may be substituted with the above-mentioned group).

Preferred as $X_1$ among them is an oxygen atom, a sulfur atom or a group $NR^{5a}$ (wherein $R^{5a}$ represents a group selected from the group consisting of hydrogen, halogen, hydroxy, N—$C_1$–$C_6$ alkylsulfonylamino, $C_1$–$C_6$ alkoxy, $C_1$–$C_6$ alkoxycarbonyl, $C_2$–$C_6$ alkanoyl, carbamoyl and N—$C_1$–$C_{10}$ alkylcarbamoyl; or a straight-chain saturated $C_1$–$C_9$ aliphatic group, a straight-chain unsaturated $C_1$–$C_9$ aliphatic group, a branched saturated $C_1$–$C_9$ aliphatic group or a branched unsaturated $C_1$–$C_9$ aliphatic group, each of which groups may be substituted with the above-mentioned group).

Particularly preferred as $X_1$ among them is an oxygen atom or a group $NR^{5b}$ (wherein $R^{5b}$ represents a group selected from the group consisting of hydrogen, hydroxy, $C_1$–$C_6$ alkoxy, $C_1$–$C_6$ alkoxycarbonyl and N—$C_1$–$C_{10}$ alkylcarbamoyl; or a straight-chain saturated $C_1$–$C_9$ aliphatic group, a straight-chain unsaturated $C_1$–$C_9$ aliphatic group, a branched saturated $C_1$–$C_9$ aliphatic group or a branched unsaturated $C_1$–$C_9$ aliphatic group, each of which groups may be substituted with the above-mentioned group).

$X_2$ represents for example an oxygen atom or a sulfur atom.

Y represents for example an oxygen atom, a sulfur atom, a group $NR^5$ or a group $CR^6R^7$ (wherein $R^6$ is a group selected from the group consisting of hydrogen, halogen, hydroxy, N—$C_1$–$C_6$ alkylsulfonylamino, $C_1$–$C_6$ alkoxy, $C_1$–$C_6$ alkoxycarbonyl, $C_2$–$C_6$ alkanoyl, carbamoyl and N—$C_1$–$C_{10}$ alkylcarbamoyl; or a straight-chain saturated $C_1$–$C_9$ aliphatic group, a straight-chain unsaturated $C_1$–$C_9$ aliphatic group, a branched saturated $C_1$–$C_9$ aliphatic group or a branched unsaturated $C_1$–$C_9$ aliphatic group, each of which groups may be substituted with the above-mentioned group, $R^7$ represents hydrogen or $C_1$–$C_6$ alkyl, and $R^5$ is as defined above).

Preferred as Y among them is an oxygen atom, a sulfur atom, a group $NR^{5a}$ or a group $CR^{6a}R^{7a}$ (wherein $R^{6a}$ is a group selected from the group consisting of hydrogen, halogen, hydroxy, N—$C_1$–$C_6$ alkylsulfonylamino, $C_1$–$C_6$ alkoxy, $C_1$–$C_6$ alkoxycarbonyl, $C_2$–$C_6$ alkanoyl, carbamoyl and N—$C_1$–$C_{10}$ alkylcarbamoyl; or a straight-chain saturated $C_1$–$C_9$ aliphatic group, a straight-chain unsaturated $C_1$–$C_9$ aliphatic group, a branched saturated $C_1$–$C_9$ aliphatic group or a branched unsaturated $C_1$–$C_9$ aliphatic group, each of which groups may be substituted with the above-mentioned group, $R^{7a}$ represents hydrogen or $C_1$–$C_6$ alkyl, and $R^{5a}$ is as defined above).

Particularly preferred as Y among them is an oxygen atom, a sulfur atom or a group $CR^{6b}R^{7b}$ (wherein $R^{6b}$ is a group selected from the group consisting of hydrogen, hydroxy, $C_1$–$C_6$ alkoxy, $C_1$–$C_6$ alkoxycarbonyl and N—$C_1$–$C_{10}$ alkylcarbamoyl; or a straight-chain saturated $C_1$–$C_9$ aliphatic group, a straight-chain unsaturated $C_1$–$C_9$ aliphatic group, a branched saturated $C_1$–$C_9$ aliphatic group or a branched unsaturated $C_1$–$C_9$ aliphatic group, each of which groups may be substituted with the above-mentioned group, and $R^{7b}$ represents hydrogen or $C_1$–$C_6$ alkyl)

Z represents for example a bi- or tricyclic saturated or unsaturated $C_6$–$C_{15}$ condensed carbocyclic group selected from the group consisting of condensed aryl, acenaphthylenyl, adamantyl, anthryl, indanyl, indenyl, $C_6$–$C_8$ cycloalkanyl, $C_6$–$C_8$ cycloalkadienyl, $C_6$–$C_8$ cycloalkenyl, norbornyl, phenanthryl and fluorenyl; a 6-membered heterocyclic group selected from the group consisting of isoquinolyl, isoindolyl, indazolyl, indolyl, indolizinyl, ethylenedioxyphenyl, quinazolinyl, quinoxalinyl, quinolidinyl, quinolyl, cumaronyl, chromenyl, thionaphthenyl, naphthyridinyl, pyridyl, pyrazinyl, pyrimidinyl, pyridazinyl, pyranyl, phthalazinyl, benzimidazolyl, benzoxazolyl, benzothiazolyl, benzotriazolyl, benzofuranyl and methylenedioxyphenyl; or a bi- or tricyclic condensed aromatic heterocyclic group having per one ring 1 to 5 hetero atoms selected from the group consisting of nitrogen atoms, oxygen atoms and sulfur atoms.

Preferred as Z among them is a bi- or tricyclic saturated or unsaturated $C_6$–$C_{15}$ condensed carbocyclic group selected from the group consisting of condensed aryl, adamantyl, anthryl, indanyl, indenyl, $C_6$–$C_8$ cycloalkanyl, $C_6$–$C_8$ cycloalkadienyl, $C_6$–$C_8$ cycloalkenyl, norbornyl and phenanthryl; a 6-membered heterocyclic group selected from the group consisting of ethylenedioxyphenyl, pyridyl, pyrazinyl, pyrimidinyl, pyridazinyl, benzimidazolyl, benzoxazolyl, benzothiazolyl, benzotriazolyl, benzofuranyl and methylenedioxyphenyl; or a bi- or tricyclic condensed aromatic heterocyclic group having per one ring 1 to 5 hetero atoms selected from the group consisting of nitrogen atoms, oxygen atoms and sulfur atoms.

Particularly preferred as Z among them is a bi- or tricyclic saturated or unsaturated $C_6$–$C_{15}$ condensed carbocyclic group selected from the group consisting of condensed aryl, anthryl, $C_6$–$C_8$ cycloalkanyl, $C_6$–$C_8$ cycloalkadienyl and $C_6$–$C_8$ cycloalkenyl; a 6-membered heterocyclic group selected from the group consisting of ethylenedioxyphenyl, pyridyl, pyrazinyl, pyrimidinyl, pyridazinyl and methylenedioxyphenyl; or a bi- or tricyclic condensed aromatic heterocyclic group having per one ring 1 to 5 hetero atoms selected from the group consisting of nitrogen atoms, oxygen atoms and sulfur atoms.

Next, description is made on the compounds of the general formula [I] of the invention.

Among compounds represented by the general formula [I]

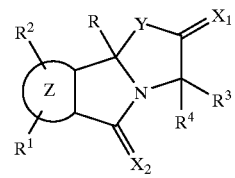

[I]

(wherein R, $R^1$, $R^2$, $R^3$, $R^4$, $X_1$, $X_2$, Y and Z are as defined above), preferred are compounds represented by the general formula [I-a]

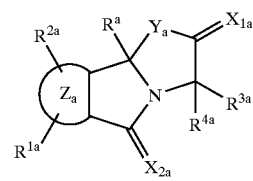

[I-a]

[wherein, $R^a$ represents (1) an aryl group; (2) a mono- to tricyclic $C_7$–$C_{15}$ aromatic carbocyclic group selected from the group consisting of adamantyl, anthryl, indenyl, norbornyl and phenanthryl; (3) a 5- or 6-membered heterocyclic group selected from the group consisting of the aforementioned series of groups A'; or (4) a monocyclic to tricyclic aromatic heterocyclic group having per one ring 1 to 5 hetero atoms selected from the group consisting of nitrogen atoms, oxygen atoms and sulfur atoms, selected from the group consisting of the aforementioned series of groups B', each of which groups (1) to (4) may have as substituents one or more groups selected from the group consisting of groups selected from the group consisting of the aforementioned series of groups C', $R^{1a}$ and $R^{2a}$ are the same or different, and represent groups selected from the group consisting of the aforementioned series of groups D'; or straight-chain saturated $C_1$–$C_9$ aliphatic groups, straight-chain unsaturated $C_1$–$C_9$ aliphatic groups, branched saturated $C_1$–$C_9$ aliphatic groups, branched unsaturated $C_1$–$C_9$ aliphatic groups, or $C_1$–$C_6$ alkoxy groups, each of which groups may optionally be substituted with the above-mentioned group, $R^{3a}$ and $R^{4a}$ are the same or different, and represent
(1) groups selected from the group consisting of the aforementioned series of groups E',
(2) groups selected from the group consisting of straight-chain saturated $C_1$–$C_9$ aliphatic groups, straight-chain unsaturated $C_1$–$C_9$ aliphatic groups, branched saturated $C_1$–$C_9$ aliphatic groups, and branched unsaturated $C_1$–$C_9$ aliphatic groups, each of which groups may optionally be substituted with the above-mentioned group, or
(3) (3-1) aryl groups; (3-2) mono- to tricyclic $C_7$–$C_{15}$ aromatic carbocyclic groups selected from the group consisting of adamantyl, anthryl, indenyl, norbornyl and phenanthryl; (3-3) 5- or 6-membered heterocyclic groups selected from the group consisting of the aforementioned series of groups A'; (3-4) monocyclic to tricyclic aromatic heterocyclic groups having per one ring 1 to 5 hetero atoms selected from the group consisting of nitrogen atoms, oxygen atoms and sulfur atoms, selected from the group consisting of the aforementioned series of groups B'; or (3-5) straight-chain saturated $C_1$–$C_9$ aliphatic groups, straight-chain unsaturated $C_1$–$C_9$ aliphatic groups, branched saturated $C_1$–$C_9$ aliphatic groups or branched unsaturated $C_1$–$C_9$ aliphatic groups, each of which groups may be substituted with the above-mentioned aryl group; aromatic carbocyclic group, heterocyclic group or aromatic heterocyclic group;

each of which groups (3-1) to (3-5) may optionally have one or more substituents selected from the group consisting of the aforementioned series of groups C', or (4) $R^{3a}$ and $R^{4a}$ combine together to form straight-chain saturated $C_1$–$C_9$ aliphatic groups, straight-chain unsaturated $C_1$–$C_9$ aliphatic groups, branched saturated $C_1$–$C_9$ aliphatic groups, branched unsaturated $C_1$–$C_9$ aliphatic groups, 5- or 6-membered saturated carbocyclic groups, or 5- or 6-membered unsaturated carbocyclic groups, $X_{1a}$ represents an oxygen atom, a sulfur atom, or a group $NR^{5a}$ (wherein $R^{5a}$ represents a group selected from the group consisting of hydrogen, halogen, hydroxy, N—$C_1$–$C_6$ alkylsulfonylamino, $C_1$–$C_6$ alkoxy, $C_1$–$C_6$ alkoxycarbonyl, $C_2$–$C_6$ alkanoyl, carbamoyl and N—$C_1$–$C_{10}$ alkylcarbamoyl; or a straight-chain saturated $C_1$–$C_9$ aliphatic group, a straight-chain unsaturated $C_1$–$C_9$ aliphatic group, a branched saturated $C_1$–$C_9$ aliphatic group or a branched unsaturated $C_1$–$C_9$ aliphatic group, each of which groups may be substituted with the above-mentioned group), $X_{2a}$ represents an oxygen atom or a sulfur atom, $Y_a$ represents an oxygen atom, a sulfur atom, a group $NR^{5a}$ or a group $CR^{6a}R^{7a}$ (wherein $R^{6a}$ is a group selected from the group consisting of hydrogen, halogen, hydroxy, N—$C_1$–$C_6$ alkylsulfonylamino, $C_1$–$C_6$ alkoxy, $C_1$–$C_6$ alkoxycarbonyl, $C_2$–$C_6$ alkanoyl, carbamoyl and N—$C_1$–$C_{10}$ alkylcarbamoyl; or a straight-chain saturated $C_1$–$C_9$ aliphatic group, a straight-chain unsaturated $C_1$–$C_9$ aliphatic group, a branched saturated $C_1$–$C_9$ aliphatic group or a branched unsaturated $C_1$–$C_9$ aliphatic group, each of which groups may be substituted with the above-mentioned group, $R^{7a}$ represents hydrogen or $C_1$–$C_6$ alkyl, and $R^{5a}$ is as defined above), and $Z_a$ represents a bi- or tricyclic saturated or unsaturated $C_6$–$C_{15}$ condensed carbocyclic group selected- from the group consisting of condensed aryl, adamantyl, anthryl, indanyl, indenyl, $C_6$–$C_8$ cycloalkanyl, $C_6$–$C_8$ cycloalkadienyl, $C_6$–$C_8$ cycloalkenyl, norbornyl and phenanthryl; a 6-membered heterocyclic group selected from the group consisting of ethylenedioxyphenyl, pyridyl, pyrazinyl, pyrimidinyl, pyridazinyl, benzimidazolyl, benzoxazolyl, benzothiazolyl, benzotriazolyl, benzofuranyl and methylenedioxyphenyl; or a bi- or tricyclic condensed aromatic heterocyclic group having per one ring 1 to 5 hetero atoms selected from the group consisting of nitrogen atoms, oxygen atoms and sulfur atoms].

Among compounds represented by the general formula [I], particularly preferred are compounds represented by the general formula [I-b]

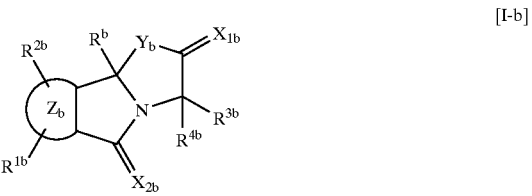

[I-b]

[wherein, $R^b$ represents (1) an aryl group; (2) a mono- to tricyclic $C_7$–$C_{15}$ aromatic carbocyclic group selected from the group consisting of anthryl and phenanthryl; (3) a 5- or 6-membered heterocyclic group selected from the group consisting of thienyl, pyridyl, pyrazinyl, pyrimidinyl, furyl, tetrahydrofuranyl and morpholino; or (4) a monocyclic to tricyclic aromatic heterocyclic group having per one ring 1 to 5 hetero atoms selected from the group consisting of nitrogen atoms, oxygen atoms and sulfur atoms, selected from the group consisting of ethylenedioxyphenyl, dibenzofuranyl, dibenzothiophenyl and methylenedioxyphenyl, each of which groups (1) to (4) may have one or more substituents selected from the group consisting of the aforementioned series of groups C", $R^{1b}$ and $R^{2b}$ are the same or different, and represent substituents selected from the group consisting of hydrogen, amino, nitro, halogen, hydroxy, aryl, N-arylamino, N—$C_1$–$C_6$ alkylamino, N,N-di-$C_1$–$C_6$ alkylamino, N—$C_1$–$C_{10}$ alkylcarbamoyl, $C_1$–$C_6$ alkoxy, $C_1$–$C_6$ alkoxycarbonyl and N—$C_3$–$C_6$ cycloalkylamino; or straight-chain saturated $C_1$–$C_9$ aliphatic groups, straight-chain unsaturated $C_1$–$C_9$ aliphatic groups, branched saturated $C_1$–$C_9$ aliphatic groups or branched unsaturated $C_1$–$C_9$ aliphatic groups, or $C_1$–$C_6$ alkoxy groups, each of which groups may be substituted with the above group, $R^{3b}$ and $R^{4b}$ are the same or different, and represent
(1) groups selected from the group consisting of hydrogen; azido, amidino, amino, carbamoyl, carboxyl, guanidino, cyano, sulfamoyl, sulfo, nitro, halogen, hydroxy, formyl, cyclic saturated $C_3$–$C_9$ aliphatic groups, cyclic unsaturated $C_3$–$C_9$ aliphatic groups, N—$C_1$–$C_6$ alkylamino, N—$C_1$–$C_{10}$ alkylcarbamoyl, $C_1$–$C_6$ alkylthio, $C_1$–$C_6$ alkoxy and $C_1$–$C_6$ alkoxycarbonyl,
(2) groups selected from the group consisting of straight-chain saturated $C_1$–$C_9$ aliphatic groups, straight-chain unsaturated $C_1$–$C_9$ aliphatic groups, branched saturated $C_1$–$C_9$ aliphatic groups and branched unsaturated $C_1$–$C_9$ aliphatic groups, each of which groups may be substituted with the above group, or
(3) (3-1) aryl groups; (3-2) mono- to tricyclic $C_7$–$C_{15}$ aromatic carbocyclic groups selected from the group consisting of anthryl and phenanthryl; (3-3) 5- or 6-membered heterocyclic groups selected from the group consisting of thienyl, pyridyl, pyrazinyl, pyrimidinyl, furyl, tetrahydrofuranyl and morpholino; (3-4) monocyclic to tricyclic aromatic heterocyclic groups having per one ring 1 to 5 hetero atoms selected from the group consisting of nitrogen atoms, oxygen atoms and sulfur atoms, selected from the group consisting of ethylenedioxyphenyl, dibenzofuranyl, dibenzothiophenyl and methylenedioxyphenyl; or (3-5) straight-chain saturated $C_1$–$C_9$ aliphatic groups, straight-chain unsaturated $C_1$–$C_9$ aliphatic groups, branched saturated $C_1$–$C_9$ aliphatic groups or branched unsaturated $C_1$–$C_9$ aliphatic groups, each of which groups may be substituted with the above-mentioned aryl group, aromatic carbocyclic group, heterocyclic group or aromatic heterocyclic group;

each of which groups (3-1) to (3-5) may optionally have one or more substituents selected from the group consisting of the aforementioned series of groups C", or (4) $R^{3b}$ and $R^{4b}$ combine together to form a straight-chain unsaturated $C_1$–$C_9$ aliphatic group or a 5- or 6-membered saturated carbocyclic group, $X_{1b}$ represents an oxygen atom, or a group $NR^{5b}$ (wherein $R^{5b}$ represents a group selected from the group consisting of hydrogen, hydroxy, $C_1$–$C_6$ alkoxy, $C_1$–$C_6$ alkoxycarbonyl and N—$C_1$–$C_{10}$ alkylcarbamoyl; or a straight-chain saturated $C_1$–$C_9$ aliphatic group, a straight-chain unsaturated $C_1$–$C_9$ aliphatic group, a branched saturated $C_1$–$C_9$ aliphatic group or a branched unsaturated $C_1$–$C_9$ aliphatic group, each of which groups may be substituted with the above-mentioned group), $X_{2b}$ represents an oxygen atom or a sulfur atom, $Y_b$ represents an oxygen atom, a sulfur atom or a group $CR^{6b}R^{7b}$ (wherein $R^{6b}$ is a group selected from the group consisting of hydrogen, hydroxy, $C_1$–$C_6$ alkoxy, $C_1$–$C_6$ alkoxycarbonyl and N—$C_1$–$C_{10}$ alkylcarbamoyl; or a straight-chain saturated $C_1$–$C_9$ aliphatic group, a straight-chain unsaturated $C_1$–$C_9$ aliphatic group, a branched saturated $C_1$–$C_9$ aliphatic group or a branched unsaturated $C_1$–$C_9$ aliphatic group, each of which groups may be substituted with the above-mentioned group, and $R^{7b}$ represents hydrogen or $C_1$–$C_6$ alkyl), and $Z_b$ represents a bi- or tricyclic saturated or unsaturated $C_6$–$C_{15}$ condensed carbocyclic group selected from the group consisting of condensed aryl, anthryl, $C_6$–$C_8$ cycloalkanyl, $C_6$–$C_8$ cycloalkadienyl and $C_6$–$C_8$ cycloalkenyl; a 6-membered heterocyclic group selected from the group consisting of ethylenedioxyphenyl, pyridyl, pyrazinyl, pyrimidinyl, pyridazinyl and methylenedioxyphenyl; or a bi- or tricyclic condensed aromatic heterocyclic group having per one ring 1 to 5 hetero atoms selected from the group consisting of nitrogen atoms, oxygen atoms and sulfur atoms].

Further, compounds represented by the following general formula [I-c] are compounds disclosed in base application for the priority of the present application, and are included in the compounds of the general formula [I] of the invention.

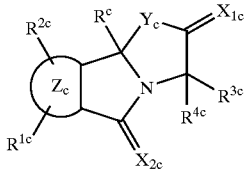

[I-c]

[wherein, $R^c$ represents an aryl group, a mono- to tricyclic $C_7$–$C_{15}$ aromatic carbocyclic group (provided that an aryl group is excluded), a 5- or 6-membered heterocyclic group, or a monocyclic to tricyclic aromatic heterocyclic groups having per one ring 1 to 5 hetero atoms selected from the group consisting of nitrogen atoms, oxygen atoms and sulfur atoms (provided that a 5- or 6-membered heterocyclic group is excluded), $R^{1c}$ and $R^{2c}$ are the same or different, and represent groups selected from the group consisting of hydrogen, azido, amino, carbamoyl, carbamoylamino, carbamoyloxy, carboxyl, cyano, sulfamoyl, sulfo, nitro, halogen, hydroxy, formyl, formylamino, cyclic saturated or unsaturated $C_3$–$C_9$ aliphatic groups, aralkyl, N-aralkylamino, aralkyloxy, aralkylcarbonyl, aryl, N-arylamino, aryloxy, arylsulfonyl, N-arylsulfonylamino, N-arylsulfonylamino $C_1$–$C_6$ alkylamino, N-arylsulfonylamino $C_1$–$C_{10}$ alkylcarbamoyl, arylsulfonylamino $C_1$–$C_6$ alkoxycarbonyl, $C_2$–$C_6$ alkanoyl, N—$C_2$–$C_6$ alkanoylamino, aroyl, N-aroylamino, N-aroyl $C_1$–$C_6$ alkylamino, N-aroyl $C_1$–$C_{10}$ alkylcarbamoyl, N—$C_1$–$C_6$ alkylamino, N,N-di-$C_1$–$C_6$ alkylamino, N—$C_1$–$C_{10}$ alkylcarbamoyl, N,N-di-$C_1$–$C_{10}$ alkylcarbamoyl, N—$C_1$–$C_6$ alkylsulfamoyl, $C_1$–$C_6$ alkylsulfinyl, $C_1$–$C_6$ alkylsulfonyl, $C_1$–$C_6$ alkylthio, $C_1$–$C_6$ alkoxy, $C_1$–$C_6$ alkoxycarbonyl, N—$C_3$–$C_6$ cycloalkylamino, $C_3$–$C_6$ cycloalkyloxy and N—$C_3$–$C_6$ cycloalkylcarbamoyl; or straight-chain or branched and saturated or unsaturated $C_1$–$C_9$ aliphatic groups, N—$C_1$–$C_6$ alkylamino groups, $C_1$–$C_6$ alkylthio groups, or $C_1$–$C_6$ alkoxy groups, each of which groups may be substituted with the above group, $R^{3c}$ and $R^{4c}$ may be the same or different, and represent (1) groups selected from the group consisting of hydrogen, azido, amidino, amino, carbamoyl, carbamoylamino, carbamoyloxy, carboxyl, guanidino, cyano, sulfamoyl, sulfo, nitro, halogen, hydroxy, formyl, formylamino, cyclic saturated $C_3$–$C_9$ aliphatic groups, cyclic unsaturated $C_3$–$C_9$ aliphatic groups, $C_2$–$C_6$ alkanoyl, N—$C_2$–$C_6$ alkanoylamino, N—$C_1$–$C_6$ alkylamino, N,N-di-$C_1$–$C_6$ alkylamino, N—$C_1$–$C_{10}$ alkylcarbamoyl, N,N-di-$C_1$–$C_{10}$ alkylcarbamoyl, $C_1$–$C_6$ alkylthio, N—$C_1$–$C_6$ alkylsulfamoyl, $C_1$–$C_6$ alkylsulfinyl, $C_1$–$C_6$ alkylsulfonyl, $C_1$–$C_6$ alkoxy, $C_1$–$C_6$ alkoxycarbonyl, N—$C_3$–$C_6$ cycloalkylamino, $C_3$–$C_6$ cycloalkyloxy and N—$C_3$–$C_6$ cycloalkylcarbamoyl, (2) straight-chain or branched and saturated or unsaturated $C_1$–$C_9$ aliphatic groups optionally be substituted with the above-mentioned group, (3) (3-1) aryl groups; (3-2) monocyclic to tricyclic $C_7$–$C_{15}$ aromatic carbocyclic groups (excluding aryl groups); (3-3) 5- or 6-membered heterocyclic groups; (3-4) monocyclic to tricyclic aromatic heterocyclic groups having per one ring 1 to 5 hetero atoms selected from the group consisting of nitrogen atoms, oxygen atoms and sulfur atoms (excluding 5- or 6-membered heterocyclic groups); or (3-5) straight-chain or branched and saturated or unsaturated $C_1$–$C_9$ aliphatic groups optionally substituted with the above-mentioned aryl group, aromatic carbocyclic group, heterocyclic group or aromatic heterocyclic group;

each of which groups (3-1) to (3-5) may optionally be substituted with substituent(s), or (4) $R^{3c}$ and $R^{4c}$ combine together to form a straight-chain or branched unsaturated $C_1$–$C_9$ aliphatic group, or a 5- or 6-membered saturated or unsaturated carbocyclic group, $X_{1c}$ and $X_{2c}$ are the same or different, and represent an oxygen atom or a sulfur atom, $Y_c$ represents an oxygen atom, a sulfur atom, a group $CHR^{5c}$ or a group $NR^{5c}$ (wherein $R^{5c}$ represents a group selected from the group consisting of hydrogen, halogen, hydroxy, $C_1$–$C_6$ alkoxy, $C_2$–$C_6$ alkanoyl, carbamoyl and N—$C_1$–$C_{10}$ alkylcarbamoyl; or a straight-chain or branched and saturated or unsaturated $C_1$–$C_9$ aliphatic group optionally substituted with the above-mentioned group), and $Z_c$ represents a condensed aryl group; a bi- or tricyclic saturated or unsaturated $C_6$–$C_{15}$ condensed carbocyclic group (excluding a condensed aryl group); a 6-membered heterocyclic group; or a bi- or tricyclic condensed aromatic heterocyclic group having per one ring 1 to 5 hetero atoms selected from the group consisting of nitrogen atoms, oxygen atoms and sulfur atoms (excluding a 6-membered heterocyclic group)].

The compounds of the general formula [I] include compounds represented by the general formula [I-1]

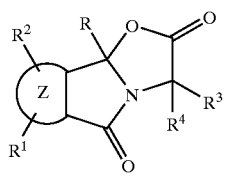

[I-1]

(wherein R, $R^1$, $R^2$, $R^3$, $R^4$, and Z are as defined before), compounds represented by the general formula [I-2]

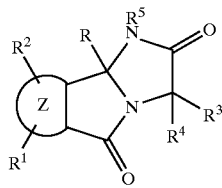

[I-2]

(wherein R, $R^1$, $R^2$, $R^3$, $R^4$, $R^5$, and Z are as defined before), compounds represented by the general formula [I-3]

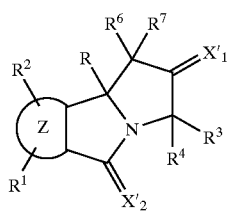

[I-3]

(wherein $X'_1$ represents an oxygen atom or a group $N(R^5)$, $X'_2$ represents an oxygen atom or a sulfur atom, and R, $R^1$, $R^2$, $R^3$, $R^4$, $R^5$, $R^6$, $R^7$ and Z are as defined before). and compounds represented by the general formula [I-4]

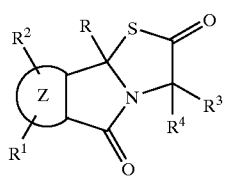

[I-4]

(wherein R, $R^1$, $R^2$, $R^3$, $R^4$ and Z are as defined before), and preferred among them are compounds of the general formula [I-1], compounds of the general formula [I-3] and compounds of the general formula [I-4], and particularly preferred among them are compounds of the general formula [I-1] and compounds of the general formula [I-3].

Representative examples of the compounds of the general formula [I] of the invention are shown in tables 1 to 45.

TABLE 1

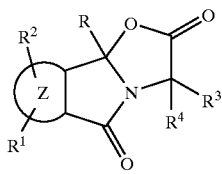

[I-1]

| Compound No. | $R^1$ | $R^2$ | $R^3$ | $R^4$ | Z | R |
|---|---|---|---|---|---|---|
| 1001 | H | H | i-Pr | H | Ph | 2-MeO—Ph |
| 1002 | H | H | i-Pr | H | Ph | Ph |
| 1003 | H | H | i-Pr | H | Ph | 2-NH$_2$—Ph |
| 1004 | H | H | i-Pr | H | Ph | 4-F—Ph |
| 1005 | H | H | i-Pr | H | Ph | 4-Et$_2$N—Ph |
| 1006 | H | H | i-Pr | H | Ph | 4-Cl—Ph |
| 1007 | H | H | i-Pr | H | Ph | 4-HO—Ph |
| 1008 | H | H | i-Pr | H | Ph | 3-MeO—Ph |
| 1009 | H | H | i-Pr | H | Ph | 3-HO—Ph |
| 1010 | H | H | i-Pr | H | Ph | 3-NH$_2$—Ph |
| 1011 | H | H | i-Pr | H | Ph | 4-MeO—Ph |
| 1012 | H | H | i-Pr | H | Ph | 4-Me—Ph |
| 1013 | H | H | i-Pr | H | Ph | 3-Me—Ph |
| 1014 | H | H | i-Pr | H | Ph | 4-tBuO$_2$CCH$_2$O—Ph |
| 1015 | H | H | i-Pr | H | Ph | 4-HO$_2$CCH$_2$O—Ph |
| 1016 | H | H | i-Pr | H | Ph | 4-tBuO$_2$C(CH$_2$)$_5$O—Ph |
| 1017 | H | H | i-Pr | H | Ph | 4-HO$_2$C(CH$_2$)$_5$O—Ph |
| 1018 | H | H | i-Pr | H | Ph | 4-HO(CH$_2$)$_3$O—Ph |
| 1019 | H | H | i-Pr | H | Ph | 4-HO(CH$_2$)$_2$O—Ph |
| 1020 | H | H | i-Pr | H | Ph | 4-HOC(Me)$_2$(CH$_2$)$_2$O—Ph |
| 1021 | H | H | i-Pr | H | Ph | 4-PhCH$_2$O—Ph |
| 1022 | H | H | i-Pr | H | Ph | 4-MeNHCOCH$_2$O—Ph |
| 1023 | H | H | i-Pr | H | Ph | 4-EtNHCOCH$_2$O—Ph |
| 1024 | H | H | i-Pr | H | Ph | 4-nPrNHCOCH$_2$O—Ph |
| 1025 | H | H | i-Pr | H | Ph | 4-nBuNHCOCH$_2$O—Ph |
| 1026 | H | H | i-Pr | H | Ph | 4-CH$_2$=CHCH$_2$NHCOCH$_2$O—Ph |
| 1027 | H | H | i-Pr | H | Ph | 4-Me(CH$_2$)$_9$NHCOCH$_2$O—Ph |
| 1028 | H | H | i-Pr | H | Ph | 4-N$_3$(CH$_2$)$_3$O—Ph |
| 1029 | H | H | i-Pr | H | Ph | 4-tBuO$_2$CCH(Me)O—Ph |
| 1030 | H | H | i-Pr | H | Ph | 4-nPrNHCOCH(Me)O—Ph |
| 1031 | H | H | i-Pr | H | Ph | 4-F$_3$CSO$_3$—Ph |
| 1032 | H | H | i-Pr | H | Ph | 4-tBuO$_2$CCH=CHPh |
| 1033 | H | H | i-Pr | H | Ph | 4-nPrNHCOCH=CH—Ph |
| 1034 | H | H | i-Pr | H | Ph | 4-nPrCH(Me)NHCOCH$_2$O—Ph |
| 1035 | H | H | i-Pr | H | Ph | 4-EtCH(Me)NHCOCH$_2$O—Ph |
| 1036 | H | H | i-Pr | H | Ph | 4-MeOCH$_2$O—Ph |
| 1037 | H | H | i-Pr | H | Ph | 4-EtCOCH$_2$O—Ph |
| 1038 | H | H | i-Pr | H | Ph | 3-tBuO$_2$CCH$_2$O—Ph |
| 1039 | H | H | i-Pr | H | Ph | 3-HO$_2$CCH$_2$O—Ph |
| 1040 | H | H | i-Pr | H | Ph | 3-nPrNHCOCH$_2$O—Ph |
| 1041 | H | H | i-Pr | H | Ph | 4-H2NC(Me)$_2$CH$_2$O$_2$CCH$_2$O—Ph |
| 1042 | H | H | i-Pr | H | Ph | 4-morpholinoCOCH$_2$O—Ph |
| 1043 | H | H | i-Pr | H | Ph | 4-(4-Cl—Ph)—COCH$_2$O—Ph |
| 1044 | H | H | i-Pr | H | Ph | 4-PhCOCH$_2$O—Ph |
| 1045 | H | H | i-Pr | H | Ph | 4-(4-pyridyl)-CH$_2$NHCOCH$_2$O—Ph |
| 1046 | H | H | i-Pr | H | Ph | 4-H$_2$NCH$_2$CH$_2$NHCOCH$_2$O—Ph |

TABLE 2

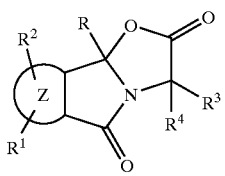

[I-1]

| Compound No. | R¹ | R² | R³ | R⁴ | Z | R |
|---|---|---|---|---|---|---|
| 1047 | H | H | i-Pr | H | Ph | 4-Cl-3-NO$_2$—Ph |
| 1048 | H | H | i-Pr | H | Ph | 4-Cl-3-F—Ph |
| 1049 | H | H | i-Pr | H | Ph | 4-Cl-3-Me—Ph |
| 1050 | H | H | i-Pr | H | Ph | 3-NH$_2$-4-Cl—Ph |
| 1051 | H | H | i-Pr | H | Ph | 3-Cl-4-MeO—Ph |
| 1052 | H | H | i-Pr | H | Ph | 3-Cl-4-Me—Ph |
| 1053 | H | H | i-Pr | H | Ph | 4-Br-3-Cl—Ph |
| 1054 | H | H | i-Pr | H | Ph | 4-Br-2-Cl—Ph |
| 1055 | H | H | i-Pr | H | Ph | 4-F-3-Me—Ph |
| 1056 | H | H | i-Pr | H | Ph | 3-F-4-Me—Ph |
| 1057 | H | H | i-Pr | H | Ph | 3-Br-4-HO—Ph |
| 1058 | H | H | i-Pr | H | Ph | 3-Br-4-MeO—Ph |
| 1059 | H | H | i-Pr | H | Ph | 3-Br-4-F—Ph |
| 1060 | H | H | i-Pr | H | Ph | 3-F-4-PhPh |
| 1061 | H | H | i-Pr | H | Ph | 4-HO-3-I—Ph |
| 1062 | H | H | i-Pr | H | Ph | 5-HO-2-I—Ph |
| 1063 | H | H | i-Pr | H | Ph | 3-I-4-MeO—Ph |
| 1064 | H | H | i-Pr | H | Ph | 2-I-5-MeO—Ph |
| 1065 | H | H | i-Pr | H | Ph | 4-MeO-3-Me—Ph |
| 1066 | H | H | i-Pr | H | Ph | 4-HO(CH$_2$)$_3$O-3-I—Ph |
| 1067 | H | H | i-Pr | H | Ph | 4-HO(CH$_2$)$_2$O-3-I—Ph |
| 1068 | H | H | i-Pr | H | Ph | 4-HOC(Me)$_2$(CH$_2$)$_2$O-3-I—Ph |
| 1069 | H | H | i-Pr | H | Ph | 4-tBuO$_2$O(CH$_2$)$_4$O-3-I—Ph |
| 1070 | H | H | i-Pr | H | Ph | 3-I-4-PhCH$_2$O—Ph |
| 1071 | H | H | i-Pr | H | Ph | 4-H$_2$NCOCH$_2$O-3-I—Ph |
| 1072 | H | H | i-Pr | H | Ph | 3-I-4-MeNHCOCH$_2$O—Ph |
| 1073 | H | H | i-Pr | H | Ph | 4-EtNHCOCH$_2$O-3-I—Ph |
| 1074 | H | H | i-Pr | H | Ph | 3-I-4-nPrNHCOCH$_2$O—Ph |
| 1075 | H | H | i-Pr | H | Ph | 3-I-4-iPrNHCOCH$_2$O—Ph |
| 1076 | H | H | i-Pr | H | Ph | 4-nBuNHCOCH$_2$O-3-I—Ph |
| 1077 | H | H | i-Pr | H | Ph | 4-tBuNHCOCH$_2$O-3-I—Ph |
| 1078 | H | H | i-Pr | H | Ph | 4-iBuNHCOCH$_2$O—Ph |
| 1079 | H | H | i-Pr | H | Ph | 4-tBuO$_2$CCH$_2$O-3-I—Ph |
| 1080 | H | H | i-Pr | H | Ph | 3-I-4-PhCH$_2$NHCOCH$_2$O—Ph |
| 1081 | H | H | i-Pr | H | Ph | 3-I-4-(2-tetrahydrofuryl)CH$_2$NHCOCH$_2$O—Ph |
| 1082 | H | H | i-Pr | H | Ph | 4-cycloPrNHCOCH$_2$O-3-I—Ph |
| 1083 | H | H | i-Pr | H | Ph | 4-cycloPentylNHCOCH$_2$O-3-I—Ph |
| 1084 | H | H | i-Pr | H | Ph | 4-cycloHexylNHCOCH$_2$O-3-I—Ph |
| 1085 | H | H | i-Pr | H | Ph | 4-cycloPrNHCOCH$_2$O-3-F—Ph |
| 1086 | H | H | i-Pr | H | Ph | 4-Me(CH$_2$)$_9$NHCOCH$_2$O-3-I—Ph |
| 1087 | H | H | i-Pr | H | Ph | 4-HO$_2$CCH$_2$O-3-I—Ph |
| 1088 | H | H | i-Pr | H | Ph | 4-N$_3$(CH$_2$)$_3$O-3-I—Ph |
| 1089 | H | H | i-Pr | H | Ph | 3-I-4-nPrNHCO(CH$_2$)$_4$O—Ph |
| 1090 | H | H | i-Pr | H | Ph | 4-Et$_2$NCOCH$_2$O-3-I—Ph |
| 1091 | H | H | i-Pr | H | Ph | 3-I-4-nPrN(Me)COCH$_2$O—Ph |
| 1092 | H | H | i-Pr | H | Ph | 3-Cl-4-nPrNHCOCH$_2$O—Ph |

TABLE 3

[I-1]

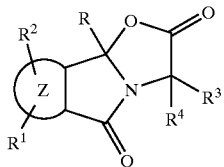

| Compound No. | R¹ | R² | R³ | R⁴ | Z | R |
|---|---|---|---|---|---|---|
| 1093 | H | H | i-Pr | H | Ph | 3-Br-4-nPrNHCOCH$_2$O—Ph |
| 1094 | H | H | i-Pr | H | Ph | 3-F-4-nPrNHCOCH$_2$O—Ph |
| 1095 | H | H | i-Pr | H | Ph | 3-Me-4-nPrNHCOCH$_2$O—Ph |
| 1096 | H | H | i-Pr | H | Ph | 4-EtNHCOCH$_2$O-3-F—Ph |
| 1097 | H | H | i-Pr | H | Ph | 3-I-4-iPrNHCOC(Me)$_2$CH$_2$O—Ph |
| 1098 | H | H | i-Pr | H | Ph | 3-Br-4-CH$_2$=CHCH$_2$NHCOCH$_2$O—Ph |
| 1099 | H | H | i-Pr | H | Ph | 4-iBuNHCOCH$_2$O-3-F—Ph |
| 1100 | H | H | i-Pr | H | Ph | 3-tBuO$_2$CCH=CH-4-nPrNHCOCH$_2$O—Ph |
| 1101 | H | H | i-Pr | H | Ph | 3-HO$_2$CCH=CH-4-nPrNHCOCH$_2$O—Ph |
| 1102 | H | H | i-Pr | H | Ph | 3-I-4-MeOCH$_2$CH$_2$NHCOCH$_2$O—Ph |
| 1103 | H | H | i-Pr | H | Ph | 3-F-4-HO—Ph |
| 1104 | H | H | i-Pr | H | Ph | 3-F-4-MeO—Ph |
| 1105 | H | H | i-Pr | H | Ph | 3,4-methylenedioxyPh |
| 1106 | H | H | i-Pr | H | Ph | 3,4-ethylenedioxyPh |
| 1107 | H | H | i-Pr | H | Ph | 3,4-Cl$_2$—Ph |
| 1108 | H | H | i-Pr | H | Ph | 3,4-Me$_2$—Ph |
| 1109 | H | H | i-Pr | H | Ph | 3,4-F$_2$—Ph |
| 1110 | H | H | i-Pr | H | Ph | 3,4-(MeO)$_2$—Ph |
| 1111 | H | H | i-Pr | H | Ph | 3,5-(MeO)$_2$—Ph |
| 1112 | H | H | i-Pr | H | Ph | 3,5-Me$_2$—Ph |
| 1113 | H | H | i-Pr | H | Ph | 3,5-I$_2$-4-HO—Ph |
| 1114 | H | H | i-Pr | H | Ph | 2,4-I$_2$-5-HO—Ph |
| 1115 | H | H | i-Pr | H | Ph | 3,5-I$_2$-4-MeO—Ph |
| 1116 | H | H | i-Pr | H | Ph | 2,4-I$_2$-5-MeO—Ph |
| 1117 | H | H | i-Pr | H | Ph | 2,4,6-Me$_3$—Ph |
| 1118 | H | H | i-Pr | H | Ph | 4-HO(CH$_2$)$_3$O-3,5-I$_2$Ph |
| 1119 | H | H | i-Pr | H | Ph | 3,5-I$_2$-4-nPrNHCOCH$_2$O—Ph |
| 1120 | H | H | i-Pr | H | Ph | 2-thienyl |
| 1121 | H | H | i-Pr | H | Ph | 2-furyl |
| 1122 | H | H | i-Pr | H | Ph | 3-pyridyl |
| 1123 | H | H | i-Pr | H | Ph | 2-naphthyl |
| 1124 | H | H | i-Pr | H | Ph | 5-F-1-naphthyl |
| 1125 | H | H | i-Pr | H | Ph | dibenzothiophene-2-yl |
| 1126 | 6-F | H | i-Pr | H | Ph | Ph |
| 1127 | 7-F | H | i-Pr | H | Ph | Ph |
| 1128 | 8-F | H | i-Pr | H | Ph | Ph |
| 1129 | 9-F | H | i-Pr | H | Ph | Ph |
| 1130 | 6-MeO | H | i-Pr | H | Ph | Ph |
| 1131 | 9-MeO | H | i-Pr | H | Ph | Ph |
| 1132 | 6-OH | H | i-Pr | H | Ph | Ph |
| 1133 | 9-OH | H | i-Pr | H | Ph | Ph |
| 1134 | 7-NO$_2$ | H | i-Pr | H | Ph | Ph |
| 1135 | 8-NO$_2$ | H | i-Pr | H | Ph | Ph |
| 1136 | 9-NO$_2$ | H | i-Pr | H | Ph | Ph |
| 1137 | 6-NHPh | H | i-Pr | H | Ph | Ph |
| 1138 | 7-Me$_2$N | H | i-Pr | H | Ph | Ph |

TABLE 4

[I-1]

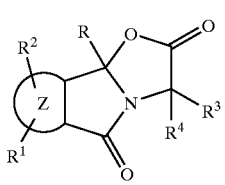

| Compound No. | R¹ | R² | R³ | R⁴ | Z | R |
|---|---|---|---|---|---|---|
| 1139 | 7-Me | H | i-Pr | H | Ph | Ph |
| 1140 | 8-Me | H | i-Pr | H | Ph | Ph |

TABLE 4-continued

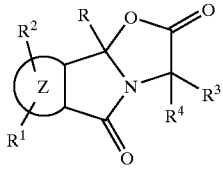

[I-1]

| Compound No. | R¹ | R² | R³ | R⁴ | Z | R |
|---|---|---|---|---|---|---|
| 1141 | 7-t-Bu | H | i-Pr | H | Ph | Ph |
| 1142 | 8-t-Bu | H | i-Pr | H | Ph | Ph |
| 1143 | 7-Br | H | i-Pr | H | Ph | Ph |
| 1144 | 8-Br | H | i-Pr | H | Ph | Ph |
| 1145 | 7-Cl | H | i-Pr | H | Ph | Ph |
| 1146 | 8-Cl | H | i-Pr | H | Ph | Ph |
| 1147 | 7-Cl | 8-Cl | i-Pr | H | Ph | Ph |
| 1148 | 6-Cl | 9-Cl | i-Pr | H | Ph | Ph |
| 1149 | 6-OH | 9-I | i-Pr | H | Ph | Ph |
| 1150 | H | H | i-Pr | H | 1,2-naphthyl | Ph |
| 1151 | H | H | i-Pr | H | 2,3-naphthyl | Ph |
| 1152 | H | H | i-Pr | H | cyclohexenyl | Ph |
| 1153 | H | H | D-Leucine | H | Ph | Ph |
| 1154 | H | H | L-Leucine | H | Ph | Ph |
| 1155 | H | H | D-NorLeucine | H | Ph | Ph |
| 1156 | H | H | L-NorLeucine | H | Ph | Ph |
| 1157 | H | H | D-AlloLeucine | H | Ph | Ph |
| 1158 | H | H | L-AlloLeucine | H | Ph | Ph |
| 1159 | H | H | D-NorValine | H | Ph | Ph |
| 1160 | H | H | L-NorValine | H | Ph | Ph |
| 1161 | H | H | D-Alanine | H | Ph | Ph |
| 1162 | H | H | L-Alanine | H | Ph | Ph |
| 1163 | H | H | D-Arginine | H | Ph | Ph |
| 1164 | H | H | L-Arginine | H | Ph | Ph |
| 1165 | H | H | D-Asparagine | H | Ph | Ph |
| 1166 | H | H | L-Asparagine | H | Ph | Ph |
| 1167 | H | H | D-Glutamic Acid | H | Ph | Ph |
| 1168 | H | H | L-Glutamic Acid | H | Ph | Ph |
| 1169 | H | H | D-Glutamine | H | Ph | Ph |
| 1170 | H | H | L-Glutamine | H | Ph | Ph |
| 1171 | H | H | D-Histidine | H | Ph | Ph |
| 1172 | H | H | L-Histidine | H | Ph | Ph |
| 1173 | H | H | D-Methionine | H | Ph | Ph |
| 1174 | H | H | L-Methionine | H | Ph | Ph |
| 1175 | H | H | D-Tryptophan | H | Ph | Ph |
| 1176 | H | H | L-Tryptophan | H | Ph | Ph |
| 1177 | H | H | D-Tyrosine | H | Ph | Ph |
| 1178 | H | H | L-Tyrosine | H | Ph | Ph |
| 1179 | H | H | D-Homo Phenylalanine | H | Ph | Ph |
| 1180 | H | H | L-Homo Phenylalanine | H | Ph | Ph |
| 1181 | H | H | D-Leucine | H | Ph | 4-Cl—Ph |
| 1182 | H | H | L-Leucine | H | Ph | 4-Cl—Ph |
| 1183 | H | H | D-NorLeucine | H | Ph | 4-Cl—Ph |

TABLE 5

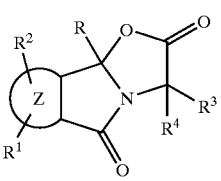

[1-1]

| Compound No. | R¹ | R² | R³ | R⁴ | Z | R |
|---|---|---|---|---|---|---|
| 1184 | H | H | L-NorLeucine | H | Ph | 4-Cl—Ph |
| 1185 | H | H | D-AlloLeucine | H | Ph | 4-Cl—Ph |
| 1186 | H | H | L-AlloLeucine | H | Ph | 4-Cl—Ph |

TABLE 5-continued

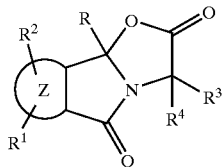

[1-1]

| Compound No. | R¹ | R² | R³ | R⁴ | Z | R |
|---|---|---|---|---|---|---|
| 1187 | H | H | D-NorValine | H | Ph | 4-Cl—Ph |
| 1188 | H | H | L-NorValine | H | Ph | 4-Cl—Ph |
| 1189 | H | H | D-Alanine | H | Ph | 4-Cl—Ph |
| 1190 | H | H | L-Alanine | H | Ph | 4-Cl—Ph |
| 1191 | H | H | D-Arginine | H | Ph | 4-Cl—Ph |
| 1192 | H | H | L-Arginine | H | Ph | 4-Cl—Ph |
| 1193 | H | H | D-Asparagine | H | Ph | 4-Cl—Ph |
| 1194 | H | H | L-Asparagine | H | Ph | 4-Cl—Ph |
| 1195 | H | H | D-Glutamic Acid | H | Ph | 4-Cl—Ph |
| 1196 | H | H | L-Glutamic Acid | H | Ph | 4-Cl—Ph |
| 1197 | H | H | D-Glutamine | H | Ph | 4-Cl—Ph |
| 1198 | H | H | L-Glutamine | H | Ph | 4-Cl—Ph |
| 1199 | H | H | D-Histidine | H | Ph | 4-Cl—Ph |
| 1200 | H | H | L-Histidine | H | Ph | 4-Cl—Ph |
| 1201 | H | H | D-Methionine | H | Ph | 4-Cl—Ph |
| 1202 | H | H | L-Methionine | H | Ph | 4-Cl—Ph |
| 1203 | H | H | D-Tryptophan | H | Ph | 4-Cl—Ph |
| 1204 | H | H | L-Tryptophan | H | Ph | 4-Cl—Ph |
| 1205 | H | H | D-Tyrosine | H | Ph | 4-Cl—Ph |
| 1206 | H | H | L-Tyrosine | H | Ph | 4-Cl—Ph |
| 1207 | H | H | D-Homo Phenylalanine | H | Ph | 4-Cl—Ph |
| 1208 | H | H | L-Homo Phenylalanine | H | Ph | 4-Cl—Ph |
| 1209 | H | H | t-Bu | H | Ph | Ph |
| 1210 | H | H | (CH₃)₂(OH)C | H | Ph | Ph |
| 1211 | H | H | CH₃(MeO)CH | H | Ph | Ph |
| 1212 | H | H | 4-HO—Ph | H | Ph | Ph |
| 1213 | H | H | 4-HO-3-I—Ph | H | Ph | Ph |
| 1214 | H | H | 4-HO-3,5-I₂—Ph | H | Ph | Ph |
| 1215 | H | H | 4-HO-3-I—PhCH₂ | H | Ph | Ph |
| 1216 | H | H | 4-HO-3,5-I₂—PhCH₂ | H | Ph | Ph |
| 1217 | H | H | 1-naphthylmethyl | H | Ph | Ph |
| 1218 | H | H | 4-F—PhCH₂ | H | Ph | Ph |
| 1219 | H | H | 1-naphthylmethyl | H | Ph | 4-Cl—Ph |
| 1220 | H | H | 4-F—PhCH₂ | H | Ph | 4-Cl—Ph |
| 1221 | H | H | i-Pr | Me | Ph | 4-Cl—Ph |
| 1222 | H | H | Me | Me | Ph | Ph |
| 1223 | H | H | (Combined with R⁴) CH₂= | — | Ph | Ph |
| 1224 | H | H | (Combined with R⁴) MeCH= | — | Ph | Ph |
| 1225 | H | H | (Combined with R⁴) (CH₂)₄ | — | Ph | Ph |
| 1226 | H | H | i-Pr | H | Ph | 4-n-PrNHCOCH₂CH₂O—Ph |
| 1227 | H | H | i-Pr | H | Ph | 4-i-PrNHCOCH₂CH₂O—Ph |
| 1228 | H | H | i-Pr | H | Ph | 4-EtNHCOCH₂CH₂O—Ph |

TABLE 6

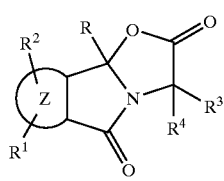

[I-1]

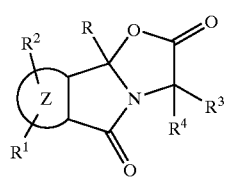

[I-1]

| Compound No. | R¹ | R² | R³ | R⁴ | Z | R |
|---|---|---|---|---|---|---|
| 1229 | H | H | i-Pr | H | Ph | 4-EtCH(Me)NHCOCH₂CH₂O—Ph |
| 1230 | H | H | i-Pr | H | Ph | 3-Cl-4-i-PrNHCOCH₂O—Ph |
| 1231 | H | H | i-Pr | H | Ph | 3-Cl-4-EtNHCOCH₂O—Ph |
| 1232 | H | H | i-Pr | H | Ph | 3-Cl-4-EtCH(Me)NHCOCH₂O—Ph |
| 1233 | H | H | i-Pr | H | Ph | 4-i-PrNHCOCH₂O-3-Me—Ph |
| 1234 | H | H | i-Pr | H | Ph | 4-EtNHCOCH₂O-3-Me—Ph |

TABLE 6-continued

[I-1]

| Compound No. | R¹ | R² | R³ | R⁴ | Z | R |
|---|---|---|---|---|---|---|
| 1235 | H | H | i-Pr | H | Ph | 4-EtCH(Me)NHCOCH₂O-3-Me—Ph |
| 1236 | H | H | i-Pr | H | Ph | 4-cycloPrNHCOCH₂CH₂O—Ph |
| 1237 | H | H | i-Pr | H | Ph | 4-cycloPentylNHCOCH₂CH₂O—Ph |
| 1238 | H | H | i-Pr | H | Ph | 3-I-4-n-PrNHCOCH₂CH₂O—Ph |
| 1239 | H | H | i-Pr | H | Ph | 3-I-4-i-PrNHCOCH₂CH₂O—Ph |
| 1240 | H | H | i-Pr | H | Ph | 4-EtNHCOCH₂CH₂O-3-I—Ph |
| 1241 | H | H | i-Pr | H | Ph | 4-EtCH(Me)NHCOCH₂CH₂O-3-I—Ph |
| 1242 | H | H | i-Pr | H | Ph | 4-EtCOCH₂CH₂O-3-I—Ph |
| 1243 | H | H | i-Pr | H | Ph | 4-cycloPrNHCOCH₂CH₂O-3-I—Ph |
| 1244 | H | H | i-Pr | H | Ph | 4-cycloPentylNHCOCH₂CH₂O-3-I—Ph |
| 1245 | H | H | i-Pr | H | Ph | 3-F-4-n-PrNHCOCH₂CH₂O—Ph |
| 1246 | H | H | i-Pr | H | Ph | 3-F-4-i-PrNHCOCH₂CH₂O—Ph |
| 1247 | H | H | i-Pr | H | Ph | 4-EtNHCOCH₂CH₂O-3-F—Ph |
| 1248 | H | H | i-Pr | H | Ph | 4-EtCH(Me)NHCOCH₂CH₂O-3-F—Ph |
| 1249 | H | H | i-Pr | H | Ph | 4-EtCOCH₂CH₂O-3-F—Ph |
| 1250 | H | H | i-Pr | H | Ph | 3-F-4-i-BuNHCOCH₂CH₂O—Ph |
| 1251 | H | H | i-Pr | H | Ph | 4-cycloPrNHCOCH₂CH₂O-3-F—Ph |
| 1252 | H | H | i-Pr | H | Ph | 3-Br-4-n-PrNHCOCH₂CH₂O—Ph |
| 1253 | H | H | i-Pr | H | Ph | 3-Br-4-i-PrNHCOCH₂CH₂O—Ph |
| 1254 | H | H | i-Pr | H | Ph | 3-Br-4-EtNHCOCH₂CH₂O—Ph |
| 1255 | H | H | i-Pr | H | Ph | 3-Br-4-i-BuNHCOOH₂CH₂O—Ph |
| 1256 | H | H | i-Pr | H | Ph | 3-Cl-4-n-PrNHCOCH₂CH₂O—Ph |
| 1257 | H | H | i-Pr | H | Ph | 3-Cl-4-i-PrNHCOCH₂CH₂O—Ph |
| 1258 | H | H | i-Pr | H | Ph | 3-Cl-4-EtNHCOCH₂CH₂O—Ph |
| 1259 | H | H | i-Pr | H | Ph | 3-Cl-4-EtCH(Me)NHCOCH₂CH₂O—Ph |
| 1260 | H | H | i-Pr | H | Ph | 3-Cl-4-cycloPrNHCOCH₂CH₂O—Ph |
| 1261 | H | H | i-Pr | H | Ph | 3-Cl-4-cycloPentylNHCOCH₂CH₂O—Ph |
| 1262 | H | H | i-Pr | H | Ph | 3-Me-4-n-PrNHCOCH₂CH₂O—Ph |
| 1263 | H | H | i-Pr | H | Ph | 4-i-PrNHCOCH₂CH₂O-3-Me—Ph |
| 1264 | H | H | i-Pr | H | Ph | 4-EtNHCOCH₂CH₂O-3-Me—Ph |
| 1265 | H | H | i-Pr | H | Ph | 3-Me-4-MeNHCOCH₂CH₂O—Ph |
| 1266 | H | H | i-Pr | H | Ph | 3-Me-4-n-BuNHCOCH₂CH₂O—Ph |
| 1267 | H | H | i-Pr | H | Ph | 4-EtCH(Me)NHCOCH₂CH₂O-3-Me—Ph |
| 1268 | H | H | i-Pr | H | Ph | 4-EtCOCH₂CH₂O-3-Me—Ph |
| 1269 | H | H | i-Pr | H | Ph | 4-i-BuNHCOCH₂CH₂O-3-Me—Ph |
| 1270 | H | H | i-Pr | H | Ph | 3-Me-4-t-BuNHCOCH₂CH₂O—Ph |
| 1271 | H | H | i-Pr | H | Ph | 4-cycloPrNHCOCH₂CH₂O-3-Me—Ph |
| 1272 | H | H | i-Pr | H | Ph | 4-cycloPentylNHCOCH₂CH₂O-3-Me—Ph |
| 1273 | H | H | Me | H | Ph | 3-Cl-4-n-PrNHCOCH₂O—Ph |

TABLE 7

[I-1]

| Compound No. | R¹ | R² | R³ | R⁴ | Z | R |
|---|---|---|---|---|---|---|
| 1274 | H | H | Me | H | Ph | 3-Cl-4-i-PrNHCOCH₂O—Ph |
| 1275 | H | H | Me | H | Ph | 3-Cl-4-EtNHCOCH₂O—Ph |
| 1276 | H | H | Me | H | Ph | 3-Cl-4-EtCH(Me)NHCOCH₂O—Ph |
| 1277 | H | H | Me | H | Ph | 3-Cl-4-cycloPrNHCOCH₂O—Ph |
| 1278 | H | H | Me | H | Ph | 3-Cl-4-cycloPentylNHCOCH₂O—Ph |
| 1279 | H | H | Et | H | Ph | 3-Me-4-n-PrNHCOCH₂O—Ph |
| 1280 | H | H | Et | H | Ph | 4-i-PrNHCOCH₂O-3-Me—Ph |
| 1281 | H | H | Et | H | Ph | 4-EtNHCOCH₂O-3-Me—Ph |
| 1282 | H | H | Et | H | Ph | 3-Me-4-MeNHCOCH₂O—Ph |
| 1283 | H | H | Et | H | Ph | 3-Me-4-n-BuNHCOCH₂O—Ph |
| 1284 | H | H | Et | H | Ph | 4-EtCH(Me)NHCOCH₂O-3-Me—Ph |
| 1285 | H | H | Et | H | Ph | 4-EtCOCH₂O-3-Me—Ph |
| 1286 | H | H | Et | H | Ph | 4-i-BuNHCOCH₂O-3-Me—Ph |
| 1287 | H | H | Pr | H | Ph | 3-Cl-4-n-PrNHCOCH₂O—Ph |
| 1288 | H | H | Pr | H | Ph | 3-Cl-4-i-PrNHCOCH₂O—Ph |
| 1289 | H | H | Pr | H | Ph | 3-Cl-4-EtNHCOCH₂O—Ph |
| 1290 | H | H | Pr | H | Ph | 3-Cl-4-EtCH(Me)NHCOCH₂O—Ph |
| 1291 | H | H | Pr | H | Ph | 3-Cl-4-cycloPrNHCOCH₂O—Ph |
| 1292 | H | H | Pr | H | Ph | 3-Cl-4-cycloPentylNHCOCH₂O—Ph |
| 1293 | H | H | Bu | H | Ph | 3-Me-4-n-PrNHCOCH₂O—Ph |
| 1294 | H | H | Bu | H | Ph | 4-i-PrNHCOCH₂O-3-Me—Ph |
| 1295 | H | H | Bu | H | Ph | 4-EtNHCOCH₂O-3-Me—Ph |
| 1296 | H | H | Bu | H | Ph | 3-Me-4-MeNHCOCH₂O—Ph |
| 1297 | H | H | Bu | H | Ph | 3-Me-4-n-BuNHCOCH₂O—Ph |
| 1298 | H | H | Bu | H | Ph | 4-EtCH(Me)NHCOCH₂O-3-Me—Ph |
| 1299 | H | H | Bu | H | Ph | 4-EtCOCH₂O-3-Me—Ph |
| 1300 | H | H | Bu | H | Ph | 4-i-BuNHCOCH₂O-3-Me—Ph |
| 1301 | H | H | i-Bu | H | Ph | 3-Cl-4-n-PrNHCOCH₂O—Ph |
| 1302 | H | H | i-Bu | H | Ph | 3-Cl-4-i-PrNHCOCH₂O—Ph |
| 1303 | H | H | i-Bu | H | Ph | 3-Cl-4-EtNHCOCH₂O—Ph |
| 1304 | H | H | i-Bu | H | Ph | 3-Cl-4-EtCH(Me)NHCOCH₂O—Ph |
| 1305 | H | H | i-Bu | H | Ph | 3-Cl-4-cycloPrNHCOCH₂O—Ph |
| 1306 | H | H | i-Bu | H | Ph | 3-Cl-4-cycloPentylNHCOCH₂O—Ph |
| 1307 | H | H | t-Bu | H | Ph | 3-Me-4-n-PrNHCOCH₂O—Ph |
| 1308 | H | H | t-Bu | H | Ph | 4-i-PrNHCOCH₂O-3-Me—Ph |
| 1309 | H | H | t-Bu | H | Ph | 4-EtNHCOCH₂O-3-Me—Ph |
| 1310 | H | H | t-Bu | H | Ph | 3-Me-4-MeNHCOCH₂O—Ph |
| 1311 | H | H | PhCH₂ | H | Ph | 3-Me-4-n-BuNHCOCH₂O—Ph |
| 1312 | H | H | PhCH₂ | H | Ph | 4-EtCH(Me)NHCOCH₂O-3-Me—Ph |
| 1313 | H | H | PhCH₂ | H | Ph | 4-EtCOCH₂O-3-Me—Ph |
| 1314 | H | H | PhCH₂ | H | Ph | 4-i-BuNHCOCH₂O-3-Me—Ph |
| 1315 | H | H | i-Pr | Me | Ph | 3-Cl-4-n-PrNHCOCH₂O—Ph |
| 1316 | H | H | i-Pr | Me | Ph | 3-Cl-4-i-PrNHCOCH₂O—Ph |
| 1317 | H | H | i-Pr | Me | Ph | 3-Cl-4-EtNHCOCH₂O—Ph |
| 1318 | H | H | i-Pr | Me | Ph | 3-Cl-4-EtCH(Me)NHCOCH₂O—Ph |

TABLE 8

[I-9]

| Compound No. | R¹ | R² | R³ | R⁴ | Z | R |
|---|---|---|---|---|---|---|
| 1319 | H | H | i-Pr | Me | Ph | 3-Cl-4-cycloPrNHCOCH$_2$O—Ph |
| 1320 | H | H | i-Pr | Me | Ph | 3-Cl-4-cycloPentylNHCOCH$_2$O—Ph |
| 1321 | H | H | i-Pr | H | 2,3-Pyridyl | 3-Me-4-n-PrNHCOCH$_2$O—Ph |
| 1322 | H | H | i-Pr | H | 2,3-Pyridyl | 4-i-PrNHCOCH$_2$O-3-Me—Ph |
| 1323 | H | H | i-Pr | H | 2,3-Pyridyl | 4-EtNHCOCH$_2$O-3-Me—Ph |
| 1324 | H | H | i-Pr | H | 2,3-Pyridyl | 3-Me-4-MeNHCOCH$_2$O—Ph |
| 1325 | H | H | i-Pr | H | 2,3-Pyridyl | 3-Me-4-n-BuNHCOCH$_2$O—Ph |
| 1326 | H | H | i-Pr | H | 2,3-Pyridyl | 4-EtCH(Me)NHCOCH$_2$O-3-Me—Ph |
| 1327 | H | H | i-Pr | H | 2,3-Pyridyl | 4-EtCOCH$_2$O-3-Me—Ph |
| 1328 | H | H | i-Pr | H | 2,3-Pyridyl | 4-i-BuNHCOCH$_2$O-3-Me—Ph |
| 1329 | H | H | i-Pr | H | 2,3-Pyridyl | 3-Cl-4-n-PrNHCOCH$_2$O—Ph |
| 1330 | H | H | i-Pr | H | 3,4-Pyridyl | 3-Cl-4-i-PrNHCOCH$_2$O—Ph |
| 1331 | H | H | i-Pr | H | 3,4-Pyridyl | 3-Cl-4-EtNHCOCH$_2$O—Ph |
| 1332 | H | H | i-Pr | H | 3,4-Pyridyl | 3-Cl-4-EtCH(Me)NHCOCH$_2$O—Ph |
| 1333 | H | H | i-Pr | H | 3,4-Pyridyl | 3-Cl-4-cycloPrNHCOCH$_2$O—Ph |
| 1334 | H | H | i-Pr | H | 3,4-Pyridyl | 3-Cl-4-cycloPentylNHCOCH$_2$O—Ph |
| 1335 | H | H | i-Pr | H | Ph | 4-F-5-n-PrNHCOCH$_2$O-(2-pyridyl) |
| 1336 | H | H | i-Pr | H | Ph | 4-F-5-i-PrNHCOCH$_{22}$O-(2-pyridyl) |
| 1337 | H | H | i-Pr | H | Ph | 4-EtNHCOCH$_2$O-3-F-(2-pyridyl) |
| 1338 | H | H | i-Pr | H | Ph | 4-EtCH(Me)NHCOCH$_2$O-3-F-(2-pyridyl) |
| 1339 | H | H | i-Pr | H | Ph | 4-EtCOCH$_2$O-3-F-(2-pyridyl) |
| 1340 | H | H | i-Pr | H | Ph | 3-F-4-i-BuNHCOCH$_2$O-(2-pyridyl) |
| 1341 | H | H | i-Pr | H | Ph | 4-cycloPrNHCOCH$_2$O-3-F-(2-pyridyl) |
| 1342 | H | H | i-Pr | H | Ph | 5-I-6-n-PrNHCOCH$_2$O-(3-pyridyl) |
| 1343 | H | H | i-Pr | H | Ph | 5-I-6-i-PrNHCOCH$_2$O-(3-pyridyl) |
| 1344 | H | H | i-Pr | H | Ph | 6-EtNHCOCH$_2$O-5-I-(3-pyridyl) |
| 1345 | H | H | i-Pr | H | Ph | 6-EtCH(Me)NHCOCH$_2$O-5-I-(3-pyridyl) |
| 1346 | H | H | i-Pr | H | Ph | 6-EtCOCH$_2$O-5-I-(3-pyridyl) |
| 1347 | H | H | i-Pr | H | Ph | 6-cycloPrNHCOCH$_2$O-5-I-(3-pyridyl) |
| 1348 | H | H | i-Pr | H | Ph | 3-NO$_2$-4-n-PrNHCOCH$_2$O—Ph |
| 1349 | H | H | i-Pr | H | Ph | 3-NO$_2$-4-i-PrNHCOCH$_2$O—Ph |
| 1350 | H | H | i-Pr | H | Ph | 4-EtNHCOCH$_2$O-3-NO$_2$—Ph |
| 1351 | H | H | i-Pr | H | Ph | 4-EtCH(Me)NHCOCH$_2$O-3-NO$_2$—Ph |
| 1352 | H | H | i-Pr | H | Ph | 4-EtCOCH$_2$O-3-NO$_2$—Ph |
| 1353 | H | H | i-Pr | H | Ph | 4-i-BuNHCOCH$_2$O-3-NO$_2$—Ph |
| 1354 | H | H | i-Pr | H | Ph | 4-cycloPrNHCOCH$_2$O-3-NO$_2$—Ph |
| 1355 | H | H | i-Pr | H | Ph | 3-MeO-4-n-PrNHCOCH$_2$O—Ph |
| 1356 | H | H | i-Pr | H | Ph | 3-MeO-4-i-PrNHCOCH$_2$O—Ph |
| 1357 | H | H | i-Pr | H | Ph | 4-EtNHCOCH$_2$O-3-MeO—Ph |
| 1358 | H | H | i-Pr | H | Ph | 4-EtCH(Me)NHCOCH$_2$O-3-MeO—Ph |
| 1359 | H | H | i-Pr | H | Ph | 4-EtCOCH$_2$O-3-MeO—Ph |
| 1360 | H | H | i-Pr | H | Ph | 3-MeO-4-i-BuNHCOCH$_2$O—Ph |
| 1361 | H | H | i-Pr | H | Ph | 4-cycloPrNHCOCH$_2$O-3-MeO—Ph |
| 1362 | H | H | i-Pr | H | Ph | 3-HO-4-n-PrNHCOCH$_2$O—Ph |
| 1363 | H | H | i-Pr | H | Ph | 3-HO-4-i-PrNHCOCH$_2$O—Ph |

TABLE 9

[I-1]

| Compound No. | R¹ | R² | R³ | R⁴ | Z | R |
|---|---|---|---|---|---|---|
| 1364 | H | H | i-Pr | H | Ph | 4-EtNHCOCH$_2$O-3-HO—Ph |
| 1365 | H | H | i-Pr | H | Ph | 4-EtCH(Me)NHCOCH$_2$O-3-HO—Ph |
| 1366 | H | H | i-Pr | H | Ph | 4-EtCOCH$_2$O-3-HO—Ph |
| 1367 | H | H | i-Pr | H | Ph | 3-HO-4-i-BuNHCOCH$_2$O—Ph |
| 1368 | H | H | i-Pr | H | Ph | 4-cycloPrNHCOCH$_2$O-3-HO—Ph |
| 1369 | H | H | i-Pr | H | Ph | 3-H$_2$NCH$_2$CH$_2$NHCOCH$_2$O—Ph |

TABLE 9-continued

[I-1]

| Compound No. | R¹ | R² | R³ | R⁴ | Z | R |
|---|---|---|---|---|---|---|
| 1370 | H | H | i-Pr | H | Ph | 2-H₂NCH₂CH₂NHCOCH₂O—Ph |
| 1371 | H | H | i-Pr | H | Ph | 4-MeNHCH₂CH₂NHCOCH₂O—Ph |
| 1372 | H | H | i-Pr | H | Ph | 3-MeNHCH₂CH₂NHCOCH₂O—Ph |
| 1373 | H | H | i-Pr | H | Ph | 2-MeNHCH₂CH₂NHCOCH₂O—Ph |
| 1374 | H | H | i-Pr | H | Ph | 4-Me₂NCH₂CH₂NHCOCH₂O—Ph |
| 1375 | H | H | i-Pr | H | Ph | 3-Me₂NCH₂CH₂NHCOCH₂O—Ph |
| 1376 | H | H | i-Pr | H | Ph | 2-Me₂NCH₂CH₂NHCOCH₂O—Ph |
| 1377 | H | H | i-Pr | H | Ph | 4-H₂NCH₂CH₂NHCOCH₂O-3-Cl—Ph |
| 1378 | H | H | i-Pr | H | Ph | 3-H₂NCH₂CH₂NHCOCH₂O-4-Cl—Ph |
| 1379 | H | H | i-Pr | H | Ph | 2-H₂NCH₂CH₂NHCOCH₂O-4-Cl—Ph |
| 1380 | H | H | i-Pr | H | Ph | 4-MeNHCH₂CH₂NHCOCH₂O-3-Me—Ph |
| 1381 | H | H | i-Pr | H | Ph | 3-MeNHCH₂CH₂NHCOCH₂O-4-Me—Ph |
| 1382 | H | H | i-Pr | H | Ph | 2-MeNHCH₂CH₂NHCOCH₂O-4-Me—Ph |
| 1383 | H | H | i-Pr | H | Ph | 4-Me₂NCH₂CH₂NHCOCH₂O-3-F—Ph |
| 1384 | H | H | i-Pr | H | Ph | 3-Me₂NCH₂CH₂NHCOCH₂O-4-F—Ph |
| 1385 | H | H | i-Pr | H | Ph | 2-Me₂NCH₂CH₂NHCOCH₂O-4-F—Ph |
| 1386 | H | H | i-Pr | H | Ph | 4-H₂NCOCH₂-3-I—Ph |
| 1387 | H | H | i-Pr | H | Ph | 3-I-4-MeNHCOCH₂—Ph |
| 1388 | H | H | i-Pr | H | Ph | 4-EtNHCOCH₂-3-I—Ph |
| 1389 | H | H | i-Pr | H | Ph | 3-I-4-nPrNHCOCH₂—Ph |
| 1390 | H | H | i-Pr | H | Ph | 3-I-4-iPrNHCOCH₂—Ph |
| 1391 | H | H | i-Pr | H | Ph | 4-nBuNHCOCH₂-3-I—Ph |
| 1392 | H | H | i-Pr | H | Ph | 4-tBuNHCOCH₂-3-I—Ph |
| 1393 | H | H | i-Pr | H | Ph | 4-iBuNHCOCH₂—Ph |
| 1394 | H | H | i-Pr | H | Ph | 4-tBuO₂CCH₂-3-I—Ph |
| 1395 | H | H | i-Pr | H | Ph | 3-I-4-PhCH₂NHCOCH₂—Ph |
| 1396 | H | H | i-Pr | H | Ph | 3-I-4-(2-tetrahydrofuryl)CH₂NHCOCH₂— |
| 1397 | H | H | i-Pr | H | Ph | 4-cycloPrNHCOCH₂-3-I—Ph |
| 1398 | H | H | i-Pr | H | Ph | 4-cycloPentylNHCOCH₂-3-I—Ph |
| 1399 | H | H | i-Pr | H | Ph | 4-cycloHexylNHCOCH₂-3-I—Ph |
| 1400 | H | H | i-Pr | H | Ph | 4-cycloPrNHCOCH₂-3-F—Ph |
| 1401 | H | H | i-Pr | H | Ph | 3-Cl-4-i-PrNHCOCH₂CH₂—Ph |
| 1402 | H | H | i-Pr | H | Ph | 3-Cl-4-EtNHCOCH₂CH₂—Ph |
| 1403 | H | H | i-Pr | H | Ph | 3-Cl-4-EtCH(Me)NHCOCH₂CH₂—Ph |
| 1404 | H | H | i-Pr | H | Ph | 4-i-PrNHCO-3-Me—Ph |
| 1405 | H | H | i-Pr | H | Ph | 4-EtNHCO-3-Me—Ph |
| 1406 | H | H | i-Pr | H | Ph | 4-EtCH(Me)NHCO-3-Me—Ph |
| 1407 | H | H | i-Pr | H | Ph | 3-Cl-4-i-PrNHCH₂CH₂O—Ph |
| 1408 | H | H | i-Pr | H | Ph | 3-Cl-4-EtNHCH₂CH₂O—Ph |
| 1409 | H | H | i-Pr | H | Ph | 3-Cl-4-EtCH(Me)NHCH₂CH₂O—Ph |

TABLE 10

[I-1]

| Compound No. | R¹ | R² | R³ | R⁴ | Z | R |
|---|---|---|---|---|---|---|
| 1410 | H | H | i-Pr | H | 2,3-anthryl | 4-nBuNHCOCH₂O—Ph |
| 1411 | H | H | i-Pr | H | 2,3-indenyl | 4-nPrNHCOCH₂O—Ph |
| 1412 | H | H | i-Pr | H | 2,3-naphthyl | 4-nPrNHCOCH₂O—Ph |
| 1413 | H | H | i-Pr | H | 2,3-pyrazinyl | 4-nPrNHCOCH₂O—Ph |
| 1414 | H | H | i-Pr | H | Ph | 3-PhO-4-nPrNHCOCH₂O—Ph |
| 1415 | H | H | i-Pr | H | Ph | 3-PhCH₂O-4-MeO₂CNH₂CH₂CH₂NHCOCH₂O—Ph |
| 1416 | H | H | i-Pr | H | Ph | 3-Ph₂N-4-nPrNHCOCH₂O—Ph |
| 1417 | H | H | i-Pr | H | Ph | 3-PhCH₂CH₂N-4-nPrNHCOCH₂O—Ph |
| 1418 | H | H | i-Pr | H | Ph | 3-PhCH₂CH₂N-4-nPrNHCOCH₂O—Ph |
| 1419 | H | H | i-Pr | H | Ph | 3-PhSO₃-4-nPrNHCOCH₂O—Ph |
| 1420 | H | H | i-Pr | H | Ph | 3-Me-4-nPrNHCOCH₂S—Ph |
| 1421 | H | H | i-Pr | H | Ph | 3-PhNHSO₂-4-nPrNHCOCH₂O—Ph |

TABLE 10-continued

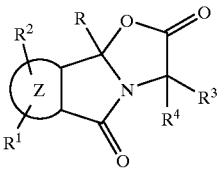

[I-1]

| Compound No. | R¹ | R² | R³ | R⁴ | Z | R |
|---|---|---|---|---|---|---|
| 1422 | H | H | i-Pr | H | Ph | 3-PhCH₂CO-4-nPrNHCOCH₂O—Ph |
| 1423 | H | H | H₂NCO—PhCH₂ | H | Ph | 4-nPrNHCOCH₂O—Ph |
| 1424 | H | H | MeCO—PhCH₂ | H | Ph | 4-nPrNHCOCH₂O—Ph |
| 1425 | H | H | H₂NCH₂CH₂ | H | Ph | 4-nPrNHCOCH₂O—Ph |
| 1426 | H | H | MeO₂C—PhCH₂ | H | Ph | 4-nPrNHCOCH₂O—Ph |
| 1427 | H | H | D-Glutamic Acid | H | Ph | 3-Me-4-nPrNHCOCH₂O—Ph |
| 1428 | H | H | L-Glutamic Acid | H | Ph | 3-Me-4-nPrNHCOCH₂O—Ph |
| 1429 | H | H | (3-Pyridyl)CH₂ | H | Ph | 3-Me-4-nPrNHCOCH₂O—Ph |
| 1430 | H | H | i-Pr | H | Ph | 4-n-PrNHCOCH₂O-3-CH₂CH—Ph |
| 1431 | H | H | i-Pr | H | Ph | 4-n-PrNHCOCH₂O-3-(2-Pyridyl)-Ph |
| 1432 | H | H | i-Pr | H | Ph | 4-n-PrNHCOCH₂O-3-(3-Pyridyl)-Ph |
| 1433 | H | H | i-Pr | H | Ph | 4-n-PrNHCOCH₂O-3-(4-Pyridyl)-Ph |
| 1434 | H | H | i-Pr | H | Ph | 3-Ph-4-n-PrNHCOCH₂O—Ph |
| 1435 | H | H | i-Pr | H | Ph | 3-Et-4-n-PrNHCOCH₂O—Ph |
| 1436 | H | H | i-Pr | H | Ph | 3-n-Bu-4-n-PrNHCOCH₂O—Ph |
| 1437 | H | H | i-Pr | H | Ph | 3-MeO-6-Me—Ph |
| 1438 | H | H | i-Pr | H | Ph | 3-HO-6-Me—Ph |
| 1439 | H | H | i-Pr | H | Ph | 6-Me-3-n-PrNHCOCH₂O—Ph |

TABLE 11

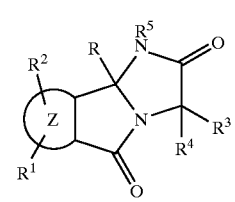

[I-2]

| Compound No. | R¹ | R² | R³ | R⁴ | R⁵ | Z | R |
|---|---|---|---|---|---|---|---|
| 2001 | H | H | i-Pr | H | H | Ph | 2-MeO—Ph |
| 2002 | H | H | i-Pr | H | H | Ph | Ph |
| 2003 | H | H | i-Pr | H | H | Ph | 2-NH₂—Ph |
| 2004 | H | H | i-Pr | H | H | Ph | 4-F—Ph |
| 2005 | H | H | i-Pr | H | H | Ph | 4-Et₂N—Ph |
| 2006 | H | H | i-Pr | H | H | Ph | 4-Cl—Ph |
| 2007 | H | H | i-Pr | H | H | Ph | 4-HO—Ph |
| 2008 | H | H | i-Pr | H | H | Ph | 3-MeO—Ph |
| 2009 | H | H | i-Pr | H | H | Ph | 3-HO—Ph |
| 2010 | H | H | i-Pr | H | H | Ph | 3-NH₂—Ph |
| 2011 | H | H | i-Pr | H | H | Ph | 4-MeO—Ph |
| 2012 | H | H | i-Pr | H | H | Ph | 4-Me—Ph |
| 2013 | H | H | i-Pr | H | H | Ph | 3-Me—Ph |
| 2014 | H | H | i-Pr | H | H | Ph | 4-tBuO₂CCH₂O—Ph |
| 2015 | H | H | i-Pr | H | H | Ph | 4-HO₂CCH₂O—Ph |
| 2016 | H | H | i-Pr | H | H | Ph | 4-tBuO₂C(CH₂)₅O—Ph |
| 2017 | H | H | i-Pr | H | H | Ph | 4-HO₂C(CH₂)₅O—Ph |
| 2018 | H | H | i-Pr | H | H | Ph | 4-HO(CH₂)₃O—Ph |
| 2019 | H | H | i-Pr | H | H | Ph | 4-HO(CH₂)₂O—Ph |
| 2020 | H | H | i-Pr | H | H | Ph | 4-HOC(Me)₂(CH₂)₂O—Ph |
| 2021 | H | H | i-Pr | H | H | Ph | 4-PhCH₂O—Ph |
| 2022 | H | H | i-Pr | H | H | Ph | 4-MeNHCOCH₂O—Ph |
| 2023 | H | H | i-Pr | H | H | Ph | 4-EtNHCOCH₂O—Ph |
| 2024 | H | H | i-Pr | H | H | Ph | 4-nPrNHCOCH₂O—Ph |
| 2025 | H | H | i-Pr | H | H | Ph | 4-nBuNHCOCH₂O—Ph |
| 2026 | H | H | i-Pr | H | H | Ph | 4-CH₂=CHCH₂NHCOCH₂O—Ph |
| 2027 | H | H | i-Pr | H | H | Ph | 4-Me(CH₂)₉NHCOCH₂O—Ph |
| 2028 | H | H | i-Pr | H | H | Ph | 4-N₃(CH₂)₃O—Ph |
| 2029 | H | H | i-Pr | H | H | Ph | 4-tBuO₂CCH(Me)O—Ph |
| 2030 | H | H | i-Pr | H | H | Ph | 4-nPrNHCOCH(Me)O—Ph |
| 2031 | H | H | i-Pr | H | H | Ph | 4-F₃CSO₃—Ph |
| 2032 | H | H | i-Pr | H | H | Ph | 4-tBuO₂CCH=CHPh |
| 2033 | H | H | i-Pr | H | H | Ph | 4-nPrNHCOCH=CH—Ph |
| 2034 | H | H | i-Pr | H | H | Ph | 4-nPrCH(Me)NHCOCH₂O—Ph |
| 2035 | H | H | i-Pr | H | H | Ph | 4-EtCH(Me)NHCOCH₂O—Ph |
| 2036 | H | H | i-Pr | H | H | Ph | 4-MeOCH₂O—Ph |
| 2037 | H | H | i-Pr | H | H | Ph | 4-EtCOCH₂O—Ph |
| 2038 | H | H | i-Pr | H | H | Ph | 3-tBuO₂CCH₂O—Ph |
| 2039 | H | H | i-Pr | H | H | Ph | 3-HO₂CCH₂O—Ph |
| 2040 | H | H | i-Pr | H | H | Ph | 3-nPrNHCOCH₂O—Ph |
| 2041 | H | H | i-Pr | H | H | Ph | 4-H₂NC(Me)₂CH₂O₂CCH₂O—Ph |
| 2042 | H | H | i-Pr | H | H | Ph | 4-morpholinoCOCH₂O—Ph |
| 2043 | H | H | i-Pr | H | H | Ph | 4-(4-Cl—Ph)—COCH₂O—Ph |
| 2044 | H | H | i-Pr | H | H | Ph | 4-PhCOCH₂O—Ph |
| 2045 | H | H | i-Pr | H | H | Ph | 4-(4-pyridyl)-CH₂NHCOCH₂O—Ph |
| 2046 | H | H | i-Pr | H | H | Ph | 4-H₂NCH₂CH₂NHCOCH₂O—Ph |
| 2047 | H | H | i-Pr | H | H | Ph | 4-Cl-3-NO₂—Ph |

TABLE 12

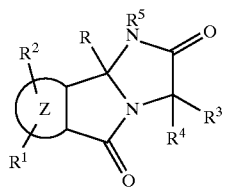

[I-2]

| Compound No. | R¹ | R² | R³ | R⁴ | R⁵ | Z | R |
|---|---|---|---|---|---|---|---|
| 2048 | H | H | i-Pr | H | H | Ph | 4-Cl-3-F—Ph |
| 2049 | H | H | i-Pr | H | H | Ph | 4-Cl-3-Me—Ph |
| 2050 | H | H | i-Pr | H | H | Ph | 3-NH$_2$-4-Cl—Ph |
| 2051 | H | H | i-Pr | H | H | Ph | 3-Cl-4-MeO—Ph |
| 2052 | H | H | i-Pr | H | H | Ph | 3-Cl-4-Me—Ph |
| 2053 | H | H | i-Pr | H | H | Ph | 4-Br-3-Cl—Ph |
| 2054 | H | H | i-Pr | H | H | Ph | 4-Br-2-CF—Ph |
| 2055 | H | H | i-Pr | H | H | Ph | 4-F-3-Me—Ph |
| 2056 | H | H | i-Pr | H | H | Ph | 3-F-4-Me—Ph |
| 2057 | H | H | i-Pr | H | H | Ph | 3-Br-4-HO—Ph |
| 2058 | H | H | i-Pr | H | H | Ph | 3-Br-4-MeO—Ph |
| 2059 | H | H | i-Pr | H | H | Ph | 3-Br-4-F—Ph |
| 2060 | H | H | i-Pr | H | H | Ph | 3-F-4-PhPh |
| 2061 | H | H | i-Pr | H | H | Ph | 4-HO-3-I—Ph |
| 2062 | H | H | i-Pr | H | H | Ph | 5-HO-2-I—Ph |
| 2063 | H | H | i-Pr | H | H | Ph | 3-I-4-MeO—Ph |
| 2064 | H | H | i-Pr | H | H | Ph | 2-I-5-MeO—Ph |
| 2065 | H | H | i-Pr | H | H | Ph | 4-MeO-3-Me—Ph |
| 2066 | H | H | i-Pr | H | H | Ph | 4-HO(CH$_2$)$_3$O-3-I—Ph |
| 2067 | H | H | i-Pr | H | H | Ph | 4-HO(CH$_2$)$_2$O-3-I—Ph |
| 2068 | H | H | i-Pr | H | H | Ph | 4-HOC(Me)$_2$(CH$_2$)$_2$O-3-I—Ph |
| 2069 | H | H | i-Pr | H | H | Ph | 4-tBuO$_2$C(CH$_2$)$_4$O-3-I—Ph |
| 2070 | H | H | i-Pr | H | H | Ph | 3-I-4-PhCH$_2$O—Ph |
| 2071 | H | H | i-Pr | H | H | Ph | 4-H$_2$NCOCH$_2$O-3-I—Ph |
| 2072 | H | H | i-Pr | H | H | Ph | 3-I-4-MeNHCOCH$_2$O—Ph |
| 2073 | H | H | i-Pr | H | H | Ph | 4-EtNHCOCH$_2$O-3-I—Ph |
| 2074 | H | H | i-Pr | H | H | Ph | 3-I-4-nPrNHCOCH$_2$O—Ph |
| 2075 | H | H | i-Pr | H | H | Ph | 3-I-4-iPrNHCOCH$_2$O—Ph |
| 2076 | H | H | i-Pr | H | H | Ph | 4-nBuNHCOCH$_2$O-3-I—Ph |
| 2077 | H | H | i-Pr | H | H | Ph | 4-tBuNHCOCH$_2$O-3-I—Ph |
| 2078 | H | H | i-Pr | H | H | Ph | 4-iBuNHCOCH$_2$O—Ph |
| 2079 | H | H | i-Pr | H | H | Ph | 4-tBuO$_2$CCH$_2$O-3-I—Ph |
| 2080 | H | H | i-Pr | H | H | Ph | 3-I-4-PhCH$_2$NHCOCH$_2$O—Ph |
| 2081 | H | H | i-Pr | H | H | Ph | 3-I-4-(2-tetrahydrofuryl)CH$_2$NHCOCH$_2$O—Ph |
| 2082 | H | H | i-Pr | H | H | Ph | 4-cycloPrNHCOCH$_2$O-3-I—Ph |
| 2083 | H | H | i-Pr | H | H | Ph | 4-cycloPentylNHCOCH$_2$O-3-I—Ph |
| 2084 | H | H | i-Pr | H | H | Ph | 4-cycloHexylNHCOCH$_2$O-3-I—Ph |
| 2085 | H | H | i-Pr | H | H | Ph | 4-cycloPrNHCOCH$_2$O-3-I—Ph |
| 2086 | H | H | i-Pr | H | H | Ph | 4-Me(CH$_2$)$_9$NHCOCH$_2$O-3-I—Ph |
| 2087 | H | H | i-Pr | H | H | Ph | 4-HO$_2$CCH$_2$O-3-I—Ph |
| 2088 | H | H | i-Pr | H | H | Ph | 4-N$_3$(CH$_2$)$_3$O-3-I—Ph |
| 2089 | H | H | i-Pr | H | H | Ph | 3-I-4-nPrNHCO(CH$_2$)$_4$O—Ph |
| 2090 | H | H | i-Pr | H | H | Ph | 4-Et$_2$NCOCH$_2$O-3-I—Ph |
| 2091 | H | H | i-Pr | H | H | Ph | 3-I-4-nPrN(Me)COCH$_2$O—Ph |
| 2092 | H | H | i-Pr | H | H | Ph | 3-Cl-4-nPrNHCOCH$_2$O—Ph |
| 2093 | H | H | i-Pr | H | H | Ph | 3-Br-4-nPrNHCOCH$_2$O—Ph |
| 2094 | H | H | i-Pr | H | H | Ph | 3-F-4-nPrNHCOCH$_2$O—Ph |

TABLE 13

[I-2]

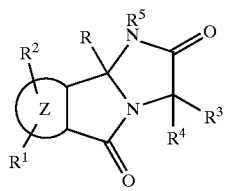

| Compound No. | $R^1$ | $R^2$ | $R^3$ | $R^4$ | $R^5$ | Z | R |
|---|---|---|---|---|---|---|---|
| 2095 | H | H | i-Pr | H | H | Ph | 3-Me-4-nPrNHCOCH$_2$O—Ph |
| 2096 | H | H | i-Pr | H | H | Ph | 4-EtNHCOCH$_2$O-3-F—Ph |
| 2097 | H | H | i-Pr | H | H | Ph | 3-I-4-iPrNHCOC(Me)$_2$CH$_2$O—Ph |
| 2098 | H | H | i-Pr | H | H | Ph | 3-Br-4-CH$_2$=CHCH$_2$NHCOCH$_2$O—Ph |
| 2099 | H | H | i-Pr | H | H | Ph | 4-iBuNHCOCH$_2$O-3-F—Ph |
| 2100 | H | H | i-Pr | H | H | Ph | 3-tBuO$_2$CCH=CH-4-nPrNHCOCH$_2$O—Ph |
| 2101 | H | H | i-Pr | H | H | Ph | 3-HO$_2$CCH=CH-4-nPrNHCOCH$_2$O—Ph |
| 2102 | H | H | i-Pr | H | H | Ph | 3-I-4-MeOCH$_2$CH$_2$NHCOCH$_2$O—Ph |
| 2103 | H | H | i-Pr | H | H | Ph | 3-F-4-HO—Ph |
| 2104 | H | H | i-Pr | H | H | Ph | 3-F-4-MeO—Ph |
| 2105 | H | H | i-Pr | H | H | Ph | 3,4-methylenedioxyPh |
| 2106 | H | H | i-Pr | H | H | Ph | 3,4-ethylenedioxyPh |
| 2107 | H | H | i-Pr | H | H | Ph | 3,4-Cl$_2$—Ph |
| 2108 | H | H | i-Pr | H | H | Ph | 3,4-Me$_2$—Ph |
| 2109 | H | H | i-Pr | H | H | Ph | 3,4-F$_2$—Ph |
| 2110 | H | H | i-Pr | H | H | Ph | 3,4-(MeO)$_2$—Ph |
| 2111 | H | H | i-Pr | H | H | Ph | 3,5-(MeO)$_2$—Ph |
| 2112 | H | H | i-Pr | H | H | Ph | 3,5-Me$_2$—Ph |
| 2113 | H | H | i-Pr | H | H | Ph | 3,5-I$_2$-4-HO—Ph |
| 2114 | H | H | i-Pr | H | H | Ph | 2,4-I$_2$-5-HO—Ph |
| 2115 | H | H | i-Pr | H | H | Ph | 3,5-I$_2$-4-MeO—Ph |
| 2116 | H | H | i-Pr | H | H | Ph | 2,4-I$_2$-5-MeO—Ph |
| 2117 | H | H | i-Pr | H | H | Ph | 2,4,6-Me$_3$—Ph |
| 2118 | H | H | i-Pr | H | H | Ph | 4-HO(CH$_2$)$_3$O-3,5-I$_2$Ph |
| 2119 | H | H | i-Pr | H | H | Ph | 3,5-I$_2$-4-nPrNHCOCH$_2$O—Ph |
| 2120 | H | H | i-Pr | H | H | Ph | 2-thienyl |
| 2121 | H | H | i-Pr | H | H | Ph | 2-furyl |
| 2122 | H | H | i-Pr | H | H | Ph | 3-pyridyl |
| 2123 | H | H | i-Pr | H | H | Ph | 2-naphthyl |
| 2124 | H | H | i-Pr | H | H | Ph | 5-F-1-naphthyl |
| 2125 | H | H | i-Pr | H | H | Ph | dibenzothiophene-2-yl |
| 2126 | 6-F | H | i-Pr | H | H | Ph | Ph |
| 2127 | 7-F | H | i-Pr | H | H | Ph | Ph |
| 2128 | 8-F | H | i-Pr | H | H | Ph | Ph |
| 2129 | 9-F | H | i-Pr | H | H | Ph | Ph |
| 2130 | 6-MeO | H | i-Pr | H | H | Ph | Ph |
| 2131 | 9-MeO | H | i-Pr | H | H | Ph | Ph |
| 2132 | 6-OH | H | i-Pr | H | H | Ph | Ph |
| 2133 | 9-OH | H | i-Pr | H | H | Ph | Ph |
| 2134 | 7-NO$_2$ | H | i-Pr | H | H | Ph | Ph |
| 2135 | 8-NO$_2$ | H | i-Pr | H | H | Ph | Ph |
| 2136 | 9-NO$_2$ | H | i-Pr | H | H | Ph | Ph |
| 2137 | 6-NHPh | H | i-Pr | H | H | Ph | Ph |
| 2138 | 7-Me$_2$N | H | i-Pr | H | H | Ph | Ph |
| 2139 | 7-Me | H | i-Pr | H | H | Ph | Ph |
| 2140 | 8-Me | H | i-Pr | H | H | Ph | Ph |
| 2141 | 7-t-Bu | H | i-Pr | H | H | Ph | Ph |

TABLE 14

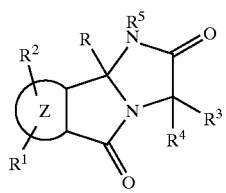

[I-2]

| Compound No. | R¹ | R² | R³ | R⁴ | R⁵ | Z | R |
|---|---|---|---|---|---|---|---|
| 2142 | 8-t-Bu | H | i-Pr | H | H | Ph | Ph |
| 2143 | 7-Br | H | i-Pr | H | H | Ph | Ph |
| 2144 | 8-Br | H | i-Pr | H | H | Ph | Ph |
| 2145 | 7-Cl | H | i-Pr | H | H | Ph | Ph |
| 2146 | 8-Cl | H | i-Pr | H | H | Ph | Ph |
| 2147 | 7-Cl | 8-Cl | i-Pr | H | H | Ph | Ph |
| 2148 | 6-Cl | 9-Cl | i-Pr | H | H | Ph | Ph |
| 2149 | 6-OH | 9-I | i-Pr | H | H | Ph | Ph |
| 2150 | H | H | i-Pr | H | H | 1,2-naphthyl | Ph |
| 2151 | H | H | i-Pr | H | H | 2,3-naphthyl | Ph |
| 2152 | H | H | i-Pr | H | H | cyclohexenyl | Ph |
| 2153 | H | H | D-Leucine | H | H | Ph | Ph |
| 2154 | H | H | L-Leucine | H | H | Ph | Ph |
| 2155 | H | H | D-NorLeucine | H | H | Ph | Ph |
| 2156 | H | H | L-NorLeucine | H | H | Ph | Ph |
| 2157 | H | H | D-AlloLeucine | H | H | Ph | Ph |
| 2158 | H | H | L-AlloLeucine | H | H | Ph | Ph |
| 2159 | H | H | D-NorValine | H | H | Ph | Ph |
| 2160 | H | H | L-NorValine | H | H | Ph | Ph |
| 2161 | H | H | D-Alanine | H | H | Ph | Ph |
| 2162 | H | H | L-Alanine | H | H | Ph | Ph |
| 2163 | H | H | D-Arginine | H | H | Ph | Ph |
| 2164 | H | H | L-Arginine | H | H | Ph | Ph |
| 2165 | H | H | D-Asparagine | H | H | Ph | Ph |
| 2166 | H | H | L-Asparagine | H | H | Ph | Ph |
| 2167 | H | H | D-Glutamic Acid | H | H | Ph | Ph |
| 2168 | H | H | L-Glutamic Acid | H | H | Ph | Ph |
| 2169 | H | H | D-Glutamine | H | H | Ph | Ph |
| 2170 | H | H | L-Glutamine | H | H | Ph | Ph |
| 2171 | H | H | D-Histidine | H | H | Ph | Ph |
| 2172 | H | H | L-Histidine | H | H | Ph | Ph |
| 2173 | H | H | D-Methionine | H | H | Ph | Ph |
| 2174 | H | H | L-Methionine | H | H | Ph | Ph |
| 2175 | H | H | D-Tryptophan | H | H | Ph | Ph |
| 2176 | H | H | L-Tryptophan | H | H | Ph | Ph |
| 2177 | H | H | D-Tyrosine | H | H | Ph | Ph |
| 2178 | H | H | L-Tyrosine | H | H | Ph | Ph |
| 2179 | H | H | D-Homo Phenylalanine | H | H | Ph | Ph |
| 2180 | H | H | L-Homo Phenylalanine | H | H | Ph | Ph |
| 2181 | H | H | D-Leucine | H | H | Ph | 4-Cl—Ph |
| 2182 | H | H | L-Leucine | H | H | Ph | 4-Cl—Ph |
| 2183 | H | H | D-NorLeucine | H | H | Ph | 4-Cl—Ph |
| 2184 | H | H | L-NorLeucine | H | H | Ph | 4-Cl—Ph |
| 2185 | H | H | D-AlloLeucine | H | H | Ph | 4-Cl—Ph |
| 2186 | H | H | L-AlloLeucine | H | H | Ph | 4-Cl—Ph |
| 2187 | H | H | D-NorValine | H | H | Ph | 4-Cl—Ph |

TABLE 15

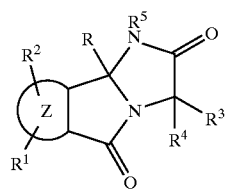

[I-2]

| Compound No. | R¹ | R² | R³ | R⁴ | R⁵ | Z | R |
|---|---|---|---|---|---|---|---|
| 2188 | H | H | L-NorValine | H | H | Ph | 4-Cl—Ph |
| 2189 | H | H | D-Alanine | H | H | Ph | 4-Cl—Ph |
| 2190 | H | H | L-Alanine | H | H | Ph | 4-Cl—Ph |
| 2191 | H | H | D-Arginine | H | H | Ph | 4-Cl—Ph |
| 2192 | H | H | L-Arginine | H | H | Ph | 4-Cl—Ph |
| 2193 | H | H | D-Asparagine | H | H | Ph | 4-Cl—Ph |
| 2194 | H | H | L-Asparagine | H | H | Ph | 4-Cl—Ph |
| 2195 | H | H | D-Glutamic Acid | H | H | Ph | 4-Cl—Ph |
| 2196 | H | H | L-Glutamic Acid | H | H | Ph | 4-Cl—Ph |
| 2197 | H | H | D-Glutamine | H | H | Ph | 4-Cl—Ph |
| 2198 | H | H | L-Glutamine | H | H | Ph | 4-Cl—Ph |
| 2199 | H | H | D-Histidine | H | H | Ph | 4-Cl—Ph |
| 2200 | H | H | L-Histidine | H | H | Ph | 4-Cl—Ph |
| 2201 | H | H | D-Methionine | H | H | Ph | 4-Cl—Ph |
| 2202 | H | H | L-Methionine | H | H | Ph | 4-Cl—Ph |
| 2203 | H | H | D-Tryptophan | H | H | Ph | 4-Cl—Ph |
| 2204 | H | H | L-Tryptophan | H | H | Ph | 4-Cl—Ph |
| 2205 | H | H | D-Tyrosine | H | H | Ph | 4-Cl—Ph |
| 2206 | H | H | L-Tyrosine | H | H | Ph | 4-Cl—Ph |
| 2207 | H | H | D-Homo Phenylalanine | H | H | Ph | 4-Cl—Ph |
| 2208 | H | H | L-Homo Phenylalanine | H | H | Ph | 4-Cl—Ph |
| 2209 | H | H | t-Bu | H | H | Ph | Ph |
| 2210 | H | H | (CH₃)₂(OH)C | H | H | Ph | Ph |
| 2211 | H | H | CH₃(MeO)CH | H | H | Ph | Ph |
| 2212 | H | H | 4-HO—Ph | H | H | Ph | Ph |
| 2213 | H | H | 4-HO-3-I—Ph | H | H | Ph | Ph |
| 2214 | H | H | 4-HO-3,5-I₂—Ph | H | H | Ph | Ph |
| 2215 | H | H | 4-HO-3-I—PhCH₂ | H | H | Ph | Ph |
| 2216 | H | H | 4-HO-3,5-I₂—PhCH₂ | H | H | Ph | Ph |
| 2217 | H | H | 1-naphthylmethyl | H | H | Ph | Ph |
| 2218 | H | H | 4-F—PhCH₂ | H | H | Ph | Ph |
| 2219 | H | H | 1-naphthylmethyl | H | H | Ph | 4-Cl—Ph |
| 2220 | H | H | 4-F—PhCH₂ | H | H | Ph | 4-Cl—Ph |
| 2221 | H | H | i-Pr | Me | H | Ph | 4-Cl—Ph |
| 2222 | H | H | Me | Me | H | Ph | Ph |
| 2223 | H | H | (Combined with R⁴) CH₂= | — | H | Ph | Ph |
| 2224 | H | H | (Combined with R⁴) MeCH= | — | H | Ph | Ph |
| 2225 | H | H | (Combined with R⁴) (CH₂)₄ | — | H | Ph | Ph |
| 2226 | H | H | i-Pr | H | H | Ph | 4-n-PrNHCOCH₂CH₂O—Ph |
| 2227 | H | H | i-Pr | H | H | Ph | 4-i-PrNHCOCH₂CH₂O—Ph |
| 2228 | H | H | i-Pr | H | H | Ph | 4-EtNHCOCH₂CH₂O—Ph |
| 2229 | H | H | i-Pr | H | H | Ph | 4-EtCH(Me)NHCOCH₂CH₂O—Ph |
| 2230 | H | H | i-Pr | H | H | Ph | 3-Cl-4-i-PrNHCOCH₂O—Ph |
| 2231 | H | H | i-Pr | H | H | Ph | 3-Cl-4-EtNHCOCH₂O—Ph |
| 2232 | H | H | i-Pr | H | H | Ph | 3-Cl-4-EtCH(Me)NHCOCH₂O—Ph |
| 2233 | H | H | i-Pr | H | H | Ph | 4-i-PrNHCOCH₂O-3-Me—Ph |

TABLE 16

[I-2]

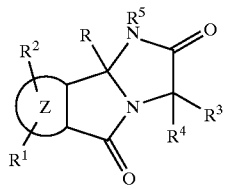

| Compound No. | R¹ | R² | R³ | R⁴ | R⁵ | Z | R |
|---|---|---|---|---|---|---|---|
| 2234 | H | H | i-Pr | H | H | Ph | 4-EtNHCOCH$_2$O-3-Me—Ph |
| 2235 | H | H | i-Pr | H | H | Ph | 4-EtCH(Me)NHCOCH$_2$O-3-Me—Ph |
| 2236 | H | H | i-Pr | H | H | Ph | 4-cycloPrNHCOCH$_2$CH$_2$O—Ph |
| 2237 | H | H | i-Pr | H | H | Ph | 4-cycloPentylNHCOCH$_2$CH$_2$O—Ph |
| 2238 | H | H | i-Pr | H | H | Ph | 3-I-4-n-PrNHCOCH$_2$CH$_2$O—Ph |
| 2239 | H | H | i-Pr | H | H | Ph | 3-I-4-i-PrNHCOCH$_2$CH$_2$O—Ph |
| 2240 | H | H | i-Pr | H | H | Ph | 4-EtNHCOCH$_2$CH$_2$O-3-I—Ph |
| 2241 | H | H | i-Pr | H | H | Ph | 4-EtCH(Me)NHCOCH$_2$CH$_2$O-3-I—Ph |
| 2242 | H | H | i-Pr | H | H | Ph | 4-EtCOCH$_2$CH$_2$O-3-I—Ph |
| 2243 | H | H | i-Pr | H | H | Ph | 4-cycloPrNHCOCH$_2$CH$_2$O-3-I—Ph |
| 2244 | H | H | i-Pr | H | H | Ph | 4-cycloPentylNHCOCH$_2$CH$_2$O-3-I—Ph |
| 2245 | H | H | i-Pr | H | H | Ph | 3-F-4-n-PrNHCOCH$_2$CH$_2$O—Ph |
| 2246 | H | H | i-Pr | H | H | Ph | 3-F-4-i-PrNHCOCH$_2$CH$_2$O—Ph |
| 2247 | H | H | i-Pr | H | H | Ph | 4-EtNHCOCH$_2$CH$_2$O-3-F—Ph |
| 2248 | H | H | i-Pr | H | H | Ph | 4-EtCH(Me)NHCOCH$_2$CH$_2$O-3-F—Ph |
| 2249 | H | H | i-Pr | H | H | Ph | 4-EtCOCH$_2$CH$_2$O-3-F—Ph |
| 2250 | H | H | i-Pr | H | H | Ph | 3-F-4-i-BuNHCOCH$_2$CH$_2$O—Ph |
| 2251 | H | H | i-Pr | H | H | Ph | 4-cycloPrNHCOCH$_2$CH$_2$O-3-F—Ph |
| 2252 | H | H | i-Pr | H | H | Ph | 3-Br-4-n-PrNHCOCH$_2$CH$_2$O—Ph |
| 2253 | H | H | i-Pr | H | H | Ph | 3-Br-4-i-PrNHCOCH$_2$CH$_2$O—Ph |
| 2254 | H | H | i-Pr | H | H | Ph | 3-Br-4-EtNHCOCH$_2$CH$_2$O—Ph |
| 2255 | H | H | i-Pr | H | H | Ph | 3-Br-4-i-BuNHCOCH$_2$CH$_2$O—Ph |
| 2256 | H | H | i-Pr | H | H | Ph | 3-Cl-4-n-PrNHCOCH$_2$CH$_2$O—Ph |
| 2257 | H | H | i-Pr | H | H | Ph | 3-Cl-4-i-PrNHCOCH$_2$CH$_2$O—Ph |
| 2258 | H | H | i-Pr | H | H | Ph | 3-Cl-4-EtNHCOCH$_2$CH$_2$O—Ph |
| 2259 | H | H | i-Pr | H | H | Ph | 3-Cl-4-EtCH(Me)NHCOCH$_2$CH$_2$O—Ph |
| 2260 | H | H | i-Pr | H | H | Ph | 3-Cl-4-cycloPrNHCOCH$_2$CH$_2$O—Ph |
| 2261 | H | H | i-Pr | H | H | Ph | 3-Cl-4-cycloPentylNHCOCH$_2$CH$_2$O—Ph |
| 2262 | H | H | i-Pr | H | H | Ph | 3-Me-4-n-PrNHCOCH$_2$CH$_2$O—Ph |
| 2263 | H | H | i-Pr | H | H | Ph | 4-i-PrNHCOCH$_2$CH$_2$O-3-Me—Ph |
| 2264 | H | H | i-Pr | H | H | Ph | 4-EtNHCOCH$_2$CH$_2$O-3-Me—Ph |
| 2265 | H | H | i-Pr | H | H | Ph | 3-Me-4-MeNHCOCH$_2$CH$_2$O—Ph |
| 2266 | H | H | i-Pr | H | H | Ph | 3-Me-4-n-BuNHCOCH$_2$CH$_2$O—Ph |
| 2267 | H | H | i-Pr | H | H | Ph | 4-EtCH(Me)NHCOCH$_2$CH$_2$O-3-Me—Ph |
| 2268 | H | H | i-Pr | H | H | Ph | 4-EtCOCH$_2$CH$_2$O-3-Me—Ph |
| 2269 | H | H | i-Pr | H | H | Ph | 4-i-BuNHCOCH$_2$CH$_2$O-3-Me—Ph |
| 2270 | H | H | i-Pr | H | H | Ph | 3-Me-4-t-BuNHCOCH$_2$CH$_2$O—Ph |
| 2271 | H | H | i-Pr | H | H | Ph | 4-cycloPrNHCOCH$_2$CH$_2$O-3-Me—Ph |
| 2272 | H | H | i-Pr | H | H | Ph | 4-cycloPentylNHCOCH$_2$CH$_2$O-3-Me—Ph |
| 2273 | H | H | Me | H | H | Ph | 3-Cl-4-n-PrNHCOCH$_2$O—Ph |
| 2274 | H | H | Me | H | H | Ph | 3-Cl-4-i-PrNHCOCH$_2$O—Ph |
| 2275 | H | H | Me | H | H | Ph | 3-Cl-4-EtNHCOCH$_2$O—Ph |
| 2276 | H | H | Me | H | H | Ph | 3-Cl-4-EtCH(Me)NHCOCH$_2$O—Ph |
| 2277 | H | H | Me | H | H | Ph | 3-Cl-4-cycloPrNHCOCH$_2$O—Ph |
| 2278 | H | H | Me | H | H | Ph | 3-Cl-4-cycloPentylNHCOCH$_2$O—Ph |
| 2279 | H | H | Et | H | H | Ph | 3-Me-4-n-PrNHCOCH$_2$O—Ph |

TABLE 17

[I-2]

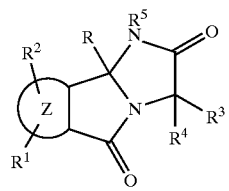

| Compound No. | R¹ | R² | R³ | R⁴ | R⁵ | Z | R |
|---|---|---|---|---|---|---|---|
| 2280 | H | H | Et | H | H | Ph | 4-i-PrNHCOCH$_2$O-3-Me—Ph |
| 2281 | H | H | Et | H | H | Ph | 4-EtNHCOCH$_2$O-3-Me—Ph |
| 2282 | H | H | Et | H | H | Ph | 3-Me-4-MeNHCOCH$_2$O—Ph |
| 2283 | H | H | Et | H | H | Ph | 3-Me-4-n-BuNHCOCH$_2$O—Ph |
| 2284 | H | H | Et | H | H | Ph | 4-EtCH(Me)NHCOCH$_2$O-3-Me—Ph |
| 2285 | H | H | Et | H | H | Ph | 4-EtCOCH$_2$O-3-Me—Ph |
| 2286 | H | H | Et | H | H | Ph | 4-i-BuNHCOCH$_2$O-3-Me—Ph |
| 2287 | H | H | Pr | H | H | Ph | 3-Cl-4-n-PrNHCOCH$_2$O—Ph |
| 2288 | H | H | Pr | H | H | Ph | 3-Cl-4-i-PrNHCOOH$_2$O—Ph |
| 2289 | H | H | Pr | H | H | Ph | 3-Cl-4-EtNHCOCH$_2$O—Ph |
| 2290 | H | H | Pr | H | H | Ph | 3-Cl-4-EtCH(Me)NHCOCH$_2$O—Ph |
| 2291 | H | H | Pr | H | H | Ph | 3-Cl-4-cycloPrNHCOCH$_2$O—Ph |
| 2292 | H | H | Pr | H | H | Ph | 3-Cl-4-cycloPentylNHCOCH$_2$O—Ph |
| 2293 | H | H | Bu | H | H | Ph | 3-Me-4-n-PrNHCOCH$_2$O—Ph |
| 2294 | H | H | Bu | H | H | Ph | 4-i-PrNHCOCH$_2$O-3-Me—Ph |
| 2295 | H | H | Bu | H | H | Ph | 4-EtNHCOCH$_2$O-3-Me—Ph |
| 2296 | H | H | Bu | H | H | Ph | 3-Me-4-MeNHCOCH$_2$O—Ph |
| 2297 | H | H | Bu | H | H | Ph | 3-Me-4-n-BuNHCOCH$_2$O—Ph |
| 2298 | H | H | Bu | H | H | Ph | 4-EtCH(Me)NHCOCH$_2$O-3-Me—Ph |
| 2299 | H | H | Bu | H | H | Ph | 4-EtCOCH$_2$O-3-Me—Ph |
| 2300 | H | H | Bu | H | H | Ph | 4-i-BuNHCOCH$_2$O-3-Me—Ph |
| 2301 | H | H | i-Bu | H | H | Ph | 3-Cl-4-n-PrNHCOCH$_2$O—Ph |
| 2302 | H | H | i-Bu | H | H | Ph | 3-Cl-4-i-PrNHCOCH$_2$O—Ph |
| 2303 | H | H | i-Bu | H | H | Ph | 3-Cl-4-EtNHCOCH$_2$O—Ph |
| 2304 | H | H | i-Bu | H | H | Ph | 3-Cl-4-EtCH(Me)NHCOCH$_2$O—Ph |
| 2305 | H | H | i-Bu | H | H | Ph | 3-Cl-4-cycloPrNHCOCH$_2$O—Ph |
| 2306 | H | H | i-Bu | H | H | Ph | 3-Cl-4-cycloPentylNHCOCH$_2$O—Ph |
| 2307 | H | H | t-Bu | H | H | Ph | 3-Me-4-n-PrNHCOCH$_2$O—Ph |
| 2308 | H | H | t-Bu | H | H | Ph | 4-i-PrNHCOCH$_2$O-3-Me—Ph |
| 2309 | H | H | t-Bu | H | H | Ph | 4-EtNHCOCH$_2$O-3-Me—Ph |
| 2310 | H | H | t-Bu | H | H | Ph | 3-Me-4-MeNHCOCH$_2$O—Ph |
| 2311 | H | H | PhCH$_2$ | H | H | Ph | 3-Me-4-n-BuNHCOCH$_2$O—Ph |
| 2312 | H | H | PhCH$_2$ | H | H | Ph | 4-EtCH(Me)NHCOCH$_2$O-3-Me—Ph |
| 2313 | H | H | PhCH$_2$ | H | H | Ph | 4-EtCOCH$_2$O-3-Me—Ph |
| 2314 | H | H | PhCH$_2$ | H | H | Ph | 4-i-BuNHCOCH$_2$O-3-Me—Ph |
| 2315 | H | H | i-Pr | Me | H | Ph | 3-Cl-4-n-PrNHCOCH$_2$O—Ph |
| 2316 | H | H | i-Pr | Me | H | Ph | 3-Cl-4-i-PrNHCOCH$_2$O—Ph |
| 2317 | H | H | i-Pr | Me | H | Ph | 3-Cl-4-EtNHCOCH$_2$O—Ph |
| 2318 | H | H | i-Pr | Me | H | Ph | 3-Cl-4-EtCH(Me)NHCOCH$_2$O—Ph |
| 2319 | H | H | i-Pr | Me | H | Ph | 3-Cl-4-cycloPrNHCOCH$_2$O—Ph |
| 2320 | H | H | i-Pr | Me | H | Ph | 3-Cl-4-cycloPentylNHCOCH$_2$O—Ph |
| 2321 | H | H | i-Pr | H | H | 2,3-Pyridyl | 3-Me-4-n-PrNHCOCH$_2$O—Ph |
| 2322 | H | H | i-Pr | H | H | 2,3-Pyridyl | 4-i-PrNHCOCH$_2$O-3-Me—Ph |
| 2323 | H | H | i-Pr | H | H | 2,3-Pyridyl | 4-EtNHCOCH$_2$O-3-Me—Ph |
| 2324 | H | H | i-Pr | H | H | 2,3-Pyridyl | 3-Me-4-MeNHCOCH$_2$O—Ph |
| 2325 | H | H | i-Pr | H | H | 2,3-Pyridyl | 3-Me-4-n-BuNHCOCH$_2$O—Ph |

TABLE 18

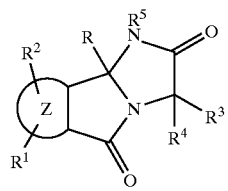

[I-2]

| Compound No. | R¹ | R² | R³ | R⁴ | R⁵ | Z | R |
|---|---|---|---|---|---|---|---|
| 2326 | H | H | i-Pr | H | H | 2,3-Pyridyl | 4-EtCH(Me)NHCOCH$_2$O-3-Me—Ph |
| 2327 | H | H | i-Pr | H | H | 2,3-Pyridyl | 4-EtCOCH$_2$O-3-Me—Ph |
| 2328 | H | H | i-Pr | H | H | 2,3-Pyridyl | 4-i-BuNHCOCH$_2$O-3-Me—Ph |
| 2329 | H | H | i-Pr | H | H | 2,3-Pyridyl | 3-Cl-4-n-PrNHCOCH$_2$O—Ph |
| 2330 | H | H | i-Pr | H | H | 3,4-Pyridyl | 3-Cl-4-i-PrNHCOCH$_2$O—Ph |
| 2331 | H | H | i-Pr | H | H | 3,4-Pyridyl | 3-Cl-4-EtNHCOCH$_2$O—Ph |
| 2332 | H | H | i-Pr | H | H | 3,4-Pyridyl | 3-Cl-4-EtCH(Me)NHCOCH$_2$O—Ph |
| 2333 | H | H | i-Pr | H | H | 3,4-Pyridyl | 3-Cl-4-cycloPrNHCOCH$_2$O—Ph |
| 2334 | H | H | i-Pr | H | H | 3,4-Pyridyl | 3-Cl-4-cycloPentylNHCOCH$_2$O—Ph |
| 2335 | H | H | i-Pr | H | H | Ph | 4-F-5-n-PrNHCOCH$_2$O-(2-pyridyl) |
| 2336 | H | H | i-Pr | H | H | Ph | 4-F-5-i-PrNHCOCH$_{22}$O-(2-pyridyl) |
| 2337 | H | H | i-Pr | H | H | Ph | 4-EtNHCOCH$_2$O-3-F-(2-pyridyl) |
| 2338 | H | H | i-Pr | H | H | Ph | 4-EtCH(Me)NHCOCH$_2$O-3-F-(2-pyridyl) |
| 2339 | H | H | i-Pr | H | H | Ph | 4-EtCOCH$_2$O-3-F-(2-pyridyl) |
| 2340 | H | H | i-Pr | H | H | Ph | 3-F-4-i-BuNHCOCH$_2$O-(2-pyridyl) |
| 2341 | H | H | i-Pr | H | H | Ph | 4-cycloPrNHCOCH$_2$O-3-F-(2-pyridyl) |
| 2342 | H | H | i-Pr | H | H | Ph | 5-I-6-n-PrNHCOCH$_2$O-(3-pyridyl) |
| 2343 | H | H | i-Pr | H | H | Ph | 5-I-6-i-PrNHCOCH$_2$O-(3-pyridyl) |
| 2344 | H | H | i-Pr | H | H | Ph | 6-EtNHCOCH$_2$O-5-I-(3-pyridyl) |
| 2345 | H | H | i-Pr | H | H | Ph | 6-EtCH(Me)NHCOCH$_2$O-5-I-(3-pyridyl) |
| 2346 | H | H | i-Pr | H | H | Ph | 6-EtCOCH$_2$O-5-I-(3-pyridyl) |
| 2347 | H | H | i-Pr | H | H | Ph | 6-cycloPrNHCOCH$_2$O-5-I-(3-pyridy |
| 2348 | H | H | i-Pr | H | H | Ph | 3-NO$_2$-4-n-PrNHCOCH$_2$O—Ph |
| 2349 | H | H | i-Pr | H | H | Ph | 3-NO$_2$-4-i-PrNHCOCH$_2$O—Ph |
| 2350 | H | H | i-Pr | H | H | Ph | 4-EtNHCOCH$_2$O-3-NO$_2$—Ph |
| 2351 | H | H | i-Pr | H | H | Ph | 4-EtCH(Me)NHCOCH$_2$O-3-NO$_2$—Ph |
| 2352 | H | H | i-Pr | H | H | Ph | 4-EtCOCH$_2$O-3-NO$_2$—Ph |
| 2353 | H | H | i-Pr | H | H | Ph | 4-i-BuNHCOCH$_2$O-3-NO$_2$—Ph |
| 2354 | H | H | i-Pr | H | H | Ph | 4-cycloPrNHCOCH$_2$O-3-NO$_2$—Ph |
| 2355 | H | H | i-Pr | H | H | Ph | 3-MeO-4-n-PrNHCOCH$_2$O—Ph |
| 2356 | H | H | i-Pr | H | H | Ph | 3-MeO-4-i-PrNHCOCH$_2$O—Ph |
| 2357 | H | H | i-Pr | H | H | Ph | 4-EtNHCOCH$_2$O-3-MeO—Ph |
| 2358 | H | H | i-Pr | H | H | Ph | 4-EtCH(Me)NHCOCH$_2$O-3-MeO—Ph |
| 2359 | H | H | i-Pr | H | H | Ph | 4-EtCOCH$_2$O-3-MeO—Ph |
| 2360 | H | H | i-Pr | H | H | Ph | 3-MeO-4-i-BuNHCOCH$_2$O—Ph |
| 2361 | H | H | i-Pr | H | H | Ph | 4-cycloPrNHCOCH$_2$O-3-MeO—Ph |
| 2362 | H | H | i-Pr | H | H | Ph | 3-HO-4-n-PrNHCOCH$_2$O—Ph |
| 2363 | H | H | i-Pr | H | H | Ph | 3-HO-4-i-PrNHCOCH$_2$O—Ph |
| 2364 | H | H | i-Pr | H | H | Ph | 4-EtNHCOCH$_2$O-3-HO—Ph |
| 2365 | H | H | i-Pr | H | H | Ph | 4-EtCH(Me)NHCOCH$_2$O-3-HO—Ph |
| 2366 | H | H | i-Pr | H | H | Ph | 4-EtCOCH$_2$O-3-HO—Ph |
| 2367 | H | H | i-Pr | H | H | Ph | 3-HO-4-i-BuNHCOCH$_2$O—Ph |
| 2368 | H | H | i-Pr | H | H | Ph | 4-cycloPrNHCOCH$_2$O-3-HO—Ph |
| 2369 | H | H | i-Pr | H | H | Ph | 3-H$_2$NCH$_2$CH$_2$NHCOCH$_2$O—Ph |
| 2370 | H | H | i-Pr | H | H | Ph | 2-H$_2$NCH$_2$CH$_2$NHCOCH$_2$O—Ph |
| 2371 | H | H | i-Pr | H | H | Ph | 4-MeNHCH$_2$CH$_2$NHCOCH$_2$O—Ph |

TABLE 19

[I-2]

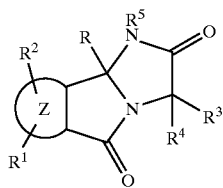

| Compound No. | R¹ | R² | R³ | R⁴ | R⁵ | Z | R |
|---|---|---|---|---|---|---|---|
| 2372 | H | H | i-Pr | H | H | Ph | 3-MeNHCH$_2$CH$_2$NHCOCH$_2$O—Ph |
| 2373 | H | H | i-Pr | H | H | Ph | 2-MeNHCH$_2$CH$_2$NHCOCH$_2$O—Ph |
| 2374 | H | H | i-Pr | H | H | Ph | 4-Me$_2$NCH$_2$CH$_2$NHCOCH$_2$O—Ph |
| 2375 | H | H | i-Pr | H | H | Ph | 3-Me$_2$NCH$_2$CH$_2$NHCOCH$_2$O—Ph |
| 2376 | H | H | i-Pr | H | H | Ph | 2-Me$_2$NCH$_2$CH$_2$NHCOCH$_2$O—Ph |
| 2377 | H | H | i-Pr | H | H | Ph | 4-H$_2$NCH$_2$CH$_2$NHCOCH$_2$O-3-Cl—Ph |
| 2378 | H | H | i-Pr | H | H | Ph | 3-H$_2$NCH$_2$CH$_2$NHCOCH$_2$O-4-Cl—Ph |
| 2379 | H | H | i-Pr | H | H | Ph | 2-H$_2$NCH$_2$CH$_2$NHCOCH$_2$O-4-Cl—Ph |
| 2380 | H | H | i-Pr | H | H | Ph | 4-MeNHCH$_2$CH$_2$NHCOCH$_2$O-3-Me—Ph |
| 2381 | H | H | i-Pr | H | H | Ph | 3-MeNHCH$_2$CH$_2$NHCOCH$_2$O-4-Me—Ph |
| 2382 | H | H | i-Pr | H | H | Ph | 2-MeNHCH$_2$CH$_2$NHCOCH$_2$O-4-MePh |
| 2383 | H | H | i-Pr | H | H | Ph | 4-Me$_2$NCH$_2$CH$_2$NHCOCH$_2$O-3-F—Ph |
| 2384 | H | H | i-Pr | H | H | Ph | 3-Me$_2$NCH$_2$CH$_2$NHCOCH$_2$O-4-F—Ph |
| 2385 | H | H | i-Pr | H | H | Ph | 2-Me$_2$NCH$_2$CH$_2$NHCOCH$_2$O-4-F—Ph |
| 2386 | H | H | i-Pr | H | H | Ph | 4-H$_2$NCOCH$_2$-3-I—Ph |
| 2387 | H | H | i-Pr | H | H | Ph | 3-I-4-MeNHCOCH$_2$—Ph |
| 2388 | H | H | i-Pr | H | H | Ph | 4-EtNHCOCH$_2$-3-I—Ph |
| 2389 | H | H | i-Pr | H | H | Ph | 3-I-4-nPrNHCOCH$_2$—Ph |
| 2390 | H | H | i-Pr | H | H | Ph | 3-I-4-iPrNHCOCH$_2$—Ph |
| 2391 | H | H | i-Pr | H | H | Ph | 4-nBuNHCOCH$_2$-3-I—Ph |
| 2392 | H | H | i-Pr | H | H | Ph | 4-tBuNHCOCH$_2$-3-I—Ph |
| 2393 | H | H | i-Pr | H | H | Ph | 4-iBuNHCOCH$_2$—Ph |
| 2394 | H | H | i-Pr | H | H | Ph | 4-tBuO$_2$CCH$_2$-3-I—Ph |
| 2395 | H | H | i-Pr | H | H | Ph | 3-I-4-PhCH$_2$NHCOCH$_2$—Ph |
| 2396 | H | H | i-Pr | H | H | Ph | 3-I-4-(2-tetrahydrafuryl)CH$_2$NHCOCH$_2$—Ph |
| 2397 | H | H | i-Pr | H | H | Ph | 4-cycloPrNHCOCH$_2$-3-I—Ph |
| 2398 | H | H | i-Pr | H | H | Ph | 4-cycloPentylNHCOCH$_2$-3-I—Ph |
| 2399 | H | H | i-Pr | H | H | Ph | 4-cycloHexylNHCOCH$_2$-3-I—Ph |
| 2400 | H | H | i-Pr | H | H | Ph | 4-cycloPrNHCOCH$_2$-3-F—Ph |
| 2401 | H | H | i-Pr | H | H | Ph | 3-Cl-4-i-PrNHCOCH$_2$CH$_2$—Ph |
| 2402 | H | H | i-Pr | H | H | Ph | 3-Cl-4-EtNHCOCH$_2$CH$_2$—Ph |
| 2403 | H | H | i-Pr | H | H | Ph | 3-Cl-4-EtCH(Me)NHCOCH$_2$CH$_2$—Ph |
| 2404 | H | H | i-Pr | H | H | Ph | 4-i-PrNHCO-3-Me—Ph |
| 2405 | H | H | i-Pr | H | H | Ph | 4-EtNHCO-3-Me—Ph |
| 2406 | H | H | i-Pr | H | H | Ph | 4-EtCH(Me)NHCO-3-Me—Ph |
| 2407 | H | H | i-Pr | H | H | Ph | 3-Cl-4-i-PrNHCH$_2$CH$_2$O—Ph |
| 2408 | H | H | i-Pr | H | H | Ph | 3-Cl-4-EtNHCH$_2$CH$_2$O—Ph |
| 2409 | H | H | i-Pr | H | H | Ph | 3-Cl-4-EtCH(Me)NHCH$_2$CH$_2$O—Ph |
| 2410 | H | H | i-Pr | H | Me | Ph | 3-Cl-4-n-PrNHCOCH$_2$O—Ph |
| 2411 | H | H | i-Pr | H | Me | Ph | 3-Cl-4-i-PrNHCOCH$_2$O—Ph |
| 2412 | H | H | i-Pr | H | Me | Ph | 3-Cl-4-EtNHCOCH$_2$O—Ph |
| 2413 | H | H | i-Pr | H | Me | Ph | 3-Cl-4-EtCH(Me)NHCOCH$_2$O—Ph |
| 2414 | H | H | i-Pr | H | Me | Ph | 3-Cl-4-cycloPrNHCOCH$_2$O—Ph |
| 2415 | H | H | i-Pr | H | Me | Ph | 3-Cl-4-cycloPentylNHCOCH$_2$O—Ph |
| 2416 | H | H | i-Pr | H | Et | Ph | 3-Me-4-n-PrNHCOCH$_2$O—Ph |
| 2417 | H | H | i-Pr | H | Et | Ph | 4-i-PrNHCOCH$_2$O-3-Me—Ph |

TABLE 20

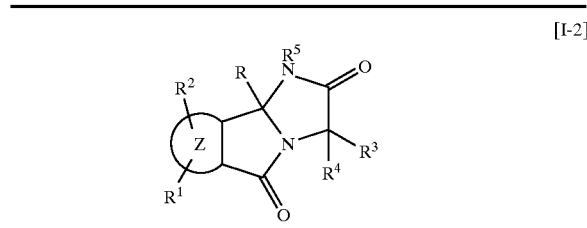

[I-2]

| Compound No. | R¹ | R² | R³ | R⁴ | R⁵ | Z | R |
|---|---|---|---|---|---|---|---|
| 2418 | H | H | i-Pr | H | Et | Ph | 4-EtNHCOCH₂O-3-Me—Ph |
| 2419 | H | H | i-Pr | H | Et | Ph | 3-Me-4-MeNHCOCH₂O—Ph |
| 2420 | H | H | i-Pr | H | Et | Ph | 3-Me-4-n-BuNHCOCH₂O—Ph |
| 2421 | H | H | i-Pr | H | Et | Ph | 4-EtCH(Me)NHCOCH₂O-3-Me—Ph |
| 2422 | H | H | i-Pr | H | Et | Ph | 4-EtCOCH₂O-3-Me—Ph |
| 2423 | H | H | i-Pr | H | Et | Ph | 4-i-BuNHCOCH₂O-3-Me—Ph |
| 2424 | H | H | i-Pr | H | Ac | Ph | 3-Cl-4-n-PrNHCOCH₂O—Ph |
| 2425 | H | H | i-Pr | H | Ac | Ph | 3-Cl-4-i-PrNHCOCH₂O—Ph |
| 2426 | H | H | i-Pr | H | Ac | Ph | 3-Cl-4-EtNHCOCH₂O—Ph |
| 2427 | H | H | i-Pr | H | Ac | Ph | 3-Cl-4-EtCH(Me)NHCOCH₂O—Ph |
| 2428 | H | H | i-Pr | H | Ac | Ph | 3-Cl-4-cycloPrNHCOCH₂O—Ph |
| 2429 | H | H | i-Pr | H | Ac | Ph | 3-Cl-4-cycloPentylNHCOCH₂O—Ph |
| 2430 | H | H | i-Pr | H | OH | Ph | 3-Me-4-n-PrNHCOCH₂O—Ph |
| 2431 | H | H | i-Pr | H | OH | Ph | 4-i-PrNHCOCH₂O-3-Me—Ph |
| 2432 | H | H | i-Pr | H | OH | Ph | 4-EtNHCOCH₂O-3-Me—Ph |
| 2433 | H | H | i-Pr | H | OH | Ph | 3-Me-4-MeNHCOCH₂O—Ph |
| 2434 | H | H | i-Pr | H | OH | Ph | 3-Me-4-n-BuNHCOCH₂O—Ph |
| 2435 | H | H | i-Pr | H | OH | Ph | 4-EtCH(Me)NHCOCH₂O-3-Me—Ph |
| 2436 | H | H | i-Pr | H | OH | Ph | 4-EtCOCH₂O-3-Me—Ph |
| 2437 | H | H | i-Pr | H | OH | Ph | 4-i-BuNHCOCH₂O-3-Me—Ph |
| 2438 | H | H | i-Pr | H | OMe | Ph | 3-Cl-4-n-PrNHCOCH₂O—Ph |
| 2439 | H | H | i-Pr | H | OMe | Ph | 3-Cl-4-i-PrNHCOCH₂O—Ph |
| 2440 | H | H | i-Pr | H | OMe | Ph | 3-Cl-4-EtNHCOCH₂O—Ph |
| 2441 | H | H | i-Pr | H | OMe | Ph | 3-Cl-4-EtCH(Me)NHCOCH₂O—Ph |
| 2442 | H | H | i-Pr | H | OMe | Ph | 3-Cl-4-cycloPrNHCOCH₂O—Ph |
| 2443 | H | H | i-Pr | H | OMe | Ph | 3-Cl-4-cycloPentylNHCOCH₂O—Ph |
| 2444 | H | H | i-Pr | H | OEt | Ph | 3-Me-4-n-PrNHCOCH₂O—Ph |
| 2445 | H | H | i-Pr | H | OEt | Ph | 4-i-PrNHCOCH₂O-3-Me—Ph |
| 2446 | H | H | i-Pr | H | OEt | Ph | 4-EtNHCOCH₂O-3-Me—Ph |
| 2447 | H | H | i-Pr | H | OEt | Ph | 3-Me-4-MeNHCOCH₂O—Ph |
| 2448 | H | H | i-Pr | H | OEt | Ph | 3-Me-4-n-BuNHCOCH₂O—Ph |
| 2449 | H | H | i-Pr | H | OEt | Ph | 4-EtCH(Me)NHCOCH₂O-3-Me—Ph |
| 2450 | H | H | i-Pr | H | OEt | Ph | 4-EtCOCH₂O-3-Me—Ph |
| 2451 | H | H | i-Pr | H | OEt | Ph | 4-i-BuNHCOCH₂O-3-Me—Ph |
| 2452 | H | H | i-Pr | H | Pr | Ph | 3-Cl-4-n-PrNHCOCH₂O—Ph |
| 2453 | H | H | i-Pr | H | Pr | Ph | 3-Cl-4-i-PrNHCOCH₂O—Ph |
| 2454 | H | H | i-Pr | H | Pr | Ph | 3-Cl-4-EtNHCOCH₂O—Ph |
| 2455 | H | H | i-Pr | H | Pr | Ph | 3-Cl-4-EtCH(Me)NHCOCH₂O—Ph |
| 2456 | H | H | i-Pr | H | Pr | Ph | 3-Cl-4-cycloPrNHCOCH₂O—Ph |
| 2457 | H | H | i-Pr | H | Pr | Ph | 3-Cl-4-cycloPentylNHCOCH₂O—Ph |
| 2458 | H | H | i-Pr | H | i-Pr | Ph | 3-Me-4-n-PrNHCOCH₂O—Ph |
| 2459 | H | H | i-Pr | H | i-Pr | Ph | 4-i-PrNHCOCH₂O-3-Me—Ph |
| 2460 | H | H | i-Pr | H | i-Pr | Ph | 4-EtNHCOCH₂O-3-Me—Ph |
| 2461 | H | H | i-Pr | H | i-Pr | Ph | 3-Me-4-MeNHCOCH₂O—Ph |
| 2462 | H | H | i-Pr | H | i-Pr | Ph | 3-Me-4-n-BuNHCOCH₂O—Ph |
| 2463 | H | H | i-Pr | H | i-Pr | Ph | 4-EtCH(Me)NHCOCH₂O-3-Me—Ph |

TABLE 21

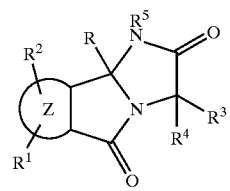

[I-2]

| Compound No. | R¹ | R² | R³ | R⁴ | R⁵ | Z | R |
|---|---|---|---|---|---|---|---|
| 2464 | H | H | i-Pr | H | H | 4,5-ethylenedioxy-Ph | 4-nBuNHCOCH₂O—Ph |
| 2465 | H | H | i-Pr | H | H | Ph | 3-PhCO₂-4-nPrNHCOCH₂O—Ph |
| 2466 | H | H | i-Pr | H | H | Ph | 3-cycloPrNH-4-nPrNHCOCH₂O—Ph |
| 2467 | H | H | i-Pr | H | H | Ph | 4-nPrNHCOCH₂O-pyrimidin-5-yl |

TABLE 21-continued

[I-2]

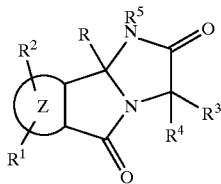

| Compound No. | R¹ | R² | R³ | R⁴ | R⁵ | Z | R |
|---|---|---|---|---|---|---|---|
| 2468 | H | H | MeSO$_2$NHCH$_2$CH$_2$ | H | H | Ph | 4-nPrNHCOCH$_2$O—Ph |
| 2469 | H | H | MeOCH$_2$CH$_2$ | H | H | Ph | 4-nPrNHCOCH$_2$O—Ph |
| 2470 | H | H | MeO$_2$CCH=CH | H | H | Ph | 4-nPrNHCOCH$_2$O—Ph |
| 2471 | H | H | i-Pr | H | Me | Ph | 4-nPrNHCOCH$_2$O—Ph |
| 2472 | H | H | i-Pr | H | nPrNHCOCH$_2$ | Ph | 4-nPrNHCOCH$_2$O—Ph |
| 2473 | H | H | i-Pr | H | H$_2$NCOCH$_2$ | Ph | 4-nPrNHCOCH$_2$O—Ph |
| 2474 | H | H | i-Pr | H | MeSO$_2$NHCOCH$_2$ | Ph | 4-nPrNHCOCH$_2$O—Ph |
| 2475 | H | H | i-Pr | H | MeO$_2$CCH$_2$ | Ph | 4-nPrNHCOCH$_2$O—Ph |
| 2476 | H | H | i-Pr | H | HOCH$_2$CH$_2$ | Ph | 4-nPrNHCOCH$_2$O—Ph |

TABLE 22

[I-3]

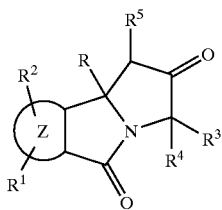

TABLE 22-continued

[I-3]

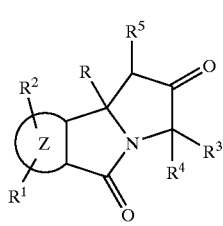

| Compound No. | R¹ | R² | R³ | R⁴ | R⁶ | Z | R |
|---|---|---|---|---|---|---|---|
| 3001 | H | H | i-Pr | H | H | Ph | 2-MeO—Ph |
| 3002 | H | H | i-Pr | H | H | Ph | Ph |
| 3003 | H | H | i-Pr | H | H | Ph | 2-NH$_2$—Ph |
| 3004 | H | H | i-Pr | H | H | Ph | 4-F—Ph |
| 3005 | H | H | i-Pr | H | H | Ph | 4-Et$_2$N—Ph |
| 3006 | H | H | i-Pr | H | H | Ph | 4-Cl—Ph |
| 3007 | H | H | i-Pr | H | H | Ph | 4-HO—Ph |
| 3008 | H | H | i-Pr | H | H | Ph | 3-MeO—Ph |
| 3009 | H | H | i-Pr | H | H | Ph | 3-HO—Ph |
| 3010 | H | H | i-Pr | H | H | Ph | 3-NH$_2$—Ph |
| 3011 | H | H | i-Pr | H | H | Ph | 4-MeO—Ph |
| 3012 | H | H | i-Pr | H | H | Ph | 4-Me—Ph |
| 3013 | H | H | i-Pr | H | H | Ph | 3-Me—Ph |
| 3014 | H | H | i-Pr | H | H | Ph | 4-tBuO$_2$CCH$_2$O—Ph |
| 3015 | H | H | i-Pr | H | H | Ph | 4-HO$_2$CCH$_2$O—Ph |
| 3016 | H | H | i-Pr | H | H | Ph | 4-tBuO$_2$C(CH$_2$)$_5$O—Ph |
| 3017 | H | H | i-Pr | H | H | Ph | 4-HO$_2$C(CH$_2$)$_5$O—Ph |
| 3018 | H | H | i-Pr | H | H | Ph | 4-HO(CH$_2$)$_3$O—Ph |
| 3019 | H | H | i-Pr | H | H | Ph | 4-HO(CH$_2$)$_2$O—Ph |
| 3020 | H | H | i-Pr | H | H | Ph | 4-HOC(Me)$_2$(CH$_2$)$_2$O—Ph |
| 3021 | H | H | i-Pr | H | H | Ph | 4-PhCH$_2$O—Ph |
| 3022 | H | H | i-Pr | H | H | Ph | 4-MeNHCOCH$_2$O—Ph |
| 3023 | H | H | i-Pr | H | H | Ph | 4-EtNHCOCH$_2$O—Ph |
| 3024 | H | H | i-Pr | H | H | Ph | 4-nPrNHCOCH$_2$O—Ph |
| 3025 | H | H | i-Pr | H | H | Ph | 4-nBuNHCOCH$_2$O—Ph |
| 3026 | H | H | i-Pr | H | H | Ph | 4-CH$_2$=CHCH$_2$NHCOCH$_2$O—Ph |
| 3027 | H | H | i-Pr | H | H | Ph | 4-Me(CH$_2$)$_9$NHCOCH$_2$O—Ph |
| 3028 | H | H | i-Pr | H | H | Ph | 4-N$_3$(CH$_2$)$_3$O—Ph |
| 3029 | H | H | i-Pr | H | H | Ph | 4-tBuO$_2$CCH(Me)O—Ph |
| 3030 | H | H | i-Pr | H | H | Ph | 4-nPrNHCOCH(Me)O—Ph |
| 3031 | H | H | i-Pr | H | H | Ph | 4-F$_3$CSO$_3$—Ph |
| 3032 | H | H | i-Pr | H | H | Ph | 4-tBuO$_2$CCH=CHPh |
| 3033 | H | H | i-Pr | H | H | Ph | 4-nPrNHCOCH=CH—Ph |
| 3034 | H | H | i-Pr | H | H | Ph | 4-nPrCH(Me)NHCOCH$_2$O—Ph |
| 3035 | H | H | i-Pr | H | H | Ph | 4-EtCH(Me)NHCOCH$_2$O—Ph |
| 3036 | H | H | i-Pr | H | H | Ph | 4-MeOCH$_2$O—Ph |
| 3037 | H | H | i-Pr | H | H | Ph | 4-EtCOCH$_2$O—Ph |
| 3038 | H | H | i-Pr | H | H | Ph | 3-tBuO$_2$CCH$_2$O—Ph |
| 3039 | H | H | i-Pr | H | H | Ph | 3-HO$_2$CCH$_2$O—Ph |
| 3040 | H | H | i-Pr | H | H | Ph | 3-nPrNHCOCH$_2$O—Ph |
| 3041 | H | H | i-Pr | H | H | Ph | 4-H$_2$NC(Me)$_2$CH$_2$O$_2$CCH$_2$O—Ph |
| 3042 | H | H | i-Pr | H | H | Ph | 4-morpholinoCOCH$_2$O—Ph |
| 3043 | H | H | i-Pr | H | H | Ph | 4-(4-Cl—Ph)—COCH$_2$O—Ph |
| 3044 | H | H | i-Pr | H | H | Ph | 4-PhCOCH$_2$O—Ph |
| 3045 | H | H | i-Pr | H | H | Ph | 4-(4-pyridyl)-CH$_2$NHCOCH$_2$O— |
| 3046 | H | H | i-Pr | H | H | Ph | 4-H$_2$NCH$_2$CH$_2$NHCOCH$_2$O—Ph |
| 3047 | H | H | i-Pr | H | H | Ph | 4-Cl-3-NO$_2$—Ph |

TABLE 23

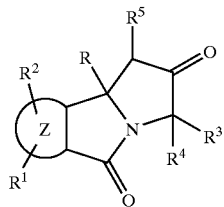

[I-3]

| Compound No. | R¹ | R² | R³ | R⁴ | R⁶ | Z | R |
|---|---|---|---|---|---|---|---|
| 3048 | H | H | i-Pr | H | H | Ph | 4-Cl-3-F—Ph |
| 3049 | H | H | i-Pr | H | H | Ph | 4-Cl-3-Me—Ph |
| 3050 | H | H | i-Pr | H | H | Ph | 3-NH$_2$-4-Cl—Ph |
| 3051 | H | H | i-Pr | H | H | Ph | 3-Cl-4-MeO—Ph |
| 3052 | H | H | i-Pr | H | H | Ph | 3-Cl-4-Me—Ph |
| 3053 | H | H | i-Pr | H | H | Ph | 4-Br-3-Cl—Ph |
| 3054 | H | H | i-Pr | H | H | Ph | 4-Br-2-Cl—Ph |
| 3055 | H | H | i-Pr | H | H | Ph | 4-F-3-Me—Ph |
| 3056 | H | H | i-Pr | H | H | Ph | 3-F-4-Me—Ph |
| 3057 | H | H | i-Pr | H | H | Ph | 3-Br-4-HO—Ph |
| 3058 | H | H | i-Pr | H | H | Ph | 3-Br-4-MeO—Ph |
| 3059 | H | H | i-Pr | H | H | Ph | 3-Br-4-F—Ph |
| 3060 | H | H | i-Pr | H | H | Ph | 3-F-4-PhPh |
| 3061 | H | H | i-Pr | H | H | Ph | 4-HO-3-I—Ph |
| 3062 | H | H | i-Pr | H | H | Ph | 5-HO-2-I—Ph |
| 3063 | H | H | i-Pr | H | H | Ph | 3-I-4-MeO—Ph |
| 3064 | H | H | i-Pr | H | H | Ph | 2-I-5-MeO—Ph |
| 3065 | H | H | i-Pr | H | H | Ph | 4-MeO-3-Me—Ph |
| 3066 | H | H | i-Pr | H | H | Ph | 4-HO(CH$_2$)$_3$O-3-I—Ph |
| 3067 | H | H | i-Pr | H | H | Ph | 4-HO(CH$_2$)$_2$O-3-I—Ph |
| 3068 | H | H | i-Pr | H | H | Ph | 4-HOC(Me)$_2$(CH$_2$)$_2$O-3-I—Ph |
| 3069 | H | H | i-Pr | H | H | Ph | 4-tBuO$_2$C(CH$_2$)$_4$O-3-I—Ph |
| 3070 | H | H | i-Pr | H | H | Ph | 3-I-4-PhCH$_2$O—Ph |
| 3071 | H | H | i-Pr | H | H | Ph | 4-H$_2$NCOCH$_2$O-3-I—Ph |
| 3072 | H | H | i-Pr | H | H | Ph | 3-I-4-MeNHCOCH$_2$O—Ph |
| 3073 | H | H | i-Pr | H | H | Ph | 4-EtNHCOCH$_2$O-3-I—Ph |
| 3074 | H | H | i-Pr | H | H | Ph | 3-I-4-nPrNHCOCH$_2$O—Ph |
| 3075 | H | H | i-Pr | H | H | Ph | 3-I-4-iPrNHCOCH$_2$O—Ph |
| 3076 | H | H | i-Pr | H | H | Ph | 4-nBuNHCOCH$_2$O-3-I—Ph |
| 3077 | H | H | i-Pr | H | H | Ph | 4-tBuNHCOCH$_2$O-3-I—Ph |
| 3078 | H | H | i-Pr | H | H | Ph | 4-iBuNHCOCH$_2$O—Ph |
| 3079 | H | H | i-Pr | H | H | Ph | 4-tBuO$_2$CCH$_2$O-3-I—Ph |
| 3080 | H | H | i-Pr | H | H | Ph | 3-I-4-PhCH$_2$NHCOCH$_2$O—Ph |
| 3081 | H | H | i-Pr | H | H | Ph | 3-I-4-(2-tetrahydrofuryl)CH$_2$NHCOCH$_2$O—Ph |
| 3082 | H | H | i-Pr | H | H | Ph | 4-cycloPrNHCOCH$_2$O-3-I—Ph |
| 3083 | H | H | i-Pr | H | H | Ph | 4-cycloPentylNHCOCH$_2$O-3-I—Ph |
| 3084 | H | H | i-Pr | H | H | Ph | 4-cycloHexylNHCOCH$_2$O-3-I—Ph |
| 3085 | H | H | i-Pr | H | H | Ph | 4-cycloPrNHCOCH$_2$O-3-F—Ph |
| 3086 | H | H | i-Pr | H | H | Ph | 4-Me(CH$_2$)$_9$NHCOCH$_2$O-3-I—Ph |
| 3087 | H | H | i-Pr | H | H | Ph | 4-HO$_2$CCH$_2$O-3-I—Ph |
| 3088 | H | H | i-Pr | H | H | Ph | 4-N$_3$(CH$_2$)$_3$O-3-I—Ph |
| 3089 | H | H | i-Pr | H | H | Ph | 3-I-4-nPrNHCO(CH$_2$)$_4$O—Ph |
| 3090 | H | H | i-Pr | H | H | Ph | 4-Et$_2$NCOCH$_2$O-3-I—Ph |
| 3091 | H | H | i-Pr | H | H | Ph | 3-I-4-nPrN(Me)COCH$_2$O—Ph |
| 3092 | H | H | i-Pr | H | H | Ph | 3-Cl-4-nPrNHCOCH$_2$O—Ph |
| 3093 | H | H | i-Pr | H | H | Ph | 3-Br-4-nPrNHCOCH$_2$O—Ph |
| 3094 | H | H | i-Pr | H | H | Ph | 3-F-4-nPrNHCOCH$_2$O—Ph |

TABLE 24

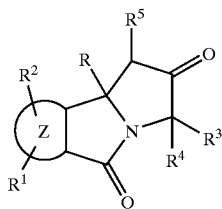

[I-3]

| Compound No. | R¹ | R² | R³ | R⁴ | R⁶ | Z | R |
|---|---|---|---|---|---|---|---|
| 3095 | H | H | i-Pr | H | H | Ph | 3-Me-4-nPrNHCOCH$_2$O—Ph |
| 3096 | H | H | i-Pr | H | H | Ph | 4-EtNHCOCH$_2$O-3-F—Ph |
| 3097 | H | H | i-Pr | H | H | Ph | 3-I-4-iPrNHCOC(Me)$_2$CH$_2$O—Ph |
| 3098 | H | H | i-Pr | H | H | Ph | 3-Br-4-CH$_2$=CHCH$_2$NHCOCH$_2$O—Ph |
| 3099 | H | H | i-Pr | H | H | Ph | 4-iBuNHCOCH$_2$O-3-F—Ph |
| 3100 | H | H | i-Pr | H | H | Ph | 3-tBuO$_2$CCH=CH-4-nPrNHCOCH$_2$O—Ph |
| 3101 | H | H | i-Pr | H | H | Ph | 3-HO$_2$CCH=CH-4-nPrNHCOCH$_2$O—Ph |
| 3102 | H | H | i-Pr | H | H | Ph | 3-I-4-MeOCH$_2$CH$_2$NHCOCH$_2$O—Ph |
| 3103 | H | H | i-Pr | H | H | Ph | 3-F-4-HO—Ph |
| 3104 | H | H | i-Pr | H | H | Ph | 3-F-4-MeO—Ph |
| 3105 | H | H | i-Pr | H | H | Ph | 3,4-methylenedioxyPh |
| 3106 | H | H | i-Pr | H | H | Ph | 3,4-ethylenedioxyPh |
| 3107 | H | H | i-Pr | H | H | Ph | 3,4-Cl$_2$—Ph |
| 3108 | H | H | i-Pr | H | H | Ph | 3,4-Me$_2$—Ph |
| 3109 | H | H | i-Pr | H | H | Ph | 3,4-F$_2$—Ph |
| 3110 | H | H | i-Pr | H | H | Ph | 3,4-(MeO)$_2$—Ph |
| 3111 | H | H | i-Pr | H | H | Ph | 3,5-(MeO)$_2$—Ph |
| 3112 | H | H | i-Pr | H | H | Ph | 3,5-Me$_2$—Ph |
| 3113 | H | H | i-Pr | H | H | Ph | 3,5-I$_2$-4-HO—Ph |
| 3114 | H | H | i-Pr | H | H | Ph | 2,4-I$_2$-5-HO—Ph |
| 3115 | H | H | i-Pr | H | H | Ph | 3,5-I$_2$-4-MeO—Ph |
| 3116 | H | H | i-Pr | H | H | Ph | 2,4-I$_2$-5-MeO—Ph |
| 3117 | H | H | i-Pr | H | H | Ph | 2,4,6-Me$_3$—Ph |
| 3118 | H | H | i-Pr | H | H | Ph | 4-HO(CH$_2$)$_3$O-3,5-I$_2$Ph |
| 3119 | H | H | i-Pr | H | H | Ph | 3,5-I$_2$-4-nPrNHCOCH$_2$O—Ph |
| 3120 | H | H | i-Pr | H | H | Ph | 2-thienyl |
| 3121 | H | H | i-Pr | H | H | Ph | 2-furyl |
| 3122 | H | H | i-Pr | H | H | Ph | 3-pyridyl |
| 3123 | H | H | i-Pr | H | H | Ph | 2-naphthyl |
| 3124 | H | H | i-Pr | H | H | Ph | 5-F-1-naphthyl |
| 3125 | H | H | i-Pr | H | H | Ph | dibenzothiophene-2-yl |
| 3126 | 6-F | H | i-Pr | H | H | Ph | Ph |
| 3127 | 7-F | H | i-Pr | H | H | Ph | Ph |
| 3128 | 8-F | H | i-Pr | H | H | Ph | Ph |
| 3129 | 9-F | H | i-Pr | H | H | Ph | Ph |
| 3130 | 6-MeO | H | i-Pr | H | H | Ph | Ph |
| 3131 | 9-MeO | H | i-Pr | H | H | Ph | Ph |
| 3132 | 6-OH | H | i-Pr | H | H | Ph | Ph |
| 3133 | 9-OH | H | i-Pr | H | H | Ph | Ph |
| 3134 | 7-NO$_2$ | H | i-Pr | H | H | Ph | Ph |
| 3135 | 8-NO$_2$ | H | i-Pr | H | H | Ph | Ph |
| 3136 | 9-NO$_2$ | H | i-Pr | H | H | Ph | Ph |
| 3137 | 6-NHPh | H | i-Pr | H | H | Ph | Ph |
| 3138 | 7-Me$_2$N | H | i-Pr | H | H | Ph | Ph |
| 3139 | 7-Me | H | i-Pr | H | H | Ph | Ph |
| 3140 | 8-Me | H | i-Pr | H | H | Ph | Ph |
| 3141 | 7-t-Bu | H | i-Pr | H | H | Ph | Ph |

TABLE 25

[I-3]

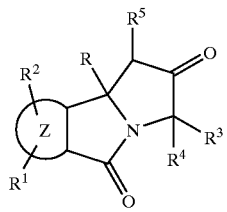

| Compound No. | R$^1$ | R$^2$ | R$^3$ | R$^4$ | R$^6$ | Z | R |
|---|---|---|---|---|---|---|---|
| 3142 | 8-t-Bu | H | i-Pr | H | H | Ph | Ph |
| 3143 | 7-Br | H | i-Pr | H | H | Ph | Ph |
| 3144 | 8-Br | H | i-Pr | H | H | Ph | Ph |
| 3145 | 7-Cl | H | i-Pr | H | H | Ph | Ph |
| 3146 | 8-Cl | H | i-Pr | H | H | Ph | Ph |
| 3147 | 7-Cl | 8-Cl | i-Pr | H | H | Ph | Ph |
| 3148 | 6-Cl | 9-Cl | i-Pr | H | H | Ph | Ph |
| 3149 | 6-OH | 9-I | i-Pr | H | H | Ph | Ph |
| 3150 | H | H | i-Pr | H | H | 1,2-naphthyl | Ph |
| 3151 | H | H | i-Pr | H | H | 2,3-naphthyl | Ph |
| 3152 | H | H | i-Pr | H | H | cyclo-hexenyl | Ph |
| 3153 | H | H | D-Leucine | H | H | Ph | Ph |
| 3154 | H | H | L-Leucine | H | H | Ph | Ph |
| 3155 | H | H | D-NorLeucine | H | H | Ph | Ph |
| 3156 | H | H | L-NorLeucine | H | H | Ph | Ph |
| 3157 | H | H | D-AlloLeucine | H | H | Ph | Ph |
| 3158 | H | H | L-AlloLeucine | H | H | Ph | Ph |
| 3159 | H | H | D-NorValine | H | H | Ph | Ph |
| 3160 | H | H | L-NorValine | H | H | Ph | Ph |
| 3161 | H | H | D-Alanine | H | H | Ph | Ph |
| 3162 | H | H | L-Alanine | H | H | Ph | Ph |
| 3163 | H | H | D-Arginine | H | H | Ph | Ph |
| 3164 | H | H | L-Arginine | H | H | Ph | Ph |
| 3165 | H | H | D-Asparagine | H | H | Ph | Ph |
| 3166 | H | H | L-Asparagine | H | H | Ph | Ph |
| 3167 | H | H | D-Glutamic Acid | H | H | Ph | Ph |
| 3168 | H | H | L-Glutamic Acid | H | H | Ph | Ph |
| 3169 | H | H | D-Glutamine | H | H | Ph | Ph |
| 3170 | H | H | L-Glutamine | H | H | Ph | Ph |
| 3171 | H | H | D-Histidine | H | H | Ph | Ph |
| 3172 | H | H | L-Histidine | H | H | Ph | Ph |
| 3173 | H | H | D-Methionine | H | H | Ph | Ph |
| 3174 | H | H | L-Methionine | H | H | Ph | Ph |
| 3175 | H | H | D-Tryptophan | H | H | Ph | Ph |
| 3176 | H | H | L-Tryptophan | H | H | Ph | Ph |
| 3177 | H | H | D-Tyrosine | H | H | Ph | Ph |
| 3178 | H | H | L-Tyrosine | H | H | Ph | Ph |
| 3179 | H | H | Homo Phenylalar | H | H | Ph | Ph |
| 3180 | H | H | Homo Phenylalar | H | H | Ph | Ph |
| 3181 | H | H | D-Leucine | H | H | Ph | 4-Cl—Ph |
| 3182 | H | H | L-Leucine | H | H | Ph | 4-Cl—Ph |
| 3183 | H | H | D-NorLeucine | H | H | Ph | 4-Cl—Ph |
| 3184 | H | H | L-NorLeucine | H | H | Ph | 4-Cl—Ph |
| 3185 | H | H | D-AlloLeucine | H | H | Ph | 4-Cl—Ph |
| 3186 | H | H | L-AlloLeucine | H | H | Ph | 4-Cl—Ph |
| 3187 | H | H | D-NorValine | H | H | Ph | 4-Cl—Ph |

TABLE 26

[I-3]

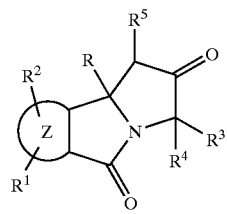

| Compound No. | R$^1$ | R$^2$ | R$^3$ | R$^4$ | R$^6$ | Z | R |
|---|---|---|---|---|---|---|---|
| 3188 | H | H | L-NorValine | H | H | Ph | 4-Cl—Ph |
| 3189 | H | H | D-Alanine | H | H | Ph | 4-Cl—Ph |
| 3190 | H | H | L-Alanine | H | H | Ph | 4-Cl—Ph |
| 3191 | H | H | D-Arginine | H | H | Ph | 4-Cl—Ph |
| 3192 | H | H | L-Arginine | H | H | Ph | 4-Cl—Ph |
| 3193 | H | H | D-Asparagine | H | H | Ph | 4-Cl—Ph |
| 3194 | H | H | L-Asparagine | H | H | Ph | 4-Cl—Ph |
| 3195 | H | H | D-Glutamic Acid | H | H | Ph | 4-Cl—Ph |
| 3196 | H | H | L-Glutamic Acid | H | H | Ph | 4-Cl—Ph |
| 3197 | H | H | D-Glutamine | H | H | Ph | 4-Cl—Ph |
| 3198 | H | H | L-Glutamine | H | H | Ph | 4-Cl—Ph |

TABLE 26-continued

[I-3]

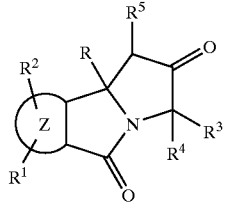

| Compound No. | R¹ | R² | R³ | R⁴ | R⁶ | Z | R |
|---|---|---|---|---|---|---|---|
| 3199 | H | H | D-Histidine | H | H | Ph | 4-Cl—Ph |
| 3200 | H | H | L-Histidine | H | H | Ph | 4-Cl—Ph |
| 3201 | H | H | D-Methionine | H | H | Ph | 4-Cl—Ph |
| 3202 | H | H | L-Methionine | H | H | Ph | 4-Cl—Ph |
| 3203 | H | H | D-Tryptophan | H | H | Ph | 4-Cl—Ph |
| 3204 | H | H | L-Tryptophan | H | H | Ph | 4-Cl—Ph |
| 3205 | H | H | D-Tyrosine | H | H | Ph | 4-Cl—Ph |
| 3206 | H | H | L-Tyrosine | H | H | Ph | 4-Cl—Ph |
| 3207 | H | H | D-Homo Phenylalanine | H | H | Ph | 4-Cl—Ph |
| 3208 | H | H | L-Homo Phenylalanine | H | H | Ph | 4-Cl—Ph |
| 3209 | H | H | t-Bu | H | H | Ph | Ph |
| 3210 | H | H | (CH₃)₂(OH)C | H | H | Ph | Ph |
| 3211 | H | H | CH₃(MeO)CH | H | H | Ph | Ph |
| 3212 | H | H | 4-HO—Ph | H | H | Ph | Ph |
| 3213 | H | H | 4-HO-3-I—Ph | H | H | Ph | Ph |
| 3214 | H | H | 4-HO-3,5-I₂—Ph | H | H | Ph | Ph |
| 3215 | H | H | 4-HO-3-I—PhCH₂ | H | H | Ph | Ph |
| 3216 | H | H | 4-HO-3,5-I₂—PhCH₂ | H | H | Ph | Ph |
| 3217 | H | H | 1-naphthylmethyl | H | H | Ph | Ph |
| 3218 | H | H | 4-F—PhCH₂ | H | H | Ph | Ph |
| 3219 | H | H | 1-naphthylmethyl | H | H | Ph | 4-Cl—Ph |
| 3220 | H | H | 4-F—PhCH₂ | H | H | Ph | 4-Cl—Ph |
| 3221 | H | H | i-Pr | Me | H | Ph | 4-Cl—Ph |
| 3222 | H | H | Me | Me | H | Ph | Ph |
| 3223 | H | H | (Combined with R⁴)CH₂= | — | H | Ph | Ph |
| 3224 | H | H | (Combined with R⁴)MeCH= | — | H | Ph | Ph |
| 3225 | H | H | (Combined with R⁴)(CH₂)₄ | — | H | Ph | Ph |
| 3226 | H | H | i-Pr | H | H | Ph | 4-n-PrNHCOCH₂CH₂O—Ph |
| 3227 | H | H | i-Pr | H | H | Ph | 4-i-PrNHCOCH₂CH₂O—Ph |
| 3228 | H | H | i-Pr | H | H | Ph | 4-EtNHCOCH₂CH₂O—Ph |
| 3229 | H | H | i-Pr | H | H | Ph | 4-EtCH(Me)NHCOCH₂CH₂O—Ph |
| 3230 | H | H | i-Pr | H | H | Ph | 3-Cl-4-i-PrNHCOCH₂O—Ph |
| 3231 | H | H | i-Pr | H | H | Ph | 3-Cl-4-EtNHCOCH₂O—Ph |
| 3232 | H | H | i-Pr | H | H | Ph | 3-Cl-4-EtCH(Me)NHCOCH₂O—Ph |
| 3233 | H | H | i-Pr | H | H | Ph | 4-i-PrNHCOCH₂O-3-Me—Ph |

TABLE 27

[I-3]

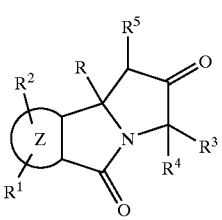

| Compound No. | R¹ | R² | R³ | R⁴ | R⁶ | Z | R |
|---|---|---|---|---|---|---|---|
| 3234 | H | H | i-Pr | H | H | Ph | 4-EtNHCOCH₂O-3-Me—Ph |
| 3235 | H | H | i-Pr | H | H | Ph | 4-EtCH(Me)NHCOCH₂O-3-Me—Ph |
| 3236 | H | H | i-Pr | H | H | Ph | 4-cycloPrNHCOCH₂CH₂O—Ph |
| 3237 | H | H | i-Pr | H | H | Ph | 4-cycloPentylNHCOCH₂CH₂O—Ph |
| 3238 | H | H | i-Pr | H | H | Ph | 3-I-4-n-PrNHCOCH₂CH₂O—Ph |
| 3239 | H | H | i-Pr | H | H | Ph | 3-I-4-i-PrNHCOCH₂CH₂O—Ph |
| 3240 | H | H | i-Pr | H | H | Ph | 4-EtNHCOCH₂CH₂O-3-I—Ph |
| 3241 | H | H | i-Pr | H | H | Ph | 4-EtCH(Me)NHCOCH₂CH₂O-3-I—Ph |

TABLE 27-continued

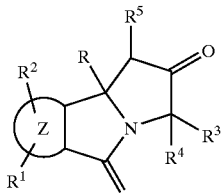

[I-3]

| Compound No. | R¹ | R² | R³ | R⁴ | R⁶ | Z | R |
|---|---|---|---|---|---|---|---|
| 3242 | H | H | i-Pr | H | H | Ph | 4-EtCOCH₂CH₂O-3-I—Ph |
| 3243 | H | H | i-Pr | H | H | Ph | 4-cycloPrNHCOCH₂CH₂O-3-I—Ph |
| 3244 | H | H | i-Pr | H | H | Ph | 4-cycloPentylNHCOCH₂CH₂O-3-I—Ph |
| 3245 | H | H | i-Pr | H | H | Ph | 3-F-4-n-PrNHCOCH₂CH₂O—Ph |
| 3246 | H | H | i-Pr | H | H | Ph | 3-F-4-i-PrNHCOCH₂CH₂O—Ph |
| 3247 | H | H | i-Pr | H | H | Ph | 4-EtNHCOCH₂CH₂O-3-F—Ph |
| 3248 | H | H | i-Pr | H | H | Ph | 4-EtCH(Me)NHCOCH₂CH₂O-3-F—Ph |
| 3249 | H | H | i-Pr | H | H | Ph | 4-EtCOCH₂CH₂O-3-F—Ph |
| 3250 | H | H | i-Pr | H | H | Ph | 3-F-4-i-BuNHCOCH₂CH₂O—Ph |
| 3251 | H | H | i-Pr | H | H | Ph | 4-cycloPrNHCOCH₂CH₂O-3-F—Ph |
| 3252 | H | H | i-Pr | H | H | Ph | 3-Br-4-n-PrNHCOCH₂CH₂O—Ph |
| 3253 | H | H | i-Pr | H | H | Ph | 3-Br-4-i-PrNHCOCH₂CH₂O—Ph |
| 3254 | H | H | i-Pr | H | H | Ph | 3-Br-4-EtNHCOCH₂CH₂O—Ph |
| 3255 | H | H | i-Pr | H | H | Ph | 3-Br-4-i-BuNHCOCH₂CH₂O—Ph |
| 3256 | H | H | i-Pr | H | H | Ph | 3-Cl-4-n-PrNHCOCH₂CH₂O—Ph |
| 3257 | H | H | i-Pr | H | H | Ph | 3-Cl-4-i-PrNHCOCH₂CH₂O—Ph |
| 3258 | H | H | i-Pr | H | H | Ph | 3-Cl-4-EtNHCOCH₂CH₂O—Ph |
| 3259 | H | H | i-Pr | H | H | Ph | 3-Cl-4-EtCH(Me)NHCOCH₂CH₂O—Ph |
| 3260 | H | H | i-Pr | H | H | Ph | 3-Cl-4-cycloPrNHCOCH₂CH₂O—Ph |
| 3261 | H | H | i-Pr | H | H | Ph | 3-Cl-4-cycloPentylNHCOCH₂CH₂O—Ph |
| 3262 | H | H | i-Pr | H | H | Ph | 3-Me-4-n-PrNHCOCH₂CH₂O—Ph |
| 3263 | H | H | i-Pr | H | H | Ph | 4-i-PrNHCOCH₂CH₂O-3-Me—Ph |
| 3264 | H | H | i-Pr | H | H | Ph | 4-EtNHCOCH₂CH₂O-3-Me—Ph |
| 3265 | H | H | i-Pr | H | H | Ph | 3-Me-4-MeNHCOCH₂CH₂O—Ph |
| 3266 | H | H | i-Pr | H | H | Ph | 3-Me-4-n-BuNHCOCH₂CH₂O—Ph |
| 3267 | H | H | i-Pr | H | H | Ph | 4-EtCH(Me)NHCOCH₂CH₂O-3-Me—Ph |
| 3268 | H | H | i-Pr | H | H | Ph | 4-EtCOCH₂CH₂O-3-Me—Ph |
| 3269 | H | H | i-Pr | H | H | Ph | 4-i-BuNHCOCH₂CH₂O-3-Me—Ph |
| 3270 | H | H | i-Pr | H | H | Ph | 3-Me-4-t-BuNHCOCH₂CH₂O—Ph |
| 3271 | H | H | i-Pr | H | H | Ph | 4-cycloPrNHCOCH₂CH₂O-3-Me—Ph |
| 3272 | H | H | i-Pr | H | H | Ph | 4-cycloPentylNHCOCH₂CH₂O-3-Me—Ph |
| 3273 | H | H | Me | H | H | Ph | 3-Cl-4-n-PrNHCOCH₂O—Ph |
| 3274 | H | H | Me | H | H | Ph | 3-Cl-4-i-PrNHCOCH₂O—Ph |
| 3275 | H | H | Me | H | H | Ph | 3-Cl-4-EtNHCOCH₂O—Ph |
| 3276 | H | H | Me | H | H | Ph | 3-Cl-4-EtCH(Me)NHCOCH₂O—Ph |
| 3277 | H | H | Me | H | H | Ph | 3-Cl-4-cycloPrNHCOCH₂O—Ph |
| 3278 | H | H | Me | H | H | Ph | 3-Cl-4-cycloPentylNHCOCH₂O—Ph |
| 3279 | H | H | Et | H | H | Ph | 3-Me-4-n-PrNHCOCH₂O—Ph |

TABLE 28

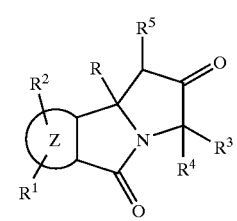

[I-3]

| Compound No. | R¹ | R² | R³ | R⁴ | R⁶ | Z | R |
|---|---|---|---|---|---|---|---|
| 3280 | H | H | Et | H | H | Ph | 4-i-PrNHCOCH₂O-3-Me—Ph |
| 3281 | H | H | Et | H | H | Ph | 4-EtNHCOCH₂O-3-Me—Ph |
| 3282 | H | H | Et | H | H | Ph | 3-Me-4-MeNHCOCH₂O—Ph |
| 3283 | H | H | Et | H | H | Ph | 3-Me-4-n-BuNHCOCH₂O—Ph |
| 3284 | H | H | Et | H | H | Ph | 4-EtCH(Me)NHCOCH₂O-3-Me—Ph |

TABLE 28-continued

[I-3]

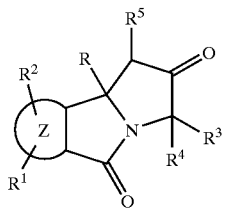

| Compound No. | R¹ | R² | R³ | R⁴ | R⁶ | Z | R |
|---|---|---|---|---|---|---|---|
| 3285 | H | H | Et | H | H | Ph | 4-EtCOCH₂O-3-Me—Ph |
| 3286 | H | H | Et | H | H | Ph | 4-i-BuNHCOCH₂O-3-Me—Ph |
| 3287 | H | H | Pr | H | H | Ph | 3-Cl-4-n-PrNHCOCH₂O—Ph |
| 3288 | H | H | Pr | H | H | Ph | 3-Cl-4-i-PrNHCOCH₂O—Ph |
| 3289 | H | H | Pr | H | H | Ph | 3-Cl-4-EtNHCOCH₂O—Ph |
| 3290 | H | H | Pr | H | H | Ph | 3-Cl-4-EtCH(Me)NHCOCH₂O—Ph |
| 3291 | H | H | Pr | H | H | Ph | 3-Cl-4-cycloPrNHCOCH₂O—Ph |
| 3292 | H | H | Pr | H | H | Ph | 3-Cl-4-cycloPentylNHCOCH₂O—Ph |
| 3293 | H | H | Bu | H | H | Ph | 3-Me-4-n-PrNHCOCH₂O—Ph |
| 3294 | H | H | Bu | H | H | Ph | 4-i-PrNHCOCH₂O-3-Me—Ph |
| 3295 | H | H | Bu | H | H | Ph | 4-EtNHCOCH₂O-3-Me—Ph |
| 3296 | H | H | Bu | H | H | Ph | 3-Me-4-MeNHCOCH₂O—Ph |
| 3297 | H | H | Bu | H | H | Ph | 3-Me-4-n-BuNHCOCH₂O—Ph |
| 3298 | H | H | Bu | H | H | Ph | 4-EtCH(Me)NHCOCH₂O-3-Me—Ph |
| 3299 | H | H | Bu | H | H | Ph | 4-EtCOCH₂O-3-Me—Ph |
| 3300 | H | H | Bu | H | H | Ph | 4-i-BuNHCOCH₂O-3-Me—Ph |
| 3301 | H | H | i-Bu | H | H | Ph | 3-Cl-4-n-PrNHCOCH₂O—Ph |
| 3302 | H | H | i-Bu | H | H | Ph | 3-Cl-4-HPrNHCOCH₂O—Ph |
| 3303 | H | H | i-Bu | H | H | Ph | 3-Cl-4-EtNHCOCH₂O—Ph |
| 3304 | H | H | i-Bu | H | H | Ph | 3-Cl-4-EtCH(Me)NHCOCH₂O—Ph |
| 3305 | H | H | i-Bu | H | H | Ph | 3-Cl-4-cycloPrNHCOCH₂O—Ph |
| 3306 | H | H | i-Bu | H | H | Ph | 3-Cl-4-cycloPentylNHCOCH₂O—Ph |
| 3307 | H | H | t-Bu | H | H | Ph | 3-Me-4-n-PrNHCOCH₂O—Ph |
| 3308 | H | H | t-Bu | H | H | Ph | 4-i-PrNHCOCH₂O-3-Me—Ph |
| 3309 | H | H | t-Bu | H | H | Ph | 4-EtNHCOCH₂O-3-Me—Ph |
| 3310 | H | H | t-Bu | H | H | Ph | 3-Me-4-MeNHCOCH₂O—Ph |
| 3311 | H | H | PhCH₂ | H | H | Ph | 3-Me-4-n-BuNHCOCH₂O—Ph |
| 3312 | H | H | PhCH₂ | H | H | Ph | 4-EtCH(Me)NHCOCH₂O-3-Me—Ph |
| 3313 | H | H | PhCH₂ | H | H | Ph | 4-EtCOCH₂O-3-Me—Ph |
| 3314 | H | H | PhCH₂ | H | H | Ph | 4-i-BuNHCOCH₂O-3-Me—Ph |
| 3315 | H | H | i-Pr | Me | H | Ph | 3-Cl-4-n-PrNHCOCH₂O—Ph |
| 3316 | H | H | i-Pr | Me | H | Ph | 3-Cl-4-i-PrNHCOCH₂O—Ph |
| 3317 | H | H | i-Pr | Me | H | Ph | 3-Cl-4-EtNHCOCH₂O—Ph |
| 3318 | H | H | i-Pr | Me | H | Ph | 3-Cl-4-EtCH(Me)NHCOCH₂O—Ph |
| 3319 | H | H | i-Pr | Me | H | Ph | 3-Cl-4-cycloPrNHCOCH₂O—Ph |
| 3320 | H | H | i-Pr | Me | H | Ph | 3-Cl-4-cycloPentylNHCOCH₂O—Ph |
| 3321 | H | H | i-Pr | H | H | 2,3-Pyridyl | 3-Me-4-n-PrNHCOCH₂O—Ph |
| 3322 | H | H | i-Pr | H | H | 2,3-Pyridyl | 4-i-PrNHCOCH₂O-3-Me—Ph |
| 3323 | H | H | i-Pr | H | H | 2,3-Pyridyl | 4-EtNHCOCH₂O-3-Me—Ph |
| 3324 | H | H | i-Pr | H | H | 2,3-Pyridyl | 3-Me-4-MeNHCOCH₂O—Ph |
| 3325 | H | H | i-Pr | H | H | 2,3-Pyridyl | 3-Me-4-n-BuNHCOCH₂O—Ph |

TABLE 29

[I-3]

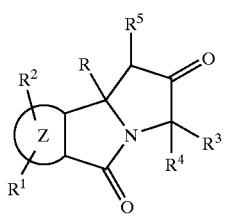

| Compound No | R¹ | R² | R³ | R⁴ | R⁶ | Z | R |
|---|---|---|---|---|---|---|---|
| 3326 | H | H | i-Pr | H | H | 2,3-Pyridyl | 4-EtCH(Me)NHCOCH₂O-3-Me—Ph |
| 3327 | H | H | i-Pr | H | H | 2,3-Pyridyl | 4-EtCOCH₂O-3-Me—Ph |

TABLE 29-continued

[I-3]

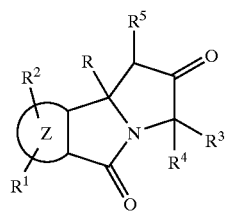

| Compound No | R¹ | R² | R³ | R⁴ | R⁶ | Z | R |
|---|---|---|---|---|---|---|---|
| 3328 | H | H | i-Pr | H | H | 2,3-Pyridyl | 4-i-BuNHCOCH$_2$O-3-Me—Ph |
| 3329 | H | H | i-Pr | H | H | 2,3-Pyridyl | 3-Cl-4-n-PrNHCOCH$_2$O—Ph |
| 3330 | H | H | i-Pr | H | H | 3,4-Pyridyl | 3-Cl-4-i-PrNHCOCH$_2$O—Ph |
| 3331 | H | H | i-Pr | H | H | 3,4-Pyridyl | 3-Cl-4-EtNHCOCH$_2$O—Ph |
| 3332 | H | H | i-Pr | H | H | 3,4-Pyridyl | 3-Cl-4-EtCH(Me)NHCOCH$_2$O—Ph |
| 3333 | H | H | i-Pr | H | H | 3,4-Pyridyl | 3-Cl-4-cycloPrNHCOCH$_2$O—Ph |
| 3334 | H | H | i-Pr | H | H | 3,4-Pyridyl | 3-Cl-4-cycloPentylNHCOCH$_2$O—Ph |
| 3335 | H | H | i-Pr | H | H | Ph | 4-F-5-n-PrNHCOCH$_2$O-(2-pyridyl) |
| 3336 | H | H | i-Pr | H | H | Ph | 4-F-5-i-PrNHCOCH$_2$$_2$O-(2-pyridyl) |
| 3337 | H | H | i-Pr | H | H | Ph | 4-EtNHCOCH$_2$O-3-F-(2-pyridyl) |
| 3338 | H | H | i-Pr | H | H | Ph | 4-EtCH(Me)NHCOCH$_2$O-3-F-(2-pyridyl) |
| 3339 | H | H | i-Pr | H | H | Ph | 4-EtCOCH$_2$O-3-F-(2-pyridyl) |
| 3340 | H | H | i-Pr | H | H | Ph | 3-F-4-i-BuNHCOCH$_2$O-(2-pyridyl) |
| 3341 | H | H | i-Pr | H | H | Ph | 4-cycloPrNHCOCH$_2$O-3-F-(2-pyridyl) |
| 3342 | H | H | i-Pr | H | H | Ph | 5-I-6-n-PrNHCOCH$_2$O-(3-pyridyl) |
| 3343 | H | H | i-Pr | H | H | Ph | 5-I-6-i-PrNHCOCH$_2$O-(3-pyridyl) |
| 3344 | H | H | i-Pr | H | H | Ph | 6-EtNHCOCH$_2$O-5-I-(3-pyridyl) |
| 3345 | H | H | i-Pr | H | H | Ph | 6-EtCH(Me)NHCOCH$_2$O-5-I-(3-pyridyl) |
| 3346 | H | H | i-Pr | H | H | Ph | 6-EtCOCH$_2$O-5-I-(3-pyridyl) |
| 3347 | H | H | i-Pr | H | H | Ph | 6-cycloPrNHCOCH$_2$O-5-H(3-pyridyl) |
| 3348 | H | H | i-Pr | H | H | Ph | 3-NO$_2$-4-n-PrNHCOCH$_2$O—Ph |
| 3349 | H | H | i-Pr | H | H | Ph | 3-NO$_2$-4-i-PrNHCOCH$_2$O—Ph |
| 3350 | H | H | i-Pr | H | H | Ph | 4-EtNHCOCH$_2$O-3-NO$_2$—Ph |
| 3351 | H | H | i-Pr | H | H | Ph | 4-EtCH(Me)NHCOCH$_2$O-3-NO$_2$—Ph |
| 3352 | H | H | i-Pr | H | H | Ph | 4-EtCOCH$_2$O-3-NO$_2$—Ph |
| 3353 | H | H | i-Pr | H | H | Ph | 4-i-BuNHCOCH$_2$O-3-NO$_2$—Ph |
| 3354 | H | H | i-Pr | H | H | Ph | 4-cycloPrNHCOCH$_2$O-3-NO$_2$—Ph |
| 3355 | H | H | i-Pr | H | H | Ph | 3-MeO-4-n-PrNHCOCH$_2$O—Ph |
| 3356 | H | H | i-Pr | H | H | Ph | 3-MeO-4-i-PrNHCOCH$_2$O—Ph |
| 3357 | H | H | i-Pr | H | H | Ph | 4-EtNHCOCH$_2$O-3-MeO—Ph |
| 3358 | H | H | i-Pr | H | H | Ph | 4-EtCH(Me)NHCOCH$_2$O-3-MeO—Ph |
| 3359 | H | H | i-Pr | H | H | Ph | 4-EtCOCH$_2$O-3-MeO—Ph |
| 3360 | H | H | i-Pr | H | H | Ph | 3-MeO-4-i-BuNHCOCH$_2$O—Ph |
| 3361 | H | H | i-Pr | H | H | Ph | 4-cycloPrNHCOCH$_2$O-3-MeO—Ph |
| 3362 | H | H | i-Pr | H | H | Ph | 3-HO-4-n-PrNHCOCH$_2$O—Ph |
| 3363 | H | H | i-Pr | H | H | Ph | 3-HO-4-i-PrNHCOCH$_2$O—Ph |
| 3364 | H | H | i-Pr | H | H | Ph | 4-EtNHCOCH$_2$O-3-HO—Ph |
| 3365 | H | H | i-Pr | H | H | Ph | 4-EtCH(Me)NHCOCH$_2$O-3-HO—Ph |
| 3366 | H | H | i-Pr | H | H | Ph | 4-EtCOCH$_2$O-3-HO—Ph |
| 3367 | H | H | i-Pr | H | H | Ph | 3-HO-4-i-BuNHCOCH$_2$O—Ph |
| 3368 | H | H | i-Pr | H | H | Ph | 4-cycloPrNHCOCH$_2$O-3-HO—Ph |
| 3369 | H | H | i-Pr | H | H | Ph | 3-H$_2$NCH$_2$CH$_2$NHCOCH$_2$O—Ph |
| 3370 | H | H | i-Pr | H | H | Ph | 2-H$_2$NCH$_2$CH$_2$NHCOCH$_2$O—Ph |
| 3371 | H | H | i-Pr | H | H | Ph | 4-MeNHCH$_2$CH$_2$NHCOCH$_2$O—Ph |

TABLE 30

[I-3]

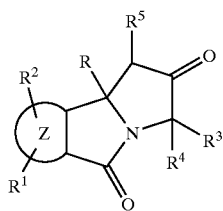

| Compound No. | $R^1$ | $R^2$ | $R^3$ | $R^6$ | Z | R |
|---|---|---|---|---|---|---|
| 3372 | H | H | i-Pr | H | H | Ph | 3-MeNHCH$_2$CH$_2$NHCOCH$_2$O—Ph |
| 3373 | H | H | i-Pr | H | H | Ph | 2-MeNHCH$_2$CH$_2$NHCOCH$_2$O—Ph |
| 3374 | H | H | i-Pr | H | H | Ph | 4-Me$_2$NCH$_2$CH$_2$NHCOCH$_2$O—Ph |
| 3375 | H | H | i-Pr | H | H | Ph | 3-Me$_2$NCH$_2$CH$_2$NHCOH$_2$O—Ph |
| 3376 | H | H | i-Pr | H | H | Ph | 2-Me$_2$NCH$_2$CH$_2$NHCOCH$_2$O—Ph |
| 3377 | H | H | i-Pr | H | H | Ph | 4-H$_2$NCH$_2$CH$_2$NHCOCH$_2$O-3-Cl—Ph |
| 3378 | H | H | i-Pr | H | H | Ph | 3-H$_2$NCH$_2$CH$_2$NHCOCH$_2$O-4-Cl—Ph |
| 3379 | H | H | i-Pr | H | H | Ph | 2-H$_2$NCH$_2$CH$_2$NHCOCH$_2$O-4-Cl—Ph |
| 3380 | H | H | i-Pr | H | H | Ph | 4-MeNHCH$_2$CH$_2$NHCOCH$_2$O-3-Me—Ph |
| 3381 | H | H | i-Pr | H | H | Ph | 3-MeNHCH$_2$CH$_2$NHCOCH$_2$O-4-Me—Ph |
| 3382 | H | H | i-Pr | H | H | Ph | 2-MeNHCH$_2$CH$_2$NHCOCH$_2$O-4-MePh |
| 3383 | H | H | i-Pr | H | H | Ph | 4-Me$_2$NCH$_2$CH$_2$NHCOCH$_2$O-3-F—Ph |
| 3384 | H | H | i-Pr | H | H | Ph | 3-Me$_2$NCH$_2$CH$_2$NHCOCH$_2$O-4-F—Ph |
| 3385 | H | H | i-Pr | H | H | Ph | 2-Me$_2$NCH$_2$CH$_2$NHCOCH$_2$O-4-F—Ph |
| 3386 | H | H | i-Pr | H | H | Ph | 4-H$_2$NCOCH$_2$-3-I—Ph |
| 3387 | H | H | i-Pr | H | H | Ph | 3-I-4-MeNHCOCH$_2$—Ph |
| 3388 | H | H | i-Pr | H | H | Ph | 4-EtNHCOCH$_2$-3-I—Ph |
| 3389 | H | H | i-Pr | H | H | Ph | 3-I-4-nPrNHCOCH$_2$—Ph |
| 3390 | H | H | i-Pr | H | H | Ph | 3-I-4-iPrNHCOCH$_2$—Ph |
| 3391 | H | H | i-Pr | H | H | Ph | 4-nBuNHCOCH$_2$-3-I—Ph |
| 3392 | H | H | i-Pr | H | H | Ph | 4-tBuNHCOCH$_2$-3-I—Ph |
| 3393 | H | H | i-Pr | H | H | Ph | 4-iBuNHCOCH$_2$—Ph |
| 3394 | H | H | i-Pr | H | H | Ph | 4-tBuO$_2$CCH$_2$-3-I—Ph |
| 3395 | H | H | i-Pr | H | H | Ph | 3-I-4-PhCH$_2$NHCOCH$_2$—Ph |
| 3396 | H | H | i-Pr | H | H | Ph | 3-I-4-(2-tetrahydrofuryl)CH$_2$NHCOCH$_2$—Ph |
| 3397 | H | H | i-Pr | H | H | Ph | 4-cycloPrNHCOCH$_2$-3-I—Ph |
| 3398 | H | H | i-Pr | H | H | Ph | 4-cycloPentylNHCOCH$_2$-3-I—Ph |
| 3399 | H | H | i-Pr | H | H | Ph | 4-cycloHexylNHCOCH$_2$-3-I—Ph |
| 3400 | H | H | i-Pr | H | H | Ph | 4-cycloPrNHCOCH$_2$-3-F—Ph |
| 3401 | H | H | i-Pr | H | H | Ph | 3-Cl-4-i-PrNHCOCH$_2$CH$_2$—Ph |
| 3402 | H | H | i-Pr | H | H | Ph | 3-Cl-4-EtNHCOCH$_2$CH$_2$—Ph |
| 3403 | H | H | i-Pr | H | H | Ph | 3-Cl-4-EtCH(Me)NHCOCH$_2$CH$_2$—Ph |
| 3404 | H | H | i-Pr | H | H | Ph | 4-i-PrNHCO-3-Me—Ph |
| 3405 | H | H | i-Pr | H | H | Ph | 4-EtNHCO-3-Me—Ph |
| 3406 | H | H | i-Pr | H | H | Ph | 4-EtCH(Me)NHCO-3-Me—Ph |
| 3407 | H | H | i-Pr | H | H | Ph | 3-Cl-4-i-PrNHCH$_2$CH$_2$O—Ph |
| 3408 | H | H | i-Pr | H | H | Ph | 3-Cl-4-EtNHCH$_2$CH$_2$O—Ph |
| 3409 | H | H | i-Pr | H | H | Ph | 3-Cl-4-EtCH(Me)NHCH$_2$CH$_2$O—Ph |
| 3410 | H | H | i-Pr | H | Me | Ph | 3-Cl-4-n-PrNHCOCH$_2$O—Ph |
| 3411 | H | H | i-Pr | H | Me | Ph | 3-Cl-4-i-PrNHCOCH$_2$O—Ph |
| 3412 | H | H | i-Pr | H | Me | Ph | 3-Cl-4-EtNHCOCH$_2$O—Ph |
| 3413 | H | H | i-Pr | H | Me | Ph | 3-Cl-4-EtCH(Me)NHCOCH$_2$O—Ph |
| 3414 | H | H | i-Pr | H | Me | Ph | 3-Cl-4-cycloPrNHCOCH$_2$O—Ph |
| 3415 | H | H | i-Pr | H | Me | Ph | 3-Cl-4-cycloPentylNHCOCH$_2$O—Ph |
| 3416 | H | H | i-Pr | H | Et | Ph | 3-Me-4-n-PrNHCOCH$_2$O—Ph |
| 3417 | H | H | i-Pr | H | Et | Ph | 4-i-PrNHCOCH$_2$O-3-Me—Ph |

TABLE 31

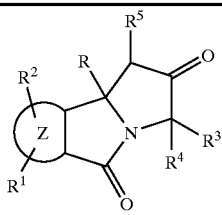

[I-3]

| Compound No. | R¹ | R² | R³ | R⁴ | R⁶ | Z | R |
|---|---|---|---|---|---|---|---|
| 3418 | H | H | i-Pr | H | Et | Ph | 4-EtNHCOCH$_2$O-3-Me—Ph |
| 3419 | H | H | i-Pr | H | Et | Ph | 3-Me-4-MeNHCOCH$_2$O—Ph |
| 3420 | H | H | i-Pr | H | Et | Ph | 3-Me-4-n-BuNHCOCH$_2$O—Ph |
| 3421 | H | H | i-Pr | H | Et | Ph | 4-EtCH(Me)NHCOCH$_2$O-3-Me—Ph |
| 3422 | H | H | i-Pr | H | Et | Ph | 4-EtCOCH$_2$O-3-Me—Ph |
| 3423 | H | H | i-Pr | H | Et | Ph | 4-i-BuNHCOCH$_2$O-3-Me—Ph |
| 3424 | H | H | i-Pr | H | Ac | Ph | 3-Cl-4-n-PrNHCOCH$_2$O—Ph |
| 3425 | H | H | i-Pr | H | Ac | Ph | 3-Cl-4-i-PrNHCOCH$_2$O—Ph |
| 3426 | H | H | i-Pr | H | Ac | Ph | 3-Cl-4-EtNHCOCH$_2$O—Ph |
| 3427 | H | H | i-Pr | H | Ac | Ph | 3-Cl-4-EtCH(Me)NHCOCH$_2$O—Ph |
| 3428 | H | H | i-Pr | H | Ac | Ph | 3-Cl-4-cycloPrNHCOCH$_2$O—Ph |
| 3429 | H | H | i-Pr | H | Ac | Ph | 3-Cl-4-cycloPentylNHCOCH$_2$O—Ph |
| 3430 | H | H | i-Pr | H | OH | Ph | 3-Me-4-n-PrNHCOCH$_2$O—Ph |
| 3431 | H | H | i-Pr | H | OH | Ph | 4-i-PrNHCOCH$_2$O-3-Me—Ph |
| 3432 | H | H | i-Pr | H | OH | Ph | 4-EtNHCOCH$_2$O-3-Me—Ph |
| 3433 | H | H | i-Pr | H | OH | Ph | 3-Me-4-MeNHCOCH$_2$O—Ph |
| 3434 | H | H | i-Pr | H | OH | Ph | 3-Me-4-n-BuNHCOCH$_2$O—Ph |
| 3435 | H | H | i-Pr | H | OH | Ph | 4-EtCH(Me)NHCOCH$_2$O-3-Me—Ph |
| 3436 | H | H | i-Pr | H | OH | Ph | 4-EtCOCH$_2$O-3-Me—Ph |
| 3437 | H | H | i-Pr | H | OH | Ph | 4-i-BuNHCOCH$_2$O-3-Me—Ph |
| 3438 | H | H | i-Pr | H | OMe | Ph | 3-Cl-4-n-PrNHCOCH$_2$O—Ph |
| 3439 | H | H | i-Pr | H | OMe | Ph | 3-Cl-4-i-PrNHCOCH$_2$O—Ph |
| 3440 | H | H | i-Pr | H | OMe | Ph | 3-Cl-4-EtNHCOCH$_2$O—Ph |
| 3441 | H | H | i-Pr | H | OMe | Ph | 3-Cl-4-EtCH(Me)NHCOCH$_2$O—Ph |
| 3442 | H | H | i-Pr | H | OMe | Ph | 3-Cl-4-cycloPrNHCOCH$_2$O—Ph |
| 3443 | H | H | i-Pr | H | OMe | Ph | 3-Cl-4-cycloPentylNHCOCH$_2$O—Ph |
| 3444 | H | H | i-Pr | H | OEt | Ph | 3-Me-4-n-PrNHCOCH$_2$O—Ph |
| 3445 | H | H | i-Pr | H | OEt | Ph | 4-i-PrNHCOCH$_2$O-3-Me—Ph |
| 3446 | H | H | i-Pr | H | OEt | Ph | 4-EtNHCOCH$_2$O-3-Me—Ph |
| 3447 | H | H | i-Pr | H | OEt | Ph | 3-Me-4-MeNHCOCH$_2$O—Ph |
| 3448 | H | H | i-Pr | H | OEt | Ph | 3-Me-4-n-BuNHCOCH$_2$O—Ph |
| 3449 | H | H | i-Pr | H | OEt | Ph | 4-EtCH(Me)NHCOCH$_2$O-3-Me—Ph |
| 3450 | H | H | i-Pr | H | OEt | Ph | 4-EtCOCH$_2$O-3-Me—Ph |
| 3451 | H | H | i-Pr | H | OEt | Ph | 4-i-BuNHCOCH$_2$O-3-Me—Ph |
| 3452 | H | H | i-Pr | H | Pr | Ph | 3-Cl-4-n-PrNHCOCH$_2$O—Ph |
| 3453 | H | H | i-Pr | H | Pr | Ph | 3-Cl-4-i-PrNHCOCH$_2$O—Ph |
| 3454 | H | H | i-Pr | H | Pr | Ph | 3-Cl-4-EtNHCOCH$_2$O—Ph |
| 3455 | H | H | i-Pr | H | Pr | Ph | 3-Cl-4-EtCH(Me)NHCOCH$_2$O—Ph |
| 3456 | H | H | i-Pr | H | Pr | Ph | 3-Cl-4-cycloPrNHCOCH$_2$O—Ph |
| 3457 | H | H | i-Pr | H | Pr | Ph | 3-Cl-4-cycloPentylNHCOCH$_2$O—Ph |
| 3458 | H | H | i-Pr | H | i-Pr | Ph | 3-Me-4-n-PrNHCOCH$_2$O—Ph |
| 3459 | H | H | i-Pr | H | i-Pr | Ph | 4-i-PrNHCOCH$_2$O-3-Me—Ph |
| 3460 | H | H | i-Pr | H | i-Pr | Ph | 4-EtNHCOCH$_2$O-3-Me—Ph |
| 3461 | H | H | i-Pr | H | i-Pr | Ph | 3-Me-4-MeNHCOCH$_2$O—Ph |
| 3462 | H | H | i-Pr | H | i-Pr | Ph | 3-Me-4-n-BuNHCOCH$_2$O—Ph |
| 3463 | H | H | i-Pr | H | i-Pr | Ph | 4-EtCH(Me)NHCOCH$_2$O-3-Me—Ph |

TABLE 32

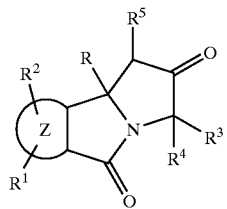

[I-3]

| Compound No. | R¹ | R² | R³ | R⁴ | R⁶ | Z | R |
|---|---|---|---|---|---|---|---|
| 3464 | H | H | i-Pr | H | H | pyrimidin-4,5-yl | 4-nBuNHCOCH$_2$O—Ph |
| 3465 | H | H | i-Pr | H | H | 5,6-benzimizazolyl | 4-PrNHCOCH$_2$O—Ph |
| 3466 | H | H | i-Pr | H | H | Ph | 3-cycloPrO-4-nPrNHCOCH$_2$O—Ph |
| 3467 | H | H | i-Pr | H | H | Ph | 3-PhSO$_2$NHCH$_2$NHCO-4-nPrNHCOCH$_2$O—Ph |
| 3468 | H | H | i-Pr | H | H | Ph | 3-MeNHSO$_2$-4-nPrNHCOCH$_2$O—Ph |
| 3469 | H | H | PhNHCOCH$_2$CH$_2$ | H | H | Ph | 4-nPrNHCOCH$_2$O—Ph |

TABLE 32-continued

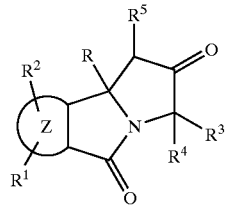

[I-3]

| Compound No. | R¹ | R² | R³ | R⁴ | R⁶ | Z | R |
|---|---|---|---|---|---|---|---|
| 3470 | H | H | MeCONHCH₂CH₂ | H | H | Ph | 4-nPrNHCOCH₂O—Ph |
| 3471 | H | H | 4-PhNHSO₂-pyrazin-2,5-y | H | H | Ph | 4-nPrNHCOCH₂O—Ph |
| 3472 | H | H | i-Pr | H | H | Ph | 3-Cl-4-HO—Ph |
| 3473 | H | H | i-Pr | H | H | Ph | 4-HO-3-MePh |
| 3474 | H | H | i-Pr | H | H | Ph | 4-HO₂CCH₂O-3-Me—Ph |
| 3475 | H | H | i-Pr | H | H | Ph | 3,5-Cl₂-4-nPrNHCOCH₂O—Ph |
| 3476 | H | H | i-Pr | H | H | Ph | 3-Me-4-nPrNHCSCH₂O—Ph |
| 3477 | H | H | i-Pr | H | H | Ph | 3,5-Cl₂-4-nPrNHCSCH₂O—Ph |
| 3478 | H | H | i-Pr | H | H | Ph | 4-nPentylNHCOCH₂O—Ph |
| 3479 | H | H | i-Pr | H | Me | Ph | 4-MeO—Ph |
| 3480 | H | H | i-Pr | H | Me | Ph | 4-HO—Ph |
| 3481 | H | H | i-Pr | H | Me | Ph | 4-nPrNHCOCH₂O—Ph |
| 3482 | H | H | i-Pr | H | Br | Ph | 4-nPrNHCOCH₂O—Ph |
| 3483 | H | H | i-Pr | H | nPrNHCOCH₂ | Ph | 4-nPrNHCOCH₂O—Ph |
| 3484 | H | H | i-Pr | H | H₂NCOCH₂ | Ph | 4-nPrNHCOCH₂O—Ph |
| 3485 | H | H | i-Pr | H | MeSO₂NHCH₂CH₂ | Ph | 4-nPrNHCOCH₂O—Ph |
| 3486 | H | H | i-Pr | H | MeO₂CCH₂ | Ph | 4-nPrNHCOCH₂O—Ph |
| 3487 | H | H | i-Pr | H | HOCH₂CH₂ | Ph | 4-nPrNHCOCH₂O—Ph |

TABLE 33

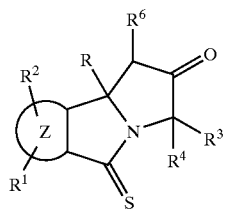

[I-3b]

| Compound No. | R¹ | R² | R³ | R⁴ | R⁶ | Z | R |
|---|---|---|---|---|---|---|---|
| 3488 | H | H | i-Pr | H | H | Ph | 3,5-Cl₂-4-nPrNHCOCH₂O—Ph |
| 3489 | H | H | i-Pr | H | H | Ph | 3,5-Cl₂-4-nPrNHCSCH₂O—Ph |
| 3490 | H | H | i-Pr | H | H | Ph | 3-Me-4-nPrNHCOCH₂O—Ph |
| 3491 | H | H | i-Pr | H | H | Ph | 3-Cl-4-nPrNHCOCH₂O—Ph |
| 3492 | H | H | i-Pr | H | H | pyrimidin-4,5-yl | 4-nBuNHCOCH₂O—Ph |
| 3493 | H | H | i-Pr | H | H | 5,6-benzimizazolyl | 4-nPrNHCOCH₂O—Ph |
| 3494 | H | H | i-Pr | H | H | Ph | 3-MeSO-4-nPrNHCOCH₂O—Ph |
| 3495 | Et₂N | H | i-Pr | H | H | Ph | 4-nPrNHCOCH₂O—Ph |
| 3496 | Ph | H | i-Pr | H | H | Ph | 4-nPrNHCOCH₂O—Ph |
| 3497 | H | H | MeSO₂CH₂CH₂ | H | H | Ph | 4-nPrNHCOCH₂O—Ph |
| 3498 | H | H | PhNHSO₃CH₂—Ph | H | H | Ph | 4-nPrNHCOCH₂O—Ph |

TABLE 34

[I-3c]

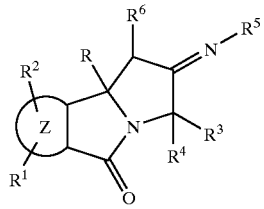

| Compound No. | R¹ | R² | R³ | R⁴ | R⁵ | Z | R | R⁶ |
|---|---|---|---|---|---|---|---|---|
| 3499 | H | H | i-Pr | H | MeO | Ph | 3-Me-4-nPrNHCOCH₂O—Ph | H |
| 3500 | H | H | i-Pr | H | HO | Ph | 3-Cl-4-nPrNHCOCH₂O—Ph | H |
| 3501 | H | H | i-Pr | H | Me | Ph | 4-nPrNHCOCH₂O—Ph | H |
| 3502 | H | H | i-Pr | H | MeO | Ph | 4-MeOCOCH₂NHCOCH₂O—Ph | H |
| 3503 | H | H | i-Pr | H | MeO | Ph | 4-PhCONHCH₂NHCOCH₂O—Ph | Me |
| 3504 | H | H | i-Pr | H | MeO | Ph | 4-PhCOCH₂NHCOCH₂O—Ph | H |
| 3505 | H | H | i-Pr | H | HOCH₂CH₂ | Ph | 4-nPrNHCOCH₂O—Ph | H |
| 3506 | H | H | i-Pr | H | MeO₂CCH₂ | Ph | 4-nPrNHCOCH₂O—Ph | H |
| 3507 | H | H | 2-Pyridyl-PhCH₂ | H | H | Ph | 4-nPrNHCOCH₂O—Ph | H |
| 3508 | H | H | MeNHCOCH₂O—PhCH₂ | H | H | Ph | 4-nPrNHCOCH₂—Ph | H |

TABLE 35

[I-3d]

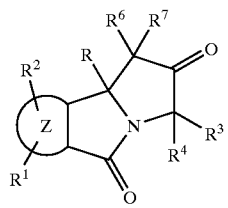

| Compound No. | R¹ | R² | R³ | R⁴ | R⁶ | Z | R | R⁷ |
|---|---|---|---|---|---|---|---|---|
| 3509 | H | H | i-Pr | H | Me | Ph | 4-MeO—Ph | Me |
| 3510 | H | H | i-Pr | H | Me | Ph | 4-HO—Ph | Me |
| 3511 | H | H | i-Pr | H | Me | Ph | 4-nPrNHCOCH₂O—Ph | Me |
| 3512 | H | H | i-Pr | H | HO | Ph | 4-nPrNHCOCH₂O—Ph | Me |
| 3513 | H | H | i-Pr | H | MeCO | Ph | 4-nPrNHCOCH₂O—Ph | Me |
| 3514 | H | H | i-Pr | H | H₂NCO | Ph | 4-nPrNHCOCH₂O—Ph | Me |
| 3515 | H | H | i-Pr | H | MeCOCH₂ | Ph | 4-nPrNHCOCH₂O—Ph | Me |
| 3516 | H | H | i-Pr | H | MeO₂CCH₂ | Ph | 4-nPrNHCOCH₂O—Ph | Me |
| 3517 | H | H | i-Pr | H | Me | Ph | 4-nPrNHCOCH₂O—Ph | Et |
| 3518 | H | H | i-Pr | H | Me | Ph | 4-nPrNHCOCH₂O—Ph | Pr |
| 3519 | H | H | 4-MeO—Ph | H | Me | Ph | 4-nPrNHCOCH₂O—Ph | Me |
| 3520 | H | H | (2-pyridyl)CH₂NHCO—Ph | H | Me | Ph | 4-nPrNHCOCH₂O—Ph | Me |
| 3521 | H | H | (3,4-methylenedioxyPh)—Ph | H | Me | Ph | 4-nPrNHCOCH₂O—Ph | Me |

TABLE 36

[I-4]

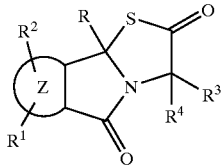

| Compound No. | R¹ | R² | R³ | R⁴ | Z | R |
|---|---|---|---|---|---|---|
| 4001 | H | H | i-Pr | H | Ph | 2-MeO—Ph |
| 4002 | H | H | i-Pr | H | Ph | Ph |
| 4003 | H | H | i-Pr | H | Ph | 2-NH₂—Ph |
| 4004 | H | H | i-Pr | H | Ph | 4-F—Ph |
| 4005 | H | H | i-Pr | H | Ph | 4-Et₂N—Ph |
| 4006 | H | H | i-Pr | H | Ph | 4-Cl—Ph |
| 4007 | H | H | i-Pr | H | Ph | 4-HO—Ph |
| 4008 | H | H | i-Pr | H | Ph | 3-MeO—Ph |
| 4009 | H | H | i-Pr | H | Ph | 3-HO—Ph |
| 4010 | H | H | i-Pr | H | Ph | 3-NH₂—Ph |
| 4011 | H | H | i-Pr | H | Ph | 4-MeO—Ph |
| 4012 | H | H | i-Pr | H | Ph | 4-Me—Ph |
| 4013 | H | H | i-Pr | H | Ph | 3-Me—Ph |
| 4014 | H | H | i-Pr | H | Ph | 4-tBuO₂CCH₂O—Ph |
| 4015 | H | H | i-Pr | H | Ph | 4-HO₂CCH₂O—Ph |
| 4016 | H | H | i-Pr | H | Ph | 4-tBuO₂C(CH₂)₅O—Ph |
| 4017 | H | H | i-Pr | H | Ph | 4-HO₂C(CH₂)₅O—Ph |
| 4018 | H | H | i-Pr | H | Ph | 4-HO(CH₂)₃O—Ph |
| 4019 | H | H | i-Pr | H | Ph | 4-HO(CH₂)₂O—Ph |
| 4020 | H | H | i-Pr | H | Ph | 4-HOC(Me)₂(CH₂)₂O—Ph |
| 4021 | H | H | i-Pr | H | Ph | 4-PhCH₂O—Ph |
| 4022 | H | H | i-Pr | H | Ph | 4-MeNHCOCH₂O—Ph |
| 4023 | H | H | i-Pr | H | Ph | 4-EtNHCOCH₂O—Ph |
| 4024 | H | H | i-Pr | H | Ph | 4-nPrNHCOCH₂O—Ph |
| 4025 | H | H | i-Pr | H | Ph | 4-nBuNHCOCH₂O—Ph |
| 4026 | H | H | i-Pr | H | Ph | 4-CH₂=CHCH₂NHCOCH₂O—Ph |

TABLE 36-continued

[I-4]

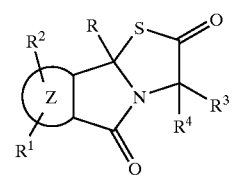

| Compound No. | R¹ | R² | R³ | R⁴ | Z | R |
|---|---|---|---|---|---|---|
| 4027 | H | H | i-Pr | H | Ph | 4-Me(CH₂)₉NHCOCH₂O—Ph |
| 4028 | H | H | i-Pr | H | Ph | 4-N₃(CH₂)₃O—Ph |
| 4029 | H | H | i-Pr | H | Ph | 4-tBuO₂CCH(Me)O—Ph |
| 4030 | H | H | i-Pr | H | Ph | 4-nPrNHCOCH(Me)O—Ph |
| 4031 | H | H | i-Pr | H | Ph | 4-F₃CSO₃—Ph |
| 4032 | H | H | i-Pr | H | Ph | 4-tBuO₂CCH=CHPh |
| 4033 | H | H | i-Pr | H | Ph | 4-nPrNHCOCH=CH—Ph |
| 4034 | H | H | i-Pr | H | Ph | 4-nPrCH(Me)NHCOCH₂O—Ph |
| 4035 | H | H | i-Pr | H | Ph | 4-EtCH(Me)NHCOCH₂O—Ph |
| 4036 | H | H | i-Pr | H | Ph | 4-MeOCH₂O—Ph |
| 4037 | H | H | i-Pr | H | Ph | 4-EtCOCH₂O—Ph |
| 4038 | H | H | i-Pr | H | Ph | 3-tBuO₂CCH₂O—Ph |
| 4039 | H | H | i-Pr | H | Ph | 3-HO₂CCH₂O—Ph |
| 4040 | H | H | i-Pr | H | Ph | 3-nPrNHCOCH₂O—Ph |
| 4041 | H | H | i-Pr | H | Ph | 4-H₂NC(Me)₂CH₂O₂CCH₂O—Ph |
| 4042 | H | H | i-Pr | H | Ph | 4-morpholinoCOCH₂O—Ph |
| 4043 | H | H | i-Pr | H | Ph | 4-(4-Cl-Ph)-COCH₂O—Ph |
| 4044 | H | H | i-Pr | H | Ph | 4-PhCOCH₂O—Ph |
| 4045 | H | H | i-Pr | H | Ph | 4-(4-pyridyl)-CH₂NHCOCH₂O—Ph |
| 4046 | H | H | i-Pr | H | Ph | 4-H₂NCH₂CH₂NHCOCH₂O—Ph |

TABLE 37

[I-4]

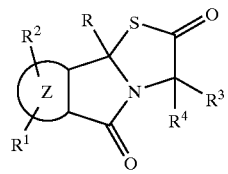

| Compound No. | R¹ | R² | R³ | R⁴ | Z | R |
|---|---|---|---|---|---|---|
| 4047 | H | H | i-Pr | H | Ph | 4-Cl-3-NO₂—Ph |
| 4048 | H | H | i-Pr | H | Ph | 4-Cl-3-F—Ph |
| 4049 | H | H | i-Pr | H | Ph | 4-Cl-3-Me—Ph |
| 4050 | H | H | i-Pr | H | Ph | 3-NH₂-4-Cl—Ph |
| 4051 | H | H | i-Pr | H | Ph | 3-Cl-4-MeO—Ph |
| 4052 | H | H | i-Pr | H | Ph | 3-Cl-4-Me—Ph |
| 4053 | H | H | i-Pr | H | Ph | 4-Br-3-Cl—Ph |
| 4054 | H | H | i-Pr | H | Ph | 4-Br-2-Cl—Ph |
| 4055 | H | H | i-Pr | H | Ph | 4-F-3-Me—Ph |
| 4056 | H | H | i-Pr | H | Ph | 3-F-4-Me—Ph |
| 4057 | H | H | i-Pr | H | Ph | 3-Br-4-HO—Ph |
| 4058 | H | H | i-Pr | H | Ph | 3-Br-4-MeO—Ph |

TABLE 37-continued

[I-4]

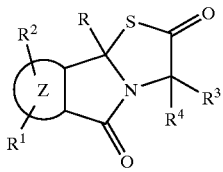

| Compound No. | $R^1$ | $R^2$ | $R^3$ | $R^4$ | Z | R |
|---|---|---|---|---|---|---|
| 4059 | H | H | i-Pr | H | Ph | 3-Br-4-F—Ph |
| 4060 | H | H | i-Pr | H | Ph | 3-F-4-PhPh |
| 4061 | H | H | i-Pr | H | Ph | 4-HO-3-I—Ph |
| 4062 | H | H | i-Pr | H | Ph | 5-HO-2-I—Ph |
| 4063 | H | H | i-Pr | H | Ph | 3-I-4-MeO—Ph |
| 4064 | H | H | i-Pr | H | Ph | 2-I-5-MeO—Ph |
| 4065 | H | H | i-Pr | H | Ph | 4-MeO-3-Me—Ph |
| 4066 | H | H | i-Pr | H | Ph | 4-HO(CH$_2$)$_3$O-3-I—Ph |
| 4067 | H | H | i-Pr | H | Ph | 4-HO(CH$_2$)$_2$O-3-I—Ph |
| 4068 | H | H | i-Pr | H | Ph | 4-HOC(Me)$_2$(CH$_2$)$_2$O-3-I—Ph |
| 4069 | H | H | i-Pr | H | Ph | 4-tBuO$_2$C(CH$_2$)$_4$O-3-I—Ph |
| 4070 | H | H | i-Pr | H | Ph | 3-I-4-PhCH$_2$O—Ph |
| 4071 | H | H | i-Pr | H | Ph | 4-H$_2$NCOCH$_2$O-3-I—Ph |
| 4072 | H | H | i-Pr | H | Ph | 3-I-4-MeNHCOCH$_2$O—Ph |
| 4073 | H | H | i-Pr | H | Ph | 4-EtNHCOCH$_2$O-3-I—Ph |
| 4074 | H | H | i-Pr | H | Ph | 3-I-4-nPrNHCOCH$_2$O—Ph |
| 4075 | H | H | i-Pr | H | Ph | 3-I-4-iPrNHCOCH$_2$O—Ph |
| 4076 | H | H | i-Pr | H | Ph | 4-nBuNHCOCH$_2$O-3-I—Ph |
| 4077 | H | H | i-Pr | H | Ph | 4-tBuNHCOCH$_2$O-3-I—Ph |
| 4078 | H | H | i-Pr | H | Ph | 4-iBuNHCOCH$_2$O—Ph |
| 4079 | H | H | i-Pr | H | Ph | 4-tBuO$_2$CCH$_2$O-3-I—Ph |
| 4080 | H | H | i-Pr | H | Ph | 3-I-4-PhCH$_2$NHCOCH$_2$O—Ph |
| 4081 | H | H | i-Pr | H | Ph | 3-I-4-(2-tetrahydrofurYI)CH$_2$NHCOCH$_2$O—Ph |
| 4082 | H | H | i-Pr | H | Ph | 4-cycloPrNHCOCH$_2$O-3-I—Ph |
| 4083 | H | H | i-Pr | H | Ph | 4-cycloPentylNHCOCH$_2$O-3-I—Ph |
| 4084 | H | H | i-Pr | H | Ph | 4-cycloHexylNHCOCH$_2$O-3-I—Ph |
| 4085 | H | H | i-Pr | H | Ph | 4-cycloPrNHCOCH$_2$O-3-F—Ph |
| 4086 | H | H | i-Pr | H | Ph | 4-Me(CH$_2$)$_9$NHCOCH$_2$O-3-I—Ph |
| 4087 | H | H | i-Pr | H | Ph | 4-HO$_2$CCH$_2$O-3-I—Ph |
| 4088 | H | H | i-Pr | H | Ph | 4-N$_3$(CH$_2$)$_3$O-3-I—Ph |
| 4089 | H | H | i-Pr | H | Ph | 3-I-4-nPrNHCO(CH$_2$)$_4$O—Ph |
| 4090 | H | H | i-Pr | H | Ph | 4-Et$_2$NCOCH$_2$O-3-I—Ph |
| 4091 | H | H | i-Pr | H | Ph | 3-I-4-nPrN(Me)COCH$_2$O—Ph |
| 4092 | H | H | i-Pr | H | Ph | 3-Cl-4-nPrNHCOCH$_2$O—Ph |

TABLE 38

[I-4]

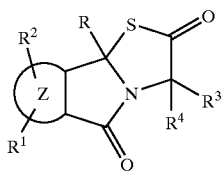

| Compound No. | $R^1$ | $R^2$ | $R^3$ | $R^4$ | Z | R |
|---|---|---|---|---|---|---|
| 4093 | H | H | i-Pr | H | Ph | 3-Br-4-nPrNHCOCH$_2$O—Ph |
| 4094 | H | H | i-Pr | H | Ph | 3-F-4-nPrNHCOCH$_2$O—Ph |
| 4095 | H | H | i-Pr | H | Ph | 3-Me-4-nPrNHCOCH$_2$O—Ph |
| 4096 | H | H | i-Pr | H | Ph | 4-EtNHCOCH$_2$O-3-F—Ph |
| 4097 | H | H | i-Pr | H | Ph | 3-I-4-iPrNHCOC(Me)$_2$CH$_2$O—Ph |
| 4098 | H | H | i-Pr | H | Ph | 3-Br-4-CH$_2$=CHCH$_2$NHCOCH$_2$O—Ph |
| 4099 | H | H | i-Pr | H | Ph | 4-iBuNHCOCH$_2$O-3-F—Ph |
| 4100 | H | H | i-Pr | H | Ph | 3-tBuO$_2$CCH=CH-4-nPrNHCOCH$_2$O—Ph |
| 4101 | H | H | i-Pr | H | Ph | 3-HO$_2$CCH=CH-4-nPrNHCOCH$_2$O—Ph |
| 4102 | H | H | i-Pr | H | Ph | 3-I-4-MeOCH$_2$CH$_2$NHCOCH$_2$O—Ph |
| 4103 | H | H | i-Pr | H | Ph | 3-F-4-HO—Ph |
| 4104 | H | H | i-Pr | H | Ph | 3-F-4-MeO—Ph |
| 4105 | H | H | i-Pr | H | Ph | 3,4-methylenedioxyPh |

TABLE 38-continued

[I-4]

| Compound No. | R¹ | R² | R³ | R⁴ | Z | R |
|---|---|---|---|---|---|---|
| 4106 | H | H | i-Pr | H | Ph | 3,4-ethylenedioxyPh |
| 4107 | H | H | i-Pr | H | Ph | 3,4-Cl$_2$—Ph |
| 4108 | H | H | i-Pr | H | Ph | 3,4-Me$_2$—Ph |
| 4109 | H | H | i-Pr | H | Ph | 3,4-F$_2$—Ph |
| 4110 | H | H | i-Pr | H | Ph | 3,4-(MeO)$_2$—Ph |
| 4111 | H | H | i-Pr | H | Ph | 3,5-(MeO)$_2$—Ph |
| 4112 | H | H | i-Pr | H | Ph | 3,5-Me$_2$—Ph |
| 4113 | H | H | i-Pr | H | Ph | 3,5-I$_2$-4-HO—Ph |
| 4114 | H | H | i-Pr | H | Ph | 2,4-I$_2$-5-HO—Ph |
| 4115 | H | H | i-Pr | H | Ph | 3,5-I$_2$-4-MeO—Ph |
| 4116 | H | H | i-Pr | H | Ph | 2,4-I$_2$-5-MeO—Ph |
| 4117 | H | H | i-Pr | H | Ph | 2,4,6-Me$_3$—Ph |
| 4118 | H | H | i-Pr | H | Ph | 4-HO(CH$_2$)$_3$O-3,5-I$_2$Ph |
| 4119 | H | H | i-Pr | H | Ph | 3,5-I$_2$-4-nPrNHCOCH$_2$O—Ph |
| 4120 | H | H | i-Pr | H | Ph | 2-thienyl |
| 4121 | H | H | i-Pr | H | Ph | 2-furyl |
| 4122 | H | H | i-Pr | H | Ph | 3-pyridyl |
| 4123 | H | H | i-Pr | H | Ph | 2-naphthyl |
| 4124 | H | H | i-Pr | H | Ph | 5-F-1-naphthyl |
| 4125 | H | H | i-Pr | H | Ph | dibenzothiophene-2-yl |
| 4126 | 6-F | H | i-Pr | H | Ph | Ph |
| 4127 | 7-F | H | i-Pr | H | Ph | Ph |
| 4128 | 8-F | H | i-Pr | H | Ph | Ph |
| 4129 | 9-F | H | i-Pr | H | Ph | Ph |
| 4130 | 6-MeO | H | i-Pr | H | Ph | Ph |
| 4131 | 9-MeO | H | i-Pr | H | Ph | Ph |
| 4132 | 6-OH | H | i-Pr | H | Ph | Ph |
| 4133 | 9-OH | H | i-Pr | H | Ph | Ph |
| 4134 | 7-NO$_2$ | H | i-Pr | H | Ph | Ph |
| 4135 | 8-NO$_2$ | H | i-Pr | H | Ph | Ph |
| 4136 | 9-NO$_2$ | H | i-Pr | H | Ph | Ph |
| 4137 | 6-NHPh | H | i-Pr | H | Ph | Ph |
| 4138 | 7-Me$_2$N | H | i-Pr | H | Ph | Ph |

TABLE 39

[I-4]

| Compound No. | R¹ | R² | R³ | R⁴ | Z | R |
|---|---|---|---|---|---|---|
| 4139 | 7-Me | H | i-Pr | H | Ph | Ph |
| 4140 | 8-Me | H | i-Pr | H | Ph | Ph |
| 4141 | 7-t-Bu | H | i-Pr | H | Ph | Ph |
| 4142 | 8-t-Bu | H | i-Pr | H | Ph | Ph |
| 4143 | 7-Br | H | i-Pr | H | Ph | Ph |
| 4144 | 8-Br | H | i-Pr | H | Ph | Ph |
| 4145 | 7-Cl | H | i-Pr | H | Ph | Ph |
| 4146 | 8-Cl | H | i-Pr | H | Ph | Ph |
| 4147 | 7-Cl | 8-Cl | i-Pr | H | Ph | Ph |
| 4148 | 6-Cl | 9-Cl | i-Pr | H | Ph | Ph |
| 4149 | 6-OH | 9-I | i-Pr | H | Ph | Ph |
| 4150 | H | H | i-Pr | H | 1,2-naphthyl | Ph |
| 4151 | H | H | i-Pr | H | 2,3-naphthyl | Ph |
| 4152 | H | H | i-Pr | H | cyclohexenyl | Ph |
| 4153 | H | H | D-Leucine | H | Ph | Ph |
| 4154 | H | H | L-Leucine | H | Ph | Ph |
| 4155 | H | H | D-NorLeucine | H | Ph | Ph |
| 4156 | H | H | L-NorLeucine | H | Ph | Ph |
| 4157 | H | H | D-AlloLeucine | H | Ph | Ph |
| 4158 | H | H | L-AlloLeucine | H | Ph | Ph |
| 4159 | H | H | D-NorValine | H | Ph | Ph |
| 4160 | H | H | L-NorValine | H | Ph | Ph |
| 4161 | H | H | D-Alanine | H | Ph | Ph |
| 4162 | H | H | L-Alanine | H | Ph | Ph |

TABLE 39-continued

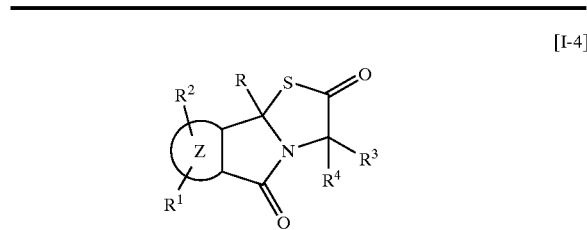

[I-4]

| Compound No. | R¹ | R² | R³ | R⁴ | Z | R |
|---|---|---|---|---|---|---|
| 4163 | H | H | D-Arginine | H | Ph | Ph |
| 4164 | H | H | L-Arginine | H | Ph | Ph |
| 4165 | H | H | D-Asparagine | H | Ph | Ph |
| 4166 | H | H | L-Asparagine | H | Ph | Ph |
| 4167 | H | H | D-Glutamic Acid | H | Ph | Ph |
| 4168 | H | H | L-Glutamic Acid | H | Ph | Ph |
| 4169 | H | H | D-Glutamine | H | Ph | Ph |
| 4170 | H | H | L-Glutamine | H | Ph | Ph |
| 4171 | H | H | D-Histidine | H | Ph | Ph |
| 4172 | H | H | L-Histidine | H | Ph | Ph |

TABLE 39-continued

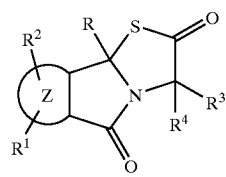

[I-4]

| Compound No. | R¹ | R² | R³ | R⁴ | Z | R |
|---|---|---|---|---|---|---|
| 4173 | H | H | D-Methionine | H | Ph | Ph |
| 4174 | H | H | L-Methionine | H | Ph | Ph |
| 4175 | H | H | D-Tryptophan | H | Ph | Ph |
| 4176 | H | H | L-Tryptophan | H | Ph | Ph |
| 4177 | H | H | D-Tyrosine | H | Ph | Ph |
| 4178 | H | H | L-Tyrosine | H | Ph | Ph |
| 4179 | H | H | D-Homo Phenylalanine | H | Ph | Ph |
| 4180 | H | H | L-Homo Phenylalanine | H | Ph | Ph |
| 4181 | H | H | D-Leucine | H | Ph | 4-Cl—Ph |
| 4182 | H | H | L-Leucine | H | Ph | 4-Cl—Ph |
| 4183 | H | H | D-NorLeucine | H | Ph | 4-Cl—Ph |

TABLE 40

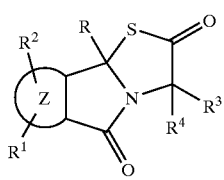

[I-4]

| Compound No. | R¹ | R² | R³ | R⁴ | Z | R |
|---|---|---|---|---|---|---|
| 4184 | H | H | L-NorLeucine | H | Ph | 4-Cl—Ph |
| 4185 | H | H | D-AlloLeucine | H | Ph | 4-Cl—Ph |
| 4186 | H | H | L-AlloLeucine | H | Ph | 4-Cl—Ph |
| 4187 | H | H | D-NorValine | H | Ph | 4-Cl—Ph |
| 4188 | H | H | L-NorValine | H | Ph | 4-Cl—Ph |
| 4189 | H | H | D-Alanine | H | Ph | 4-Cl—Ph |
| 4190 | H | H | L-Alanine | H | Ph | 4-Cl—Ph |
| 4191 | H | H | D-Arginine | H | Ph | 4-Cl—Ph |
| 4192 | H | H | L-Arginine | H | Ph | 4-Cl—Ph |
| 4193 | H | H | D-Asparagine | H | Ph | 4-Cl—Ph |
| 4194 | H | H | L-Asparagine | H | Ph | 4-Cl—Ph |
| 4195 | H | H | D-Glutamic Acid | H | Ph | 4-Cl—Ph |
| 4196 | H | H | L-Glutamic Acid | H | Ph | 4-Cl—Ph |
| 4197 | H | H | D-Glutamine | H | Ph | 4-Cl—Ph |
| 4198 | H | H | L-Glutamine | H | Ph | 4-Cl—Ph |
| 4199 | H | H | D-Histidine | H | Ph | 4-Cl—Ph |
| 4200 | H | H | L-Histidine | H | Ph | 4-Cl—Ph |
| 4201 | H | H | D-Methionine | H | Ph | 4-Cl—Ph |
| 4202 | H | H | L-Methionine | H | Ph | 4-Cl—Ph |
| 4203 | H | H | D-Tryptophan | H | Ph | 4-Cl—Ph |
| 4204 | H | H | L-Tryptophan | H | Ph | 4-Cl—Ph |
| 4205 | H | H | D-Tyrosine | H | Ph | 4-Cl—Ph |
| 4206 | H | H | L-Tyrosine | H | Ph | 4-Cl—Ph |

TABLE 40-continued

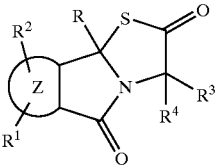

[I-4]

| Compound No. | R¹ | R² | R³ | R⁴ | Z | R |
|---|---|---|---|---|---|---|
| 4207 | H | H | D-Homo Phenylalanine | H | Ph | 4-Cl—Ph |
| 4208 | H | H | L-Homo Phenylalanine | H | Ph | 4-Cl—Ph |
| 4209 | H | H | t-Bu | H | Ph | Ph |
| 4210 | H | H | $(CH_3)_2(OH)C$ | H | Ph | Ph |
| 4211 | H | H | $CH_3(MeO)CH$ | H | Ph | Ph |
| 4212 | H | H | 4-HO—Ph | H | Ph | Ph |
| 4213 | H | H | 4-HO-3-I—Ph | H | Ph | Ph |
| 4214 | H | H | 4-HO-3,5-$I_2$—Ph | H | Ph | Ph |
| 4215 | H | H | 4-HO-3-I—$PhCH_2$ | H | Ph | Ph |
| 4216 | H | H | 4-HO-3,5-$I_2$—$PhCH_2$ | H | Ph | Ph |
| 4217 | H | H | 1-naphthylmethyl | H | Ph | Ph |
| 4218 | H | H | 4-F—$PhCH_2$ | H | Ph | Ph |
| 4219 | H | H | 1-naphthylmethyl | H | Ph | 4-Cl—Ph |
| 4220 | H | H | 4-F—$PhCH_2$ | H | Ph | 4-Cl—Ph |
| 4221 | H | H | i-Pr | Me | Ph | 4-Cl—Ph |
| 4222 | H | H | Me | Me | Ph | Ph |
| 4223 | H | H | (Combined with R⁴) $CH_2$ | — | Ph | Ph |
| 4224 | H | H | (Combined with R⁴) MeCH | — | Ph | Ph |
| 4225 | H | H | (Combined with R⁴) $(CH_2)_4$ | — | Ph | Ph |
| 4226 | H | H | i-Pr | H | Ph | 4-n-$PrNHCOCH_2CH_2O$—Ph |
| 4227 | H | H | i-Pr | H | Ph | 4-i-$PrNHCOCH_2CH_2O$—Ph |
| 4228 | H | H | i-Pr | H | Ph | 4-$EtNHCOCH_2CH_2O$—Ph |

TABLE 41

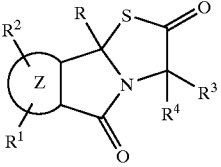

[I-4]

| Compound No. | R¹ | R² | R³ | R⁴ | Z | R |
|---|---|---|---|---|---|---|
| 4229 | H | H | i-Pr | H | Ph | 4-$EtCH(Me)NHCOCH_2CH_2O$—Ph |
| 4230 | H | H | i-Pr | H | Ph | 3-Cl-4-i-$PrNHCOCH_2O$—Ph |
| 4231 | H | H | i-Pr | H | Ph | 3-Cl-4-$EtNHCOCH_2O$—Ph |
| 4232 | H | H | i-Pr | H | Ph | 3-Cl-4-$EtCH(Me)NHCOCH_2O$—Ph |
| 4233 | H | H | i-Pr | H | Ph | 4-i-$PrNHCOCH_2O$-3-Me—Ph |
| 4234 | H | H | i-Pr | H | Ph | 4-$EtNHCOCH_2O$-3-Me—Ph |
| 4235 | H | H | i-Pr | H | Ph | 4-$EtCH(Me)NHCOCH_2O$-3-Me—Ph |
| 4236 | H | H | i-Pr | H | Ph | 4-cyclo$PrNHCOCH_2CH_2O$—Ph |
| 4237 | H | H | i-Pr | H | Ph | 4-cyclo$PentylNHCOCH_2CH_2O$—Ph |
| 4238 | H | H | i-Pr | H | Ph | 3-I-4-n-$PrNHCOCH_2CH_2O$—Ph |
| 4239 | H | H | i-Pr | H | Ph | 3-I-4-i-$PrNHCOCH_2CH_2O$—Ph |
| 4240 | H | H | i-Pr | H | Ph | 4-$EtNHCOCH_2CH_2O$-3-I—Ph |
| 4241 | H | H | i-Pr | H | Ph | 4-$EtCH(Me)NHCOCH_2CH_2O$-3-I—Ph |
| 4242 | H | H | i-Pr | H | Ph | 4-$EtCOCH_2CH_2O$-3-I—Ph |
| 4243 | H | H | i-Pr | H | Ph | 4-cyclo$PrNHCOCH_2CH_2O$-3-I—Ph |
| 4244 | H | H | i-Pr | H | Ph | 4-cyclo$PentylNHCOCH_2CH_2O$-3-I—Ph |
| 4245 | H | H | i-Pr | H | Ph | 3-F-4-n-$PrNHCOCH_2CH_2O$—Ph |
| 4246 | H | H | i-Pr | H | Ph | 3-F-4-i-$PrNHCOCH_2CH_2O$—Ph |
| 4247 | H | H | i-Pr | H | Ph | 4-$EtNHCOCH_2CH_2O$-3-F—Ph |
| 4248 | H | H | i-Pr | H | Ph | 4-$EtCH(Me)NHCOCH_2CH_2O$-3-F—Ph |
| 4249 | H | H | i-Pr | H | Ph | 4-$EtCOCH_2CH_2O$-3-F—Ph |
| 4250 | H | H | i-Pr | H | Ph | 3-F-4-i-$BuNHCOOH_2CH_2O$—Ph |
| 4251 | H | H | i-Pr | H | Ph | 4-cyclo$PrNHCOCH_2CH_2O$-3-F—Ph |
| 4252 | H | H | i-Pr | H | Ph | 3-Br-4-n-$PrNHCOCH_2CH_2O$—Ph |
| 4253 | H | H | i-Pr | H | Ph | 3-Br-4-i-$PrNHCOCH_2CH_2O$—Ph |

TABLE 41-continued

[I-4]

$$\begin{array}{c} R^2 \\ Z \\ R^1 \end{array} \begin{array}{c} R \\ S \\ N \\ R^4 \end{array} \begin{array}{c} O \\ R^3 \\ O \end{array}$$

| Compound No. | R¹ | R² | R³ | R⁴ | Z | R |
|---|---|---|---|---|---|---|
| 4254 | H | H | i-Pr | H | Ph | 3-Br-4-EtNHCOCH₂CH₂O—Ph |
| 4255 | H | H | i-Pr | H | Ph | 3-Br-4-i-BuNHCOCH₂CH₂O—Ph |
| 4256 | H | H | i-Pr | H | Ph | 3-Cl-4-n-PrNHCOCH₂CH₂O—Ph |
| 4257 | H | H | i-Pr | H | Ph | 3-Cl-4-i-PrNHCOCH₂CH₂O—Ph |
| 4258 | H | H | i-Pr | H | Ph | 3-Cl-4-EtNHCOCH₂CH₂O—Ph |
| 4259 | H | H | i-Pr | H | Ph | 3-Cl-4-EtCH(Me)NHCOCH₂CH₂O—Ph |
| 4260 | H | H | i-Pr | H | Ph | 3-Cl-4-cycloPrNHCOCH₂CH₂O—Ph |
| 4261 | H | H | i-Pr | H | Ph | 3-Cl-4-cycloPentylNHCOCH₂CH₂O—Ph |
| 4262 | H | H | i-Pr | H | Ph | 3-Me-4-n-PrNHCOCH₂CH₂O—Ph |
| 4263 | H | H | i-Pr | H | Ph | 4-i-PrNHCOCH₂CH₂O-3-Me—Ph |
| 4264 | H | H | i-Pr | H | Ph | 4-EtNHCOCH₂CH₂O-3-Me—Ph |
| 4265 | H | H | i-Pr | H | Ph | 3-Me-4-MeNHCOCH₂CH₂O—Ph |
| 4266 | H | H | i-Pr | H | Ph | 3-Me-4-n-BuNHCOCH₂CH₂O—Ph |
| 4267 | H | H | i-Pr | H | Ph | 4-EtCH(Me)NHCOCH₂CH₂O-3-Me—Ph |
| 4268 | H | H | i-Pr | H | Ph | 4-EtCOCH₂CH₂O-3-Me—Ph |
| 4269 | H | H | i-Pr | H | Ph | 4-i-BuNHCOCH₂CH₂O-3-Me—Ph |
| 4270 | H | H | i-Pr | H | Ph | 3-Me-4-t-BuNHCOCH₂CH₂O—Ph |
| 4271 | H | H | i-Pr | H | Ph | 4-cycloPrNHCOCH₂CH₂O-3-Me—Ph |
| 4272 | H | H | i-Pr | H | Ph | 4-cycloPentylNHCOCH₂CH₂O-3-MePh |
| 4273 | H | H | Me | H | Ph | 3-Cl-4-n-PrNHCOCH₂O—Ph |

TABLE 42

[I-4]

$$\begin{array}{c} R^2 \\ Z \\ R^1 \end{array} \begin{array}{c} R \\ S \\ N \\ R^4 \end{array} \begin{array}{c} O \\ R^3 \\ O \end{array}$$

| Compound No. | R¹ | R² | R³ | R⁴ | Z | R |
|---|---|---|---|---|---|---|
| 4274 | H | H | Me | H | Ph | 3-Cl-4-i-PrNHCOCH₂O—Ph |
| 4275 | H | H | Me | H | Ph | 3-Cl-4-EtNHCOCH₂O—Ph |
| 4276 | H | H | Me | H | Ph | 3-Cl-4-EtCH(Me)NHCOCH₂O—Ph |
| 4277 | H | H | Me | H | Ph | 3-Cl-4-cycloPrNHCOCH₂O—Ph |
| 4278 | H | H | Me | H | Ph | 3-Cl-4-cycloPentylNHCOCH₂O—Ph |
| 4279 | H | H | Et | H | Ph | 3-Me-4-n-PrNHCOCH₂O—Ph |
| 4280 | H | H | Et | H | Ph | 4-i-PrNHCOCH₂O-3-Me—Ph |
| 4281 | H | H | Et | H | Ph | 4-EtNHCOCH₂O-3-Me—Ph |
| 4282 | H | H | Et | H | Ph | 3-Me-4-MeNHCOCH₂O—Ph |
| 4283 | H | H | Et | H | Ph | 3-Me-4-n-BuNHCOCH₂O—Ph |
| 4284 | H | H | Et | H | Ph | 4-EtCH(Me)NHCOCH₂O-3-Me—Ph |
| 4285 | H | H | Et | H | Ph | 4-EtCOCH₂O-3-Me—Ph |
| 4286 | H | H | Et | H | Ph | 4-i-BuNHCOCH₂O-3-Me—Ph |
| 4287 | H | H | Pr | H | Ph | 3-Cl-4-n-PrNHCOCH₂O—Ph |
| 4288 | H | H | Pr | H | Ph | 3-Cl-4-i-PrNHCOCH₂O—Ph |
| 4289 | H | H | Pr | H | Ph | 3-Cl-4-EtNHCOCH₂O—Ph |
| 4290 | H | H | Pr | H | Ph | 3-Cl-4-EtCH(Me)NHCOCH₂O—Ph |
| 4291 | H | H | Pr | H | Ph | 3-Cl-4-cycloPrNHCOCH₂O—Ph |
| 4292 | H | H | Pr | H | Ph | 3-Cl-4-cycloPentylNHCOCH₂O—Ph |
| 4293 | H | H | Bu | H | Ph | 3-Me-4-n-PrNHCOCH₂O—Ph |
| 4294 | H | H | Bu | H | Ph | 4-i-PrNHCOCH₂O-3-Me—Ph |
| 4295 | H | H | Bu | H | Ph | 4-EtNHCOCH₂O-3-Me—Ph |
| 4296 | H | H | Bu | H | Ph | 3-Me-4-MeNHCOCH₂O—Ph |
| 4297 | H | H | Bu | H | Ph | 3-Me-4-n-BuNHCOCH₂O—Ph |
| 4298 | H | H | Bu | H | Ph | 4-EtCH(Me)NHCOCH₂O-3-Me—Ph |
| 4299 | H | H | Bu | H | Ph | 4-EtCOCH₂O-3-Me—Ph |
| 4300 | H | H | Bu | H | Ph | 4-i-BuNHCOCH₂O-3-Me—Ph |

TABLE 42-continued

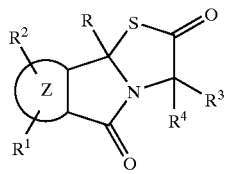

[I-4]

| Compound No. | R¹ | R² | R³ | R⁴ | Z | R |
|---|---|---|---|---|---|---|
| 4301 | H | H | i-Bu | H | Ph | 3-Cl-4-nPrNHCOCH$_2$O—Ph |
| 4302 | H | H | i-Bu | H | Ph | 3-Cl-4-i-PrNHCOCH$_2$O—Ph |
| 4303 | H | H | i-Bu | H | Ph | 3-Cl-4-EtNHCOCH$_2$O—Ph |
| 4304 | H | H | i-Bu | H | Ph | 3-Cl-4-EtOH(Me)NHCOCH$_2$O—Ph |
| 4305 | H | H | i-Bu | H | Ph | 3-Cl-4-cycloPrNHCOCH$_2$O—Ph |
| 4306 | H | H | i-Bu | H | Ph | 3-Cl-4-cycloPentylNHCOCH$_2$O—Ph |
| 4307 | H | H | t-Bu | H | Ph | 3-Me-4-n-PrNHCOCH$_2$O—Ph |
| 4308 | H | H | t-Bu | H | Ph | 4-i-PrNHCOCH$_2$O-3-Me—Ph |
| 4309 | H | H | t-Bu | H | Ph | 4-EtNHCOCH$_2$O-3-Me—Ph |
| 4310 | H | H | t-Bu | H | Ph | 3-Me-4-MeNHCOCH$_2$O—Ph |
| 4311 | H | H | PhCH$_2$ | H | Ph | 3-Me-4-n-BuNHCOCH$_2$O—Ph |
| 4312 | H | H | PhCH$_2$ | H | Ph | 4-EtOH(Me)NHCOCH$_2$O-3-Me—Ph |
| 4313 | H | H | PhCH$_2$ | H | Ph | 4-EtCOCH$_2$O-3-Me—Ph |
| 4314 | H | H | PhCH$_2$ | H | Ph | 4-i-BuNHCOCH$_2$O-3-Me—Ph |
| 4315 | H | H | i-Pr | Me | Ph | 3-Cl-4-n-PrNHCOCH$_2$O—Ph |
| 4316 | H | H | i-Pr | Me | Ph | 3-Cl-4-i-PrNHCOCH$_2$O—Ph |
| 4317 | H | H | i-Pr | Me | Ph | 3-Cl-4-EtNHCOCH$_2$O—Ph |
| 4318 | H | H | i-Pr | Me | Ph | 3-Cl-4-EtCH(Me)NHCOCH$_2$O—Ph |

TABLE 43

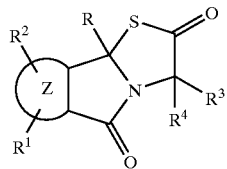

[I-4]

| Compound No. | R¹ | R² | R³ | R⁴ | Z | R |
|---|---|---|---|---|---|---|
| 4319 | H | H | i-Pr | Me | Ph | 3-Cl-4-cycloPrNHCOCH$_2$O—Ph |
| 4320 | H | H | i-Pr | Me | Ph | 3-Cl-4-cycloPentylNHCOCH$_2$O—Ph |
| 4321 | H | H | i-Pr | H | 2,3-Pyridyl | 3-Me-4-n-PrNHCOCH$_2$O—Ph |
| 4322 | H | H | i-Pr | H | 2,3-Pyridyl | 4-i-PrNHCOCH$_2$O-3-Me—Ph |
| 4323 | H | H | i-Pr | H | 2,3-Pyridyl | 4-EtNHCOCH$_2$O-3-Me—Ph |
| 4324 | H | H | i-Pr | H | 2,3-Pyridyl | 3-Me-4-MeNHCOCH$_2$O—Ph |
| 4325 | H | H | i-Pr | H | 2,3-Pyridyl | 3-Me-4-n-BuNHCOCH$_2$O—Ph |
| 4326 | H | H | i-Pr | H | 2,3-Pyridyl | 4-EtCH(Me)NHCOCH$_2$O-3-Me—Ph |
| 4327 | H | H | i-Pr | H | 2,3-Pyridyl | 4-EtCOCH$_2$O-3-Me—Ph |
| 4328 | H | H | i-Pr | H | 2,3-Pyridyl | 4-i-BuNHCOCH$_2$O-3-Me—Ph |
| 4329 | H | H | i-Pr | H | 2,3-Pyridyl | 3-Cl-4-n-PrNHCOCH$_2$O—Ph |
| 4330 | H | H | i-Pr | H | 3,4-Pyridyl | 3-Cl-4-i-PrNHCOCH$_2$O—Ph |
| 4331 | H | H | i-Pr | H | 3,4-Pyridyl | 3-Cl-4-EtNHCOCH$_2$O—Ph |
| 4332 | H | H | i-Pr | H | 3,4-Pyridyl | 3-Cl-4-EtCH(Me)NHCOCH$_2$O—Ph |
| 4333 | H | H | i-Pr | H | 3,4-Pyridyl | 3-Cl-4-cycloPrNHCOCH$_2$O—Ph |
| 4334 | H | H | i-Pr | H | 3,4-Pyridyl | 3-Cl-4-cycloPentylNHCOCH$_2$O—Ph |
| 4335 | H | H | i-Pr | H | Ph | 4-F-5-n-PrNHCOCH$_2$O-(2-pyridyl) |
| 4336 | H | H | i-Pr | H | Ph | 4-F-5-i-PrNHCOCH$_2$2O-(2-pyridyl) |
| 4337 | H | H | i-Pr | H | Ph | 4-EtNHCOCH$_2$O-3-F-(2-pyridyl) |
| 4338 | H | H | i-Pr | H | Ph | 4-EtCH(Me)NHCOCH$_2$O-3-F-(2-pyridyl) |
| 4339 | H | H | i-Pr | H | Ph | 4-EtCOCH$_2$O-3-F-(2-pyridyl) |
| 4340 | H | H | i-Pr | H | Ph | 3-F-4-i-BuNHCOCH$_2$O-(2-pyridyl) |
| 4341 | H | H | i-Pr | H | Ph | 4-cycloPrNHCOCH$_2$O-3-F-(2-pyridyl) |
| 4342 | H | H | i-Pr | H | Ph | 5-I-6-n-PrNHCOCH$_2$O-(3-pyridyl) |
| 4343 | H | H | i-Pr | H | Ph | 5-I-6-i-PrNHCOCH$_2$O-(3-pyridyl) |
| 4344 | H | H | i-Pr | H | Ph | 6-EtNHCOCH$_2$O-5-I-(3-pyridyl) |
| 4345 | H | H | i-Pr | H | Ph | 6-EtCH(Me)NHCOCH$_2$O-5-I-(3-pyridyl) |
| 4346 | H | H | i-Pr | H | Ph | 6-EtCOCH$_2$O-5-I-(3-pyridyl) |
| 4347 | H | H | i-Pr | H | Ph | 6-cycloPrNHCOCH$_2$O-5-I-(3-pyridyl) |

TABLE 43-continued

[I-4]

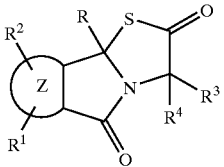

| Compound No. | R¹ | R² | R³ | R⁴ | Z | R |
|---|---|---|---|---|---|---|
| 4348 | H | H | i-Pr | H | Ph | 3-NO₂-4-n-PrNHCOCH₂O—Ph |
| 4349 | H | H | i-Pr | H | Ph | 3-NO₂-4-i-PrNHCOCH₂O—Ph |
| 4350 | H | H | i-Pr | H | Ph | 4-EtNHCOCH₂O-3-NO₂—Ph |
| 4351 | H | H | i-Pr | H | Ph | 4-EtCH(Me)NHCOCH₂O-3-NO₂—Ph |
| 4352 | H | H | i-Pr | H | Ph | 4-EtCOCH₂O-3-NO₂—Ph |
| 4353 | H | H | i-Pr | H | Ph | 4-i-BuNHCOCH₂O-3-NO₂—Ph |
| 4354 | H | H | i-Pr | H | Ph | 4-cycloPrNHCOCH₂O-3-NO₂—Ph |
| 4355 | H | H | i-Pr | H | Ph | 3-MeO-4-n-PrNHCOCH₂O—Ph |
| 4356 | H | H | i-Pr | H | Ph | 3-MeO-4-i-PrNHCOCH₂O—Ph |
| 4357 | H | H | i-Pr | H | Ph | 4-EtNHCOCH₂O-3-MeO—Ph |
| 4358 | H | H | i-Pr | H | Ph | 4-EtCH(Me)NHCOCH₂O-3-MeO—Ph |
| 4359 | H | H | i-Pr | H | Ph | 4-EtCOCH₂O-3-MeO—Ph |
| 4360 | H | H | i-Pr | H | Ph | 3-MeO-4-i-BuNHCOCH₂O—Ph |
| 4361 | H | H | i-Pr | H | Ph | 4-cycloPrNHCOCH₂O-3-MeO—Ph |
| 4362 | H | H | i-Pr | H | Ph | 3-HO-4-n-PrNHCOCH₂O—Ph |
| 4363 | H | H | i-Pr | H | Ph | 3-HO-4-i-PrNHCOCH₂O—Ph |

TABLE 44

[I-4]

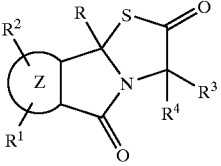

| Compound No. | R¹ | R² | R³ | R⁴ | Z | R |
|---|---|---|---|---|---|---|
| 4364 | H | H | i-Pr | H | Ph | 4-EtNHCOCH₂O-3-HO—Ph |
| 4365 | H | H | i-Pr | H | Ph | 4-EtCH(Me)NHCOCH₂O-3-HO—Ph |
| 4366 | H | H | i-Pr | H | Ph | 4-EtCOCH₂O-3-HO—Ph |
| 4367 | H | H | i-Pr | H | Ph | 3-HO-4-i-BuNHCOCH₂O—Ph |
| 4368 | H | H | i-Pr | H | Ph | 4-cycloPrNHCOCH₂O-3-HO—Ph |
| 4369 | H | H | i-Pr | H | Ph | 3-H₂NCH₂CH₂NHCOCH₂O—Ph |
| 4370 | H | H | i-Pr | H | Ph | 2-H₂NCH₂CH₂NHCOCH₂O—Ph |
| 4371 | H | H | i-Pr | H | Ph | 4-MeNHCH₂CH₂NHCOCH₂O—Ph |
| 4372 | H | H | i-Pr | H | Ph | 3-MeNHCH₂CH₂NHCOCH₂O—Ph |
| 4373 | H | H | i-Pr | H | Ph | 2-MeNHCH₂CH₂NHCOCH₂O—Ph |
| 4374 | H | H | i-Pr | H | Ph | 4-Me₂NCH₂CH₂NHCOCH₂O—Ph |
| 4375 | H | H | i-Pr | H | Ph | 3-Me₂NCH₂CH₂NHCOCH₂O—Ph |
| 4376 | H | H | i-Pr | H | Ph | 2-Me₂NCH₂CH₂NHCOCH₂O—Ph |
| 4377 | H | H | i-Pr | H | Ph | 4-H₂NCH₂CH₂NHCOCH₂O-3-Cl—Ph |
| 4378 | H | H | i-Pr | H | Ph | 3-H₂NCH₂CH₂NHCOCH₂O-4-Cl—Ph |
| 4379 | H | H | i-Pr | H | Ph | 2-H₂NCH₂CH₂NHCOCH₂O-4-Cl—Ph |
| 4380 | H | H | i-Pr | H | Ph | 4-MeNHCH₂CH₂NHCOCH₂O-3-Me—Ph |
| 4381 | H | H | i-Pr | H | Ph | 3-MeNHCH₂CH₂NHCOCH₂O-4-Me—Ph |
| 4382 | H | H | i-Pr | H | Ph | 2-MeNHCH₂CH₂NHCOCH₂O-4-MePh |
| 4383 | H | H | i-Pr | H | Ph | 4-Me₂NCH₂CH₂NHCOCH₂O-3-F—Ph |
| 4384 | H | H | i-Pr | H | Ph | 3-Me₂NCH₂CH₂NHCOCH₂O-4-F—Ph |
| 4385 | H | H | i-Pr | H | Ph | 2-Me₂NCH₂CH₂NHCOCH₂O-4-F—Ph |
| 4386 | H | H | i-Pr | H | Ph | 4-H₂NCOCH₂-3-I—Ph |
| 4387 | H | H | i-Pr | H | Ph | 3-I-4-MeNHCOCH₂—Ph |
| 4388 | H | H | i-Pr | H | Ph | 4-EtNHCOCH₂-3-I—Ph |
| 4389 | H | H | i-Pr | H | Ph | 3-I-4-nPrNHCOCH₂—Ph |
| 4390 | H | H | i-Pr | H | Ph | 3-I-4-iPrNHCOCH₂—Ph |
| 4391 | H | H | i-Pr | H | Ph | 4-nBuNHCOCH₂-3-I—Ph |
| 4392 | H | H | i-Pr | H | Ph | 4-tBuNHCOCH₂-3-I—Ph |
| 4393 | H | H | i-Pr | H | Ph | 4-iBuNHCOCH₂—Ph |
| 4394 | H | H | i-Pr | H | Ph | 4-tBuO₂CCH₂-3-I—Ph |

TABLE 44-continued

[I-4]

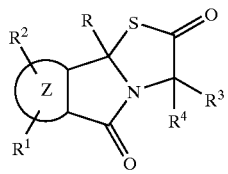

| Compound No. | R¹ | R² | R³ | R⁴ | Z | R |
|---|---|---|---|---|---|---|
| 4395 | H | H | i-Pr | H | Ph | 3-I-4—PhCH$_2$NHCOCH$_2$—Ph |
| 4396 | H | H | i-Pr | H | Ph | 3-I-4-(2-tetrahydrofuryl)CH$_2$NHCOCH$_2$—Ph |
| 4397 | H | H | i-Pr | H | Ph | 4-cycloPrNHCOCH$_2$-3-I—Ph |
| 4398 | H | H | i-Pr | H | Ph | 4-cycloPentylNHCOCH$_2$-3-I—Ph |
| 4399 | H | H | i-Pr | H | Ph | 4-cycloHexylNHCOCH$_2$-3-I—Ph |
| 4400 | H | H | i-Pr | H | Ph | 4-cycloPrNHCOCH$_2$-3-F—Ph |
| 4401 | H | H | i-Pr | H | Ph | 3-Cl-4-i-PrNHCOCH$_2$CH$_2$—Ph |
| 4402 | H | H | i-Pr | H | Ph | 3-Cl-4-EtNHCOCH$_2$CH$_2$—Ph |
| 4403 | H | H | i-Pr | H | Ph | 3-Cl-4-EtCH(Me)NHCOOH$_2$CH$_2$—Ph |
| 4404 | H | H | i-Pr | H | Ph | 4-i-PrNHCO-3-Me—Ph |
| 4405 | H | H | i-Pr | H | Ph | 4-EtNHCO-3-Me—Ph |
| 4406 | H | H | i-Pr | H | Ph | 4-EtCH(Me)NHCO-3-Me—Ph |
| 4407 | H | H | i-Pr | H | Ph | 3-Cl-4-i-PrNHCH$_2$CH$_2$O—Ph |
| 4408 | H | H | i-Pr | H | Ph | 3-Cl-4-EtNHCH$_2$CH$_2$O—Ph |
| 4409 | H | H | i-Pr | H | Ph | 3-Cl-4-EtCH(Me)NHCH$_2$CH$_2$O—Ph |

TABLE 45

[I-4]

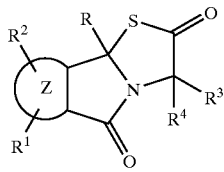

| Compound No. | R¹ | R² | R³ | R⁴ | Z | R |
|---|---|---|---|---|---|---|
| 4410 | H | H | i-Pr | H | 4,5-pyridazinyl | 4-nPrNHCOCH$_2$O—Ph |
| 4411 | H | H | i-Pr | H | 5,6-benztrizolyl | 4-nPrNHCOCH$_2$O—Ph |
| 4412 | H | H | i-Pr | H | 1,2-cyclohexyl | 4-nPrNHCOCH$_2$O—Ph |
| 4413 | H | H | i-Pr | H | 6,7-phthalazinyl | 4-nPrNHCOCH$_2$O—Ph |
| 4414 | H | H | i-Pr | H | 6,7-quinoxatinyl | 4-nPrNHCOCH$_2$O—Ph |
| 4415 | H | H | i-Pr | H | Ph | 3—PhSO$_2$-4-nPrNHCOCH$_2$O—Ph |
| 4416 | H | H | i-Pr | H | Ph | 3-EtNH$_2$-4-nPrNHCOCH$_2$O—Ph |
| 4417 | H | H | i-Pr | H | Ph | 3-Me-4-nPrNHCOCH$_2$S—Ph |
| 4418 | H | H | i-Pr | H | Ph | 3-Me-4-Et$_2$NCOCH$_2$S—Ph |
| 4419 | H | H | i-Pr | H | Ph | 4-nPrNHCOCH$_2$O-pyrazin-2-yl |
| 4420 | H | H | i-Pr | H | Ph | 3-(2,5-Pyrazinyl)-4-n-PrNHCOCH$_2$O—Ph |
| 4421 | H | H | i-Pr | H | Ph | 3-(3,4-methylenedioxyPh)-4-EtNHCOCH$_2$O—Ph |
| 4422 | H | H | i-Pr | H | Ph | 3-Me-4-nPrNHCOCH$_2$NH—Ph |
| 4423 | H | H | i-Pr | H | Ph | 3-Me-4-nPrNHCOCH$_2$S—Ph |
| 4424 | H | H | i-Pr | H | Ph | 3-Cl-4-HO—Ph |
| 4425 | H | H | n-PrNHCS—PhCH$_2$ | H | Ph | 4-nPrNHCOCH$_2$O—Ph |
| 4426 | H | H | (3-thienyl)CH$_2$ | H | Ph | 4-nPrNHCOCH$_2$O—Ph |
| 4427 | H | H | 3,4-ethytenedioxyPhCH$_2$ | H | Ph | 4-nPrNHCOCH$_2$O—Ph |

Among these compounds, preferred ones are, for example, compounds of 1002, 1011, 1014, 1023, 1024, 1033, 1035, 1037, 1046, 1050, 1056, 1063, 1070, 1071, 1072, 1073, 1074, 1075, 1076, 1077, 1078, 1081, 1082, 1083, 1085, 1091, 1092, 1093, 1094, 1095, 1096, 1098, 1102, 1104, 1107, 1119, 1122, 1126, 1129, 1130, 1137, 1150, 1152, 1182, 1183, 1184, 1185, 1209, 1210, 1219, 1251, 1257, 1268, 1276, 1285, 1295, 1310, 1316, 1413, 1426, 1429, 1430, 1432, 1433, 1435, 1328, 1333, 1338, 1348, 1356, 1364, 1371, 1380, 1383, 1388, 1391, 1404, 2002, 2011, 2023, 2024, 2050, 2056, 2074, 2092, 2094, 2096, 2251, 2268, 2285, 2295, 2316, 2333, 2348, 2364, 2380, 2388, 2391, 2410, 2422, 2456, 2462, 2467, 2468, 2471, 2474, 2476, 3001, 3002, 3007, 3011, 3014, 3015, 3020, 3023, 3024, 3033, 3039, 3047, 3050, 3051, 3056, 3057, 3058, 3063, 3065, 3072, 3073, 3074, 3076, 3078, 3082, 3083, 3092, 3093, 3094, 3095, 3096, 3103, 3104, 3107, 3117, 3226, 3241, 3246, 3258, 3266, 3296, 3307, 3319, 3412, 3418, 3464, 3468, 3471, 3475, 3476, 3477, 3479, 3480, 3481, 3482, 3484, 3485, 3486, 3487, 3488, 3489, 3492, 3493, 3495, 3499, 3500, 3501, 3505, 3506, 3509, 3510, 3511, 3513, 3515, 3516, 3517, 3518, 4002, 4011, 4023, 4024, 4050, 4056, 4063, 4073, 4074, 4092, 4094, 4096, 4257, 4276, 4295, 4316, 4333, 4348, 4364, 4380, 4388, 4404, 4410, 4416, 4417, 4419, 4420, etc, and further preferred ones are, for example, compounds of 1002, 1014, 1024, 1033, 1050, 1063, 1071, 1072, 1073, 1074, 1075, 1076, 1078, 1081, 1082, 1083, 1091, 1092, 1093, 1094, 1095, 1098, 1102, 1104, 1209, 1429, 1430, 1432, 1433, 1435, 2002, 2011, 2050, 2074, 2094, 2268, 2295, 2333, 2364, 2380, 2391, 2410, 2422, 2456, 2462, 2471, 3001, 3002, 3007, 3011, 3014, 3015, 3024, 3050, 3056. 3063, 3074, 3078, 3082, 3092, 3093, 3094, 3095, 3103, 3104, 3475, 3476, 3477, 3479, 3480, 3481, 3482, 3488, 3489, 3499, 3511, 4002, 4011, 4050, 4063, 4073, 4074, 4094, 4257, 4295, 4333, 4348, 4380, 4388, 4404 , etc.

Particularly preferred compounds among these compounds are as follows:

2-(4-(3-isopropyl-2,5-dioxo-2,3-dihydro[1,3]oxazolo[2,3-a]isoindol-9(5H)-yl)phenoxy)-N-propylacetamide (compound of 1024), 9b-(3-iodo-4-methoxyphenyl)-3-isopropyl[1,3]oxazolo[2,3-a]isoindole-2,5(3H,9bH)-dione (compound of 1063), 2-(2-iodo-4-(3-isopropyl-2,5-dioxo-2,3-dihydro[1,3]oxazolo[2,3-a]isoindol-9(5H)-yl)phenoxy)-N-methylacetamide (compound of 1072), N-ethyl-2-(2-iodo-4-(3-isopropyl-2,5-dioxo-2,3-dihydro[1,3]oxazolo[2,3-a]isoindol-9(5H)-yl)phenoxy)acetamide (compound of 1073), 2-(2-iodo-4-(3-isopropyl-2,5-dioxo-2,3-dihydro[1,3]oxazolo[2,3-a]isoindol-9(5H)-yl)phenoxy)-N-propylacetamide (compound of 1074), 2-(2-chloro-4-(3-isopropyl-2,5-dioxo-2,3-dihydro[1,3]oxazolo[2,3-a]isoindol-9(5H)-yl)phenoxy)-N-propylacetamide (compound of 1092), 2-(2-bromo-4-(3-isopropyl-2,5-dioxo-2,3-dihydro[1,3]oxazolo[2,3-a]isoindol-9(5H)-yl)phenoxy)-N-propylacetamide (compound of 1093), 2-(2-fluoro-4-(3-isopropyl-2,5-dioxo-2,3-dihydro[1,3]oxazolo[2,3-a]isoindol-9(5H)-yl)phenoxy)-N-propylacetamide (compound of 1094), 2-(4-(3-isopropyl-2,5-dioxo-2,3-dihydro[1,3]oxazolo[2,3-a]isoindol-9(5H)-yl)-2-methylphenoxy)-N-propylacetamide (compound of 1095), 2-(2-ethyl-4-(3-isopropyl-2,5-dioxo-2,3-dihydro [1,3]oxazolo[2,3-a]isoindol-9(5H)-yl)phenoxy)-N-propylacetamide (compound of 1435), 2-(2-iodo-4-(3-isopropyl-2,5-dioxo-2,3-dihydro-1H-imidazo[2,1-a]isoindol-9(5H)-yl)phenoxy)-N-propylacetamide (compound of 2074), 2-(4-(3-isopropyl-1-methyl-2,5-dioxo-2,3-dihydro-1H-imidazo[2,1-a]isoindol-9(5H)-yl)phenoxy)-N-propylacetamide (compound of 2471), 3-isopropyl-9b-(4-methoxyphenyl)-1H-pyrrolo[2,1-a]isoindole-2,5(3 H,9bH)-dione (compound of 3011), 2-(4-(3-isopropyl-2,5-dioxo-2,3-dihydro-1H-pyrrolo[2,1-a]isoindol-9(5H)-yl)phenoxy)-N-propylacetamide (compound of 3024), 9b-(3-fluoro-4-methylphenyl)-3-isopropyl-1H-pyrrolo[2,1-a]isoindole-2,5(3H,9bH)-dione (compound of 3056), 2-(2-iodo-4-(3-isopropyl-2,5-dioxo-2,3-dihydro-1H-pyrrolo[2,1-a]isoindol-9(5H)-yl)phenoxy)-N-propylacetamide (compound of 3074), 2-(2-chloro-4-(3-isopropyl-2,5-dioxo-2,3-dihydro-1H-pyrrolo[2,1-a]isoindol-9(5H)-yl)phenoxy-N-propylacetamide (compound of 3092), 2-(2-bromo-4-(3-isopropyl-2,5-dioxo-2,3-dihydro-1H-pyrrolo[2,1-a]isoindol-9(5H)-yl)phenoxy)-N-propylacetamide (compound of 3093), 2-(2-fluoro-4-(3-isopropyl-2,5-dioxo-2,3-dihydro-1H-pyrrolo[2,1-a]isoindol-9(5H)-yl)phenoxy)-N-propylacetamide (compound of 3094), 2-(4-(3-isopropyl-2,5-dioxo-2,3-dihydro-1H-pyrrolo[2,1-a]isoindol-9(5H)-yl)-2-methylphenoxy)-N-propylacetamide (compound of 3095), 2-(4-(3-isopropyl-2,5-dioxo-2,3-dihydro-1H-pyrrolo[2,1-a]isoindol-9(5H)-yl)-2-methylphenoxy)-N-propylethanethioamide (compound of 3476), 2-(2,6-dichloro-4-(3-isopropyl-2,5-dioxo-2,3-dihydro-1H-pyrrolo[2,1-a]isoindol-9(5H)-yl)phenoxy)-N-propylethanethioamide (compound of 3477), 2-(4-(3-isopropyl-1-methyl-2,5-dioxo-2,3-dihydro-1H-pyrrolo[2,1-a]isoindol-9(5H)-yl)phenoxy)-N-propylacetamide (compound of 3481), 2-(2,6-dichloro-4-(3-isopropyl-2-oxo-5-thioxo-2,3-dihydro-1H-pyrrolo[2,1-a]isoindol-9(5H)-yl)phenoxy)-N-propylethanethioamide (compound of 3489), 2-(4-(3-isopropyl-2-(methoxyimino)-5-oxo-1H-pyrrolo[2,1-a]isoindol-9(3H,5H)-yl)-2-methylphenoxy)-N-propylacetamide (compound of 3499), 2-(4-(3-isopropyl-1,1-dimethyl-2,5-dioxo-2,3-dihydro-1H-pyrrolo[2,1-a]isoindol-9(5H)-yl)phenoxy)-N-propylacetamide (compound of 3511), 9b-(3-iodo-4-methoxyphenyl)-3-isopropyl[1,3]thiazolo[2,3-a]isoindole-2,5(3H,9bH)-dione (compound of 4063), N-ethyl-2-(2-iodo-4-(3-isopropyl-2,5-dioxo-2,3-dihydro[1,3]thiazolo[2,3-a]isoindol-9(5H)-yl)phenoxy)acetamide (compound of 4073), 2-(2-iodo-4-(3-isopropyl-2,5-dioxo-2,3-dihydro[1,3]thiazolo[2,3-a]isoindol-9(5H)-yl)phenoxy)-N-propylacetamide (compound of 4074), etc.

Next, description is made on processes for preparing compounds of the general formula [I] of the invention.

Preparation Process A

This preparation process is for preparation of the compounds of the general formula [I-1], the compounds of the general formula [I-2] or the compounds of the general formula [I-3] of the invention, wherein Y is an oxygen atom, a group $NR^5$ or a group $CR^6R^7$ (wherein $R^5$, $R^6$ and $R^7$ are as defined above) in the compounds of the general formula [I]. The compounds of the general formula [I-1] or the compounds of the general formula [I-2] of the invention can not only be synthesized in a usual liquid phase, but also using a solid phase, for example using the combinatorial synthetic method or the parallel synthetic method, remarkably developing in the recent years.

(First Step)

A carboxylic acid or thiocarboxylic acid represented by the general formula [II]

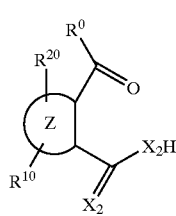

[II]

[wherein, $R^0$ represents (1) an aryl group; (2) a mono- to tricyclic $C_7$–$C_{15}$ aromatic carbocyclic group selected from the group consisting of acenaphthylenyl, adamantyl, anthryl, indenyl, norbornyl and phenanthryl; (3) a 5- or 6-membered heterocyclic group selected from the group consisting of the aforementioned series of groups A; or (4) a monocyclic to tricyclic aromatic heterocyclic groups having per one ring 1 to 5 hetero atoms selected from the group consisting of nitrogen atoms, oxygen atoms and sulfur atoms, selected from the group consisting of the aforementioned series of groups B, each of which groups (1) to (4) may optionally have one or more substituents selected from the group consisting of the aforementioned series of groups C provided that amino, carboxyl, hydroxyl, N-amino $C_1$–$C_{10}$ alkylcarbamoyl and amino $C_1$–$C_6$ alkoxycarbonyl may optionally be protected, $R^{10}$ and $R^{20}$ are the same or different, and represent groups selected from the group consisting of the aforementioned series of groups D provided that amino, carboxyl and hydroxyl may optionally be protected; or straight-chain saturated $C_1$–$C_9$ aliphatic groups, straight-chain unsaturated $C_1$–$C_9$ aliphatic groups, branched saturated $C_1$–$C_9$ aliphatic groups or branched unsaturated $C_1$–$C_9$ aliphatic groups, N—$C_1$–$C_6$ alkylamino groups, $C_1$–$C_6$ alkylthio groups or $C_1$–$C_6$ alkoxy groups, each of which groups may optionally be substituted with the above-mentioned group, and $X_2$ and Z are as defined above]

is reacted with an amine compounds represented by the general formula [III]

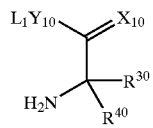

[III]

[wherein, $Y_{10}$ represents an oxygen atom, a group $NR^{50}$ or a group $CR^{60}R^7$, and herein, $R^{50}$ represents a group selected from the group consisting of hydrogen, a protective group for amino groups, halogen, optionally protected hydroxyl, N—$C_1$–$C_6$ alkylsulfonylamino, $C_1$–$C_6$ alkoxy, $C_1$–$C_6$ alkoxycarbonyl, $C_2$–$C_6$ alkanoyl, carbamoyl and N—$C_1$–$C_{10}$ carbamoyl; or a straight-chain saturated $C_1$–$C_9$ aliphatic group, a straight-chain unsaturated $C_1$–$C_9$ aliphatic group, a branched saturated $C_1$–$C_9$ aliphatic group or a branched unsaturated $C_1$–$C_9$ aliphatic groups, each of which groups may optionally be substituted with the above-mentioned group, $R^{60}$ represents a group selected from the group consisting of hydrogen, halogen, optionally protected hydroxyl, N—$C_1$–$C_6$ alkylsulfonylamino, $C_1$–$C_6$ alkoxy, $C_1$–$C_6$ alkoxycarbonyl, $C_2$–$C_6$ alkanoyl, carbamoyl and N—$C_1$–$C_{10}$ carbamoyl; or a straight-chain saturated $C_1$–$C_9$ aliphatic group, a straight-chain unsaturated $C_1$–$C_9$ aliphatic group, a branched saturated $C_1$–$C_9$ aliphatic group or a branched unsaturated $C_1$–$C_9$ aliphatic groups, each of which groups may optionally be substituted with the above-mentioned group, $R^7$ is as defined before, $R^{30}$ and $R^{40}$ are the same or different, and represent (1) groups selected from the group consisting of the aforementioned series of groups E provided that amino, carboxyl and hydroxyl may optionally be protected, (2) groups selected from the group consisting of straight-chain saturated $C_1$–$C_9$ aliphatic groups, straight-chain unsaturated $C_1$–$C_9$ aliphatic groups, branched saturated $C_1$–$C_9$ aliphatic groups and branched unsaturated $C_1$–$C_9$ aliphatic groups, each of which groups may optionally be substituted with the above-mentioned group, (3) (3-1) aryl groups; (3-2) mono- to tricyclic $C_7$–$C_{15}$ aromatic carbocyclic groups selected from the group consisting of acenaphthylenyl, adamantyl, anthryl, indenyl, norbornyl and phenanthryl; (3-3) 5- or 6-membered heterocyclic groups selected from the group consisting of the aforementioned series of groups A; (3-4) monocyclic to tricyclic aromatic heterocyclic groups having per one ring 1 to 5 hetero atoms selected from the group consisting of nitrogen atoms, oxygen atoms and sulfur atoms, selected from the group consisting of the aforementioned series of groups B; or (3-5) straight-chain saturated $C_1$–$C_9$ aliphatic groups, straight-chain unsaturated $C_1$–$C_9$ aliphatic groups, branched saturated $C_1$–$C_9$ aliphatic groups or branched unsaturated $C_1$–$C_9$ aliphatic groups, each of which groups may optionally be substituted with the above-mentioned aryl group, aromatic carbocyclic group, heterocyclic group or aromatic heterocyclic group, each of which groups (3-1) to (3-5) may optionally have one or more substituents selected from the group consisting of the aforementioned series of groups C provided that amino, carboxyl, hydroxyl, N-amino $C_1$–$C_{10}$ alkylcarbamoyl and amino $C_1$–$C_6$ alkoxycarbonyl may be protected, or (4) $R^{30}$ and $R^{40}$ combine together to form a straight-chain saturated $C_1$–$C_9$ aliphatic group, a straight-chain unsaturated $C_1$–$C_9$ aliphatic group, a branched saturated $C_1$–$C_9$ aliphatic group, a branched unsaturated $C_1$–$C_9$ aliphatic group, a 5- or 6-membered saturated carbocyclic group or a 5- or 6-membered unsaturated carbocyclic group, $L_1$ represents a hydrogen atom, a protective group for carboxyl groups, a protective group for amino groups, or a resin carrier of a carboxyl group or an amino group in peptide solid phase synthesis, $X_{10}$ represents an oxygen atom, a sulfur atom or a group $NR^{50}$ (wherein $R^{50}$ is as defined above)], and the protective group of amino groups, the protective group of hydroxy groups or the protective group of carboxyl groups [specifically, the protective groups when $Y_{10}$ (namely $R^{50}$) or $L_1$ has the protective group of amino groups, the protective group of hydroxy groups or the protective group of carboxyl groups] is removed if needed (when $L_1$ is a protective group for amino groups, $R^{50}$ only represents a straight-chain or branched and saturated or unsaturated $C_1$–$C_9$ aliphatic group) to form a compound represented by the general formula [IV']

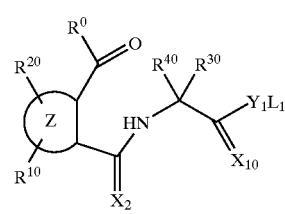

[IV']

[wherein, $Y_1$ represents an oxygen atom, a group $NR^5$ or a group $CR^6R^7$ (wherein, $R^5$, $R^6$ and $R^7$ are as defined before), and $R^0$, $R^{10}$, $R^{20}$, $R^{30}$, $R^{40}$, $L_1$, $X_2$, $X_{10}$ and Z are as defined above).

The compounds represented by the general formula [IV'] are in an equilibrium state with compounds represented by the general formula [V']

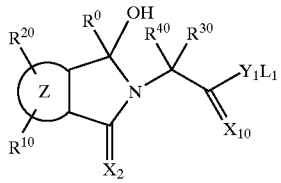

(wherein, $R^0$, $R^{10}$, $R^{20}$, $R^{30}$, $R^{40}$, $L_1$, $X_2$, $X_{10}$, $Y_1$ and Z are as defined above). The compounds of the general formula [IV'] and the compounds of the general formula [V'] are useful as intermediates for preparation of the compounds of the general formula [I] of the invention, and when they are used in reactions, they are usually used as an equilibrium mixture.

As resin carriers for carboxyl groups or amino groups in solid phase synthesis of peptides, polyethylene-divinylbenzene copolymers, polystyrene-divinylbenzene copolymers, etc. can for example be mentioned. Resins comprising these polymers having inserted therein a polyethylene glycol can also be used. Among them, p-benzyloxybenzyl alcohol resins (Wang™ Resin) are preferred as resin carriers for carboxyl groups, and Trityl Chloride Resins are preferred as resin carriers for amino groups.

Reagents used in reactions can suitably be increased or decreased depending on the starting compounds and reaction conditions. Usually, the reaction between a carboxylic acid or thiocarboxylic acid of the general formula [II] and an amine derivative of the general formula [III] can be carried out in a dehydrated inert organic solvent, if needed in the presence of a base, a condensation assistant and/or a condensing agent, at −100° C. to the boiling point of the solvent, preferably 0 to 30° C. for 0.5 to 96 hours, preferably 3 to 24 hours. Then, when the condensed compound has the protective groups for amino groups, protective groups for hydroxy groups or protective groups for carboxyl groups, the protective groups are suitably be removed to complete the reactions.

As inert organic solvents used in the reactions are not particularly limited so long as the reactions are not badly influenced thereby, but specifically, there can for example be mentioned methylene chloride, chloroform, 1,2-dichloroethane, trichloroethane, N,N-dimethylformamide, ethyl acetate, methyl acetate, acetonitrile, acetic anhydride, methyl alcohol, ethyl alcohol, benzene, xylene, water, acetic acid, toluene, 1,4-dioxane. tetrahydrofuran, etc., and in view of ensuring suitable reaction temperature, methylene chloride, chloroform, 1,2-dichloroethane, acetonitrile, N,N-dimethylformamide, 1,4-dioxane, toluene, etc. are preferred.

As bases used in the reaction, there can for example be mentioned tertiary aliphatic amines such as trimethylamine, triethylamine, N,N-diisopropylethylamine, N-methylmorpholine, N-methylpyrrolidine, N-methylpiperidine, N,N-dimethylaniline 1,8-diazabicyclo[5.4.0]undec-7-ene (DBU) and 1,5-azabicyclo[4.3.0]non-5-ene (DBN); aromatic amines such as pyridine, 4-dimethylaminopyridine, picoline, lutidine, quinoline and isoquinoline; alkali metals such as metallic potassium, metallic sodium and metallic lithium; alkali metal hydrides such as sodium hydride and potassium hydride; alkylated alkali metals such as butyllithium; alkali metal alkoxides such as potassium tert-butoxide, sodium ethoxide and sodium methoxide; alkali metal hydroxides such as potassium hydroxide and sodium hydroxide; alkali metal carbonates such as potassium carbonate, etc., and preferred among them are tertiary aliphatic amines, and particularly preferred are triethylamine, N,N-diisopropylethylamine, etc.

As condensation assistants used in the reaction, there can for example be mentioned N-hydroxybenzotriazole hydrate, N-hydroxysuccinimide, N-hydroxy-5-nobornene-2,3-dicarboxyimide, 3-hydroxy-3,4-dihydro-4-oxo-1,2,3-benzotriazole, etc., and preferred among them are N-hydroxybenzotriazole, etc.

Condensing agents used in the reaction, there can for example be mentioned thionyl chloride, N,N-dicyclohexylcarbodiimide, 1-methyl-2-bromopyridium iodide, N,N'-carbonyldiimidazole, diphenylphosphoryl chloride, diphenylphosphoryl azide, N,N'-disuccinimidyl carbonate, N,N'-disuccinimidyl oxalate, 1-ethyl-3-(3-dimethylaminopropyl)carbodiimide hydrochloride, ethyl chloroformate, isobutyl chloroformate, benzotriazo-1-lyl-oxy-tris(dimethylamino)phosphonium hexafluorophosphate, etc., and preferred among them are N,N-dicyclohexylcarbodiimide, 1-ethyl-3-(3-dimethylaminopropyl)carbodiimide hydrochloride, ethyl chloroformate, isobutyl chloroformate, etc.

Reagents used in the reaction can suitably be incresed or decreased depending on the starting compounds and the reaction conditions, but usually, 0.02 to 50 equivalents. preferably 0.2 to 2 equivalents of an amine derivative of the general formula [III], 1 to 50 equivalents, preferably 3 to 5 equivalents of a base, 1 to 50 equivalents, preferably 1 to 5 equivalents of a condensation assistant and/or 1 to 50 equivalents, preferably 1 to 5 equivalents of a condensing agent are used based on a carboxylic acid or thiocarboxylic acid of the general formula [II]. The base, condensation assistant and condensing agent can each be used alone or a combination of two or more.

(Second Step)

Next, an equilibrium mixture of a compound represented by the general formula [IV']

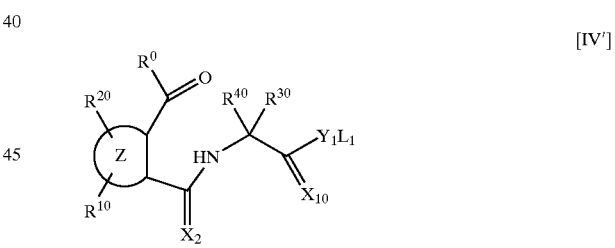

(wherein, $R^0$, $R^{10}$, $R^{20}$, $R^{30}$, $R^{40}$, $L_1$, $X_2$, $X_{10}$, $Y_1$ and Z are as defined above) and a compound represented by the general formula [V']

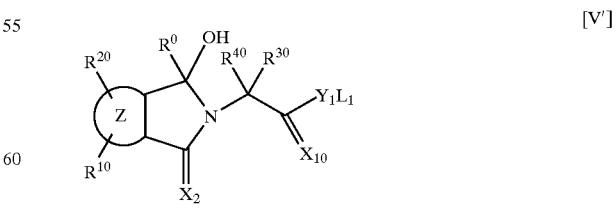

(wherein, $R^0$, $R^{10}$, $R^{20}$, $R^{30}$, $R^{40}$, $L_1$, $X_2$, $X_{10}$, $Y_1$ and Z are as defined above) is reacted with an acid in an inert organic solvent to form a compound represented by the general formula [VIII']

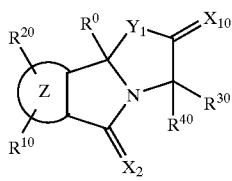

(wherein, $R^0$, $R^{10}$, $R^{20}$, $R^{30}$, $R^{40}$, $X_2$, $X_{10}$, $Y_1$ and Z are as defined above), and the protective groups are suitably removed to form a compound represented by the general formula [I']

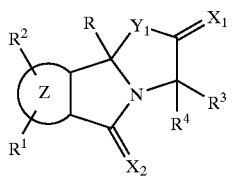

(wherein, R, $R^1$, $R^2$, $R^3$, $R^4$, $X_1$, $X_2$, $Y_1$ and Z are as defined above), namely a compound of the general formula [I-1], a compound of the general formula [I-2] or a compound of the general formula [I-3] or a pharmaceutically acceptable salt thereof. When $L_1$ is a resin carrier for carboxyl groups or amino groups in solid phase synthesis of peptides, by removing the resin carrier after the reaction with the acid, a compound of the general formula [I-1] or a compound of the general formula [I-2] can be prepared. A compound of the general formula [I'] wherein $X_1$ is $NR^5$ (wherein, $R^5$ is as defined before) or $Y_1$ is $NR^5$ or $CR^6R^7$ (wherein, $R^5$, $R^6$ and $R^7$ are as defined before) can usually be prepared using a starting compound having such a substituent, but a desired compound of the general formula [I'] can also be prepared by preparing a compound of the general formula [VIII'] wherein $X_{10}$ is an oxygen atom or NH or $Y_1$ is NH or $CHR^7$ (wherein, $R^7$ is as defined before), and then, by conventional methods, replacing the oxygen atom with $NR^5$ (wherein, $R^5$ is as defined before) or introducing $R^5$ or $R^6$ (wherein, $R^5$ and $R^6$ are as defined before) in NH or $CHR^7$ (wherein, $R^7$ is as defined before). As the introduction methods, there can for example be mentioned a reaction wherein a carbonyl group is reacted with methoxyamine hydrochloride to convert it to a methoxime group, a reaction wherein a group $CHR^7$ (wherein, $R^7$ is as defined before) is reacted with an alkyl metal reagent and then the reaction product is treated with an alkyl halide to give a group $CR^6R^7$ (wherein, $R^6$ and $R^7$ are as defined before), etc.

Reagents used in the reaction can suitably be increased or decreased depending on the starting compounds and the reaction conditions Usually, the reaction can be carried out by reacting an equilibrium mixture between a compound of the general formula [IV] and a compound of the general formula [V] with a catalytic amount of an acid in a dehydrated inert organic solvent, at $-100°$ C. to the boiling point of the solvent, preferably 0 to $30°$ C. for 0.5 to 96 hours, preferably 2 to 24 hours. Then, when the protective groups for amino groups exist, they are suitably removed to complete the reaction.

As to protective groups protecting functional groups other than $L_1$, N-protective groups, protective groups for carboxyl groups, protective groups for hydroxy groups, etc. can simultaneously be removed by suitably selecting a method to remove protective groups, reaction conditions, etc. It is also possible to selectively remove one of N-protective groups, protective groups for carboxyl groups, protective groups for hydroxy groups. The order of removal of the protective groups is not particularly limited.

As protective groups for hydroxyl groups, there can for example be mentioned lower alkylsilyl groups such as tert-butyldimethylsilyl and tert-butyldiphenylsilyl; lower alkoxymethyl groups such as methoxymethyl and 2-methoxyethoxymethyl; aralkyl groups such as benzyl and p-methoxybenzyl; acyl groups such as formyl and acetyl, etc., and tert-butyldimethylsilyl, acetyl, etc. are preferred.

As protective groups for amino groups, there can for example be mentioned aralkyl groups such as benzyl and p-nitrobenzyl; acyl groups such as formyl and acetyl; lower alkoxycarbonyl groups such as ethoxycarbonyl and tert-butoxycarbonyl; aralkyloxycarbonyl groups such as benzyloxycarbonyl and p-nitrobenzyloxycarbonyl, etc., and p-nitrobenzyl, tert-butoxycarbonyl, benzyloxycarbonyl, etc. are preferred.

As protective groups for carboxyl groups, there can for example be mentioned lower alkyl groups such as methyl, ethyl and tert-butyl; aralkyl groups such as benzyl and p-methoxybenzyl, etc., and methyl, ethyl, tert-butyl, benzyl, etc. are preferred.

Methods for removing the protective groups are varied depending on their kinds and the stability of compounds, but removal of the protective groups can be carried out by methods described in literatures (e.g., see "Protective Groups in Organic Synthesis" written by T. W. Green, John Wiley & Sons Co. (1981)) or by a little modified ones thereof, for example by solvolysis using an acid or a base, chemical reduction using a metal hydride complex or the like, catalytic reduction using palladium-carbon catalysts, Raney nickel catalysts or the like, etc.

Inert organic solvents used in the invention are not particularly limited so long as the reaction is not badly influenced, and the aforementioned inert organic solvents can be mentioned.

As acids used in the invention, there can for example be mentioned inorganic acids such as hydrochloric acid, nitric acid, hydrobromic acid, sulfuric acid, hydrofluoric acid and perchloric acid; Lewis acids such as trifluoroboric acid; sulfonic acids such as p-toluenesulfonic acid, trifluoromethanesulfonic acid and methanesulfonic acid; organic acids such as formic acid, trifluoroacetic acid and acetic acid, etc., and Lewis acids such as trifluoroboric acid, and organic acids such as trifluoroacetic acid, etc. are preferred.

After completion of the reaction, by purifying the product by usual known methods, a compound of the general formula [I-1], [I-2] or [I-3] can be obtained. Isolation and purification of the compound of the general formula [I-1], [I-2] or [I-3] can be carried out by known separation means such as extraction with solvents, recrystallization and chromatography.

Preparation Process B

This preparation process is for preparation of the compounds of the general formula [I-4] of the invention, namely the compounds of the general formula [I] wherein Y is a sulfur atom.

An equilibrium mixture between a compound represented by the general formula [IV"]

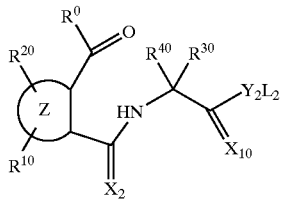

[IV"]

(wherein, $Y_2$ represents an oxygen atom, $L_2$ represents a hydrogen atom, and $R^0$, $R^{10}$, $R^{20}$, $R^{30}$, $R^{40}$, $X_2$, $X_{10}$ and Z are as defined before) and a compound represented by the general formula [V"]

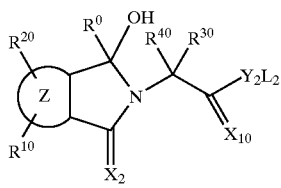

[V"]

(wherein, $R^0$, $R^{10}$, $R^{20}$, $R^{30}$, $R^{40}$, $L_2$, $X_2$, $X_{10}$, $Y_2$ and Z are as defined before) is reacted with a sulfurizing agent to form an equilibrium mixture between a compound represented by the general formula [VI"]

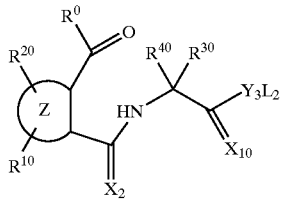

[VI"]

(wherein, $Y_3$ represents a sulfur atom, and $R^0$, $R^{10}$, $R^{20}$, $R^{30}$, $R^{40}$, $L_2$, $X_2$, $X_{10}$ and Z are as defined before) and a compound represented by the general formula [VII"]

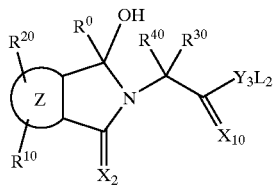

[VII"]

(wherein, $R^0$, $R^{10}$, $R^{20}$, $R^{30}$, $R^{40}$, $L_2$, $X_2$, $X_{10}$, $Y_3$ and Z are as defined before), and then, the formed equilibrium mixture is reacted with an acid in an inert organic solvent at a temperature of from room temperature to the boiling point of the solvent to form a compound represented by the general formula [VIII"]

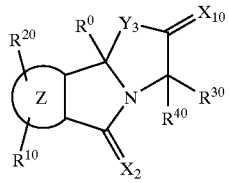

[VIII"]

(wherein, $R^0$, $R^{10}$, $R^{20}$, $R^{30}$, $R^{40}$, $X_2$, $X_{10}$, $Y_3$ and Z are as defined before), and the protective groups are suitably removed to obtain a compound represented by the general formula [I"]

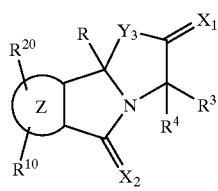

[I"]

(wherein, R, $R^1$, $R^2$, $R^3$, $R^4$, $X_1$, $X_2$, $Y_3$ and Z are as defined before) or a pharmaceutically acceptable salt thereof.

Reagents used in the reaction can suitably be increased or decreased depending on the starting compounds and the reaction conditions. Usually, an equilibrium mixture between a compound of the general formula [IV"] and a compound of the general formula [V"] is reacted with a sulfurizing agent in a dehydrated inert organic solvent at −100° C. to the boiling point of the solvent, preferably 0 to 30° C. for 0.5 to 96 hours, preferably 1 to 12 hours to form an equilibrium mixture between a compound of the general formula [VI"] and a compound of the general formula [VII"], and then reaction is carried out in the same manner as in the second step in Preparation process A to form a compound of the general formula [VIII"], and then after suitable removal of the protective groups, purification is carried out according to suitable methods to obtain a compound of the general formula [I"], namely a compound of the general formula [I-4]. Isolation and purification of the compound of the general formula [I-4] or the salt thereof from the reaction mixture can be carried out by known separation means such as extraction with solvents, recrystallization and chromatography, as in Preparation process A.

A carboxylic acid or thiocarboxylic acid of the general formula [II] is known in literatures, or can be prepared by reacting an aryl halide represented by the general formula [IX]

$R^0$—X  [IX]

(wherein, X represents a halogen atom, and $R^0$ is as defined before) with metallic magnesium in a dehydrated etherial solvent such as diethyl ether or tetrahydrofuran at from a low temperature to the boiling point of the solvent to prepare a Grignard's reagent, and then reacting the Grignard's reagent with an optionally substituted acid anhydride in a dehydrated inert organic solvent at a low temperature to room temperature.

A compound of the general formula [II] can also be prepared by subjecting an arene compound of the general formula [X]

$R^0$—H  [X]

(wherein, $R^0$ is as defined before) and a substituted or unsubstituted acid anhydride to Friedel-Crafts' acylation reaction, if necessary in the presence of an aforementioned acid.

Compounds of the general formula [III] are known in literatures, or are amino acids or amino acid derivatives derivable from the amino acids, represented by the general formula [III]

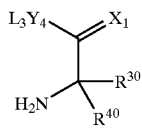
[III]

(wherein, $Y_4$ represents an oxygen atom, L3 represents a hydrogen atom, a protective group for carboxy groups or a resin carrier of carboxyl groups in solid phase synthesis of peptides, and $R^{30}$, $R^{40}$ and $X_1$ are as defined before).

A compounds of the general formula [III] can be prepared by reacting an amino acid, or a carboxylic acid or thiocarboxylic acid, which is an amino acid derivative derivable from the amino acid, represented by the general formula [XI]

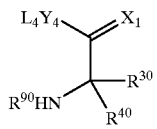
[XI]

(wherein, $L_4$ represents a hydrogen atom or a protective group for carboxyl groups, $R^{90}$ represents a hydrogen atom or a protective group for amino groups, and $R^{30}$, $R^{40}$, $X_1$ and $Y_4$ are as defined before)
with an amine derivative represented by the general formula [XII]

$R^{50}NH—R^{80}$  [XII]

(wherein, $R^{80}$ represents a protective group for amino groups or a resin carrier of amino groups in solid phase synthesis of peptides, and $R^{50}$ is as defined before), and then, in the case of $R^{90}$ being a protective group for amino groups, removing the protective group for amino groups.

A compounds of the general formula [III] can also be prepared by reacting an amino acid or amino acid derivative represented by the general formula [XIII]

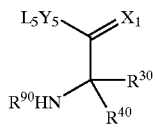
[XIII]

(wherein, $Y_5$ represents an oxygen atom or a nitrogen atom, $L_5$ represents a protective group for carboxyl groups, a hydrogen atom or a protective group for amino groups, and $R^{30}$, $R^{40}$, $R^{90}$ and $X_1$ are as defined before) with a Grignard's reagent represented by the general formula [XIV]

$R^{60}R^7CH—MgX$  [XIV]

(wherein, X represents a halogen atom, and $R^{60}$ and $R^7$ are as defined before), and then, in the case of $R^{90}$ being a protective group for amino groups, removing the protective group for amino groups.

For specifically demonstrating the usefulness of the invention, the compound of Example 1002 was used, and after administration of the compound, an influence of the compound on the GLP-1 concentration in the plasma was examined. The test method and the results are shown below.

(Test Method)

Male Wistar rats (9 weeks old, n=6) bred under the condition of free access to food and water were fasted overnight before the test, and a suspension of a test compound in 1% carboxymethylcellulose solution was administered. As a control group, 1% carboxymethylcellulose solution was orally administered to the rats. Thirty minutes after the administration of the test compound, blood was withdrawn, and subjected to centrifugation to separate the plasma. The GLP-1 concentration in the plasma was determined by the radioimmunoassay method using commercially available anti GLP-1 antibody (Cosmo Co., Ltd.). The obtained values were analyzed using Student T test, and the statistical significant difference was calculated. The results are shown in the following Table 46.

=Test Results=

TABLE 46

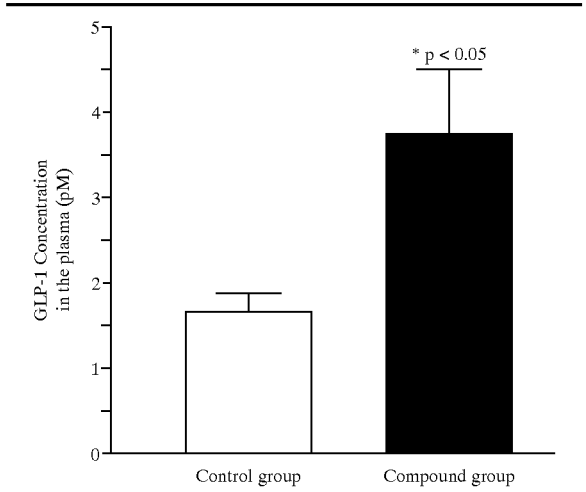

As apparent from the above result, at 30 minutes after the administration, in the group to which 30 mg/kg of the compound was administered, significantly higher GLP-1 concentration in the blood (plasma) was observed in comparison with the control group. From the result, it is demonstrated that the compounds of the invention have an activity to be able to achieve high GLP-1 concentration in the blood of rats.

Since the compounds of the invention have an activity to bring about high GLP-1 concentration in the blood, they are useful as drugs for treating diabetes, prophylactic agents for chronic complications of diabetes, or drugs against obesity.

The compounds of the general formula [I] of the invention can be used as an effective ingredient in drugs, particularly agents for treating diabetes, prophylactic agents for chronic complications of diabetes, or drugs against obesity. The compounds of the invention in medicaments, particularly agents for treating diabetes, prophylactic agents for chronic complications of diabetes, or drugs against obesity, include pharmaceutically acceptable conventional ones, for example, compounds represented by the general formula [I]

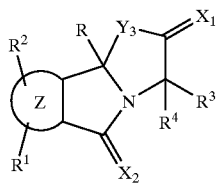

[I]

(wherein, R, $R^1$, $R^2$, $R^3$, $R^4$, $X_1$, $X_2$, Y and Z are as defined before), pharmaceutically acceptable esters or salts in carboxyl groups on R, $R^1$, $R^2$, $R^3$ or $R^4$, pharmaceutically acceptable salts in hydroxyl groups on R, $R^1$, $R^2$, $R^3$ or $R^4$, pharmaceutically acceptable salts in amino groups on R, $R^1$, $R^1$, $R^3$ or $R^4$.

As salts in the carboxyl groups or the hydroxyl groups, there can for example be mentioned alkali metal salts such as sodium salts and potassium salts, alkaline earth metal salts such as calcium salts and magnesium salts.

As acid addition salts in the amino groups, there can for example be mentioned inorganic salts such as hydrochlorides, sulfates, nitrates, phosphates, carbonates, bicarbonates and perchlorates, organic acid salts such as acetates, propionates, lactates, maleates, flimarates, tartrates, malates, citrates and ascorbates, sulfonates such as methanesulfonates, isethionates, benzenesulfonates and toluenesulfonates, acidic amino acid salts such as aspartates and glutamates, etc.

When compounds of the invention are used as agents for treating diabetes, prophylactic agents for chronic complications of diabetes, or drugs against obesity, they can also be used as their pharmacologically acceptable salts. As typical examples of pharmacologically acceptable salts, there can for example be mentioned salts with alkali metals such as sodium and potassium.

Preparation of pharmacologically acceptable salts of compounds of the invention can be carried out by appropriately combining processes usually used in the field of organic synthetic chemistry. Specifically, there can be mentioned subjecting solutions of compounds of the invention in a free form to acidimetry using an alkali solution, etc.

As dosage forms of the compounds of the invention when used as agents for treating diabetes, prophylactic agents for chronic complications of diabetes, or drugs against obesity, various forms can be selected, and there can for example be mentioned oral agents such as tablets, capsules, powders, granules and liquid medicines, sterilized liquid parenteral agents such as solutions and suspensions, etc.

Solid pharmaceutical preparations such as tablets, capsules, granules and powders can be prepared using compounds of the invention alone, but can also be prepared further using suitable additives. As the suitable additives, there can be mentioned conventional additives, for example, sugars such as lactose and glucose, starches such as corn, wheats and rices, fatty acids such as stearic acid, inorganic salts such as sodium metasilicate, magnesium aluminate and anhydrous calcium phosphate, synthetic macromolecules such as polyvinylpyrrolidone and polyalkylene glycols, fatty acid salts such as calcium stearate and magnesium stearate, alcohols such as stearyl alcohol and benzyl alcohol, synthetic cellulose derivatives such as methylcellulose, carboxymethylcellulose, ethylcellulose and hydroxypropylmethylcellulose, and further, water, gelatin, talc, vegetable oils, gum arabic, etc.

These solid pharmaceutical preparations such as tablets, capsules, granules and powders can contain, generally 0.1 to 100% by weight, preferably 5 to 100% by weight of the effective ingredient. Liquid pharmaceutical preparations can be prepared as forms of suspensions, syrups, injections, etc. using suitable additives usually used in liquid pharmaceutical preparations, such as water, alcohols or vegetable oils including soybean oil, peanut oil and sesame oil. Particularly, as solvents suitable in parenteral administration, there can for example be mentioned distilled water for injection, aqueous lidocaine hydrochloride solution (for intramuscular injection), physiological saline, aqueous glucose solution, ethanol, liquids for intravenous injection (e.g. aqueous solutions of citric acid, sodium citrate, etc.), electrolyte solutions (e.g., for intravenous injection by drip, for intravenous injection), etc., or their mixed solutions.

Liquid pharmaceutical preparations such as suspensions and syrups for oral administration can contain 0.5 to 10% by weight of an effective ingredient.

The actually preferred dose of the compounds of the invention can appropriately be increased or decreased depending on kinds of compounds used, kinds of compositions prepared, application frequency, particular sites to be treated, and states of diseases of patients. For example, the dose of each compound per day and per one adult is 0.1 to 1,000 mg in the case of oral administration, and 0.01 to 500 mg in the case of parenteral administration. The frequency of administration is varied depending on administration methods and symptoms, but the administration can be made in a time or in divided 2 to 5 times.

BEST MODE FOR CARRYING OUT THE INVENTION

The invention is further specifically described below according to examples, but the invention is not limited thereby at all.

In thin layer chromatography in examples, Silicagel $60F_{245}$(Merck) was used as plates, and UV detectors as detection means. Wakogel™ C-300 (Wako Pure Chemical) was used as silica gel for columns, and LC-SORB™ SP-B-ODS (Chemco) or YMC-GEL™ ODS-AQ 120-S50 (Yamamura Chemical Laboratory) as silica gel for reverse-phase columns.

i-Bu: isobutyl group, n-Bu: n-butyl group, t-Bu: t-butyl group
Me: methyl group, Et: ethyl group, Ph: phenyl group
i-Pr: isopropyl group, n-Pr: n-propyl group, $CDCl_3$: heavy chloroform
methanol-$d_4$: heavy methanol, DMSO-$d_6$: heavy dimethylsulfoxide

EXAMPLES

Example 1001

9b-(2-Methoxyphenyl)-3-(1-methylethyl) [1,3] oxazolo[2-3-a]isoindole-2,5(3H,9bH)-dione
(Compound of $R^1$:H; $R^2$:H; $R^3$:i-Pr; $R^4$:H; Z:Ph; R:2-MeO-Ph in the Following General Formula [I-1])

A solution in tetrahydrofuran (17 ml) of a Grignard's reagent prepared from magnesium (120 mg, 5.1 mmol) and 2-bromoanisole (0.55 ml, 4.4 mmol) was added dropwise to a solution of phthalic anhydride (500 mg, 3.4 mmol) in tetrahydrofuran (12 ml) in an atmosphere of nitrogen at −70° C. over a period of 10 minutes. The reaction mixture was stirred at −70° C. for 2.5 hours, and aqueous saturated ammonium chloride solution was added. The mixture was extracted with ethyl acetate, and the organic layer was washed with aqueous saturated sodium chloride solution, dried and concentrated under reduced pressure to obtain crude 2-(2-methoxybenzoyl)benzoic acid (770 mg, yield: 90%).

1-Hydroxybenzotriazole hydrate (490 mg, 3.6 mmol) and 1-(3-dimethylaminopropyl)-3-ethylcarbodiimide hydrochloride (690 mg, 3.6 mmol) were added to a solution of 2-(2-methoxybenzoyl)benzoic acid (750 mg, 3.0 mmol), D-valine methyl ester hydrochloride (550 mg, 3.4 mmol) and triethylamine (1.26 ml, 9.1 mmol) in methylene chloride (40 ml) under ice cooling, and the reaction mixture was stirred at room temperature for 3 hours. Aqueous saturated ammonium chloride solution was added to the reaction mixture, and the mixture was extracted with chloroform. The organic layer was washed with aqueous saturated sodium chloride solution, dried and concentrated under reduced pressure. The resulting residue was dissolved in methanol (15 ml), 4N aqueous sodium hydroxide solution (8 ml) was added, and the reaction mixture was stirred at room temperature for 12 hours and concentrated under reduced pressure. 1N Aqueous hydrochloric acid solution (40 ml) and ethyl acetate were added to the resulting residue, and the organic layer was dried and concentrated under reduced pressure. The resulting unpurified carboxylic acid was dissolved in methylene chloride (6 ml), trifluoroacetic acid (5 ml) was added, and the reaction mixture was stirred at room temperature for 2 hours. The reaction mixture was concentrated under reduced pressure, the residue was subjected three times to azeotropic distillation with toluene, and the mixture was concentrated under reduced pressure. The resulting residue was purified by silica gel column chromatography (hexane: ethyl acetate=3:2) to obtain the captioned compound (470 mg, yield: 46%) as light yellow oily matter).

$^1$HNMR(CDCl$_3$) δ:0.85(3H,d,J=6.6 Hz),1.10(3H,d,J=6.6 Hz),1.56–1.66(1H,m),3.48(3H,s),4.17(1H,d,J=10.5 Hz), 6.83(1H,d,J=7.8 Hz),7.04(1H,t,J=7.8 Hz),7.34–7.36(1H,m), 7.38(1H,t,J=7.8 Hz),7.53–7.60(2H,m),7.75(1H,d,J=7.8 Hz), 7.89–7.92(1H,m) FAB-MS(m/e):338[M+H]$^+$

In the same manner as in Example 1001, compounds of Examples 1002 to 1222. 1413, and 1427 to 1439 corresponding to the compound numbers of the compounds of the general formula [I-1] in the aforementioned compound lists were obtained. Physical constants of these compounds are shown below.

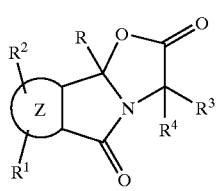

[I-1]

Example 1002

$R^1$:H;$R^2$:H;$R^3$:i-Pr;$R^4$:H;Z:Ph;R:Ph $^1$HNMR(CDCl$_3$) δ:0.92(3H,d,J=6.6 Hz), 1.11 (3H,d,J= 6.7 Hz),1.56–1.67(1H,m),4.22(1H,d, J=9.8 Hz),7.33(1H,dd, J=2.7,5.8 Hz),7.37–7.62(7H,m),7.92(1H,dd,J=2.8,5.8 Hz) FAB-MS(m/e):308[M+H]$^+$

Example 1003

$R^1$:H;$R^2$ :H;$R^3$:i-Pr;$R^4$:H;Z:Ph;R:2-NH$_2$-Ph
ESI-MS(m/e):323[M+H]$^+$

Example 1004

$R^1$:H;$R^2$:H;$R^3$:i-Pr;$R^4$:H;Z:Ph;R:4-F-Ph
ESI-MS(m/e):326[M+H]$^+$

Example 1005

$R^1$:H;$R^2$:H;$R^3$:i-Pr;$R^4$:H;Z:Ph;R:4-Et$_2$N-Ph
ESI-MS(m/e):379[M+H]$^+$

Example 1006

$R^1$:H;$R^2$ :H;$R^3$:i-Pr;$R^4$:H;Z:Ph;R:4-Cl-Ph $^1$HNMR(CDCl$_3$) δ:0.92(3H,d,J=6.6 Hz),1.12(3H,d,J=7.2 Hz),1.54–1.70(1H,m),4.21(1H, d,J=9.4 Hz),7.32(1H,ddd,J= 0.6,2.4,5.4 Hz),7.37(2H,d,J=9.0 Hz),7.43(2H,d,J=9.0 Hz), 7.58–7.62(2H,m),7.91(1H,ddd,J=0.6,2.4,5.4 Hz) FAB-MS (m/e):342[M+H]$^+$

Example 1007

$R^1$:H;$R^2$:H;$R^3$:i-Pr;$R^4$:H;Z:Ph;R:4-HO-Ph $^1$HNMR(CDCl$_3$) δ:0.93(3H,d,J=6.7 Hz),1.11(3H,d,J=6.7 Hz),1.59–1.75(1H,m),4.19(1H,d,J=9.9 Hz),6.85(2H,d,J=8.8 Hz),7.33–7.37(3H,m),7.57–7.60(2H,m),7.88–7.91(1H,m) FAB-MS(m/e):324[M+H]$^+$

Example 1008

$R^1$:H;$R^2$:H;$R^3$:i-Pr;$R^4$:H;Z:Ph;R:3-MeO-Ph $^1$HNMR(CDCl$_3$) δ:0.96(3H,d,J=6.6 Hz), 1.12(3H,d,J=6.6 Hz),1.63–1.71(1H,m),3.79(3H,s),4.21(1H,d,J=9.9 Hz),6.90 (1H,dd,J=1.4,8.0 Hz),7.02(1H,d,J=1.4 Hz),7.08(1H,d, J=8.0 Hz),7.31(1H,t,J=8.0 Hz),7.36–7.38(1H,m),7.56–7.62(2H, m),7.89-7.92(1H,m) FAB-MS(m/e):338[M+H]$^+$

Example 1009

$R^1$:H;$R^2$:H;$R^3$:i-Pr;$R^4$:H;Z:Ph;R:3-HO-Ph $^1$HNMR(CDCl$_3$) δ:0.95(3H,d,J=6.6 Hz),1.12(3H,d,J=6.6 Hz),1.67–1.72(1H,m),4.21(1H,d,J=9.9 Hz),6.85(1H,ddd,J= 0.9,2.5,7.9 Hz),6.97(1H,d,J=2.5 Hz),7.06(1H,dd,J=0.9,7.9 Hz),7.27(1H,t,J=7.9 Hz),7.34–7.38(1H,m),7.54–7.62(2H, m),7.85–7.88(1H,m) FAB-MS(m/e):324[M+H]$^+$

Example 1010

$R^1$:H;$R^2$:H;$R^3$:i-Pr;$R^4$:H;Z:Ph;R:3-NH$_2$-Ph
ESI-MS(m/e):323[M+H]$^+$

Example 1011

$R^1$:H;$R^2$:H;$R^3$:i-Pr;$R^4$:H;Z:Ph;R:4-MeO-Ph $^1$HNMR(CDCl$_3$) δ:0.93(3H,d,J=6.7 Hz),1.11(3H,d,J=6.7 Hz),1.63–1.69(1H,m),3.82(3H,s),4.19(1H,d,J=9.9 Hz),6.89 (2H,d,J=8.8 Hz),7.32–7.37(1H,m),7.40(2H,d,J=8.8 Hz). 7.57–7.60 (2H,m),7.89–7.92(1H,m) FAB-MS(m/e):338[M+ H]$^+$

Example 1012

$R^1$:H;$R^2$:H;$R^3$:i-Pr;$R^4$:H;Z:Ph;R:4-Me-Ph $^1$HNMR(CDCl$_3$) δ:0.94(3H,d,J=6.6 Hz),1.11(3H,d,J=6.7 Hz),1.57–1.72(1H,m),2.36(3H,s),4.20(1H,d,J=10.0 Hz), 7.22(1H,d,J=8.5 Hz),7.32–7.36(1H,m),7.37(1H,d, J=8.5 Hz),7.55–7.61(2H,m),7.88–7.95(1H,m) FAB-MS(m/e):322 [M+H]$^+$

Example 1013

R$^1$:H;R$^2$:H;R$^3$:i-Pr;R$^4$:H;Z:Ph;R:3-Me-Ph $^1$HNMR(CDCl$_3$) δ:0.86(3H,d,J=6.7 Hz),1.03(3H,d,J=6.7 Hz),1.52–1.60(1H,m),2.27(3H,s),4.13(1H,d,J=9.9 Hz), 7.09–7.20(4H,m,),7.20–7.29(1H,m),7.47–7.53(2H,m), 7.82–7.84 (1H,m) FAB-MS(m/e):322[M+H]$^+$

Example 1014

R$^1$:H;R$^2$:H;R$^3$:i-Pr;R$^4$:H;Z:Ph;R:t-BuO$_2$CCH$_2$O-Ph $^1$HNMR(CDCl$_3$) δ:0.92(3H,d,J=6.7 Hz),1.10(3H,d,J=6.7 Hz),1.47(9H,s),1.60–1.68(1H,m),4.19(1H,d,J=9.9 Hz),4.52 (2H,s),6.89(2H,d,J=8.8 Hz),7.40(2H,d,J=8.8 Hz), 7.32–7.91 (4H,m) FAB-MS(m/e):438[M+H]$^+$

Example 1015

R$^1$:H;R$^2$:H;R$^3$:i-Pr;R$^4$:H;Z:Ph;R:HO$_2$CCH$_2$O-Ph $^1$HNMR(CDCl$_3$) δ:0.93(3H,d,J=6.6 Hz),1.11(3H,d,J=6.6 Hz),1.60–1.70(1H,m),4.19(1H,d,J=9.9 Hz),4.69(2H,s),6.84 (2H,d,J=9.0 Hz),7.43(2H,d,J=9.0 Hz),7.31–7.92(4H,m) FAB-MS(m/e):382[M+H]$^+$

Example 1016

R$^1$:H;R$^2$:H;R$^3$:i-Pr;R$^4$:H;Z:Ph; R:4-tBuO$_2$C(CH$_2$)$_5$O-Ph $^1$HNMR(CDCl$_3$) δ:0.94(3H,d,J=6.6 Hz),1.11(3H,d,J=6.6 Hz),1.439–1.441(9H,m),1.49–1.84(7H,m),2.24(2H,t,J=7.2 Hz),3.95(2H,t,J=6.4 Hz),4.19(1H,d,J=10.1 Hz),6.87(2H,d,J =8.4 Hz),7.32–7.35(1H,m),7.38(2H,d,J=8.4 Hz),7.55–7.60 (2H,m),7.88–7.91(1H,m) FAB-MS(m/e):494[M+H]$^+$

Example 1017

R$^1$:H;R$^2$:H;R$^3$:i-Pr;R$^4$:H;Z:Ph; R:4-HO$_2$C(CH$_2$)$_5$O-Ph $^1$HNMR(CDCl$_3$) δ:0.83(3H,d,J=6.7 Hz),1.10(3H,d,J=6.7 Hz),1.47–1.85(7H,m)2.39(2H,t,J=7.8 Hz),3.85(2H,t,J=7.2 Hz),4.18(1H,d,J=10.7 Hz),6.87(2H,d,J=8.9 Hz), 7.31–7.39 (1H,m),7.39(2H,d,J=8.9 Hz),7.54–7.61(2H,m),7.87–7.92 (1H,m) FAB-MS(m/e):438[M+H]$^+$

Example 1018

R$^1$:H;R$^2$:H;R$^3$:i-Pr;R$^4$:H;Z:Ph;R:4-HO(CH$_2$)$_3$O-Ph $^1$HNMR(CDCl$_3$) δ:0.93(3H,d,J=6.7 Hz),1.11(3H,d,J=6.7 Hz),1.61–1.711 (1H,m),2.04(2H, quintet,J=5.9 Hz),3.86 (2H,t,J=5.9 Hz),4.12(2H,t,J=5.9 Hz),4.20(1H,d,J=9.8 Hz), 6.90(2H, d,J=8.8 Hz),7.32–7.91 (6H,m) FAB-MS(m/e):382 [M+H]$^+$

Example 1019

R$^1$:H;R$^2$:H;R$^3$:i-Pr;R$^4$:H;Z:Ph;R:4-HO(CH$_2$)$_2$O-Ph $^1$HNMR(CDCl$_3$) δ:0.95(3H,d,J=6.7 Hz),1.13(3H,d,J=6.7 Hz),1.63–1.71(1H,m), 3.99(2H,t,J=4.4 Hz),4.11(2H,t,J=4.4 Hz),4.22(1H,d,J=9.9 Hz),6.94(2H,d,J=8.9 Hz),7.29–7.93 (6H,m) FAB-MS(m/e):368[M+H]$^+$

Example 1020

R$^1$:H;R$^2$:H;R$^3$:i-Pr;R$^4$:H;Z:Ph; R:4-HOC(Me)$_2$(CH$_2$)$_2$O-Ph $^1$HNMR(CDCl$_3$) δ:0.95(3H,d,J=6.7 Hz),1.13(3H,d,J=6.7 Hz),1.32(6H,s),1.61–1.68(1H,m),2.01(2H,t,J=6.4 Hz),4.19 (2H,t,J=6.4 Hz),4.21(1H,d,J=9.9 Hz),6.91 (2H,d,J=8.9Hz),7.41(2H,d,J=8.9 Hz),7.33–7.92(4H,m) FAB-MS(m/e) :410[M+H]$^+$

Example 1021

R$^1$:H;R$^2$:H;R$^3$:i-Pr;R$^4$:H;Z:Ph;R:4-PhCH$_2$O-Ph $^1$HNMR(CDCl$_3$) δ:0.94(3H,d,J=6.6 Hz),1.12(3H,d,J=6.6 Hz),1.60–1.75(1H,m),4.20(1H,d, J=9.9 Hz),5.06(2H,s),6.98 (2H,d,J=8.9 Hz),7.33–7.92(11H,m) FAB-MS(m/e):414[M+H]$^+$

Example 1022

R$^1$:H;R$^2$:H;R$^3$:i-Pr;R$^4$:H;Z:Ph; R:4-MeNHCOCH$_2$O-Ph $^1$HNMR(CDCl$_3$) δ:0.92(3H,d,J=6.7 Hz),1.11(3H,d,J=6.7 Hz),1.60–1.68(1H,m),2.92(3H,d,J=5.1 Hz),4.20(1H,d,J=9.9 Hz),4.50(2H,s),6.56–6.59(1H,m),6.93(2H,d,J=8.9 Hz), 7.32–7.36(1H,m),7.45(2H,d,J=8.9 Hz),7.57–7.63(2H,m), 7.90–7.93(1H,m) FAB-MS(m/e):395[M+H]$^+$

Example 1023

R$^1$:H;R$^2$:H;R$^3$:i-Pr;R$^4$:H;Z:Ph; R:4-EtNHCOCH$_2$O-Ph $^1$HNMR(CDCl$_3$) δ:0.92(3H,d,J=6.7 Hz),1.11(3H,d,J=6.7 Hz)1.18(3H,t,J=7.3 Hz), 1.60–1.70(1H,m),3.40(2H,dt,J= 5.9,7.3 Hz),4.20(1H,d,J=9.8 Hz),4.48(2H,s),6.53(1H,brs), 6.93(2H,d,J=9.0 Hz),7.31–7.92(6H,m) FAB-MS(m/e):409 [M+H]$^+$

Example 1024

R$^1$:H;R$^2$:H;R$^3$:i-Pr;R$^4$:H;Z:Ph;R:4-n-PrNHCOCH$_2$O-Ph $^1$HNMR(CDCl$_3$) δ:0.89–0.94(6H,m),1.12(3H,d,J=7.2 Hz),1.53–1.66(3H,m),3.32 (2H,dt, J=7.2 Hz),4.21(1H,d,J= 9.9 Hz),4.50(2H,s),6.53(1H,br),6.95(2H,d,J=8.9 Hz), 7.31–7.93(6H,m) FAB-MS(m/e):414[M+H]$^+$

Example 1025

R$^1$:H;R$^2$:H;R$^3$:i-Pr;R$^4$:H;Z:Ph;R:4-n-BuNHCOCH$_2$O-Ph $^1$HNMR(CDCl$_3$) δ:0.92(3H,t,J=7.2 Hz),0.92(3H,d,J=6.6 Hz),1.11(3H,d,J=6.6 Hz),1.26–1.40(2H,m),1.48–1.70(3H, m),3.35(2H,q,J=6.8 Hz),4.21(1H,d,J=9.8 Hz),4.49(2H,s), 6.52-6.53(1H,m),6.94(2H,d,J=9.0 Hz),7.31–7.36(1H,m), 7.45(2H,d,J=9.0 Hz),7.57–7.63(2H,m),7.88–7.93(1H,m) FAB-MS(m/e):437[M+H]$^+$

Example 1026

R$^1$:H;R$^2$:H;R$^3$:i-Pr;R$^4$:H;Z:Ph;R:4-CH$_2$=CHCH$_2$NHCOCH$_2$O-Ph $^1$HNMR(CDCl$_3$) δ:0.93(3H,d,J=6.7 Hz),1.13(3H,d,J=6.7 Hz),1.61–1.67(1H,m),3.98–4.02(2H,m),4.22(1H,d,J=9.8 Hz),4.54(2H,s),5.82–5.91(1H,m),6.65(1H,br),6.96(2H,d, J=8.9 Hz),7.33–7.94(6H,m) ESI-MS(m/e):421[M+H]$^+$

Example 1027

R$^1$:H;R$^2$:H;R$^3$:i-Pr;R$^4$:H;Z:Ph; R:4-Me(CH$_2$)$_9$NHCOCH$_2$O-Ph $^1$HNMR(CDCl$_3$) δ :0.87(3H,t,J=6.5 Hz),0.92(3H,d,J=6.6 Hz),1.11(3H,d,J=6.6 Hz),1.25–1.67(7H,m),3.33(2H,dt,J=

6.8 Hz),4.20(1H,d,J=9.8 Hz),4.48(2H,s),6.61(1H,br),6.93 (2H, d,J=9.0 Hz),7.32–7.92(6H,m) FAB-MS(m/e):521[M+ H]$^+$

Example 1028

$R^1$:H;$R^2$:H;$R^3$:i-Pr;$R^4$:H;Z:Ph;R:4-$N_3(CH_2)_3$O-Ph $^1$HNMR(CDCl$_3$) δ :0.96(3H,d,J=6.6 Hz),1.14(3H,d,J=6.6 Hz),1.60–1.69(1H,m),2.07–2.12(2H,m),3.54(2H,t,J=6.6 Hz),4.07(2H,t,J=6.2 Hz),4.21(1H,d,J=9.9 Hz),6.92(2H,d,J= 8.9 Hz),7.34–7.94(6H,m) FAB-MS(m/e):407[M+H]$^+$

Example 1029

$R^1$:H;$R^2$:H;$R^3$:i-Pr;$R^4$:H;Z:Ph; R:4-t-BuO$_2$CCH(Me)O-Ph $^1$HNMR(CDCl$_3$) δ :0.91(3H,d,J=6.7 Hz),1.10(3H,d,J=6.7 Hz),1.38–1.79(13H,m),4.19(1H,d,J=9.9 Hz),4.61–4.64(1H, m),6.86(2H,d,J=8.9 Hz),7.31–7.34(1H,m),7.38(2H,d, J=8.9 Hz),7.57–7.62(2H,m),7.88–7.91(1H,m) FAB-MS(m/e):452 [M+H]$^+$

Example 1030

$R^1$:H;$R^2$:H;$R^3$:i-Pr;$R^4$:H;Z:Ph;R:4-n-PrNHCOCH (Me)O-Ph $^1$HNMR(CDCl$_3$) δ :0.78–0.89(3H,m),0.95(3H,d,J=6.8 Hz),1.11(3H,d,J=6.8 Hz),1.40–1.74(6H,m),3.11–3.32(2H, m),4.20(1H,d,J=9.3 Hz),4.64–4.70(1H,m),6.33–6.34(1H, m), 6.91(2H,d,J=8.2 Hz),7.29–7.38(1H,m),7.39–7.43(2H, m),7.56–7.62(2H,m),7.87–7.92(1H,m) FAB-MS(m/e):437 [M+H]$^+$

Example 1031

$R^1$:H;$R^2$:H;$R^3$:i-Pr;$R^4$:H;Z:Ph;R:4-$F_3$CSO$_3$-Ph $^1$HNMR(CDCl$_3$) δ :0.89(3H,d,J=6.7 Hz),1.12(3H,d,J=6.7 Hz),1.59–1.67(1H,m),4.24(1H,d,J=9.6 Hz),7.31–7.34(1H, m),7.33(2H,d,J=8.9 Hz),7.59–7.66(2H,m),7.61(2H,d, J=8.9 Hz),7.92–7.95(1H,m) FAB-MS(m/e):456[M+H]$^+$

Example 1032

$R^1$:H;$R^2$:H;$R^3$:i-Pr;$R^4$:H;Z:Ph;R:4-t-BuO$_2$CCH=CH-Ph $^1$HNMR(CDCl$_3$) δ :0.91(3H,d,J=6.6 Hz),1.11(3H,d,J=6.6 Hz),1.44(9H,s),1.50–1.66(1H,m),4.21(1H,d,J=9.7 Hz),6.38 (1H,d,J=1 6.0 Hz),7.32–7.36(1H,m),7.51–7.55(4H,m), 7.58–7.64(3H,m),7.90–7.94(1H,m) FAB-MS(m/e):434[M+ H]$^+$

Example 1033

$R^1$:H;$R^2$:H;$R^3$:i-Pr;$R^4$:H;Z:Ph;R:4-n-PrNHCOCH=CH-Ph $^1$HNMR(CDCl$_3$) δ :0.92(3H,d,J=6.7 Hz),0.97(3H,t,J=7.4 Hz),1.11(3H,d,J=6.7 Hz),1.56–1.75(3H,m),3.36(2H,q,J=6.7 Hz),4.22(1H,d,J=9.9 Hz),5.69(1H,s),6.41(1H,d,J=15.7 Hz), 7.31–7.36(1H,m),7.47–7.54(4H,m),7.59–7.63(2H,m),7.61 (1H,d,J=15.7 Hz),7.90–7.95(1H,m) FAB-MS(m/e):419[M+ H]$^+$

Example 1034

$R^1$:H;$R^2$:H;$R^3$:i-Pr;$R^4$:H;Z:Ph;R:4-n-PrCH(Me) NHCOCH$_2$O-Ph $^1$HNMR(CDCl$_3$) δ :0.91 (3H,t,J=5.3 Hz),0.93(3H,d,J=6.6 Hz),1.12(3H,d,J=6.6 Hz), 1.16(3H,d,J=6.6 Hz),1.27–1.48 (4H,m),1.61–1.69(1H,m),4.07–4.12(1H,m),4.22 (1H,d, J=9.8 Hz),4.48(2H,s),6.26(1H,br),6.95(2H,d,J=8.9 Hz), 7.32–7.94(6H,m) FAB-MS(m/e):451[M+H]$^+$

Example 1035

$R^1$:H;$R^2$:;H;$R^3$:i-Pr;$R^4$:H;Z:Ph;R:4-EtCH(Me) NHCOCH$_2$O-Ph $^1$HNMR(CDCl$_3$) δ :0.87(3H,t,J=7.5 Hz),0.92(3H,d,J=6.6 Hz),1.11(3H,d,J=6.7 Hz),1.15(3H,d,J=6.6 Hz),1.46–1.52 (2H,m),1.60–1.70(1H,m),3.98–4.03(1H,m),4.21(1H,d, J=9.8 Hz),4.48(2H,s),6.24(1H,br),6.94(2H,d,J=8.9 Hz), 7.31–7.93(6H,m) FAB-MS(m/e):437[M+H]$^+$

Example 1036

$R^1$:H;$R^2$:H;$R^3$:i-Pr;$R^4$:H;Z:Ph;R:4-MeOCH$_2$O-Ph $^1$HNMR(CDCl$_3$) δ :0.97(3H,d,J=6.9 Hz),1.13(3H,d,J=6.9 Hz),1.60–1.70(1H,m),3.49(3H,s),4.20(1H,d,J=9.6 Hz),5.19 (2H,s),7.05(2H,d,J=8.4 Hz),7.35–7.93(6H,m) ESI-MS(m/e):368[M+H]$^+$

Example 1037

$R^1$:H;$R^2$:H;$R^3$:i-Pr;$R^4$:H;Z:Ph;R:4-EtCOCH$_2$O-Ph $^1$HNMR(CDCl$_3$) δ :0.93(3H,d,J=6.6 Hz),1.12(3H,d,J=6.6 Hz),1.12(3H,t,J=7.3 Hz), 1.60–1.68(1H,m),2.26(2H,q,J7.3 Hz),4.20(1H,d,J=9.9 Hz),4.58(2H,s),6.89(2H,d,J=8.9 Hz), 7.32–7.92(6H,m) ESI-MS(m/e):394[M+H]$^+$

Example 1038

$R^1$:H;$R^2$:H;$R^3$:i-Pr;$R^4$:H;Z:Ph;R:3-tBuO$_2$CCH$_2$O-Ph $^1$HNMR(CDCl$_3$) δ :0.94(3H,d,J=6.7 Hz),1.11(3H,d,J=6.7 Hz),1.46(9H,s),1.61–1.73(1H,m),4.20(1H,d,J=9.9 Hz),4.50 (2H,s),6.89(1H,dd,J=2.3,8.1 Hz),7.02(1H,dd,J=1.1,2.3 Hz), 7.10(1H,dd,J=1.1,8.1 Hz),7.31(1H,t,J=8.1 Hz),7.33–7.37 (1H,m),7.56–7.61(2H,m), 7.87–7.92 (1H,m) FAB-MS(m/e): 438[M+H]$^+$

Example 1039

$R^1$:H;$R^2$:H;$R^3$:i-Pr;$R^4$:H;Z:Ph;R:3-HO$_2$CCH$_2$O-Ph $^1$HNMR(CDCl$_3$) δ :0.93(3H,d,J=6.6 Hz),1.10(3H,d,J=6.6 Hz),1.59–1.69(1H,m),4.20(1H,d,J=9.0 Hz),4.68(2H,s), 6.90–6.94(1H,m),7.08–7.26(3H,m),7.31–7.36(1H,m), 7.57–7.62(2H, m),7.88–7.93(1H,m) FAB-MS(m/e):382[M+ H]$^+$

Example 1040

$R^1$:H;$R^2$:H;$R^3$:i-Pr;$R^4$:H-Z:Ph;R:3-n-PrNHCOCH$_2$O-Ph $^1$HNMR(CDCl$_3$) δ :0.93(3H,t,J=7.4 Hz),0.94(3H,d,J=6.6 Hz),1.12(3H,d,J=6.6 Hz),1.52–1.72(3H,m),3.32(2H,q,J=6.8 Hz),4.22(1H,d,J=9.8 Hz),4.47(2H,s),6.56–6.58(1H,m),6.91 (1H,dd,J=2.2,7.6 Hz),7.11(1H,dd,J=1.1,2.2 Hz),7.14(1H,dd, J=1.1,7.8 Hz),7.33–7.38(2H,m),7.58–7.64(2H,m),7.91–7.94 (1H,m) FAB-MS(m/e):423[M+H]$^+$

Example 1041

$R^1$:H;$R^2$:H;$R^3$:i-Pr;$R^4$:H;Z:Ph;R:4-H$_2$NC(Me)$_2$CH$_2$O$_2$CCH$_2$O-Ph FAB-MS(m/e):453[M+H]$^+$

Example 1042

$R^1$:H;$R^2$:H;$R^3$:i-Pr;$R^4$:H;Z:Ph;R:4-morpholinoCOCH$_2$O-Ph $^1$HNMR(CDCl$_3$) δ :0.94(3H,d,J=6.7 Hz),1.13(3H,d,J=6.7 Hz),1.60–1.68(1H,m),3.59–3.69(8H,m),4.21(1H,d,J=9.8

Example 1043

R$^1$:H;R$^2$:H;R$^3$:i-Pr;R$^4$:H;Z:Ph;R:4-(4-Cl-Ph)-COCH$_2$O-Ph $^1$HNMR(CDCl$_3$) δ :0.93(3H,d,J=6.6Hz),1.11(3H,d,J=6.6 Hz),1.62–1.66(1H,m),4.19(1H,d,J=9.9 Hz),5.25(2H,s),6.93 (2H,d,J=8.9 Hz),7.32–7.97(10H,m) ESI-MS(m/e):476[M+H]$^+$

Example 1044

R$^1$:H;R$^2$:H;R$^3$:i-Pr;R$^4$:H;Z:Ph;R:4-PhCOCH$_2$O-Ph $^1$HNMR(CDCl$_3$) δ :0.93(3H,d,J=6.7 Hz),1.11(3H,d,J=6.7 Hz),1.61–1.70(1H,m),4.19(1H,d, J=9.9 Hz),5.31 (2H,s), 6.94(2H,d,J=9.0 Hz),7.33–8.01(11H,m) ESI-MS(m/e):442 [M+H]$^+$

Example 1045

R$^1$:H;R$^2$:H;R$^3$:i-Pr;R$^4$:H;Z:Ph;R:4-(4-pyridyl)-CH$_2$NHCOCH$_2$O-Ph $^1$HNMR(CDCl$_3$) δ :0.92(3H,d,J=6.5 Hz),1.12(3H,d,J=6.5 Hz),1.61–1.67(1H,m),4.21(1H,d,J=9.7 Hz),4.57(1H,d,J=6.4 Hz),4.60(2H,s),6.96(2H,d,J=8.9 Hz),7.20–8.57(10H,m) ESI-MS(m/e):472[M+H]$^+$

Example 1046

R$^1$:H;R$^2$:H;R$^3$:i-Pr;R$^4$:H;Z:Ph;R:4-H$_2$NCH$_2$CH$_2$NHCOCH$_2$O-Ph $^1$HNMR(methanol-d$_4$) δ :0.87–1.09(6H,m),1.57–2.15 (1H,m),3.06–3.12(2H,m),3.52–3.59(2H,m),4.20(1H,d,J= 9.5Hz),4.54–4.64(2H,m),6.90–7.91 (8H,m) FAB-MS(m/e): 424[M+H]$^+$

Example 1047

R$^1$:H;R$^2$:H;R$^3$:i-Pr;R$^4$:H;Z:Ph;R:4-Cl-3-NO$_2$-Ph

ESI-MS(m/e):387[M+H]$^+$

Example 1048

R$^1$:H;R$^2$:H;R$^3$:i-Pr;R$^4$:H;Z:Ph;R:4-Cl-3-F-Ph $^1$HNMR(CDCl$_3$) δ :0.94(3H,d,J=6.6 Hz),1.13(3H,d,J=6.6 Hz),1.59–1.72(1H,m),4.22(1H,d,J=9.4 Hz),7.24–7.36(3H, m),7.44(1H,t,J=7.7 Hz),7.59–7.65(2H,m),7.90–7.94(1H,m) FAB-MS(m/e):360[M+H]$^+$

Example 1049

R$^1$:H;R$^2$:H;R$^1$:i-Pr;R$^4$:H;Z:Ph;R:4-Cl-3-Me-Ph $^1$HNMR(CDCl$_3$) δ :0.94(3H,d,J=6.7 Hz),1.12(3H,d,J=6.7 Hz),1.58–1.72(1H,m),2.38(3H, s),4.20(1H,d,J=9.9 Hz), 7.21–7.27(1H,m),7.31–7.35(1H,m),7.35(2H,d,J=8.5 Hz), 7.57–7.63 (2H,m),7.88–7.95(1H,m) FAB-MS(m/e):356[M+H]$^+$

Example 1050

R$^1$:H;R$^2$:H;R$^3$:i-Pr;R$^4$:H;Z:Ph;R:3-NH$_2$-4-Cl-Ph $^1$HNMR(CDCl$_3$) δ :0.96(3H,d,J=6.6 Hz),1.13(3H,d,J= 6.5Hz),1.60–1.77(1H,m),4.19(1H,d,J=9.9 Hz),6.75(1H,dd, J=2.4,8.2 Hz),6.92(1H,d,J=2.4,Hz),7.23(1H,d,J=8.2,Hz), 7.33–7.39 (1H,m),7.57–7.63(2H,m),7.86–7.93(1H,m) FAB-MS(m/e):357[M+H]$^+$

Example 1051

R$^1$:H;R$^2$:H;R$^3$:i-Pr;R$^4$:H;Z:Ph;R:3-Cl-4-MeO-Ph $^1$HNMR(CDCl$_3$) δ :0.95(3H,d,J=6.7 Hz),1.13(3H,d,J=6.7 Hz)1.57–1.65(1H,m),3.91(3H, s),4.20(1H,d,J=9.9 Hz),6.92 (1H,d,J=8.6 Hz),7.33–7.93(6H,m) FAB-MS(m/e):372[M+H]$^+$

Example 1052

R$^1$:H;R$^2$:H;R$^3$:i-Pr;R$^4$:H;Z:Ph;R:3-Cl-4-Me-Ph $^1$HNMR(CDCl$_3$) δ :0.95(3H,d,J=6.7 Hz),1.12(3H,d,J=6.7 Hz),1.62–1.69(1H,m),3.27(3H, s),4.20(1H,d,J=9.8 Hz), 7.26–7.33(2H,m),7.33–7.36(1H,m),7.49(1H,s),7.57–7.62 (2H,m),7.89–7.93(1H,m) FAB-MS(m/e):356[M+H]$^+$

Example 1053

R$^1$:H;R$^2$:H;R$^3$:i-Pr;R$^4$:H;Z:Ph;R:4-Br-3-Cl-Ph $^1$HNMR(CDCl$_3$) δ :0.88(3H,d,J=6.7 Hz),1.12(3H,d,J=6.7 Hz),1.50–1.60(1H,m),4.24(1H,d, J=9.6 Hz),7.50–7.95(7H, m) FAB-MS(m/e):420/422[M+H]$^+$

Example 1054

R$^1$:H;R$^2$:H;R$^3$:i-Pr;R$^4$:H;Z:Ph;R:4-Br-2-Cl-Ph $^1$HNMR(CDCl$_3$) δ :0.94(3H,d,J=6.6 Hz),1.13(3H,d,J=6.5 Hz),1.62–1.67(1H,m),4.22(1H,d, J=9.7 Hz),7.22–7.94(7H, m) FAB-MS(m/e):420/422[M+H]$^+$

Example 1055

R$^1$:H;R$^2$:H;R$^3$:i-Pr;R$^4$:H;Z:Ph;R:4-F-3-Me-Ph $^1$HNMR(CDCl$_3$) δ :0.93(3H,d,J=6.7 Hz),1.12(3H,d,J=6.7 Hz),1.61–1.68(1H,m),2.28(3H,s),4.20(1H,d,J=9.9 Hz),7.01 (1H,t,J=8.9 Hz),7.27–7.35(3H,m),7.59–7.62(2H,m), 7.90–7.93(1H,m) FAB-MS(m/e):340[M+H]$^+$

Example 1056

R$^1$:H,R$^2$:H;R$^3$:i-Pr;R$^4$:H;Z:Ph;R:3-F-4-Me-Ph $^1$HNMR(CDCl$_3$) δ :0.94(3H,d,J=6.7 Hz),1.12(3H,d,J=6.7 Hz),1.63–1.70(1H,m),2.28(3H,s),4.21(1H,d,J=9.9 Hz),7.16 (1H,d,J=7.2 Hz),7.18(1H,s),7.20(1H,d,J=7.2 Hz), 7.33–7.36 (1H,m),7.57–7.63(2H,m),7.90–7.93(1H,m) FAB-MS(m/e): 340[M+H]$^+$

Example 1057

R$^1$:H;R$^2$:H;R$^3$:i-Pr;R$^4$:H;Z:Ph;R:3-Br-4-HO-Ph $^1$HNMR(CDCl$_3$) δ :0.95(3H,d,J=6.6 Hz),1.13(3H,d,J=6.6 Hz),1.62–1.72(1H,m),4.20(1H,d,J=9.9 Hz),5.70(1H,s),7.02 (1H,d,J=8.6 Hz),7.30–7.37(1H,m),7.32(1H,d,J=8.6 Hz), 7.58–7.65 (2H,m),7.64(1H,s),7.90–7.93(1H,m) FAB-MS (m/e):402/404[M+H]$^+$

Example 1058

R$^1$:H;R$^1$:H;R$^3$:i-Pr;R$^4$:H;Z:Ph;R:3-Br-4-MeO-Ph $^1$HNMR(CDCl$_3$) δ :0.95(3H,d,J=6.7 Hz),1.13(3H,d,J=6.7 Hz),1.61–1.73(1H,m),3.91(3H, s),4.20(1H,d,J=9.9 Hz),6.90

(1H,d,J=8.6 Hz),7.32–7.38(1H,m),7.42(1H,dd,J=2.3,8.6 Hz), 7.58–7.64(2H,m),7.66(1H,d,J=2.3 Hz),7.88–7.94(1H, m) FAB-MS(m/e):416/418[M+H]$^+$

Example 1059

R$^1$:H;R$^2$:H;R$^3$:i-Pr;R$^4$:H;Z:Ph;R:3-Br-4-F-Ph

ESI-MS(m/e):404[M+H]$^+$

Example 1060

R$^1$:H;R$^2$:H;R$^3$:i-Pr;R$^4$:H;Z:Ph;R:3-F-4-Ph-Ph $^1$HNMR(CDCl$_3$) δ :0.88(3H,d,J=6.5 Hz),1.15(3H,d,J=6.5 Hz),1.65–1.80(1H,m),4.23(1H,d, J=9.9 Hz),7.28–7.56(9H, m),7.56–7.66(2H,m),7.91–7.95(1H,m) FAB-MS(m/e):402 [M+H]$^+$

Example 1061

R$^1$:H;R$^2$:H;R$^3$:i-Pr;R$^4$:H;Z:Ph;R:4-HO-3-I-Ph $^1$HNMR(CDCl$_3$) δ :0.95(3H,d,J=6.6 Hz),1.13(3H,d,J=6.6 Hz),1.63–1.69(1H,m),4.19(1H,d, J=9.9 Hz),5.71(1H,s), 6.98(1 H,d,J=8.5 Hz),7.32–7.93(6H,m) FAB-MS(m/e):450 [M+H]$^+$

Example 1062

R$^1$:H;R$^2$:H;R$^3$:i-Pr;R$^4$:H;Z:Ph;R:5-HO-2-I-Ph $^1$HNMR(CDCl$_3$) δ :0.95(3H,d,J=6.7 Hz),1.12(3H,d,J=6.7 Hz),1.63–1.75(1H,m),4.20(1H,d,J=9.9 Hz),6.04(1H,brs), 6.82(1H,dd,J=2.1,8.2 Hz),7.11(1H,d,J=2.1 Hz),7.33–7.36 (1H,m),7.55–7.62(2H,m),7.69(1H,d,J=8.2 Hz),7.84–7.87 (1H,m) FAB-MS(m/e):450[M+H]$^+$

Example 1063

R$^1$:H;R$^2$:H;R$^3$:i-Pr;R$^4$:H;Z:Ph;R:3-I-4-MeO-Ph $^1$HNMR(CDCl$_3$) δ :0.96(3H,d,J=6.6 Hz),1.13(3H,d,J=6.6 Hz),1.59–1.68(1H,m),3.89(3H,s),4.20(1H,d,J=9.9 Hz),6.81 (1H,d,J=8.6 Hz),7.34–7.93(6H,m) FAB-MS(m/e):464[M+H]$^+$

Example 1064

R$^1$:H;R$^2$:H;R$^3$:i-Pr;R$^4$:H;Z:Ph;R:2-I-5-MeO-Ph $^1$HNMR(CDCl$_3$) δ :0.98(3H,d,J=6.6 Hz),1.13(3H,d,J=6.6 Hz),1.63–1.71(1H,m), 3.86(3H,s),4.22(1H,d,J=10.1 Hz), 6.87(1H,dd,J=1.9,8.0 Hz),6.91(1H,d,J=1.9Hz),7.35–7.37 (1H,m),7.58–7.64(2H,m),7.79(1H,d,J=8.0 Hz),7.92(1H,dd, J=3.0,5.7 Hz) FAB-MS(m/e):464[M+H]$^+$

Example 1065

R$^1$:H;R$^2$:H;R$^3$:i-Pr;R$^4$:H;Z:Ph;R:4-MeO-3-Me-Ph $^1$HNMR(CDCl$_3$) δ :0.95(3H,d,J=6.6 Hz),1.11(3H,d,J=6.6 Hz),1.60–1.70(1H,m),2.18(3H,s),3.83(3H,s),4.18(1H,d,J= 10.0 Hz),6.80(1H,d,J=8.6 Hz),7.20(1H,d,J=2.6 Hz),7.30 (1H,dd,J=2.6,8.6 Hz),7.32–7.36(1H,m),7.54–7.61 (2H,m), 7.88–7.92(1H,m) FAB-MS(m/e):352[M+H]$^+$

Example 1066

R$^1$:H;R$^2$:H;R$^3$:i-Pr;R$^4$:H;Z:Ph; R:4-HO(CH$_2$)$_3$O-3-I-Ph $^1$HNMR(CDCl$_3$) δ :0.97(3H,d,J=6.7 Hz),1.14(3H,d,J=6.7 Hz),1.57–1.70(1H,m),2.13(2H, dt,J=5.6 Hz),3.95(2H,t,J= 5.6 Hz),4.20(2H,t,J=5.6 Hz),4.21(1H,d,J=9.9 Hz),6.83(1H, d,J=8.6 Hz),7.35–7.94(6H,m) FAB-MS(m/e):508[M+H]$^+$

Example 1067

R$^1$:H;R$^2$:H;R$^3$:i-Pr;R$^4$:H;Z:Ph; R:4-HO(CH$_2$)$_2$O-3-I-Ph $^1$HNMR(CDCl$_3$) δ :0.96(3H,d,J=6.7 Hz),1.15(3H,d,J=6.7 Hz),1.58–1.68(1H,m),4.01(2H,t,J=4.4 Hz),4.15(2H,t,J=4.4 Hz),4.21(1H,d,J=9.9 Hz),6.83(1H,d,J=8.6 Hz), 7.34–7.94 (6H,m) FAB-MS(m/e):494[M+H]$^+$

Example 1068

R$^1$:H;R$^2$:H;R$^3$:i-Pr;R$^4$:H;Z:Ph; R:4-HOC(Me)$_2$(CH$_2$)$_2$O-3-I-Ph $^1$HNMR(CDCl$_3$) δ :0.96(3H,d,J=6.6 Hz),1.13(3H,d,J=6.6 Hz),1.34(6H,s),1.60–1.65(1H, m),2.08(2H,t,J=6.0 Hz),4.19 (1H,d,J=9.9 Hz),4.23(2H,t,J=6.0 Hz),6.82(1H,d,J=8.7 Hz), 7.32–7.94(6H,m) FAB-MS(m/e):536[M+H]$^+$

Example 1069

R$^1$:H;R$^2$:H;R$^3$:i-Pr;R$^4$:H;Z:Ph; R:4-t-BUO$_2$C(CH$_2$)$_4$O-3-I-Ph $^1$HNMR(CDCl$_3$) δ :0.95(3H,d,J=6.6 Hz),1.12(3H,d,J=6.6 Hz),1.44(9H,s),1.60–1.67(1H,m),1.82–1.86(4H,m),2.32 (2H,t,J=6.88 Hz),4.01(2H,t,J=5.3 Hz),4.18(1H,d,J=10.0 Hz), 6.75(1H,d,J=8.6 Hz),7.32–7.91(6H,m) FAB-MS(m/e): 606[M+H]$^+$

Example 1070

R$^1$:H;R$^2$:H;R$^3$:i-Pr;R$^4$:H;Z:Ph;R:3-I-4-PhCH$_2$O-Ph $^1$HNMR(CDCl$_3$) δ :0.96(3H,d,J=6.7 Hz),1.13(3H,d,J=6.7 Hz),1.60–1.75(1H,m),4.20(1H,d, J=9.9 Hz),5.16(2H,s),6.86 (1H,d,J=8.6 Hz),7.34–7.93(11H,m) FAB-MS(m/e):540[M+H]$^+$

Example 1071

R$^1$:H;R$^2$:H;R$^3$:i-Pr;R$^4$:H;Z:Ph; R:4-H$_2$NCOCH$_2$O-3-I-Ph $^1$HNMR(CDCl$_3$) δ :0.95(3H,d,J=6.7 Hz),1.13(3H,d,J=6.7 Hz),1.61–1.69(1H,m), 4.21(1H,d,J=9.9 Hz),4.53(2H,s),5.86 (1H,br),6.78(1H,8,J=8.6 Hz),6.86(1H,br),7.33–7.94(6H,m) FAB-MS(m/e):507[M+H]$^+$

Example 1072

R$^1$:H;R$^2$:H;R$^3$:i-Pr;R$^4$:H;Z:Ph;R:3-I-4-MeNHCOCH$_2$O-Ph $^1$HNMR(CDCl$_3$) δ :0.95(3H,d,J=6.6 Hz),1.13(3H,d,J=6.6 Hz),1.61–1.69(1H,m),2.97(3H, d, J=5.0 Hz),4.21(1H,d,J= 9.8 Hz),4.53(2H,s),6.77(1H,d,J=8.6 Hz),6.87(1H,br), 7.33–7.94(6H,m) FAB-MS(m/e):521[M+H]$^+$

Example 1073

R$^1$:H;R$^2$:H;R$^3$:i-Pr;R$^4$:H;Z:Ph; R:4-EtNHCOCH$_2$O-3-I-Ph $^1$HNMR(CDCl$_3$) δ :0.95(3H,d,J=6.6 Hz),1.13(3H,d,J=6.6 Hz),1.24(3H,t,J=7.3 Hz),1.61–1.69(1H,m),3.44(2H,dt,J=7.3 Hz),4.21(1H,d,J=9.8 Hz),4.51 (2H,s),6.77(1H,d,J=8.6 Hz), 6.89(1H,br),7.33–7.94(6H,m) FAB-MS(m/e):535[M+H]$^+$

Example 1074

R¹:H;R²:H;R³:i-Pr;R⁴:H;Z:Ph;R:3-I-4-n-PrNHCOCH₂O-Ph

¹HNMR(CDCl₃) δ :0.97(3H,t,J=7.8 Hz),1.00(3H,d,J=6.7 Hz),1.13(3H,d,J=6.7 Hz), 1.57–1.69(3H,m),3.37(2H,dt,J=7.0 Hz),4.22(1H,d,J=9.8 Hz),4.52(2H,s),6.78(1H,d,J=8.6 Hz), 6.91(1H,br),7.33–7.94(6H,m) FAB-MS(m/e):549[M+H]⁺

Example 1075

R¹:H;R²:H;R³:i-Pr;R⁴:H;Z:Ph;R:3-I-4-i-PrNHCOCH₂O-Ph

¹HNMR(CDCl₃) δ :0.95(3H,d,J=6.6 Hz),1.13(3H,d,J=6.6 Hz),1.25(6H,d,J=6.3 Hz),1.61–1.69(1H,m),4.11–4.20(1H,m),4.21(1H,d,J=9.8 Hz),4.49(2H,s),6.77(1H,br),6.77(1H,d,J=9.8 Hz),7.33–7.94(6H,m) FAB-MS(m/e):549[M+H]⁺

Example 1076

R¹:H;R²:H;R³:i-Pr;R⁴:H;Z:Ph;R:4-n-BuNHCOCH₂O-3-I-Ph

¹HNMR(CDCl₃) δ :0.92–0.97(6H,m),1.12(3H,d,J=6.8 Hz),1.35–1.68(5H,m),3.39(2H,dt J=6.3 Hz),4.20(1H,d,J=9.9 Hz),4.51 (2H,s),6.76(1H,d,J=8.6 Hz),6.90(1H,br), 7.32–7.93(6H, m) FAB-MS(m/e):563[M+H]⁺

Example 1077

R¹:H;R²:H;R³:i-Pr;R⁴:H;Z:Ph;R:4-t-BuNHCOCH₂O-3-I-Ph

¹HNMR(CDCl₃) δ :0.94(3H,d,J=6.7 Hz),1.13(3H,d,J=6.7 Hz),1.44(9H,s),1.61–1.69(1H, m),4.21(1H,d,J=9.8 Hz),4.40 (2H,s),6.76(1H,d,J=8.6 Hz),6.86(1H,br),7.33–7.94(6H,m) FAB-MS(m/e):563[M+H]⁺

Example 1078

R¹:H;R²:H;R³:i-Pr;R⁴:H;Z:Ph;R:4-i-BuNHCOCH₂O-Ph

¹HNMR(CDCl₃) δ :0.88–0.96(9H,m),1.11(3H,d,J=6.7 Hz),1.60–1.83(2H,m),3.18(2H,t, J=6.5 Hz),4.20(1H,d,J=9.8 Hz),4.51 (2H,s),6.54(1H,br),6.95(2H,d,J=8.9 Hz),7.31–7.93 (6H, m) FAB-MS(m/e):437[M+H]⁺

Example 1079

R¹:H;R²:H;R³:i-Pr;R⁴:H;Z:Ph; R:4-t-BuO₂CCH₂O-3-I-Ph

¹HNMR(CDCl₃) δ :0.96(3H,d,J=6.6 Hz),1.13(3H,d,J=6.6 Hz),1.48(9H,s),1.51–1.68(1H,m),4.20(1H,d,J=9.9 Hz),4.61 (2H,s),6.69(1H,d,J=8.6 Hz),7.34–7.94(6H,m) FAB-MS(m/e):564[M+H]⁺

Example 1080

R¹:H;R²:H;R³:i-Pr;R⁴:H;Z:Ph;R:3-I-4-PhCH₂NHCOCH₂O-Ph

¹HNMR(CDCl₃) δ :0.94(3H,d,J=6.7 Hz),1.13(3H,d,J=6.7 Hz),1.63–1.66(1H,m),4.20(1H,d,J=9.8 Hz),4.58(2H,s),4.59 (2H,d,J=5.5 Hz),6.79(1H,d,J=8.6Hz),7.27–7.94(11H,m) FAB-MS(m/e):597[M+H]⁺

Example 1081

R¹:H;R²:H;R³:i-Pr;R⁴:H;Z:Ph;R:3-I-4-(2-tetrahydrofuryl)-CH₂NHCOCH₂O-Ph

¹HNMR(CDCl₃) δ :0.96(3H,d,J=6.6 Hz),1.14(3H,d,J=6.6 Hz),1.56–2.06(5H,m), 3.38–4.14(5H,m),4.22(1H,d,J=9.8 Hz),4.54(2H,s),6.78(1H,d,J=8.6 Hz),7.23(1H,br),7.33–7.96(6H,m) ESI-MS(m/e):591[M+H]⁺

Example 1082

R¹:H;R²:H;R³:i-Pr;R⁴:H;Z:Ph; R:4-cycloPrNHCOCH₂O-3-I-Ph

¹HNMR(CDCl₃) δ :0.61–0.64(2H,m),0.85–0.89(2H,m),0.95(3H,d,J=6.7 Hz),1.14(3H,d, J=6.7 Hz),1.62–1.67(1H,m),2.84–2.88(1H,m),4.22(1H,d,J=9.9 Hz),4.51 (2H,s),6.76 (1H,d, J=8.6 Hz),7.00(1H,br),7.33–7.95(6H,m) FAB-MS (m/e):547[M+H]⁺

Example 1083

R¹:H;R²:H;R³:i-Pr;R⁴:H;Z:Ph; R:4-cycloPentylNHCOCH₂O-3-I-Ph

¹HNMR(CDCl₃) δ :0.95(3H,d,J=6.6 Hz),1.13(3H,d,J=6.6 Hz),1.50–1.77(7H,m),2.00–2.03(2H,m),4.22(1H,d,J=9.6 Hz),4.24–4.36(1H,m),4.50(2H,s),6.77(1H,d,J=8.6 Hz),6.95 (1H,br),7.33–7.94(6H,m) FAB-MS(m/e):575[M+H]⁺

Example 1084

R¹:H;R²:H;R³:i-Pr;R⁴:H;Z:Ph; R:4-cycloHexylNHCOCH₂O-3-I-P)

¹HNMR(CDCl₃) δ :0.94(3H,d,J=6.7 Hz),1.12(3H,d,J=6.7 Hz),1.26–1.97(11H,m),3.89–3.93(1H,m),4.21(1H,d,J=9.7 Hz),4.99(2H,s),6.77(1H,d,J=8.6 Hz),6.89(1H,brd, J=10.0Hz),7.33–7.93(6H,m) FAB-MS(m/e):589[M+H]⁺

Example 1085

R¹:H;R²:H;R³:i-Pr;R⁴:H;Z:Ph; R:4-cycloPrNHCOCH₂O-3-F-Ph

¹HNMR(CDCl₃) δ :0.57–0.59(2H,m),0.83–0.88(2H,m),0.93(3H,d,J=6.6 Hz),1.13(3H,d, J=6.6 Hz),1.60–1.68(1H,m),2.75–2.83(1H,m),4.21(1H,d,J=9.7 Hz),4.51(2H,s),6.68 (1H,br),6.92–7.93(7H,m) ESI-MS(m/e):439[M+H]⁺

Example 1086

R¹:H;R²:H;R³:i-Pr;R⁴:H;Z:Ph; R:4-Me(CH2)₉NHCOCH2O-3-I-Ph

¹HNMR(CDCl₃) δ :0.88(3H,t,J=6.3 Hz),0.95(3H,d,J=6.6 Hz),1.13(3H,d,J=6.6 Hz), 1.20–1.40(14H,m),1.56–1.70(3H,m),3.38(2H,dt,J=6.6 Hz),4.20(1H,d,J=9.9 Hz),4.51(2H,s), 6.77(1H,d,J=8.6 Hz),6.92(1H,br),7.33–7.94(6H,m) FAB-MS(m/e):647[M+H]⁺

Example 1087

R¹:H;R²:H;R³:i-Pr;R⁴:H;Z:Ph; R:4-HO₂CCH₂O-3-I-Ph

¹HNMR(CDCl₃) δ :0.96(3H,d,J=6.6 Hz),1.13(3H,d,J=6.6 Hz),1.51–1.68(1H,m),4.20(1H,d, J=9.9 Hz),4.61 (2H,s), 6.69(1H,d,J=8.6 Hz),7.34–7.94(6H,m) FAB-MS(m/e):508 [M+H]⁺

Example 1088

R¹:H;R²:H;R³:i-Pr;R¹:H;Z:Ph; R:4-N₃(CH₂)₃O-3-I-Ph

¹HNMR(CDCl₃) δ :0.97(3H,d,J=6.6 Hz),1.13(3H,d,J=6.6 Hz),1.60–1.68(1H,m),2.09–2.13(2H,m),3.63(2H,t,J=6.5

Hz),4.11 (2H,t,J=5.3 Hz),4.20(1H,d,J=9.9 Hz),6.79(1H,d,J=8.6 Hz),7.34–7.94(6H,m) FAB-MS(m/e):533[M+H]$^+$

Example 1089

R$^1$:H;R$^1$:H;R$^3$:i-Pr;R$^4$:H;Z:Ph;R:3-I-4-n-PrNHCO(CH$_2$)$_4$O-Ph $^1$HNMR(CDCl$_3$) δ :0.92(3H,t,J=7.4 Hz),0.96(3H,d,J=6.7 Hz),1.13(3H,d,J=6.7 Hz),1.45–1.55(2H,m),1.62–1.69(1H,m),1.87–1.92(4H,m),2.28–2.32(2H,m),3.21(2H,dt,J=7.0 Hz), 4.02–4.09(2H,br),4.20(1H,d,J=9.9 Hz),5.51(1H,br),6.77(1H,d,J=8.6 Hz),7.34–7.93(6H,m) FAB-MS(m/e):591[M+H]$^+$

Example 1090

R$^1$:H;R$^2$:H;R$^3$:i-Pr;R$^4$:H;Z:Ph;R:4-Et$_2$NCOCH$_2$O-3-I-Ph $^1$HNMR(CDCl$_3$) δ :0.95(3H,d,J=6.6 Hz),1.12(6H,m),1.22(3H,t,J=7.0 Hz),1.60–1.68(1H, m),3.39–3.45(4H,m),4.19(1H,d,J=9.9 Hz),4.77(2H,s),6.88(1H,d,J=8.7 Hz),7.34–7.93(6H, m) FAB-MS(m/e):563[M+H]$^+$

Example 1091

R$^1$:H;R$^2$:H;R$^3$:i-Pr;R$^4$:H;Z:Ph;R:3-I-4-n-PrN(Me)COCH$_2$O-Ph $^1$HNMR(CDCl$_3$) δ :0.84(3H,t,J=7.3 Hz),0.98(3H,d,J=6.7 Hz),1.15(3H,d,J=6.7 Hz),1.50–1.69(3H,m),2.96(3H,s,rotomer),3.11(3H,s,rotomer),3.37(2H,t,J=7.3 Hz),4.80(1H,d,J=10.0 Hz),4.79(2H,s,rotomer),4.81 (2H,s,rotomer),6.87–7.94(7H,m,rotomer) FAB-MS(m/e):563[M+H]$^+$

Example 1092

R$^1$:H;R$^2$:H;R$^3$:i-Pr;R$^4$:H;Z:Ph;R:3-Cl-4-n-PrNHCOCH$_2$O-Ph $^1$HNMR(CDCl$_3$) δ :0.93–0.98(6H,m),1.13(3H,d,J=6.6 Hz),1.56–1.70(3H,m),3.34(2H,dt, J=6.6 Hz),4.21(1H,d,J=9.8 Hz),4.54(2H,s),6.80(1H,br),6.92(1H,d,J=8.6 Hz),7.33–7.94(6H, m) ESI-MS(m/e):457[M+H]$^+$

Example 1093

R$^1$:H;R$^2$:H;R$^3$:i-Pr;R$^4$:H;Z:Ph;R:3-Br-4-n-PrNHCOCH$_2$O-Ph $^1$HNMR(CDCl$_3$) δ :0.97(3H,t,J=7.8 Hz),0.97(3H,d,J=6.6 Hz),1.13(3H,d,J=6.6 Hz),1.56–1.69(3H,m),3.34(2H,q,J=6.6 Hz),4.22(1H,d,J=10.0 Hz),4.53(2H,s),6.87–6.89(1H,m),6.87(1H,d,J=8.5 Hz),7.34–7.36(1H,m),7.45(1H,d,J=8.5 Hz),7.60–7.63(2H,m),7.72(1H,s), 7.89–7.94(1H,m) FAB-MS(m/e):50 1/503[M+H]$^+$

Example 1094

R$^1$:H;R$^2$:H;R$^3$:i-Pr;R$^4$:H;Z:Ph;R:3-F-4-n-PrNHCOCH$_2$O-Ph $^1$HNMR(CDCl$_3$) δ :0.90–0.95(6H,m),1.12(3H,d,J=6.6 Hz),1.54–1.70(3H,m),3.32(2H,dt J=6.6 Hz),4.21 (1H,d,J=9.7 Hz),4.53(2H,s),6.65(1H,br),6.94–7.93(7H,m) FAB-MS (m/e):441[M+H]$^+$

Example 1095

R$^1$:H;R$^2$:H;R$^3$:i-Pr;R$^4$:H;Z:Ph;R:3-Me-4-n-PrNHCOCH$_2$O-Ph $^1$HNMR(CDCl$_3$) δ :0.92(3H,t,J=7.6 Hz),0.95(3H,d,J=6.8 Hz),1.11(3H,d,J=6.8 Hz),1.53–1.74(3H,m),2.28(3H,s),3.33 (2H,q,J=6.6 Hz),4.21(1H,d,J=9.9 Hz),4.49(2H,s),6.51–6.52(1H, m),6.78(1H,d,J=8.2 Hz),7.29–7.36(3H,m),7.56–7.62(2H,m),7.88–7.92(1H,m) FAB-MS(m/e):437[M+H]$^+$

Example 1096

R$^1$:H;R$^2$:H;R$^3$:i-Pr;R$^4$:H;Z:Ph;R:4-EtNHCOCH$_2$O-3-F-Ph $^1$HNMR(CDCl$_3$) δ :0.94(3H,d,J=6.6 Hz),1.13(3H,d,J=6.6 Hz),1.20(3H,t,J=7.3 Hz),1.60–1.68(1H,m),3.41 (2H,dt,J=7.3 Hz),4.21(1H,d,J=9.8 Hz),4.53(2H,s),6.63(1H,br), 6.95–7.94(7H,m) ESI-MS(m/e):427[M+H]$^+$

Example 1097

R$^1$:H;R$^2$:H;R$^3$:i-Pr;R$^4$:H;Z:Ph;R:3-I-4-i-PrNHCOC(Me)$_2$CH$_2$O-Ph $^1$HNMR(CDCl$_3$) δ :0.91 (3H,t,J=7.4 Hz),0.96(3H,d,J=6.7 Hz),1.13(3H,d,J=6.7 Hz),1.52–1.69(3H,m),3.23(2H,dt,J=5.7 Hz),3.93–3.99(2H,m),4.19(1H,d,J=11.0 Hz),6,27(1H,br), 6.77(1Hd,J=8.7 Hz),7.32–7.92(6H,m) FAB-MS(m/e): 427[M+H]$^+$

Example 1098

R$^1$:H;R$^2$:H;R$^3$:i-Pr;R$^4$:H-Z:Ph;R:3-Br-4-CH$_2$=CHCH$_2$NHCOCH$_2$O-Ph $^1$HNMR(CDCl$_3$) δ :0.94(3H,t,J=6.6 Hz),1.13(3H,d,J=6.6 Hz),1.60–1.70(1H,m),4.00–4.04(2H,m),4.22(1H,d,J=9.7 Hz),4.56(2H,s),5.18(1H,d,J=10.3 Hz),5.24(1H,d,J=19.7 Hz),5.81–5.96(1H,m),6.88–6.92(1H,m),6.89(1H,d,J=8.6 Hz),7.33–7.37(1H,m),7.45(1H,dd, J=2.3, 8.6 Hz),7.61–7.65(2H,m),7.72(1H,d,J=2.3 Hz),7.90–7.95(1H,m) FAB-MS(m/e):499/501[M+H]$^+$

Example 1099

R$^1$:H;R$^2$:H;R$^3$:i-Pr;R$^4$:H;Z:Ph;R:4-i-BuNHCOCH$_2$O-3-F-Ph $^1$HNMR(CDCl$_3$) δ :0.90(6H,d,J=6.7 Hz),0.93(3H,d,J=6.7 Hz),1.12(3H,d,J=6.7 Hz),1.59–1.69(1H,m),1.77–1.84(1H,m),3.18(2H,t,J=6.7 Hz),4.20(1H,d,J=9.7 Hz),4.54(2H,s),6.68(1H,br),6.94–7.93(7H,m) ESI-MS(m/e):455[M+H]$^+$

Example 1100

R$^1$:H;R$^2$:H;R$^3$:i-Pr;R$^4$:H;Z:Ph;R:3-t-BuO$_2$CCH=CH-4-n-PrNHCOCH$_2$OPh)

$^1$HNMR(CDCl$_3$) δ :0.88(3H,t,J=7.1 Hz),0.92(3H,d,J=6.5 Hz),1.12(3H,d,J=6.5 Hz),1.41–1.68(3H,m),1.54(9H,s),3.31 (2H,q,J=6.7 Hz),4.22(1H,d,J=9.4 Hz),4.57(2H,s),6.39–6.44(1H,m),6.41(1H,d,J=16.2 Hz),6.89(1H,d,J=8.5 Hz),7.32–7.34(1H,m),7.45(1H,dd,J=2.3, 8.5 Hz),7.58–7.64(2H,m),7.67(1H,d,J=2.3 Hz),7.86(1H,d,J=16.2 Hz),7.93–7.94 (1H,m) FAB-MS(m/e):549[M+H]$^+$

Example 1101

R$^1$:H;R$^2$:H;R$^3$:i-Pr;R$^4$:H;Z:Ph;R:3-HO$_2$CCH=CH-4-n-PrNHCOCH$_2$O-Ph $^1$HNMR(CDCl$_3$) δ :0.91(3H,t,J=7.4 Hz),0.93(3H,d,J=6.6 Hz),1.12(3H,d,J=6.6 Hz),.153–1.64(3H,m),3.32(2H,q,J=6.7 Hz),4.23(1H,d,J=9.8 Hz),4.59(2H,s),6.46–6.48(1H,m),6.51 (1H,d,J=16.1 Hz),6.92(1H,d,J=8.7 Hz),7.32–7.35(1H,m), 7.50(1H,dd,J=2.3,87 Hz),7.59–7.63(2H,m),7.70(1H,d,J=2.3 Hz),7.92–7.95(1H,m),8.01(1H,d,J=16.1 Hz) FAB-MS(m/e):493[M+H]$^+$

Example 1102

R¹:H;R²:H;R³:i-Pr;R⁴:H;Z:Ph;R:3-I-4-MeOCH₂CH₂NHCOCH₂O-Ph

¹HNMR(CDCl₃) δ :0.95(3H,d,J=6.7 Hz),1.13(3H,d,J=6.7 Hz),1.60–1.70(1H,m),3.38(3H,s),3.54–3.60(4H,m),4.21(1H,d,J=9.8 Hz),4.53(2H,s),6.77(1H,d,J=8.6 Hz),7.35–7.94(6H,m) FAB-MS(m/e):565[M+H]⁺

Example 1103

R¹:H;R²:H;R³:i-Pr;R⁴:H;Z:Ph;R:3-F-4-HO-Ph

¹HNMR(CDCl₃) δ :0.95(3H,d,J=6.6 Hz),1.13(3H,d,J=6.6 Hz),1.67–1.74(1H,m),4.21(1H,d, J=9.8 Hz),6.91–7.93(7H, m) FAB-MS(m/e):342[M+H]⁺

Example 1104

R¹:H;R²:H;R³:i-Pr;R⁴:H;Z:Ph;R:3-F-4-MeO-Ph

¹HNMR(CDCl₃) δ :0.95(3H,d,J=6.7 Hz),1.13(3H,d,J=6.7 Hz),1.63–1.69(1H,m),3.90(3H,s),4.20(1H,d,J=9.8 Hz), 6.94–7.92(7H,m) FAB-MS(m/e):356[M+H]⁺

Example 1105

R¹:H;R²:H;R³:i-Pr;R⁴:H;Z:Ph;R:3,4-methylenedioxyPh)

¹HNMR(CDCl₃) δ :0.97(3H,d,J=6.7 Hz),1.13(3H,d,J=6.7 Hz),1.65–1.79(1H,m),4.19(1H,d,J=9.9 Hz),5.99(1H,d,J=5.5 Hz),6.81(1H,d,J=8.1 Hz),6.86(1H,d,J=1.9 Hz),7.05(1H,dd,J=1.9,8.1 Hz),7.33–7.39(1H,m),7.57–7.63(2H,m),7.87–7.93(1H,m) FAB-MS(m/e):352[M+H]⁺

Example 1106

R¹:H;R²:H;R¹:i-Pr;R⁴:H;Z:Ph;R:3,4-ethylenedioxyPh)

¹HNMR(CDCl₃) δ :0.97(3H,d,J=6.6 Hz),1.13(3H,d,J=6.6 Hz),1.67–1.72(1H,m),4.18(1H,d,J=10.0 Hz),4.26(4H,s),6.85(1H,d,J=8.4 Hz),6.94(1H,dd,J=2.2,8.4 Hz),7.00(1H,d,J=2.2 Hz),7.35–7.90(4H,m) FAB-MS(m/e):366[M+H]⁺

Example 1107

R¹:H;R²:H;R³:i-Pr;R⁴:H;Z:Ph;R:3,4-Cl₂-Ph

¹HNMR(CDCl₃) δ :0.94(3H,d,J=6.5 Hz),1.13(3H,d,J=6.5 Hz),1.53–1.70(1H,m),4.22(1H,d,J=9.4 Hz),7.29–7.36(2H,m),7.48(1H,d,J=8.1,Hz),7.59–7.66(3m),7.90–7.94(1H,m) FAB-MS(m/e):376[M+H]⁺

Example 1108

R¹:H;R²:H;R³:i-Pr;R⁴:H;Z:Ph;R:3,4-Me₂-Ph

¹HNMR(CDCl₃) δ :0.95(3H,d,J=6.7 Hz),1.11(3H,d,J=6.7 Hz),1.63–1.71(1H,m),2.25(6H,s),4.18(1H,d,J=10.1 Hz),7.12–7.92(7H,m) FAB-MS(m/e):336[M+H]⁺

Example 1109

R¹:H;R²:H;R³:i-Pr;R⁴:H;Z:Ph;R:3,4-F₂-Ph

¹HNMR(CDCl₃) δ :0.93(3H,d,J=6.6 Hz),1.13(3H,d,J=6.6 Hz),1.64(1H,m),4.22(1H,d, J=9.6 Hz),7.19–7.35(4H,m),7.61–7.64(2H,m),7.90–7.94(1H,m) FAB-MS(m/e):344[M+H]⁺

Example 1110

R¹:H;R²:H;R³:i-Pr;R⁴:H;Z:Ph;R:3,4-(MeO)₂-Ph

ESI-MS(m/e):368[M+H]⁺

Example 1111

R¹:H;R²:H;R³:i-Pr;R⁴:H;Z:Ph;R:3,5-(MeO)₂-Ph

ESI-MS(m/e):368[M+H]⁺

Example 1112

R¹:H;R²:H;R³:i-Pr;R⁴:H;Z:Ph;R:3,5-Me₂-Ph

ESI-MS(m/e):336[M+H]⁺

Example 1113

R¹:H;R²:H;R³:i-Pr;R⁴:H;Z:Ph;R:3,5-I₂₋₄-HO-Ph

¹HNMR(CDCl₃) δ :0.98(3H,d,J=6.6 Hz),1.15(3H,d,J=6.6 Hz),1.61–1.72(1H,m),4.20(1H,d, J=9.9 Hz),5.79(1 H,brs), 7.35–7.94(6H,m) FAB-MS(m/e):576[M+H]⁺

Example 1114

R¹:H;R²:H:R³:i-Pr;R⁴:H;Z:Ph;R:2,4-I₂₋₅-HO-Ph

¹HNMR(CDCl₃) δ :0.95(3H,d,J=6.6 Hz),1.14(3H,d,J=6.6 Hz),1.59–1.66(1H,m),4.26(1H,d,J=9.7 Hz),7.21–7.26(1H,m),7.60–7.69(2H,m),7.70(1H,s),7.91–7.95(1H,m),8.14(1H, s) FAB-MS(m/e):576[M+H]⁺

Example 1115

R¹:H;Re:H;R³:i-Pr;R⁴:H;Z:Ph;R:3,5-I₂₋₄-MeO-Ph

¹HNMR(CDCl₃) δ :0.96(3H,d,J=6.6 Hz),1.13(3H,d,J=6.6 Hz),1.61–1.72(1H,m), 3.89+3.92 (3H,s+s,rotomer),4.19(1H,d,J=9.8 Hz),7.34–7.93(6H,m) FAB-MS(m/e):590[M+H]⁺

Example 1116

R¹:H;R²:H;R³:i-Pr;R⁴:H;Z:Ph;R:2,4-I₂₋₅-MeO-Ph

¹HNMR(CDCl₃) δ :0.94(3H,d,J=7.1 Hz),1.14(3H,d,J=7.1 Hz),1.51–1.64(1H,m),3.99(3H,s),4.26(1H,d,J=9.5 Hz), 7.22–7.25(1H,m),7.45(1H,s),7.61–7.70(2H,m),7.93–7.95(1H, m),8.23(1H,s) FAB-MS(m/e):590[M+H]⁺

Example 1117

R¹:H;R²:H;R³:i-Pr;R⁴:H;Z:Ph;R:2,4,6-Me₃-Ph

ESI-MS(m/e):350[M+H]⁺

Example 1118

R¹:H;R²:H;R³:i-Pr;R⁴:H;Z:Ph; R:4-HO(CH₂)₃O-3,5-I₂-Ph

¹HNMR(CDCl₃) δ :0.99(3H,d,J=6.6 Hz),1.16(3H,d,J=6.6 Hz),1.62–1.72(1H,m),2.17(2H,dt,J=5.7 Hz),4.00(2H,t,J=5.7 Hz),4.16(2H,t,J=5.7 Hz),4.21(1H,d,J=9.9 Hz),7.38–7.96 (6H,m) FAB-MS(m/e):634[M+H]⁺

Example 1119

R¹:H;R²:H;R³:i-Pr;R⁴:H;Z:Ph;R:3,5-I₂₋₄-n-PrNHCOCH₂O-Ph

¹HNMR(CDCl₃) δ :0.97(3H,d,J=6.7 Hz),1.00(3H,t,J=7.4 Hz),1.15(3H,d,J=6.7 Hz),1.58–1.73(3H,m),3.38(2H,q,J=6.6

Hz),4.21(1H,d,J=9.8 Hz),4.49(2H,s),6.79–6.82 (1H,m),7.38–7.40(1H,m),7.62–7.69(2H,m),7.90–7.95(1H,m),7.92 (2H,s) FAB-MS(m/e):675[M+H]$^+$

Example 1120

R$^1$:H;R$^2$:H;R$^3$:i-Pr;R$^4$:H;Z:Ph;R:2-thienyl $^1$HNMR(CDCl$_3$) δ :1.04(3H,d,J=6.6 Hz),1.17(3H,d,J=6.6 Hz),1.75–1.90(1H,m),4.18(1H,d,J=10.2 Hz),7.02(1H,dd,J=3.6,5.0 Hz),7.26(1H,dd,J=1.1,3.6 Hz),7.35(1H,dd,J=1.1, 5.0 Hz),7.45–7.55(1H,m),7.56–7.68(2H,m),7.89–7.92(1H,m) FAB-MS(m/e):314[M+H]$^+$

Example 1121

R$^1$:H;R$^2$:H;R$^3$:i-Pr;R$^4$:H;Z:Ph;R:2-furyl $^1$HNMR(CDCl$_3$) δ :1.01(3H,d,J=6.6 Hz),1.21(3H,d,J=6.6 Hz),1.92–2.06(1H,m),4.17(1H,d,J=9.7 Hz),6.39(1H,dd,J=1.8,3.3 Hz),6.40(1H,d,J=3.3 Hz),7.43(1H,d,J=1.8 Hz),7.58–7.70(3H,m),7.88–7.98(1H,m) FAB-MS(m/e):298[M+H]$^+$

Example 1122

R$^1$:H;R$^2$:H;R$^3$:i-Pr;R$^4$:H;Z:Ph;R:3-pyridyl $^1$HNMR(CDCl$_3$) δ :0.92(3H,d,J=6.7 Hz),1.12(3H,d,J=6.7 Hz),1.55–1.70(1H,m),4.24(1H,d,J=9.6 Hz),7.32–7.40(2H,m),7.60–7.65(2H,m),7.79–7.83(1H,m),7.92–7.96(1H,m),8.66(1H,d, J=4.6 Hz),8.78(1H,brs) FAB-MS(m/e):309[M+H]$^+$

Example 1123

R$^1$:H;R$^2$:H;R$^3$:i-Pr;R$^4$:H;Z:Ph;R:2-naphthyl

ESI-MS(m/e):358[M+H]$^+$

Example 1124

R$^1$:H;R$^2$:H;R$^3$:i-Pr;R$^4$:H;Z:Ph;R:5-F-1-naphthyl

ESI-MS(m/e):376[M+H]$^+$

Example 1125

R$^1$:H;R$^2$:H;R$^3$:i-Pr;R$^4$:H;Z:Ph;R:dibenzothiophene-2-yl

ESI-MS(m/e):414[M+H]$^+$

Example 1126

R$^1$:6-F;R$^2$:H;R$^3$:i-Pr;R$^4$:H;Z:Ph;R:Ph $^1$HNMR(CDCl$_3$) δ :0.91(3H,d,J=6.6 Hz),1.10(3H,d,J=6.7 Hz),1.52–1.67(1H,m),4.22(1H,d, J=9.8 Hz),7.13(1H,d,J=7.8 Hz),7.22(1H,dd,J=8.5,8.6 Hz),7.38–7.43(3H,m),7.47–7.51(2H, m),7.57(1H,ddd,J=4.7,7.8,8.5 Hz) FAB-MS (m/e):326[M+H]$^+$

Example 1127

R$^1$:7-F;R$^2$:H;R$^3$:i-Pr;R$^4$:H;Z:Ph;R:Ph $^1$HNMR(CDCl$_3$) δ :0.89(3H,d,J=6.6 Hz),1.10(3H,d,J=6.6 Hz),1.64(1H,m),4.20(1H,d, J=9.8 Hz),7.23–7.33(2H,m),7.35–7.51 (5H,m),7.54–7.58(1H,m) FAB-MS(m/e):326[M+H]$^+$

Example 1128

R$^1$:8-F;R$^2$:H;R$^3$:i-Pr;R$^4$:H;Z:Ph;R:Ph $^1$HNMR(CDCl$_3$) δ :0.92(3H,d,J=6.6 Hz),1.12(3H,d,J=6.6 Hz),1.61–1.65(1H,m),4.20(1H,d,J=9.8 Hz),6.98–7.00(1H,m),7.22–7.31(1H,m),7.38–7.49(5H,m),7.90(1H,dd,J=7.6, 11.1 Hz) FAB-MS(m/e):326[M+H]$^+$

Example 1129

R$^1$:9-F;R$^2$:H;R$^3$:i-Pr;R$^4$:H;Z:Ph;R:Ph $^1$HNMR(CDCl$_3$) δ :0.89(3H,d,J=6.6 Hz),1.10(3H,d,J=6.7 Hz),1.53–1.64(1H,m),4.19(1H,d,J=9.8 Hz),7.24(1H,dd,J=7.8,8.6 Hz),7.37–7.41(3H,m),7.50–7.54(2H,m),7.61(1H,dd, J=4.3,7.8,7.8 Hz),7.73(1H,d,J=7.8 Hz) FAB-MS(m/e): 326[M+H]$^+$

Example 1130

R$^1$:6-MeO;R$^2$:H;R$^3$:i-Pr;R$^4$:H;Z:Ph;R:Ph $^1$HNMR(CDCl$_3$) δ :0.88(3H,d,J=6.7 Hz),1.09(3H,d,J=6.7 Hz),1.58–1.68(1H,m),4.01 3H,s),4.21(1H,d,J=9.7 Hz),6.88 (1H,d,J=7.3 Hz),7.33–7.60(6H,m) FAB-MS(m/e):338[M+H]$^+$

Example 1131

R$^1$:9-MeO;R$^2$:H;R$^3$:i-Pr;R$^4$:H;Z:Ph;R:Ph $^1$HNMR(CDCl$_3$) δ :0.85(3H,d,J=6.6 Hz),1.08(3H,d,J=6.6 Hz),1.52–1.59(1H,m),3.69 3H,s),4.15(1H,d,J=9.7 Hz),7.03 (1H,dd,1.0,8.0 Hz),7.31–7.35(3H,m),7.46–7.59(3H,m),551H,d, J=7.8 Hz) FAB-MS(m/e):338[M+H]$^+$

Example 1132

R$^1$:6-OH;R$^2$:H;R$^3$:i-Pr;R$^4$:H;Z:Ph;R:Ph $^1$HNMR(CDCl$_3$) δ :0.90(3H,d,J=6.7 Hz),1.10(3H,d,J=6.7 Hz),1.52–1.70(1H,m),4.15 1H,d, J=9.7 Hz),6.83(1H,d,7.6 Hz),7.00(1H,d,J=8.3 Hz),7.34–7.51 (6H,m),8.03(1H,brs) FAB-MS(m/e):324[M+H]$^+$

Example 1133

R$^1$:9-OH;R$^2$:H;R$^3$:i-Pr;R$^4$:H;Z:Ph;R:Ph $^1$HNMR(CDCl$_3$) δ :0.79(3H,d,J=6.7 Hz),1.06(3H,d,J=6.7 Hz),1.60–1.67(1H,m),4.17 1H,d, J=9.5 Hz),7.11(1H,dd,J=1.0,8.2 Hz),7.41–7.64(7H,m),9.31(1H,brs) FAB-MS(m/e): 324[M+H]$^+$

Example 1134

R$^1$:7-NO$_2$;R$^2$:H;R$^3$:i-Pr;R$^4$:H;Z:Ph;R:Ph $^1$HNMR(CDCl$_3$) δ :0.93(3H,d,J=6.6 Hz),1.12(3H,d,J=6.6 Hz),1.58–1.68(1H,m),4.25 1H,d, J=9.9 Hz),7.41–7.55(5H,m),8.45(1H,dd,J=2.2,8.4 Hz),8.74(H,d,J=2.2 Hz) FAB-MS (m/e):353[M+H]$^+$

Example 1135

R$^1$:8-NO$_2$;R$^2$:H;R$^3$:i-Pr;R$^4$:H;Z:Ph;R:Ph $^1$HNMR(CDCl$_3$) δ :0.93(3H,d,J=6.7 Hz),1.12(3H,d,J=6.7 Hz),1.58–1.68(1H,m),4.25 1H,d,J=10.0 Hz),7.42–7.55(5H,m),8.09(1H,d,J=8.3 Hz),8.16(1H,d,J=1.8 Hz),8.46(1H,dd, J=1.8,8.3 Hz) FAB-MS(m/e):353[M+H]$^+$

Example 1136

R$^1$:9-NO$_2$;R$^2$:H;R$^3$:i-Pr;R$^4$:H;Z:Ph;R:Ph $^1$HNMR(CDCl$_3$) δ :0.76(3H,d,J=6.7 Hz),1.10(3H,d,J=6.7 Hz),1.45–1.59(1H,m),4.19 1H,d,J=10.0 Hz),7.26–7.38(5H, m),7.89(1H,dd,J=7.6,8.1 Hz),8.30(1H,d, J=0.9,.6 Hz), 0.401H, dd,J=0.9,8.1 Hz) FAB-MS(m/e):353[M+H]$^+$

Example 1137

R$^1$:6-NHPh;R$^2$:H;R$^3$:i-Pr;R$^4$:H;Z:Ph;R:Ph $^1$HNMR(CDCl$_3$) δ :0.79(3H,d,J=6.7 Hz),1.11(3H,d,J=6.6 Hz),1.50–1.56(1H,m),4.20(1H,d,J=9.5 Hz),5.55(1H,s), 6.79–6.81(2H,m),6.99–7.01(1H,m),7.19–7.27(2H,m), 7.28–7.37(2H, m),7.39–7.44(4H,m),7.46–7.52(2H,m) FAB-MS(m/e):399[M+H]$^+$

Example 1138

R$^1$:7-Me$_2$N;R$^2$:H;R$^3$:i-Pr;R$^4$:H;Z:Ph;R:Ph $^1$HNMR(CDCl$_3$) δ :0.91(3H,d,J=6.6 Hz),1.10(3H,d,J=6.6 Hz),1.55–1.66(1H,m),3.03(6H,s),4.19(1H,d,J=9.9 Hz),6.84 (1H,dd,J=2.5,8.6 Hz),7.08–7.50(7H,m) FAB-MS(m/e):351 [M+H]$^+$

Example 1139

R$^1$:7-Me;R$^2$:H;R$^3$:i-Pr;R$^4$:H;Z:Ph;R:Ph $^1$HNMR(CDCl$_3$) δ :0.91 (3H,d,J=6.6 Hz),1.10(3H,d,J= 6.6 Hz),1.55–1.65(1H,m),2.45(3H, s),4.20(1H,d,J=9.8 Hz), 7.21(1H,d,J=7.9 Hz),7.35–7.42(4H,m),7.45–7.50(2H,m), 7.70(1H,d, J=0.7 Hz) FAB-MS(m/e):322[M+H]$^+$

Example 1140

R$^1$:8-Me;R$^2$:H;R$^3$:i-Pr;R$^4$:H;Z:Ph;R:Ph $^1$HNMR(CDCl$_3$) δ :0.91(3H,d,J=6.6 Hz),1.09(3H,d,J=6.6 Hz),1.55–1.68(1H,m),2.38(3H,s),4.19(1H,d,J=9.8 Hz),7.11 (1H,s),7.35–7.45(4H,m),7.45–7.52(2H,m), 7.79(1H,d, J=7.6 Hz) FAB-MS(m/e):322[M+H]$^+$

Example 1141

R$^1$:7-t-Bu;R$^2$:H;R$^3$:i-Pr;R$^4$:H;Z:Ph;R:Ph $^1$HNMR(CDCl$_3$) δ :0.92(3H,d,J=6.7 Hz),1.10(3H,d,J=6.7 Hz),1.35(9H,s),1.63–1.67(1H,m),4.20(1H,d,J=9.9 Hz),7.26 (1H,d,J=8.4 Hz),7.37–7.52(5H,m),7.62(1H,dd, J=1.5,8.4 Hz),7.92 (1H,d,J=1.5 Hz) FAB-MS(m/e):364[M+H]$^+$

Example 1142

R$^1$:8-t-Bu;R$^2$:H;R$^3$:i-Pr;R$^4$:H;Z:Ph;R:Ph $^1$HNMR(CDCl$_3$) δ :0.92(3H,d,J=6.7 Hz),1.10(3H,d,J=6.7 Hz),1.27(9H,s),1.60–1.65(1H,m),4.19(1H,d,J=9.9 Hz),7.30 (1H,d,J=1.6 Hz),7.37–7.52(5H,m),7.61(1H,dd,J=1.6, 8.1 Hz),7.83(1H,d,J=8.1 Hz) FAB-MS(m/e):364[M+H]$^+$

Example 1143

R$^1$:7-Br;R$^2$:H;R$^3$:i-Pr;R$^4$:H;Z:Ph;R:Ph $^1$HNMR(CDCl$_3$) δ :0.91 (3H,d,J=6.6 Hz),1.09(3H,d,J= 6.65 Hz),1.58–1.65(1H,m),4.20(1H, d,J=9.8 Hz),7.40–7.50 (6H,m),7.70–7.79(2H,m) FAB-MS(m/e):386/388[M+H]$^+$

Example 1144

R$^1$:8-Br;R$^2$:H;R$^3$:i-Pr;R$^4$:H;Z:Ph;R:Ph $^1$HNMR(CDCl$_3$) δ :0.91(3H,d,J=6.7 Hz),1.10(3H,d,J=6.7 Hz),1.61–1.63(1H,m),4.20(1H,d, J=9.8 Hz),7.21(1H,d,J= 8.5 Hz),7.38–7.49(5H,m),7.70(1H,dd,J=1.9,8.1 Hz), 8.03–8.04(1H, m) FAB-MS(m/e):386/388[M+H]$^+$

Example 1145

R$^1$:7-Cl;R$^2$:H;R$^3$:i-Pr;R$^4$:H;Z:Ph;R:Ph $^1$HNMR(CDCl$_3$) δ :0.91 (3H,d,J=6.6 Hz),1.10(3H,d,J= 6.6 Hz),1.56–1.68(1H,m),4.21(1H,d,J=9.8 Hz),7.27(1H,dd, J=0.6,8.2 Hz),7.37–7.43(3H,m),7.44–7.51(2H,m), 7.55(1H, dd,J=1.9, 8.2 Hz),7.87(1H,dd,J=0.6,1.9 Hz) FAB-MS(m/e): 342[M+H]$^+$

Example 1146

R$^1$:8-Cl;R$^2$:H;R$^3$:i-Pr;R$^4$:H;Z:Ph;R:Ph $^1$HNMR(CDCl$_3$) δ :0.91(3H,d,J=6.6 Hz),1.10(3H,d,J=6.7 Hz),1.53–1.72(1H,m),4.20(1H,d,J=9.8 Hz),7.31 (1H,dd,J= 0.6, 1.7 Hz),7.39–7.48(5H,m),7.56(1H,dd,J=1.7,8.1 Hz), 7.84(1H, dd,J=0.6,8.1 Hz) FAB-MS(m/e):342[M+H]$^+$

Example 1147

R$^1$:7-Cl;R$^2$:8-Cl;R$^3$:i-Pr;R$^4$:H;Z:Ph;R:Ph $^1$HNMR(CDCl$_3$) δ :0.90(3H,d,J=6.6 Hz),1.09(3H,d,J=6.6 Hz),1.60–1.64(1H,m),4.19(1H, d, J=9.9 Hz),7.40–7.48(6H, m),7.98(1H,s) FAB-MS(m/e):376[M+H]$^+$

Example 1148

R$^1$:6-Cl;R$^2$:9-Cl;R$^3$:i-Pr;R$^4$:H;Z:Ph;R:Ph $^1$HNMR(CDCl$_3$) δ :0.76(3H,d,J=6.6 Hz),1.09(3H,d,J=6.6 Hz),1.49–1.59(1H,m),4.19(1H,d, J=9.6 Hz),7.36–7.48(6H, m),7.52(1 H,d,J=8.4 Hz) FAB-MS(m/e):376[M+H]$^+$

Example 1149

R$^1$:6-OH;R$^2$:9-I;R$^3$:i-Pr;R$^4$:H;Z:Ph;R:Ph $^1$HNMR(DMSO-d$_6$) δ :0.64(3H,d,J=6.7 Hz),0.96(3H,d, J=6.7 Hz),1.40–1.52(1H,m),4.19(1H,d,J=8.9 Hz),6.82(1H, d,J=8.5 Hz),7.30–7.40(5H,m),7.85(1H,d,J=8.5 Hz),10.56 (1H,brs) FAB-MS(m/e):450[M+H]$^+$

Example 1150

R$^1$:H;R$^2$:H;R$^3$:i-Pr;R$^4$:H;Z:1,2-naphthlyl;R:Ph $^1$HNMR(CDCl$_3$) δ :0.80(3H,d,J=6.5 Hz),1.13(3H,d,J=6.5 Hz),1.55–1.70(1H,m),4.21(1H,d,J=9.1 Hz),7.30–7.40(3H, m),7.40–7.50(3H,m),7.54–7.60(1H,m),7.80(1H,d, J=8.6 Hz),7.93(1H,d,J=8.2 Hz),7.94(1H,d,J=8.2 Hz),8.08(1H,d,J= 8.2 Hz) FAB-MS(m/e):358[M+H]$^+$

Example 1151

R$^1$:H;R$^2$:H;R$^3$:i-Pr;R$^4$:H;Z:2,3-naphthlyl;R:Ph $^1$HNMR(CDCl$_3$) δ :0.96(3H,d,J=6.1 Hz),1.13(3H,d,J=6.1 Hz),1.59–1.67(1H,m),4.28(1H,d, J=10.1 Hz),7.34–7.43(3H, m),7.54–7.76(4H,m),7.76(1H,s),7.83–7.85(1H,m), 8.04–8.06(1H, m),8.54(1H,s) FAB-MS(m/e):358[M+H]$^+$

Example 1152

R$^1$:H;R$^2$:H;R$^3$:i-Pr;R$^4$:H;Z:cyclohexenyl;R:Ph $^1$HNMR(CDCl$_3$) δ :0.79(3H,d,J=6.0 Hz),1.04(3H,d,J=6.0 Hz),1.56–1.80(5H,m),2.28–2.30(4H,m),4.04(1H,d,J=9.0 Hz),7.391–7.394(5H,m) FAB-MS(m/e):312[M+H]$^+$

[I-1]

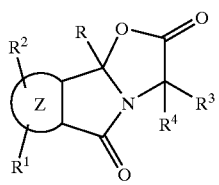

$R^3$ represents an amino acid residue.

Example 1153

$R^1$:H;$R^2$:H;$R^3$:D-Leucine;$R^4$:H;Z:Ph;R:Ph
ESI-MS(m/e):322[M+H]$^+$

Example 1154

$R^1$:H;$R^2$:H;$R^3$:L-Leucine;$R^4$:H;Z:Ph:R:Ph
ESI-MS(m/e):322[M+H]$^+$

Example 1155

$R^1$:H;$R^2$:H;$R^3$:D-NorLeucine;$R^4$:H;Z:Ph;R:Ph
ESI-MS(m/e):322[M+H]$^+$

Example 1156

$R^1$:H;$R^2$:H;$R^3$:L-NorLeucine;$R^4$:H;Z:Ph;R:Ph
ESI-MS(m/e):322[M+H]$^+$

Example 1157

$R^1$:H;$R^2$:H;$R^3$:D-AlloLeucine;$R^4$:H;Z:Ph;R:Ph
ESI-MS(m/e):322[M+H]$^+$

Example 1158

$R^1$:H;$R^2$:H;$R^3$:L-AlloLeucine;$R^4$:H;Z:Ph;R:Ph
ESI-MS(m/e):322[M+H]$^+$

Example 1159

$R^1$:H;$R^2$:H;$R^3$:D-NorValine;$R^4$:H;Z:Ph;R:Ph
ESI-MS(m/e):308[M+H]$^+$

Example 1160

$R^1$:H;$R^2$:H;$R^3$:L-NorValine;$R^4$:H;Z:Ph;R:Ph
ESI-MS(m/e):308[M+H]$^+$

Example 1161

$R^1$:H;$R^2$:H;$R^3$:D-Alanine;$R^4$:H;Z:Ph;R:Ph
ESI-MS(m/e):280[M+H]$^+$

Example 1162

$R^1$:H;$R^2$:H;$R^3$:L-Alanine;$R^4$:H;Z:Ph;R:Ph
ESI-MS(m/e):280[M+H]$^+$

Example 1163

$R^1$:H;$R^2$:H;$R^3$:D-Arginine;$R^4$:H;Z:Ph;R:Ph
ESI-MS(m/e):365[M+H]$^+$

Example 1164

$R^1$:H;$R^2$:H;$R^3$:L-Arginine;$R^4$:H;Z:Ph;R:Ph
ESI-MS(m/e):365[M+H]$^+$

Example 1165

$R^1$:H;$R^2$:H;$R^3$:D-Asparagine;$R^4$:H;Z:Ph;R:Ph
ESI-MS(m/e):323[M+H]$^+$

Example 1166

$R^1$:H;$R^2$:H;$R^3$:L-Asparagine;$R^4$:H;Z:Ph;R:Ph
ESI-MS(m/e):323[M+H]$^+$

Example 1167

$R^1$:H;$R^2$:H;$R^3$:L-Glutamic Acid;$R^4$:H;Z:Ph;R:Ph
ESI-MS(m/e):338[M+H]$^+$ Example 1168

$R^1$:H;$R^2$:H;$R^3$:L-Glutamic Acid;$R^4$:H;Z:Ph;R:Ph
ESI-MS(m/e):338[M+H]$^+$ Example 1169

$R^1$:H;$R^2$:H;$R^1$:D-Glutamine;$R^4$:H;Z:Ph;R:Ph
ESI-MS(m/e):337[M+H]$^+$

Example 1170

$R^1$:H;$R^2$:H;$R^3$:L-Glutamine;$R^4$:H;Z:Ph;R:Ph
ESI-MS(m/e):337[M+H]$^+$

Example 1171

$R^1$:H;$R^2$:H;$R^3$:D-Histidine;$R^4$:H;Z:Ph;R:Ph
ESI-MS(m/e):346[M+H]$^+$

Example 1172

$R^1$:H;$R^2$:H;$R^3$:L-Histidine;$R^4$:H;Z:Ph;R:Ph
ESI-MS(m/e):346[M+H]$^+$

Example 1173

$R^1$:H;$R^2$:H;$R^3$:D-Methionine;$R^4$:H;Z:Ph;R:Ph
ESI-MS(m/e):340[M+H]$^+$

Example 1174

$R^1$:H;$R^2$:H;$R^3$:L-Methionine;$R^4$:H;Z: Ph;R:Ph
ESI-MS(m/e):340[M+H]$^+$

Example 1175

$R^1$:H;$R^2$:H;$R^3$:D-Tryptophan;$R^4$:H;Z:Ph;R:Ph
ESI-MS(m/e):395[M+H]$^+$

Example 1176

$R^1$:H;$R^2$:H;$R^3$:L-Tryptophan;$R^4$:H;Z:Ph;R:Ph
ESI-MS(m/e):395[M+H]$^+$

Example 1177

R$^1$:H;R$^2$:H;R$^3$:D-Tyrosine;R$^4$:H;Z:Ph;R:Ph

ESI-MS(m/e):372[M+H]$^+$

Example 1178

R$^1$:H;R$^2$:H;R$^3$:L-Tyrosine;R$^4$:H;Z:Ph;R:Ph $^1$HNMR(CDCl$_3$) δ :2.45(1H,dd,J=11.5,14.5 Hz),3.07(1H, dd,J=4.4,14.5 Hz),4.92(1H,dd, J=4.4,11.5 Hz),5.31(1H,brs), 6.77(2H,d,J=8.6 Hz),6.99(2H,d,J=8.6 Hz),7.34–7.37(1H, m), 7.39–7.44(3H,m),7.46–7.50(2H,m),7.55–7.59(2H,m), 7.84–7.87(1H,m)

FAB-MS(m/e):372[M+H]$^+$

Example 1179

R$^1$:H;R$^2$:H;R$^3$:D-HomoPhenylalanine;R$^4$:H;Z:Ph;R:Ph

ESI-MS(m/e):370[M+H]$^+$

Example 1180

R$^1$:H;R$^2$:H;R$^3$: L-HomoPhenylalanine;R$^4$:H;Z:Ph;R:Ph

ESI-MS(rne):370[M+H]$^+$

Example 1181

R$^1$:H;R$^2$:H;R$^1$:D-Leucine;R$^4$:H;Z:Ph;R:4-Cl-Ph

ESI-MS(m/e):356[M+H]$^+$

Example 1182

R$^1$:H;R$^2$:H;R$^3$:L-Leucine;R$^4$:H;Z:Ph;R:4-Cl-Ph

ESI-MS(m/e):356[M+H]$^+$

Example 1183

R$^1$:H;R$^2$:H;R$^3$:D-NorLeucine;R$^4$:H;Z:Ph;R:4-Cl-Ph

ESI-MS(m/e):356[M+H]$^+$

Example 1184

R$^1$:H;R$^2$:H;R$^3$:L-NorLeucine;R$^4$:H;Z:Ph;R:4-Cl-Ph

ESI-MS(m/e):356[M+H]$^+$

Example 1185

R$^1$:H;R$^2$:H;R$^3$:D-AlloLeucine;R$^4$:H;Z:Ph;R:4-Cl-Ph

ESI-MS(m/e):356[M+H]$^+$

Example 1186

R$^1$:H;R$^2$:H;R$^3$:L-AlloLeucine;R$^4$:H;Z:Ph;R:4-Cl-Ph

ESI-MS(m/e):356[M+H]$^+$

Example 1187

R$^1$:H;R$^2$:H;R$^3$:D-NorValine;R$^4$:H;Z:Ph;R:4-Cl-Ph

ESI-MS(m/e):342[M+H]$^+$

Example 1188

R$^1$:H;R$^2$:H;R$^3$:L-NorValine;R$^4$:H;Z:Ph;R:4-Cl-Ph

ESI-MS(m/e):342[M+H]$^+$

Example 1189

R$^1$:H;R$^2$:H;R$^3$:D-Alanine;R$^4$:H;Z:Ph;R:4-Cl-Ph

ESI-MS(m/e):314[M+H]$^+$

Example 1190

R$^1$:H;R$^2$:H;R$^3$:L-Alanine;R$^4$:H;Z:Ph;R:4-Cl-Ph

ESI-MS(m/e):314[M+H]$^+$

Example 1191

R$^1$:H;R$^2$:H;R$^3$:D-Arginine;R$^4$:H;Z:Ph;R:4-Cl-Ph

ESI-MS(m/e):399[M+H]$^+$

Example 1192

R$^1$:H;R$^2$:H;R$^3$:L-Arginine;R$^4$:H;Z:Ph;R:4-Cl-Ph

ESI-MS(m/e):399[M+H]$^+$

Example 1193

R$^1$:H;R$^2$:H;R$^3$:D-Asparagine;R$^4$:H;Z:Ph;R:4-Cl-Ph

ESI-MS(m/e):357[M+H]$^+$

Example 1194

R$^1$:H;R$^2$:H;R$^3$:L-Asparagine;R$^4$:H;Z:Ph;R:4-Cl-Ph

ESI-MS(m/e):357[M+H]$^+$

Example 1195

R$^1$:H;R$^2$:H;R$^3$:D-Glutamic Acid;R$^4$:H;Z:Ph;R:4-Cl-Ph

ESI-MS(m/e):372[M+H]$^+$

Example 1196

R$^1$:H;R$^2$:H;R$^3$:L-Glutamic Acid; R$^4$:H;Z:Ph;R:4-Cl-Ph

ESI-MS(m/e):372[M+H]$^+$

Example 1197

R$^1$:H;R$^2$:H;R$^3$:D-Glutamine;R$^4$:H;Z:Ph;R:4-Cl-Ph

ESI-MS(m/e):371[M+H]$^+$

Example 1198

R$^1$:H;R$^2$:H;R$^3$:L-Glutamine;R$^4$:H;Z:Ph;R:4-Cl-Ph

ESI-MS(m/e):371[M+H]$^+$

Example 1199

R$^1$:H;R$^2$:H;R$^3$:D-Histidine;R$^4$:H;Z:Ph;R:4-Cl-Ph

ESI-MS(m/e):380[M+H]$^+$

Example 1200

R$^1$:H;R$^2$:H;R$^3$:L-Histidine;R$^4$:H;Z:Ph;R:4-Cl-Ph

ESI-MS(m/e):380[M+H]$^+$

Example 1201

R$^1$:H;R$^2$:H;R$^3$:D-Methionine;R$^4$:H;Z:Ph;R:4-Cl-Ph

ESI-MS(m/e):374[M+H]$^+$

Example 1202

R¹:H;R²:H;R³:L-Methionine;R⁴:H;Z:Ph;R:4-Cl-Ph

ESI-MS(m/e):374[M+H]⁺

Example 1203

R¹:H;R²:H;R³:D-Tryptophan;R⁴:H;Z:Ph;R:4-Cl-Ph

ESI-MS(m/e):429[M+H]⁺

Example 1204

R¹:H;R²:H;R¹:L-Tryptophan;R⁴:H;Z:Ph;R:4-Cl-Ph

ESI-MS(m/e):429[M+H]⁺

Example 1205

R¹:H;R²:H;R³:D-Tyrosine;R⁴:H;Z:Ph;R:4-Cl-Ph

ESI-MS(m/e):406[M+H]⁺

Example 1206

R¹:H;R²:H;R³:L-Tyrosine;R⁴:H;Z:Ph;R:4-Cl-Ph

ESI-MS(m/e):406[M+H]⁺

Example 1207

R¹:H;R²:H;R³:D-HomoPhenylalanine;R⁴:H;Z:Ph;R:4-Cl-Ph

ESI-MS(m/e):404[M+H]⁺

Example 1208

R¹:H;R²:H;R³:L-HomoPhenylalanine;R⁴:H;Z:Ph;R:4-Cl-Ph

ESI-MS(m/e):404[M+H]⁺

Example 1209

R¹:H;R²:H;R³:t-Bu;R⁴:H;Z:Ph;R:Ph $^1$HNMR(CDCl$_3$) δ :0.90(9H,s),4.29(1H,s),7.30(1H,ddd, J=0.8,3.2,5.6 Hz),7.34–7.41(3H, m),7.42–7.44(2H,m), 7.54–7.59(2H,m),7.91(1H,ddd,J=0.8,3.2,5.6 Hz)
ESI-MS(m/e):322[M+H]⁺

Example 1210

R¹:H;R²:H;R³:Me$_2$(OH)C;R⁴:H;Z:Ph;R:Ph $^1$HNMR(CDCl$_3$) δ :1.30(3H,s),1.45(3H,s),4.43(1H,s), 7.33–7.64(8H,m),7.93(1H,dd, J=6.0,2.6 Hz) FAB-MS(m/e):324[M+H]⁺

Example 1211

R¹:H;R²:H;R³:Me(MeO)CH;R⁴:H;Z:Ph;R:Ph $^1$HNMR(CDCl$_3$) δ :1.54(3H,d,J=6.1 Hz),3.66(3H,s),4.33 (1H,d,J=7.3 Hz),4.54(1H,dt, J=6.1,7.3 Hz),7.27–7.84(9H, m) FAB-MS(m/e):324[M+H]⁺

Example 1212

R¹:H;R²:H;R³:4-HO-Ph;R⁴:H;Z:Ph;R:Ph $^1$HNMR(CDCl$_3$) δ :4.95(1H,brs),5.73(1H,s),6.59(2H,d, J=8.4 Hz),7.05(2H,d,J=8.4 Hz), 7.22–7.43(6H,m),7.60–7.68 (2H,m),7.96–7.98(1H,m) FAB-MS(m/e):358[M+H]⁺

Example 1213

R¹:H;R²:H;R³:4-HO-3-I-Ph;R⁴:H;Z:Ph;R:Ph $^1$HNMR(CDCl$_3$) δ :5.38(1H,brs),5.68(1H,s),6.76(1H,d, J=8.5 Hz),7.14(1H,dd,J=2.2, 8.5 Hz),7.30–7.45(7H,m), 7.62–7.70(2H,m),7.96–8.00(1H,m) FAB-MS(m/e):484[M+H]⁺

Example 1214

R¹:H;R²:H;R³:4-HO-3,5-I$_2$-Ph;R⁴:FH;Z:Ph;R:Ph $^1$HNMR(CDCl$_3$) δ :5.62(1H,s),7.30–7.48(8H,m), 7.62–7.80(2H,m),7.97–8.01(1H,m) FAB-MS(m/e):610[M+H]⁺

Example 1215

R¹:H;R²:H;R³:4-HO-3-I-PhCH$_2$;R⁴:H;Z:Ph;R:Ph $^1$HNMR(CDCl$_3$) δ :2.45(1H,dd,J=9.8, 14.5 Hz),3.02(1H, dd,J=5.2, 14.5 Hz),4.84(1H,dd, J=5.2,9.8 Hz),5.61(1H,brs), 7.29–7.40(5H,m),7.42–7.43(3H,m),7.57–7.61(2H,m), 7.86–7.90(1H,m) FAB-MS(m/e):624[M+H]⁺

Example 1216

R¹:H;R²:H;R³:4-HO-3,5-I$_2$-PhCH$_2$;R⁴:H;Z:Ph;R:Ph $^1$HNMR(CDCl$_3$) δ :2.48(1H,dd,J=10.5,14.5 Hz),3.04(1H, dd,J=4.9, 14.5 Hz),4.86(1H,dd, J=4.9, 10.5 Hz),5.31 (1H, brs),6.86(1H,d,J=8.3 Hz),7.04(1H,dd,J=2.1,8.3 Hz),7.28 (1H,d,J=2.1 Hz),7.31–7.36(1H,m),7.41–7.42(5H,m), 7.57–7.60(2H,m),7.84–7.89(1H,m) FAB-MS(m/e):498[M+H]⁺

Example 1217

R¹:H;R²:H;R³:1-naphthylmethyl;R⁴:H;Z:Ph;R:Ph $^1$HNMR(CDCl$_3$) δ :2.54(1H,dd,J=9.8, 14.5 Hz),3.02(1H, dd,J=5.2,14.5 Hz),4.84(1H,dd, J=5.2,9.8 Hz),5.61(1H,brs), 7.32–7.34(1H,m),7.33–7.36(4H,m),7.39–7.43(3H,m), 7.57–7.61 (2H,m),7.87–7.89(2H,m)
FAB-MS(m/e):624[M+H]⁺

Example 1218

R¹:H;R²:H;R³:4-F-PhCH$_2$;R⁴:H;Z:Ph;R:Ph

ESI-MS(m/e):374[M+H]⁺

Example 1219

R¹:H;R²:H;R³: 1-naphthylmethyl; R⁴:H;Z:Ph;R:4-Cl-Ph

ESI-MS(m/e):406[M+H]⁺

Example 1220

R¹:H;R²:H;R³:4-F-PhCH$_2$;R⁴:H;Z:Ph;R:4-Cl-Ph

ESI-MS(m/e):408[M+H]⁺

Example 1221

R¹:H;R²:H;R³:i-Pr;R⁴:Me;Z:Ph;R:Ph $^1$HNMR(CDCl$_3$) δ :0.93(3H,d,J=6.8 Hz),0.98(3H,d,J=6.8 Hz),1.57–1.59(1H,m),1.70(3R,s),7.31–7.56(8H,m), 7.86–7.89(1H,m) FAB-MS(m/e):322[M+H]⁺

Example 1222

R$^1$:H;R$^2$:H;R$^3$:Me;R$^4$:Me;Z:Ph;R:Ph $^1$HNMR(CDCl$_3$) δ :1.27(3H,s),1.87(3H,s),7.35–7.40(4H, m),7.49–7.58(4H,m),7.86–7.89(1H,m) FAB-MS(m/e):294 [M+H]$^+$

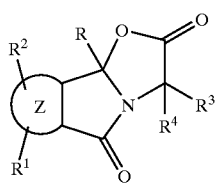

[I-1]

Example 1223

R$^1$:H;R$^2$:H;R$^3$及びR$^4$:=CH$_2$(R$^3$ and R$^4$ combine to form a =CH$_2$ group);Z:Ph;R:Ph $^1$HNMR(CDCl$_3$) δ :5.97(2H,d,J=4.3 Hz),7.35–7.42(3H, m),7.45–7.53(3H,m),7.57–7.68(2H,m),7.94–7.98(1H,m) FAB-MS(m/e):278[M+H]$^+$

Example 1224

R$^1$:H;R$^2$:H;R$^3$ and R$^4$:=CHMe(R$^3$ and R$^4$ combine to form a =CHMe group);Z:Ph;R:Ph $^1$HNMR(CDCl$_3$) δ :2.25(3H,d,J=7.3 Hz),6.66(1H,q,J=7.3 Hz),7.37–7.42(3H,m),7.48–7.54(3H,m),7.59–7.67(2H,m), 7.91–7.93(2H,m) FAB-MS(m/e):292[M+H]$^+$

Example 1225

R$^1$:H;R$^2$:H;R$^3$ and R$^4$:—(CH$_2$)$_4$—(R$^3$ and R$^4$ combine to form a (CH$_2$)$_4$— group);Z:Ph;R:Ph $^1$HNMR(CDCl$_3$) δ :1.50–2.30(7H,m),3.00–3.15(1H,m), 7.30–7.42(4H,m),7.43–7.52(2H, m),7.52–7.62(2H,m), 7.82–7.92(1H,m) FAB-MS(m/e):320[M+H]$^+$

Example 1413

R$^1$:H;R$^2$:H;R$^3$:i-Pr;R$^4$:H;Z:2,3-pyrazinyl;R:4-n-PrNHCOCH$_2$O-Ph

FAB-MS(m/e):425[M+H]$^+$

Example 1427

R$^1$:H;R$^2$:H;R$^3$:D-Glutamic Acid;R$^4$:H;Z:Ph;R:3-Me-4-n-PrNHCO—CH$_2$OPh $^1$HNMR(CDCl$_3$) δ :0.92(3H,t,J=7.4 Hz),1.54–1.61(2H, m),2.14–2.24(2H,m),2.28(3H,s), 2.58–2.65(2H,m),3.34(2H, q,J=6.6 Hz),4.50(2H,s),4.63(1H,dd,J=5.2,11.0 Hz), 6.52–6.56(1H,m),6.78(1H,d,J=8.2 Hz),7.27(1H,s),7.32(1H, d,J=8.2 Hz),7.35–7.39(1H,m),7.58–7.63(2H, m),7.89–7.92 (1H,m) FAB-MS(m/e):467[M+H]$^+$

Example 1428

R$^1$:H;R$^2$:H;R$^3$:L-Glutamic Acid;R$^4$:H;Z:Ph;R:3-Me-4-n-PrNHCO—CH$_2$OPh $^1$HNMR(CDCl$_3$) δ :0.92(3H,t,J=7.4 Hz),1.54–1.61(2H, m),2.14–2.24(2H,m),2.28(3H,s), 2.58–2.65(2H,m),3.34(2H, q,J=6.6 Hz),4.50(2H,s),4.63(1H,dd,J=5.2,11.0 Hz), 6.52–6.56(1H,m),6.78(1H,d,J=8.2 Hz),7.27(1H,s),7.32(1H, d,J=8.2 Hz),7.35–7.39(1H,m),7.58–7.63(2H, m),7.89–7.92 (1H,m) FAB-MS(m/e):467[M+H]$^+$

Example 1429

R$^1$:H;R$^2$:H;R$^3$:(3-Pyridyl)CH$_2$;R$^4$:H;Z:Ph;R:3-Me-4-n-PrNHCOCH$_2$O-Ph $^1$HNMR(CDCl$_3$) δ :0.93(3H,t,J=7.4 Hz),1.54–1.68(2H, m),2.27(3H,s),2.62(1H,dd, J=11.0,14.4 Hz),3.17(1H,dd,J= 4.7,14.4 Hz),3.33(2H,q,J=6.7 Hz),4.90(1H,dd,J=4.5,10.9 Hz),6.64–6.68(1H,m),6.82(1H,d,J=8.3 Hz),7.14(1H,d,J=1.8 Hz),7.26–7.36(3H,m),7.56–7.64(2H, m),7.72–7.75(2H,m), 7.84–7.87(1H,m) FAB-MS(m/e):486[M+H]$^+$

Example 1430

R$^1$:H;R$^2$:H;R$^3$:i-Pr;R$^4$:H;Z:Ph;R:4-n-PrNHCOCH$_2$O-3-CH$_2$=CH-Ph $^1$HNMR(CDCl$_3$) δ :0.92(3H,d,J=6.5 Hz),0.95(3H,t,J=7.3 Hz),1.12(3H,d,J=6.5 Hz),1.23–1.35(1H,m),1.50–1.67(2H, m),3.33(2H,q,J=6.8 Hz),4.21(1H,d,J=9.9 Hz),4.53(2H,s), 5.40(1H,d,J=11.2 Hz),5.76(1H,d,J=17.7 Hz),6.44–6.48(1H, m),6.85(1H,d,J=8.8 Hz),6.96(1H, dd,J=11.2,17.7 Hz), 7.27–7.40(3H,m),7.59–7.61(2H,m),7.90–7.93(1H,m) FAB-MS(m/e):449[M+H]$^+$

Example 1431

R$^1$:H;R$^2$:H;R$^3$:i-Pr;R$^4$:H;Z:Ph;R:4-n-PrNHCOCH$_2$O-3-(2-Pyridyl)-Ph $^1$HNMR(CDCl$_3$) δ :0.82(3H,t,J=7.4 Hz),0.98(3H,d,J=6.6 Hz).1.14(3H,d,J=6.6 Hz),1.43–1.55(2H,m),1.65–1.77(1H, m),3.25(2H,q,J=6.5 Hz),4.23(1H,d,J=9.9 Hz),4.62(2H,d, J=14.9 Hz),7.05(1H,d,J=8.7 Hz),7.32–7.40(2H,m), 7.50–7.63(5H,m),7.81–7.86(1H,m),7.90–7.92(1H,m), 8.195–8.197(1H,m) FAB-MS(m/e):500[M+H]$^+$

Example 1432

R$^1$:H;R$^2$:H;R$^3$:i-Pr;R$^4$:H;Z:Ph;R:4-n-PrNHCOCH$_2$O-3-(3-Pyridyl)-Ph $^1$HNMR(CDCl$_3$) δ :0.80(3H,t,J=7.4 Hz),0.99(3H,d,J=6.6 Hz),1.15(3H,d,J=6.6 Hz),1.37–1.42(2H,m),1.65–1.75(1H, m),3.18(2H,q,J=6.7 Hz),4.24(1H,d,J=9.9 Hz),4.50(2H,d, J=14.2 Hz),6.10–6.12(1H,m),6.99(1H,d,J=8.7 Hz), 7.37–7.42(2H,m),7.44(1H,d,J=2.4 Hz), 7.56–7.65(3H,m), 7.77(1H,dd,J=1.8,7.8 Hz),7.91–7.94(1H,m),8.63–8.72(2H, m) FAB-MS(m/e):500[M+H]$^+$

Example 1433

R$^1$:H;R$^2$:H;R$^3$:i-Pr;R$^4$:H;Z:Ph;R:4-n-PrNHCOCH$_2$O-3-(4-Pyridyl)-Ph $^1$HNMR(CDCl$_3$) δ :0.82(3H,t,J=7.4 Hz),0.98(3H,d,J=6.6 Hz),1.15(3H,d,J=6.6 Hz),1.38–1.48(2H,m),1.64–1.74(1H, m),3.19(2H,q,J=6.4 Hz),4.24(1H,d,J=9.9 Hz),4.52(2H,d, J=14.2 Hz),6.14–6.16(1H,m),6.99(1H,d,J=8.6 Hz), 7.36–7.44(3H,m),7.47(1H,d,J=2.4 Hz), 7.54–7.65(3H,m), 7.91–7.94(1H,m),8.69–8.76(2H,m) FAB-MS(m/e):500[M+H]$^+$

Example 1434

R$^1$:H;R$^2$:H;R$^3$:i-Pr;R$^4$:H;Z:Ph;R:3-Ph-4-n-PrNHCOCH$_2$O-Ph $^1$HNMR(CDCl$_3$) δ :0.79(3H,t,J=7.4 Hz),0.99(3H,d,J=6.6 Hz),1.15(3H,d,J=6.6 Hz),1.26–1.40(2H,m),1.65–1.76(1H, m),3.14(2H,q,J=7.1 Hz),4.23(1H,d,J=9.9 Hz),4.48(2H,d, J=14.3Hz),6.25(1H,s),6.94(1H,d,J=8.6 Hz),7.37–7.45(7H, m),7.51(1H,dd,J=2.5,8.6 Hz), 7.57–7.62(2H,m),7.89–7.92 (1H,m) FAB-MS(m/e):499[M+H]$^+$

Example 1435

R$^1$:H;R$^2$:H;R$^3$:i-Pr;R$^4$:H;Z:Ph;R:3-Et-4-n-PrNHCOCH$_2$O-Ph $^1$HNMR(CDCl$_3$) δ :0.93(3H,t,J=7.4 Hz),0.94(3H,d,J=6.6 Hz),1.11(3H,d,J=6.6 Hz),1.21(3H,t,J=7.5 Hz),1.53–1.68 (3H,m),2.61–2.73(2H,m),3.33(2H,q,J=6.6 Hz),4.20(1H,d, J=9.9 Hz),4.50(2H,s),6.48–6.49(1H,m),6.80(1H,d,J=8.6 Hz),7.28(1H,d,J=2.2 Hz),7.34(1H,dd,J=2.2,8.6 Hz), 7.341–7.347(1H,m),7.58–7.62(2H,m),7.90–7.93(1H,m) FAB-MS(m/e):451[M+H]$^+$

Example 1436

R$^1$:H;R$^2$:H;R$^3$:i-Pr;R$^4$:H;Z:Ph;R:3-n-Bu-4-n-PrNHCOCH$_2$O-Ph $^1$HNMR(CDCl$_3$) δ :0.92(3H,t,J=7.3 Hz),0.93(3H,t,J=7.3 Hz),1.11(3H,d,J=6.8 Hz),1.24–1.42(6H,m),1.28(3H,d,J=6.8 Hz),1.53–1.64(1H,m),2.51–2.71(2H,m),3.33(2H,q, J=6.6 Hz),4.20(1H,d,J=9.9 Hz),4.49(2H,s),6.47–6.49(1H,m),6.79 (1H,d,J=8.4 Hz),7.25(1H,d,J=2.4 Hz),7.33(1H,dd,J=2.4,8.4 Hz),7.33–7.36(1H,m),7.56–7.61(2H,m),7.90–7.92(1H,m) FAB-MS(m/e):479[M+H]$^+$

Example 1437

R$^1$:H;R$^2$:H;R$^3$:i-Pr;R$^4$:H;Z:Ph;R:3-MeO-6-Me-Ph $^1$HNMR(CDCl$_3$) δ :0.84(3H,d,J=6.2 Hz),1.11(3H,d,J=6.2 Hz),1.61–1.68(1H,m),1.73(3H,s),3.86(3H,s),4.23(1H,d,J= 9.6 Hz),6.82(1H,dd,J=2.1,8.2 Hz),6.99(1h,d,J=8.2 Hz), 7.30–7.31(1H,m),7.46(1H,d,J=2.1 Hz),7.60–7.61 (2H,m), 7.92–7.95(1H,m) FAB-MS(m/e):352[M+H]$^+$

Example 1438

R$^1$:H;R$^2$:H;R$^3$:i-Pr;R$^4$:H;Z:Ph;R:3-HO-6-Me-Ph $^1$HNMR(CDCl$_3$) δ :0.84(3H,d,J=6.6 Hz),1.10(3H,d,J=6.6 Hz),1.62–1.67(1H,m),1.71(3H,s),4.24(1H,d,J=9.5 Hz), 5.72–5.73(1H,m),6.81(1H,dd,J=2.3,8.0 Hz),6.94(1H,d, J=8.0 Hz),7.28–7.31(1H,m),7.42(1H,d,J=2.3 Hz),7.59–7.64 (2H,m),7.93–7.96(1H,m) FAB-MS(m/e):338[M+H]$^+$

Example 1439

R$^1$:H;R$^2$:H;R$^3$:i-Pr;R$^4$:H;Z:Ph;R:6-Me-3-n-PrNHCOCH$_2$O-Ph $^1$HNMR(CDCl$_3$) δ :0.82(3H,d,J=6.7 Hz),0.98(3H,t,J=7.4 Hz),1.12(3H,d,J=6.7 Hz),1.58–1.72(3H,m),1.75(3H,s),3.37 (2H,q,J=6.7 Hz),4.26(1H,d,J=9.4 Hz),4.51–4.52(2H,m), 6.70–6.71(1H,m),6.81(1H,dd,J=2.7,8.3 Hz),7.04(1H,d,J= 8.3 Hz),7.27–7.28(1H,m),7.30(1H,d, J=2.7 Hz),7.54–7.65 (2H,m),7.94–7.96(1H,m) FAB-MS(m/e):437[M+H]$^+$

Example 2002

3-(1-Methylethyl)-9b-phenyl-1H-imidazo[2,1-a]isoindole-2,5(3H-9bH)-dione (Compound of R$^1$:H;R$^2$:H;R$^3$:i-Pr;R$^4$:H;R$^5$:H;Z:Ph;R:Ph in the General Formula [I-2])

1-Hydroxybenzotriazole hydrate (100 mg, 0.73 mmol), 1-(3-dimethylaminopropyl)-3-ethylcarbodiimide hydrochloride (113 mg, 0.58 mmol) and 28% ammonia water (3 ml) were added to a solution of N-t-butoxycarbonyl-D-valine (106 mg, 0.49 mmol) in N,N-dimethylformamide (1 ml) at room temperature, and the reaction mixture was stirred at room temperature for 12 hours. Water and ethyl acetate were added to the reaction mixture, and the organic layer was dried and concentrated under reduced pressure. The resulting residue was purified by flash silica gel column chromatography to obtain an amide (80 mg, yield: 76%). The amide (80 mg, 0.37 mmol) was dissolved in a solution of 4N hydrochloric acid in 1,4-dioxane (2 ml), and the reaction mixture was stirred at room temperature for 1 hour and concentrated under reduced pressure. 1-Hydroxybenzotriazole hydrate (60 mg, 0.63 mmol), 1-(3-dimethylaminopropyl)-3-ethylcarbodiimide hydrochloride (85 mg, 0.44 mmol) and triethylamine (0.12 ml, 0.85 mmol) were successively added to a solution of the resulting residue and 2-benzoylbenzoic acid (83 mg, 0.37 mmol) in dimethylformamide (2 ml) at room temperature, and the reaction mixture was stirred at room temperature for 12 hours. Water and ethyl acetate were added to the reaction mixture, and the organic layer was dried and concentrated under reduced pressure. The resulting residue was purified by flash silica gel column chromatography to obtain a condensed compound (130 mg, yield: 99%). p-Toluenesulfonic acid (10 mg) was added to a solution of the obtained condensed compound (13 mg, 0.040 mmol) in toluene (2 ml) at room temperature, and the reaction mixture was stirred under reflux with heating for 4 hours. The reaction mixture was concentrated under reduced pressure, the resulting residue was subjected three times to azeotropic distillation with toluene, and the reaction mixture was concentrated under reduced pressure. The resulting residue was purified by silica gel column chromatography (hexane:ethyl acetate=2:1) to obtain the captioned compound (2.0 mg, yield: 16%) as colorless oily matter.

$^1$HNMR(CDCl$_3$) δ :0.81 (3H,d,J=6.6 Hz),1.14(3H,d,J= 6.6 Hz),1.70–1.83(1H,m),4.15(1H,d,J=8.6 Hz),7.30–7.35 (5H,m),7.50–7.54(2H,m),7.89–7.93(1H,m),8.09(1H,brs) FAB-MS(m/e):307[M+H]$^+$ In the same manner as in Example 2002, compounds of Examples 2011, 2050, 2074, 2467, 2471, 2472 and 2474 corresponding to the compound numbers of the compounds of the general formula [I-2] in the aforementioned compound lists were obtained. Physical constants of these compounds are shown below.

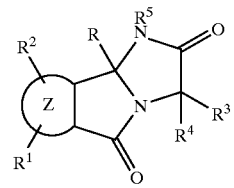

[I-2]

Example 2011

R$^1$:H;R$^2$:H;R$^3$:i-Pr;R$^4$:H;R$^5$:H;Z:Ph;R:4-MeO-Ph $^1$HNMR(CDCl$_3$) δ :0.86(3H,d,J=6.8 Hz),1.19(3H,d,J=6.8 Hz),1.77–1.85(1H,m),3.79(3H,s),4.16(1H,d,J=8.6 Hz),6.84 (2H,d,J=8.9 Hz),7.22–7.88(6H,m),9.55(1H,brs) ESI-MS(m/e):337[M+H]$^+$ Example 2050

R$^1$:H;R$^2$:H;R$^3$:i-Pr;R$^4$:H;R$^5$:H;Z:Ph;R:3-NH$_2$-4-Cl-Ph $^1$HNMR(CDCl$_3$) δ :0.89(3H,d,J=6.7 Hz),1.17(3H,d,J=6.7 Hz),1.77–1.88(1H,m),4.13(1H,d,J=8.7 Hz),6.67(1H,dd,J=

2.2,8.3 Hz),6.77(1H,d,J=2.2 Hz),7.19(1H,d,J=8.3 Hz),
7.21–7.88 (4H,m),9.02(1H,s) ESI-MS(m/e):356[M+H]$^+$

Example 2074

R$^1$:H;R$^2$:H;R$^3$:i-Pr;R$^4$:H;R$^5$:H;Z:Ph;R:3-I-4-n-PrNHCOCH$_2$O-Ph $^1$HNMR(CDCl$_3$) δ :0.86(3H,d,J=6.7 Hz),0.98(3H,t,J=7.4 Hz),1.17(3H,d,J=6.7 Hz),1.55–1.78(3H,m),3.35(2H,q,J=7.0 Hz),4.16(1H,d,J=8.8Hz),4.50(2H,s),6.73(1H,d,J=8.6 Hz), 6.92(1H,brs),7.16–7.93(6H,m),8.98(1H,brs) FAB-MS(m/e):548[M+H]$^+$ Example 2467

R$^1$:H;R$^2$:H;R$^3$:i-Pr;R$^4$:H;R$^5$:H;Z:Ph;R:4-n-PrNHCOCH$_2$O-pyrimidin-5-yl) FAB-MS(m/e):424 [M+H]$^+$ Example 2471

R$^1$:H;R$^2$:H;R$^3$:i-Pr;R$^4$:H;R$^5$:Me;Z:Ph;R:4-n-PrNHCOCH$_2$O-Ph $^1$HNMR(CDCl$_3$) δ :0.76(3H,d,J=6.6 Hz),0.91 (3H,d,J=7.4 Hz),1.17(3H,d,J=6.6 Hz),1.52–1.68(3H,m),3.13(3H,s), 3.31 (2H,dt,J=6.6,7.3 Hz),4.03(1H,d,J=10.0 Hz),4.48(2H,s), 6.53(1H,brs),6.85–8.00(8H,m) FAB-MS(m/e):436[M+H]$^+$ Example 2472

R$^1$:H;R$^2$:H;R$^3$:i-Pr;R$^4$:H;R$^5$:n-PrNHCOCH$_2$;Z:Ph;R:4-n-PrNHCO—CH$_2$OPh $^1$HNMR(CDCl$_3$) δ :0.61 (3H,t,J=7.4 Hz),0.81(3H,d,J=6.5 Hz),0.93(3H,t,J=7.4 Hz), 1.01–1.11 (2H,m),1.20(3H,d,J=6.5 Hz),1.51–1.68(3H,m),2.83–2.97(2H,m),3.32(2H,t,J=7.3 Hz), 4.17(1H,d,J=10.5 Hz),4.33(2H,d,J=16.2Hz),4.50(2H,s),5.69(1H,brs),6.52(1H,brs),6.87–8.00(8H,m) FAB-MS(m/e):521[M+H]$^+$ Example 2474

R$^1$:H;R$^2$:H;R$^3$:i-Pr;R$^4$:H;R$^5$:MeSO$_2$NHCOCH$_2$;Z:Ph;R:4-n-PrNHCO—CH$_2$O-Ph

FAB-MS(m/e):557[M+H]$^+$

Example 3011

9b-(4-Methoxyphenyl)-3-(1-methylethyl)-1H-pyrrolo[2.1-a]isoindole-2,5(3H,9bH)-dione (Compound of R$^1$:H;R$^2$:H;R$^3$:i-Pr;R$^4$:H;R$^6$:H;Z:Ph;R:4-MeO-Ph in the General Formula [I-3])

Triethylamine (55 ml, 390 mmol) and ethyl chloroformate (13 ml, 140 mmol) were added to a solution of N-t-butoxycarbonyl-D-valine (25 g, 120 mmol) in tetrahydrofuran (500 ml) at −40° C., the reaction mixture was stirred at −40° C. for 2 hours, N,O-dimethylhydroxylamine hydrochloride (23 g, 230 mmol) was added at −40° C., the mixture was stirred at 0° C. for 1 hour, and aqueous ammonium chloride solution was added. The mixture was extracted with ethyl acetate, and the organic layer was washed with aqueous saturated sodium chloride solution, dried and concentrated under reduced pressure. The resulting residue was purified by silica gel column chromatography (hexane:ethyl actate=7:3) to obtain an amide (18 g, yield: 61%). A solution (56.6 mmol) of methylmagnesium bromide (3.0 M) in diethyl ether (19.0 ml) was added dropwise to a solution of the amide (4.9 g, 18.9 mmol) in tetrahydrofuran (100 ml) at −70° C., the reaction mixture was stirred at room temperature for 2 hours, and then aqueous ammonium chloride solution was added to the reaction mixture. The mixture was extracted with ethyl acetate, and the organic layer was washed with aqueous saturated sodium chloride solution, dried and concentrated under reduced pressure. The resulting residue was purified by silica gel column chromatography (hexane:ethyl acetate=8:1) to obtain a ketone (2.0 g, yield: 50%).

The obtained ketone (2.0 g, 0.22 mmol) was dissolved in a solution of 4N hydrochloric acid in 1,4-dioxane (20 ml) at room temperature, and the reaction mixture was stirred at room temperature for 1 hour and concentrated under reduced pressure to obtain an amine hydrochloride (1.4 g, yield: 99%). The amine hydrochloride (510 mg. 3.4 mmol) was dissolved in methylene chloride (32 ml), and 1-hydroxybenzotriazole hydrate (590 mg, 4.4 mmol), 2-(4-methoxybenzoyl)benzoic acid (860 mg, 3.4 mmol). 1-(3-dimethylaminopropyl)-3-ethylcarbodiimide hydrochloride (840 mg, 4.4 mmol) and triethylamine (1.8 ml, 13.5 mmol) were successively added to the reaction mixture at room temperature. The reaction mixture was stirred at room temperature for 12 hours, and water was added to the reaction mixture. The mixture was extracted with ethyl acetate, and the organic layer was washed with aqueous saturated sodium bicarbonate solution and aqueous saturated sodium chloride solution, dried and concentrated under reduced pressure. The resulting residue was purified by silica gel column chromatography (hexane:ethyl acetate= 3:2) to obtain a condensed product (990 mg, yield: 83%). Triethylamine (2.1 ml, 15 mmol) and trimethylsilyl trifluoromethanesulfonate (2.7ml, 15 mmol) were successively added to a solution of the obtained condensed compound (890 mg, 2.5 mmol) in methylene chloride (50 ml), and the reaction mixture was stirred at room temperature for 2 hours. A boron trifluoride-diethyl ether complex (6.4 ml, 50 mmol) was added at −70° C., and the reaction mixture was stirred at room temperature for 12 hours. Water was added to the reaction mixture, and the mixture was extracted with chloroform. The organic layer was washed with aqueous saturated ammonium chloride solution and aqueous saturated sodium chloride solution, dried and concentrated under reduced pressure. The obtained residue was purified by silica gel column chromatography (hexane:ethyl acetate=4:1) to obtain the diastereomer A of the captioned compound (94 mg, yield: 11%) as colorless oily matter and the diastereomer B thereof (306 mg, yield: 36%) as colorless oily matter.

Diastereomer A $^1$HNMR(CDCl$_3$) δ :0.86(3H,d,J=7.0 Hz),1.19(3H,d,J=7.0 Hz),2.59(1H,d,J=15.9 Hz), 3.44(1H,d,J=15.9 Hz),3.63–3.71 (1H,m),3.76(3H,s),3.78(1H,d,J=3.2 Hz),6.83(2H,d, J=8.9 Hz),7.23–7.28(1H,m),7.35–7.37(1H,m),7.43–7.54(2H,m), 7.87–7.90(1H,m) ESI-MS(m/e):336[M+H]$^+$ Diastereomer B $^1$HNMR(CDCl$_3$) δ :0.85(3H,d,J=6.7 Hz),1.09(3H,d,J=6.7 Hz),1.50–1.70(1H,m),2.53(1H,d,J=17.4 Hz),3.60(1H,d,J= 17.4 Hz),3.79(3H,s),4.01(1H,d,J=9.6 Hz),6.84(2H,d,J=9.0 Hz),7.14–7.24(1H,m),7.21 (2H,d,J=9.0 Hz),7.45–7.54(2H, m),7.90–7.93(1H,m) ESI-MS(m/e):336[M+H]$^+$ In the same manner as in Example 3011, compounds of Examples 3001, 3002, 3007, 3014, 3015, 3020, 3023, 3024, 3033, 3039, 3047, 3050, 3051, 3056, 3057, 3058, 3061, 3063, 3065, 3072, 3073, 3074, 3082, 3092, 3093, 3094, 3095, 3096, 3103, 3104, 3107, 3112, 3115, 3117, 3126, 3129, 3134, 3226, 3241, 3246, 3258, 3266, 3296, 3307, 3319, 3412, 3418, 3464, 3472, 3473, 3474, 3475, 3476, 3477, 3478, 3479, 3480, 3481, 3482, 3485, 3486, 3487, 3488, 3489, 3492, 3499, 3500, 3501, 3509, 3510, 3511, 3515 and 3516 corresponding to the compound numbers of the compounds of the general formula [I-3a], the compounds of the general formula [I-3b], the general formula [I-3c] or the compounds of the general formula [I-3d] in the aforementioned compound lists were obtained. Physical constants of these compounds are shown below.

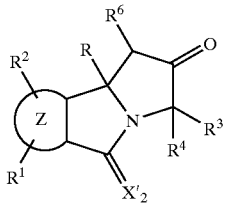

[I-3a]

Example 3001

$R^1$:H;$R^2$:H;$R^3$:i-Pr;$R^4$:H;$R^6$:H;Z:Ph;R:2-MeO-Ph
Diastereomer A $^1$HNMR(CDCl$_3$) δ :0.85(3H,d,J=7.0 Hz),1.21(3H,d,J=7.0 Hz),2.61(1H,d,J=16.7 Hz), 3.67–3.78(1H,m),3.86(1H,d,J=16.7 Hz),3.87(1H,d,J=3.2 Hz),4.01(3H,s),6.87(1H,t, J=7.4 Hz),6.94(1H,d,J=8.0 Hz),7.22–7.28(2H,m),7.41–7.50(2H, m),7.83(1H,dd,J=1.6, 7.4 Hz),7.90(1H,d,J=6.3 Hz) ESI-MS (m/e):336[M+H]$^+$
Diastereomer B $^1$HNMR(CDCl$_3$) δ :1.13(6H,d,J=6.6 Hz),1.69–1.74(1H, m),2.64(1H,d,J=18.1 Hz),3.89(3H,brs),3.97(1H,d,J=18.1 Hz),4.00(1H,d,J=10.3 Hz),6.88(1H,t,J=7.6 Hz),6.94(1H,d, J=8.2 Hz),7.30(1H,t,J=8.2 Hz),7.41–7.50(3H,m),7.61(1H, brs),7.86(1H,d,J=6.5 Hz) ESI-MS(m/e):336[M+H]$^+$

Example 3002

$R^1$:H;$R^2$:H;$R^3$:i-Pr;$R^4$:H;$R^6$:H;Z:Ph;R:Ph $^1$HNMR(CDCl$_3$) δ :0.87(3H,d,J=6.7 Hz),1.09(3H,d,J=6.6 Hz),1.49–1.70(1H,m),2.58(1H,d,J=17.6 Hz),3.66(1H,d,J=7.6 Hz),4.03(1H,d,J=9.6 Hz),7.12–7.21(1H,m),7.25–7.39 (5H,m),7.42–7.56(2H,m),7.89–7.97(1H,m) FAB-MS(m/e): 306[M+H]$^+$

Example 3007

$R^1$:H;$R^2$:H;$R^3$:i-Pr;$R^4$:H;$R^6$:H;Z:Ph;R:4-HO-Ph $^1$HNMR(CDCl$_3$) δ :0.84(3H,d,J=6.7 Hz),1.09(3H,d,J=6.7 Hz),1.51–1.64(1H,m),2.52(1H, d,J=17.3 Hz),3.59(1H,d,J=17.3 Hz),4.01(1H,d,J=9.5 Hz),5.17(1H,brs),6.79(2H,d,J=8.8Hz),7.15–7.19(1H,m),7.16(2H,d,J=8.8 Hz),7.46–7.54 (2H,m),7.90–7.93(1H,m) ESI-MS(m/e):322[M+H]$^+$

Example 3014

$R^1$:H;$R^2$:H;$R^3$:i-Pr;$R^4$:H;$R^6$:H;Z:Ph;R:4-t-BuO$_2$CCH$_2$O-Ph $^1$HNMR(CDCl$_3$) δ :0.83(3H,d,J=6.6 Hz),1.45–1.46(9H,m),1.49–1.67(1H,m),2.53(1H,d,J=17.3 Hz),3.59(1H,d,J=17.3 Hz),4.01(1H,d,J=9.6 Hz),4.48–4.49 (2H,m),6.83(2H,d,J=8.9 Hz),7.15–7.24(1H,m),7.20(2H,d, J=8.9 Hz),7.45–7.55(2H,m), 7.90–7.93(1H,m) FAB-MS(m/e):436[M+H]$^+$

Example 3015

$R^1$:H;$R^2$:H;$R^3$:i-Pr;$R^4$:H;$R^6$:H;Z:Ph;R:4-HO$_2$CCH$_2$O-Ph $^1$HNMR(CDCl$_3$) δ :0.83(3H,d,J=6.6 Hz),1.08(3H,d,J=6.6 Hz),1.47–1.59(1H,m),2.56(1H,d,J=17.2 Hz),3.61(1H,d,J=17.2 Hz),4.02(1H,d,J=9.6 Hz),4.67(2H,s),6.87(2H,d,J=8.9 Hz),7.17(1H,dd,J=1.4,6.2 Hz),7.22(2H,d,J=8.9 Hz), 7.46–7.56(2H,m),7.93(1H,dd,J=1.8, 6.2 Hz),8.65(1H,brs) FAB-MS(m/e):380[M+H]$^+$

Example 3020

$R^1$:H;$R^2$:H;$R^3$:i-Pr;$R^4$:H;$R^6$:H;Z:Ph;R:4-HOC(Me)$_2$(CH$_2$)$_2$O-Ph $^1$HNMR(CDCl$_3$) δ :0.87(3H,d,J=6.6 Hz),1.12(3H,d,J=6.6 Hz),1.32(6H,s),1.50–1.62(1H,m),1.99(2H,t,J=6.3 Hz),2.55 (1H,d,J=16.0 Hz),3.62(1H,d,J=16.0 Hz),4.02(1H,d,J=9.5 Hz),4.17(2H,t,J=6.3 Hz),6.86(1H,d,J=8.8 Hz),7.18–7.92 (6H,m) FAB-MS(m/e):408[M+H]$^+$

Example 3023

$R^1$:H;$R^2$:H;$R^3$:i-Pr;$R^4$:H;$R^6$:H;Z:Ph;R:4-EtNHCOCH$_2$O-Ph

FAB-MS(m/e):407[M+H]$^+$

Example 3024

$R^1$:H;$R^1$:H;$R^1$:i-Pr;$R^1$:H;$R^1$:H;Z:Ph;R:4-n-PrNHCOCH$_2$O-Ph $^1$HNMR(CDCl$_3$) δ :0.84(3H,d,J=6.6 Hz),0.90(3H,t,J=7.4 Hz),1.09(3H,d,J=6.6 Hz),1.49–1.61(3H,m),2.55(1H,d,J=17.4 Hz),3.30(2H,q,J=6.8 Hz),3.60(1H,d,J=17.4 Hz),4.02 (1H,d, J=9.5 Hz),4.47(2H,s),6.53(1H,brs),6.88(2H,d,J=9.0 Hz),7.16(1H,dd,J=2.2,5.7 Hz),7.27(2H,d,J=9.0 Hz), 7.46–7.55(2H,m),7.92(1H,dd,J=2.0,5.1 Hz) FAB-MS(m/e): 421[M+H]$^+$

Example 3033

$R^1$:H;$R^2$:H;$R^3$:i-Pr;$R^4$:H;$R^6$:H;Z:Ph;R:4-n-PrNHCOCH=CH-Ph FAB-MS(m/e):417[M+H]$^+$

Example 3039

$R^1$:H;$R^2$:H;$R^3$:i-Pr;$R^4$:H;$R^6$:H;Z:Ph;R:3-HO$_2$COCH$_2$O-Ph

FAB-MS(m/e):380[M+H]$^+$

Example 3047

$R^1$:H;$R^2$:H;$R^3$:i-Pr;$R^4$:H;$R^6$:H;Z:Ph;R:4-Cl-3-NO$_2$-Ph

FAB-MS(m/e):385[M+H]$^+$

Example 3050

$R^1$:H;$R^2$:H;$R^3$:i-Pr;$R^4$:H;$R^6$:H;Z:Ph;R:3-NH$_2$-4-Cl-Ph

FAB-MS(m/e):355[M+H]$^+$

Example 3051

$R^1$:H;$R^2$:H;$R^3$:i-Pr;Re:H;$R^6$:H;Z:Ph;R:3-Cl-4-MeO-Ph FAB-MS(m/e):370[M+H]$^+$

Example 3056

$R^1$:H;$R^2$:H;$R^3$:i-Pr;$R^4$:H;$R^1$:H;Z:Ph;R:3-F-4-Me-Ph $^1$HNMR(CDCl$_3$) δ :0.90(3H,d,J=6.7 Hz),1.10(3H,d,J=6.7 Hz),1.53–1.65(1H,m),2.24(3H,s),2.57(1H,d,J=17.5 Hz), 3.56(1H,d,J=17.5 Hz),4.02(1H,d,J=9.7 Hz),6.95(1H,dd,J= 1.9,10.7 Hz),7.02(1H,dd,J=1.9,7.9 Hz),7.14(1H,d,J=7.9 Hz),7.17–7.20(1H,m),7.47–7.55(2H,m),7.90–7.93(1H,m) ESI-MS(m/e):338[M+H]$^+$

Example 3057

R$^1$:H;R$^2$:H;R$^3$:i-Pr;R$^4$:H;R$^6$:H;Z:Ph; R:3-Br-4-HO-Ph $^1$HNMR(CDCl$_3$) δ :0.88(3H,d,J=6.6 Hz),1.11(3H,d,J=6.6 Hz),1.53–1.70(1H,m),2.55(1H,d,J=17.4 Hz),3.55(1H,d,J= 17.4 Hz),4.02(1H,d,J=9.6 Hz),5.81(1H,brs),6.98(1H,d,J=8.5 Hz),7.15–7.20(2H,m),7.42(1H,d,J=2.3 Hz),7.48–7.57(2H, m),7.91–7.94(1H,m) FAB-MS(m/e):400/402[M+H]$^+$ Example 3058

R$^1$:H;R$^2$:H;R$^3$:i-Pr;R$^4$:H;R$^6$:H;Z:Ph; R:3-Br-4-MeO-Ph $^1$HNMR(CDCl$_3$) δ :0.89(3H,d,J=6.6 Hz),1.11(3H,d,J=6.6 Hz),1.51–1.65(1H,m),2.55(1H,d,J=17.4 Hz),3.56(1H,d,J= 17.4 Hz),3.88(3H,s),4.02(1H,d,J=9.6Hz),6.84(1H,d,J=8.6 Hz),7.17–7.25(2H,m),7.47–7.56(3H,m),7.91–7.94(1H,m) FAB-MS(m/e):414/416[M+H]$^+$

Example 3061

R$^1$:H;R$^2$:H;R$^3$:i-Pr;R$^4$:H;R$^6$:H;Z:Ph;R:4-HO-3-I-Ph

FAB-MS(m/e):448[M+H]$^+$

Example 3063

R$^1$:H;R$^2$:H;R$^3$:i-Pr;R$^4$:H;R$^6$:H;Z:Ph; R:3-I-4-MeO-Ph $^1$HNMR(CDCl$_3$) δ :1.11(3H,d,J=6.6 Hz),1.27(3H,d,J=6.6 Hz),1.53–1.60(1H,m),2.55(1H,d,J=6.7 Hz),3.56(1H,d,J= 16.7 Hz),3.86(3H,s),4.02(1H,d,J=9.7 Hz),6.75(1H,d,J=8.6 Hz),7. 17–7.94(6H,m) FAB-MS(m/e):462[M+H]$^+$

Example 3065

R$^1$:H;R$^2$:H;R$^3$:i-Pr;R$^4$:H;R$^6$:H;Z:Ph; R:4-MeO-3-Me-Ph $^1$HNMR(CDCl$_3$) δ :0.88(3H,d,J=6.7 Hz),1.09(3H,d,J=6.7 Hz),1.39–1.62(1H,m),2.15(3H,s),2.51(1H,d,J=17.3 Hz), 3.60(1H,d,J=17.3 Hz),3.80(3H,s),4.00(1H,d,J=9.7 Hz),6.74 (1H,d,J=8.6 Hz),7.01(1H,d,J=2.6 Hz),7.10–7.21 (2H,m), 7.44–7.53(2H,m),7.90–7.93(1H,m) FAB-MS(m/e):350[M+ H]$^+$

Example 3072

R$^1$:H;R$^2$:H;R$^1$:i-Pr;R$^4$:H;R$^6$:H;Z:Ph;R:3-I-4- MeNHCOCH$_2$O-Ph

FAB-MS(m/e):519[M+H]$^+$

Example 3073

R$^1$:H;R$^2$:H;R$^3$:i-Pr;R$^4$:H;R$^6$:H;Z:Ph;R:4- EtNHCOCH$_2$O-3-I-Ph

FAB-MS(m/e):533[M+H]$^+$

Example 3074

R$^1$:H;R$^2$:H;R$^3$:i-Pr;R$^4$:H;R$^6$:H;Z:Ph;R:3-I-4-n- PrNHCOCH$_2$O-Ph $^1$HNMR(CDCl$_3$) δ :0.90(3H,d,J=6.6 Hz),0.96(3H,t,J=7.4 Hz),1.11(3H,d,J=6.6 Hz),1.53–1.67(3H,m),2.57(1H,d,J= 16.7 Hz),3.35(2H,q,J=6.6 Hz),3.55(1H,d,J=16.7 Hz),4.03 (1H,d, J=9.5 Hz),4.49(2H,s),6.73(1H,d,J=8.6 Hz),6.88–6.93 (1H,m),7.16–7.19(1H,m),7.33(1H, dd, J=2.3,8.6 Hz), 7.48–7.57(2H,m),7.73(1H,d,J=2.3 Hz),7.92–7.95(1H,m) FAB-MS(m/e):547[M+H]$^+$

Example 3082

R$^1$:H;R$^2$:H;R$^3$:i-Pr;R$^4$:H;R$^6$:H;Z:Ph; R:4-cycloPrNHCOCH$_2$O-3-I-Ph

FAB-MS(m/e):545[M+H]$^+$

Example 3092

R$^1$:H;R$^2$:H;R$^3$:i-Pr;R$^4$:H;R$^6$:H;Z:Ph; R:3-Cl-4-n-PrNHCOCH$_2$O-Ph $^1$HNMR(CDCl$_3$) δ :0.88(3H,d,J=6.6 Hz),0.94(3H,t,J=7.4 Hz),1.11(3H,d,J=6.6 Hz),1.52–1.93(3H,m),2.58(1H,d,J=6.0 Hz),3.32(2H,q,J=6.7 Hz),3.56(1H,d,J=16.0 Hz),4.03(1H, J=9.6 Hz),4.51 (2H,s),6.74–6.79(1H,m),6.87(1H,d,J=8.6 Hz),7.16–7.19(1H,m),7.24(1H,dd, J=2.4,8.6 Hz),7.36(1H, J=2.4 Hz),7.48–7.57(2H,m),7.92–7.96(1H,m) FAB-MS(m/ e):455/457[M+H]$^+$

Example 3093

R$^1$:H;R$^2$:H;R$^3$:i-Pr;R$^4$:H;R$^6$:H;Z:Ph; R:3-Br-4-n-PrNHCOCH$_2$O-Ph $^1$HNMR(CDCl$_3$) δ :0.89(3H,d,J=6.6 Hz),0.95(3H,t,J=7.4 Hz),1.11 (3H,d,J=6.6 Hz),1.52–1.65(3H,m),2.58(1H,d,J= 17.0 Hz),3.33(2H,q,J=6.6 Hz),3.56(1H,d,J=17.0 Hz),4.03 (1H,d, J=9.6 Hz),4.50(2H,s),6.82–6.85(1H,m),6.83(1H,d,J= 8.6 Hz),7.16–7.19(1H,m),7.29–7.31(1H, m),7.48–7.57(3H, m),7.88–7.94(1H,m) FAB-MS(m/e):499/501[M+H]$^+$

Example 3094

R$^1$:H;R$^2$:H;R$^3$:i-Pr;R$^4$:H;R$^6$:H;Z:Ph; R:3-F-4-n-PrNHCOCH$_2$O-Ph $^1$HNMR(CDCl$_3$) δ :0.88(3H,d,J=6.6 Hz),0.92(3H,t,J=7.4 Hz),1.11(3H,d,J=6.6 Hz),1.51–1.64(3H,m),2.58(1H,d,J= 17.5 Hz),3.30(2H,q,J=6.8 Hz),3.55(1H,d,J=17.5 Hz),4.03 (1H,d, J=9.5 Hz),4.51 (2H,s),6.61–6.64(1H,m),6.92(1H,t,J= 8.5 Hz),7.04(1H,d,J=11.9 Hz),7.07–7.18 (2H,m),7.48–7.57 (2H,m),7.91–7.98(1H,m) FAB-MS(m/e):439[M+H]$^+$

Example 3095

R$^1$:H;R$^2$:H;R$^3$:i-Pr;R$^4$:H;R$^6$:H;Z:Ph; R:3-Me-4-n-PrNHCOCH$_2$O-Ph $^1$HNMR(CDCl$_3$) δ :0.87(3H,d,J=6.7 Hz),0.92(3H,t,J=7.4 Hz),1.09(3H,d,J=6.7 Hz),1.49–1.59(3H,m),2.23(3H,s),2.54 (1H,d,J=17.3 Hz),3.21 (2H,q,J=6.7 Hz),3.58(1H,d,J=17.3 Hz),4.01(1H,d,J=9.6 Hz),4.47(2H,s),6.49–6.51(1H,m),6.73 (1H,d,J=8.6 Hz),7.08(1H,d, J=2.0 Hz),7.14–7.18(2H,m), 7.46–7.54(2H,m),7.90–7.93(1H,m) FAB-MS(m/e):435[M+ H]$^+$

Example 3096

R$^1$:H;R$^2$:H;R$^3$:i-Pr;R$^4$:H;R$^6$:H;Z:Ph; R:4-EtNHCOCH$_2$O-3-F-Ph

FAB-MS(m/e):425[M+H]$^+$

Example 3103

R$^1$:H;R$^2$:H;R$^3$:i-Pr;R$^4$:H;R$^6$:H;Z:Ph:R:3-F-4-HO-Ph $^1$HNMR(CDCl$_3$) δ :0.87(3H,d,J=6.7 Hz),1.11(3H,d,J=6.7 Hz),1.54–1.66(1H,m),2.55(1H,d,J=17.3 Hz),3.54(1H,d,J=

17.3 Hz),4.02(1H,d,J=9.6 Hz),5.38–5.41(1H,m),6.94–7.05 (3H,m),7.16–7.19(1H,m),7.47–7.57(2H,m),7.91–7.94(1H, m) FAB-MS(m/e):340[M+H]$^+$

Example 3104

R$^1$:H;R$^2$:H;R$^3$:i-Pr;R$^4$:H;R$^6$:H;Z:Ph;R:3-F4-MeO-Ph
Diastereomer A
$^1$HNMR(CDCl$_3$) δ :0.85(3H,d,J=6.9 Hz),1.19(3H,d,J=6.9 Hz),2.60(1H,d,J=16.0 Hz), 3.40(1H,d,J=16.0 Hz),3.63–3.69 (1H,m),3.78(1H,d,J=3.2 Hz),3.84(3H,s),6.89(1H,dd, J=7.3, 8.5 Hz),7.02(1H,d,J=2.3 Hz),7.09(1H,dd,J=2.3,7.3 Hz),7.36 (1H,dd,J=1.1,6.2 Hz), 7.37–7.56 (2H,m),7.89(1H,dd,J=1.9, 6.9 Hz) FAB-MS(m/e):354[M+H]$^+$
Diastereomer B
$^1$HNMR(CDCl$_3$) δ :0.87(3H,d,J=6.6 Hz),1.11(3H,d,J=6.6 Hz),1.55–1.63(1H,m),2,55(1H,d,J=17.4 Hz),3.55(1H,d,J= 17.4 Hz),3.87(3H,s),4.02(1H,d,J=9.6 Hz),6.91(1H,t,J=8.5 Hz),6.98(1H,dd,J=2.3,12.2 Hz),7.07(1H,ddd,J=1.1,2.3,8.5 Hz),7.16–7.19(1H,m),7.48–7.56(2H,m),7.91–7.94(1H,m) FAB-MS(m/e):354[M+H]$^+$

Example 3107

R$^1$:H;R$^2$:H;R$^3$:i-Pr;R$^4$:H;R$^6$:H;Z:Ph;R:3,4-Cl$_2$-Ph

FAB-MS(m/e):375[M+H]$^+$

Example 3112

R$^1$:H;R$^2$:H;R$^3$:i-Pr;R$^4$:H;R$^6$:H;Z:Ph;R:3,5-Me$_2$-Ph

FAB-MS(m/e):334[M+H]$^+$

Example 3115

R$^1$:H;R$^2$:H;R$^3$:i-Pr;R$^4$:H;R$^6$:H;Z:Ph;R:3,5-I$_{2-4}$-MeO-Ph

FAB-MS(m/e):588[M+H]$^+$

Example 3117

R$^1$:H;R$^2$:H;R$^3$:i-Pr;R$^4$:H;R$^6$:H;Z:Ph;R:2,4,6-Me$_3$-Ph

FAB-MS(m/e):348[M+H]$^+$

Example 3126

R$^1$:6-F;R$^2$:H;R$^3$:i-Pr;R$^4$:H;R$^6$:H;Z:Ph;R:Ph

FAB-MS(m/e):324[M+H]$^+$

Example 3129

R$^1$:9-F;R$^2$:H;R$^3$:i-Pr;R$^4$:H;R$^6$:H;Z:Ph;R:Ph

FAB-MS(m/e):324[M+H]$^+$

Example 3134

R$^1$:7-NO$_2$;R$^2$:H;R$^3$:i-Pr;R$^4$:H;R$^6$:H;Z:Ph;R:Ph

FAB-MS(m/e):351[M+H]$^+$

Example 3226

R$^1$:H;R$^2$:H;R$^3$:i-Pr;R$^4$:H;R$^6$:H;Z:Ph;R:4-n-PrNHCOCH$_2$CH$_2$O-Ph

FAB-MS(m/e):435[M+H]$^+$

Example 3246

R$^1$:H;R$^2$:H;R$^1$:i-Pr;R$^4$:H;R$^6$:H;Z:Ph;R:3-F-4-i-PrNHCOCH$_2$CH$_2$O-Ph

FAB-MS(m/e):453[M+H]$^+$

Example 3258

R$^1$:H;R$^2$:H;R$^3$:i-Pr;R$^4$:H;R$^6$:H;Z:Ph; R:3-Cl-4-EtNHCOCH$_2$CH$_2$O-Ph

FAB-MS(m/e):455[M+H]$^+$

Example 3266

R$^1$:H;R$^2$:H;R$^3$ :$^1$-Pr;R$^1$:H;R$^1$:H;Z:Ph; R:3-Me-4-n-BuNHCOCH$_2$CH$_2$O-Ph

FAB-MS(m/e):463[M+H]$^+$

Example 3296

R$^1$:H;R$^2$:H;R$^3$:Bu;R$^4$:H;R$^6$:H;Z:Ph; R:3-Me-4-MeNHCOCH$_2$O-Ph

FAB-MS(m/e):421[M+H]$^+$

Example 3307

R$^1$:H;R$^2$:H;R$^3$:t-Bu;R$^4$:H;R$^6$:H;Z:Ph; R:3-Me-4-n-PrNHCOCH$_2$O-Ph

FAB-MS(m/e):449[M+H]$^+$

Example 3319

R$^1$:H;R$^2$:H;R$^3$:i-Pr;R$^4$:Me;R$^6$:H;Z:Ph; R:3-Cl-4-cycloPrNHCOCH$_2$O-Ph FAB-MS(m/e):467[M+H]$^+$

Example 3324

R$^1$:H;R$^2$:H;R$^3$:i-Pr;R$^4$:H;R$^6$:H;Z:2,3-Pyridyl; R:3-Me-4-MeNHCO—CH$_2$OPh FAB-MS(m/e):408[M+H]$^+$

Example 3331

R$^1$:H;R$^2$:H;R$^3$:i-Pr;R$^4$:H;R$^6$:H;Z:3,4-Pyridyl; R:3-Cl-4-EtNHCOCH$_2$O-Ph FAB-MS(m/e):442[M+H]$^+$

Example 3337

R$^1$:H;R$^2$:H;R$^3$:i-Pr;R$^4$:H;R$^6$:H;Z:Ph; R:4-EtNHCOCH$_2$O-3-F-(2-Pyridyl))

FAB-MS(m/e):446[M+H]$^+$

Example 3344

R$^1$:H;R$^2$:H;R$^3$:i-Pr;R$^4$:H;R$^6$:H;Z:Ph; R:6-EtNHCOCH$_2$O-5-I-(3-Pyridyl))

FAB-MS(m/e):534[M+H]$^+$

Example 3351

R$^1$:H;R$^2$:H;R$^3$:i-Pr;R$^4$:H;R$^6$:H;Z:Ph; R:4-EtNHCOCH$_2$O-3-NO$_2$-Ph

FAB-MS(m/e):452[M+H]$^+$

Example 3412

R$^1$:H;R$^2$:H;R$^3$:i-Pr;R$^4$:H;R$^6$:Me;Z:Ph; R:3-Cl-4-EtNHCOCH$_2$O-Ph

FAB-MS(m/e):455[M+H]$^+$

Example 3418

R$^1$:H;R$^2$:H;R$^3$:i-Pr;R$^4$:H;R$^6$:Et;Z:Ph;
R:4-EtNHCOCH$_2$O-3-Me-Ph

FAB-MS(m/e):449[M+H]$^+$

Example 3464

R$^1$:H;R$^2$:H;R$^3$:i-Pr;R$^1$:H;
R$^6$:H;Z:pyrimidin-4,5-yl;R:4-n-BuNHCO—CH$_2$OPh FAB-MS(m/e):437[M+H]$^+$

Example 3472

R$^1$:H;R$^2$:H;R$^3$:i-Pr;R$^4$:H;R$^6$:H;Z:Ph;
R:3-Cl-4-HO-Ph $^1$HNMR(CDCl$_3$) δ :0.88(3H,d,J=6.7 Hz),1.11(3H,d,J=6.7 Hz),1.53–1.65(1H,m),2.55(1H,d, J=17.5 Hz),3.54(1H,d,J=17.5 Hz),4.01(1H,d,J=9.5 Hz),6.98(1H,d,J=8.6 Hz),7.10–7.20(1H,m),7.13(1H,dd,J=2.3 ,8.6 Hz),7.27(1H,d,J=2.3 Hz),7.47–7.57(2H,m),7.91–7.94(1H,m) FAB-MS(m/e):356[M+H]$^+$

Example 3473

R$^1$:H;R$^2$:H;R$^3$:i-Pr;R$^4$:H;R$^6$:H;Z:Ph;
R:4-HO-3-Me-Ph $^1$HNMR(CDCl$_3$) δ :0.86(3H,d,J=6.6 Hz),1.08(3H,d,J=6.6 Hz),1.53–1.61 (3H,m),2.20(3H, s),2.50(1H,d,J=17.3 Hz),3.60(1H,d,J=17.3 Hz),4.00(1H,d,J=9.7 Hz),5.98(1H,s),6.76(1H, d,J=8.2 Hz),6.99(1H,d,J=8.2 Hz),7.01(1H,s),7.18(1H,dd,J=1.5,6.4 Hz),7.44–7.54(2H,m), 7.91 (1H,dd,J=1.5,6.2 Hz) FAB-MS(m/e):336[M+H]$^+$

Example 3474

R$^1$:H;R$^2$:H;R$^3$:i-Pr;R$^4$:H;R$^6$:H;Z:Ph;
R:4-HO$_2$CCH$_2$O-3-Me-Ph $^1$HNMR(CDCl$_3$) δ :0.86(3H,d,J=6.6 Hz),1.07(3H,d,J=6.6 Hz),1.47–1.59(1H,m),2.19(3H,s),2.52(1H,d,J=17.3 Hz),3.58(1H,d,J=17.3 Hz),4.00(1H,d,J=9.8 Hz),4.60(2H,s),5.99–6.13(1H, m),6.63(1H,d,J=8.3 Hz),7.05–7.17(3H,m),7.44–7.52(2H,m),7.90–7.93(1H,m) FAB-MS(m/e):394[M+H]$^+$

Example 3475

R$^1$:H;R$^2$:H;R$^3$:i-Pr;R$^4$:H;R$^6$:H;Z:Ph;
R:3,5-Cl$_{2-4}$-n-PrNHCOCH$_2$O-Ph $^1$HNMR(CDCl$_3$) δ :0.94(3H,d,J=6.4 Hz),0.98(3H,t,J=7.5 Hz),1.13(3H,d,J=6.4 Hz),1.54–1.68(3H,m),2.63(1H,d,J=16.1 Hz),3.35(2H,q,J=6.6 Hz),3.50(1H,d,J=16.1 Hz),4.04(1H,d, J=9.7 Hz),4.51 (2H,s),6.93–6.94(1H,m),7.22–7.25(1H,m),7.33(2H,s),7.51–7.61(2H,m),7.92–7.95(1H,m) FAB-MS(m/e):489/491[M+H]$^+$

Example 3476

R$^1$:H;R$^2$:H;R$^3$:i-Pr;R$^4$:H;R$^6$:H;Z:Ph;
R:3-Me-4-n-PrNHCSCH$_2$O-Ph $^1$HNMR(CDCl$_3$) δ :0.87(3H,d,J=6.6 Hz),0.95(3H,t,J=7.5 Hz),1.09(3H,d,J=6.6 Hz),1.51–1.75(3H,m),2.23(3H,s),2.54(1H,d,J=17.4 Hz),3.59(1H,d,J=17.4 Hz),3.71 (2H,q,J=6.6 Hz),4.01(1H,d,J=9.8 Hz),4.88(2H,s),6.74(1H,d,J=8.2Hz),7.09(1H,d,J=2.2 Hz),7.14–7.17(2H,m),7.46–7.54(2H,m),7.91–7.93(1H,m),8.19–8.21(1H,m) FAB-MS(m/e):451[M+H]$^+$

Example 3477

R$^1$:H;R$^2$:i;R$^3$:i-Pr;R$^4$:H;R$^6$:H;Z:Ph;
R:3,5-Cl2–4-n-PrNHCSCH$_2$O-Ph $^1$HNMR(CDCl$_3$) δ :0.93(3H,d,J=6.8 Hz),1.04(3H,t,J=7.4 Hz),1.13(3H,d,J=6.8 Hz),1.32–1.41(1H,m),1.72–1.81(2H,m),2.62(1H,d,J=17.7 Hz),3.51(1H,d,J=17.7 Hz),3.75(2H,q,J=6.6 Hz),4.04(1H,d,J=9.7 Hz),4.89(2H,s),7.22(1H,d,J=7.9 Hz),7.33(2H,s),7.52–7.69(2H, m),7.93–7.95(1H,m),8.69–8.71(1H,m) FAB-MS(m/e):505/507[M+H]$^+$

Example 3478

R$^1$:H;R$^{2:}$H;R$^3$:i-Pr;R$^4$:H;R$^6$:H;Z:Ph;
R:4-n-Pentyl-NHCOCH$_2$O-Ph $^1$HNMR(CDCl$_3$) δ :0.83–0.96(3H,m),0.87(3H,d,J=6.7 Hz),1.10(3H,d,J=6.7 Hz),1.14–1.70(7H,m),2.56(1H,d,J=17.2 Hz),3.32(2H,q,J=6.6 Hz),3.60(1H,d,J=17.2 Hz),4.02 (1H,d, J=9.6 Hz),4.46(2H,s),6.49(1H,s),6.87(2H,d,J=9.0 Hz),7.15–7.20(1H,m),7.25–7.34(2H, m),7.48–7.54(2H,m),7.91–7.92(1H,m) FAB-MS(m/e):449[M+H]$^+$

Example 3479

R$^1$:H;R$^{2:}$H;R$^3$:i-Pr;R$^4$:H;R$^6$:Me;Z:Ph;R:4-MeO-Ph $^1$HNMR(CDCl$_3$) δ :0.69(3H,d,J=7.5 Hz),0.91 (3H,d,J=6.7 Hz),1.11(3H,d,J=6.7 Hz),1.48–1.73(1H,m),3.51(1H,q,J=7.5 Hz),3.77(3H,s),4.02(1H,d,J=9.6 Hz),6.83(2H,d,J=8.9 Hz),7.10–7.13(1H,m),7.24(2H,d,J=8.9 Hz),7.46–7.51(2H,m),7.89–7.99(1H,m) FAB-MS(m/e):350[M+H]$^+$

Example 3480

R$^1$:H;R$^1$:H;R$^3$:i-Pr;R$^4$:H;R$^6$:Me;Z:Ph;R:4-HO-Ph $^1$HNMR(CDCl$_3$) δ :0.68(3H,d,J=7.5 Hz),0.89(3H,d,J=6.6 Hz),1.10(3H,d,J=6.6 Hz),1.48–1.69(1H,m),3.52(1H,q,J=7.5 Hz),4.02(1H,dd,J=1.0,9.5 Hz),5.63(1H,s),6.79(2H,d,J=8.8 Hz),7.11–7.15(1H,m),7.18(2H,d,J=8.8 Hz),7.44–7.54(2H, m),7.90–7.92(1H,m) FAB-MS(m/e):336[M+H]$^+$

Example 3481

R$^1$:H;R$^2$:H;R$^3$:i-Pr;R$^4$:H;R.:Me;Z:Ph;
R:4-n-PrNHCOCH$_2$O-Ph $^1$HNMR(CDCl$_3$) δ :0.70(3H,d,J=7.6 Hz),0.90(3H,d,J=7.4 Hz),0.90(3H,d,J=6.6 Hz),1.11(3H,d,J=6.6 Hz),1.48–1.66 (3H,m),3.30(2H,q,J=6.8 Hz),3.50(1H,q,J=7.5 Hz),4.04(1H, dd, J=1.0,9.5 Hz),4.46(2H,s),6.50–6.51(1H,m),6.86(2H,d,J=8.9 Hz),7.09–7.12(1H,m),7.29(2H, d,J=8.9 Hz),7.46–7.52 (2H,m),7.91–7.94(1H,m) FAB-MS(m/e):435[M+H]$^+$

Example 3482

R$^1$:H;R$^2$:H;R$^3$:i-Pr;R$^4$:H;R$^6$:Br;Z:Ph;R:4-n-PrNHCOCH$_2$O-Ph $^1$HNMR(CDCl$_3$) δ :0.90(3H,d,J=6.6 Hz),0.99(3H,t,J=6.6 Hz),1.17(3H,d,J=6.6 Hz),1.51–1.74(3H,m),3.30(2H,q,J=6.7 Hz),4.36(1H,d,J=9.5 Hz),4.47(2H,s),5.14(1H,s),6.47–6.50 (1H,m),6.91 (2H,d,J=8.9 Hz),7.16–7.19(1H,m),7.34(2H,d,J=8.9 Hz),7.50–7.57(2H, m),7.91–7.94(1H,m) FAB-MS(m/e):499/501[M+H]$^+$

Example 3485

R$^1$:H;R$^2$:l;R$^3$:i-Pr;R$^4$:H;R$^6$:MeSO$_2$NHCH$_2$CH$_2$;Z:Ph;
R:4-n-PrNHCO—CH$_2$O-Ph

FAB-MS(m/e):542[M+H]$^+$

Example 3486

R$^1$:H;R$^2$:H;R$^3$:i-Pr;R$^4$:H;R$^6$:MeO$_2$CCH$_2$;Z:Ph;
R:4-n-PrNHCOCH$_2$O-Ph

FAB-MS(m/e):493[M+H]$^+$

Example 3487

R$^1$:H;R$^2$:H;R$^3$:i-Pr;R$^4$:H;R$^6$:HOCH$_2$CH$_2$;Z:Ph;R:4-n-PrNHCOCH$_2$O-Ph

FAB-MS(m/e):465[M+H]$^+$

[I-3b]

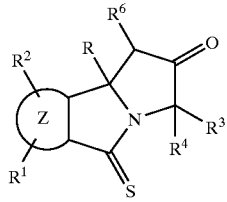

Example 3488

R$^1$:H;R$^2$:H;R$^3$:i-Pr;R$^4$:H;R$^6$:H;Z:Ph;
R:3,5-Cl$_{2-4}$-n-PrNHCOCH$_2$O-Ph $^1$HNMR(CDCl$_3$) δ :0.98(3H,t,J=7.4 Hz),1.03(3H,d,J=6.6 Hz),1.15(3H,d,J=6.6 Hz),1.52–1.67(3H,m),2.61(1H,d,J=18.0 Hz),3.35(2H,q,J=6.6 Hz),3.55(1H,d,J=18.0 Hz),4.51 (2H,s),4.57(1H,d,J=10.4 Hz),6.89–6.93(1H,m),7.53–7.61 (2H,m),8.12–8.15(1H,m) FAB-MS(m/e):505/507[M+H]$^+$

Example 3489

R$^1$:H;R$^2$:H;R$^3$:i-Pr;R$^4$:H;R$^6$:H;Z:Ph;
R:3,5-Cl$_{2-4}$-n-PrNHCSCH$_2$O-Ph $^1$HNMR(CDCl$_3$) δ :1.02(3H,d,J=6.3 Hz),1.04(3H,t,J=7.4 Hz),1.14(3H,d,J=6.3 Hz),1.52–1.59(1H,m),1.71–1.83(2H,m),2.61(1H,d,J=17.5 Hz),3.56(1H,d,J=17.5 Hz),3.75(2H,q, J=6.6 Hz),4.56(1H,d,J=10.3 Hz),4.90(2H,s),7.17–7.20(1H, m),7.23(2H,s),7.53–7.60(2H, m),8.12–8.15(1H,m) FAB-MS(m/e):521/523/525[M+H]$^+$

Example 3492

R$^1$:H;R H;R$^3$:i-Pr;R$^4$:H;
R$^6$:H;Z:pyrimidin-4,5-yl;R:4-n-BuNHCO—CH$_2$OPh FAB-MS(m/e):453[M+H]$^+$

[I-3c]

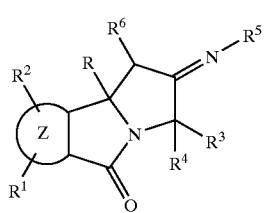

Example 3499

R$^1$:H;R$^2$:H;R$^3$:i-Pr;R$^4$:H;R$^5$:MeO;
R$^6$:H;Z:Ph;R:3-Me-4-n-PrNHCO—CH$_2$O-Ph

Geometrical Isomer A $^1$HNMR(CDCl$_3$) δ :0.92(3H,t,J=7.5 Hz),0.93(3H,d,J=6.6 Hz),1.06(3H,d,J=6.6 Hz),1.46–1.71 (3H,m),2.22(3H,s),2.63 (1H,d,J=18.1 Hz),3.31(2H,q,J=6.7 Hz),3.88(3H,s),3.93(1H, dd,J=1.0,18.1 Hz),4.38(1H,d,J=9.9 Hz),4.47(2H,s), 6.50–6.52(1H,m),6.72(1H,d, J=8.5 Hz),7.11 (1H,d,J=2.4 Hz),7.11–7.13(1H,m),7.21(1H,dd,J=2.4,8.5 Hz),7.39–7.49 (2H,m),7.81–7.84(1H,m) FAB-MS(m/e):464[M+H]$^+$ Geometrical Isomer B $^1$HNMR(CDCl$_3$) δ :0.59(3H,d,J=6.8 Hz),0.92(3H,t,J=7.4 Hz),0.97(3H,d,J=6.8 Hz),1.52–1.61(2H,m),2.04–2.12(1H, m),2.23(3H,s),2.90(1H,d,J=17.3 Hz),3.29(2H,q,J=6.7 Hz), 3.71(1H,dd,J=1.5,17.3 Hz),3.79(3H,s),4.46(2H,s),4.91 (1H, dd,J=1.2,7.6 Hz),6.50–6.51(1H,m),6.73(1H,d,J=8.5 Hz), 7.11–7.13(1H,m),7.14(1H,d,J=2.4 Hz),7.23(1H,dd,J=2.4, 8.5 Hz),7.37–7.50(2H,m),7.79–7.82(1H,m) FAB-MS(m/e): 464[M+H]$^+$

Example 3500

R$^1$:H;R$^2$:H;R$^3$:i-Pr;R$^4$:H;R$^5$:HO;R$^6$:H;Z:Ph;
R:3-Cl-4-n-PrNHCOCH$_2$O-Ph

FAB-MS(m/e):470[M+H]$^+$

Example 3501

R$^1$:H;R$^2$:H;R$^3$:i-Pr;R$^4$:H;R$^5$:Me:R$^6$::H;Z:Ph;
R:4-n-PrNHCOCH$_2$O-Ph

FAB-MS(m/e):434[M+H]$^+$

[I-3d]

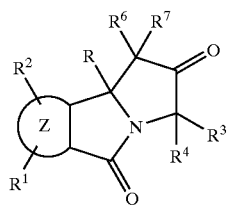

Example 3509

R$^1$:H;R$^2$:H;R$^3$:i-Pr;R$^4$:H;R$^6$:Me;R$^7$:Me;Z:Ph;
R:4-MeO-Ph $^1$HNMR(CDCl$_3$) δ :0.52(3H,s),1.01 (3H,d,J=6.6 Hz),1.29 (3H,d,J=6.6 Hz),1.44(3H,s), 1.85–1.99(1H,m),3.77(3H,s), 4.01(1H,d,J=10.3 Hz),6.78(2H,d,J=9.1 Hz),7.14(2H,d, J=9.1 Hz),7.47–7.66(3H,m),7.92–7.95(1H,m) FAB-MS(m/e):364[M+H]$^+$

Example 3510

R$^1$:H;R$^2$:H;R$^3$:i-Pr;R$^4$:H;R$^6$:Me;R$^7$:Me;Z:Ph;
R:4-HO-Ph $^1$HNMR(CDCl$_3$) δ :0.50(3H,s),0.97(3H,d,J=6.6 Hz),1.28 (3H,d,J=6.6 Hz),1.44(3H,s), 1.83–1.91(1H,m),4.01(1H,d,J= 10.3 Hz),5.91–5.92(1H,m),6.74(2H,d,J=8.9 Hz),7.04(2H,d, J=8.9 Hz),7.47(1H,d,J=7.5 Hz),7.93(1H,d,J=7.5 Hz) FAB-MS(m/e):350[M+H]$^+$

Example 3511

R[1]:H;R[2]:H;R[3]:i-Pr;R[4]:H;R[6]:Me;R[7]:Me;Z:Ph; R:4-n-PrNHCOCH$_2$O-Ph

$^1$HNMR(CDCl$_3$) δ :0.50(3H,s),0.90(3H,t,J=7.4 Hz),1.02 (3H,d,J=6.5 Hz),1.30(3H,d, J=6.5 Hz),1.43(3H,s),1.51–1.58 (2H,m),1.85–1.89(1H,m),3.29(2H,q,J=6.8 Hz),4.02(1H,d, J=10.4 Hz),4.45(2H,s),6.49–6.50(1H,m),6.82(2H,d,J=9.0 Hz),7.20(2H,d,J=9.0 Hz),7.47–7.67(3H,m),7.93–7.95(1H, m) FAB-MS(rm/e):449[M+H]hu +

Example 3515

R[1]:H;R[2]: :H;R[3]:i-Pr;R[4]:H;R[6]:MeCOCH$_2$;R[7]:Me;Z:Ph;R:4-n-PrNHCOCH$_2$O-Ph

FAB-MS(m/e):491[M+H]$^+$

Example 3516

R[1]:H;R[2]:H;R[3]:i-Pr;R[4]:H;R[6]:MeO$_2$CCH$_2$;R[7]:Me;Z:Ph;R:4-n-PrNHCOCH$_2$O-Ph

FAB-MS(m/e):507[M+H]$^+$

Example 4002

3-(1-Methylethyl)-9b-phenyl[1,3]thiazolo[2,3-a] isoindole-2,5(3H,9bH)-dione (Compound of R[1]:H;R[2]:H;R[3]:i-Pr;R[4]:H;Z:Ph;R:Ph in the general formula [I-4])

1-Hydroxybenzotriazole hydrate (3.6 g, 26.5 mmol) and 1-(3-dimethylamino-propyl)-3-ethylcarbodiimide hydrochloride (5.1 g, 26.5 mmol) were added to a solution of 2-benzoylbenzoic acid (5.0 g, 22.1 mmol), D-valine methyl ester hydrochloride (4.1 g, 24.3 mmol) and triethylamine (9.2 ml, 66.3 mmol) in methylene chloride (250 ml) under ice cooling, and the reaction mixture was stirred at room temperature for 3 hours. Aqueous saturated ammonium chloride solution was added to the reaction mixture, and the mixture was extracted with chloroform. The organic layer was washed with aqueous saturated sodium chloride solution, dried and concentrated under reduced pressure. The resulting residue was purified by silica gel column chromatography (hexane:ethyl acetate=1:1) to obtain a condensed product (4.9 g, yield: 65%). Sodium hydrosulfide n hydrate (140 mg, 2.50 mmol) was added to a solution of the obtained condensed product (212 mg, 0.62 mmol) in tetrahydrofuran (4.5 ml), the reaction mixture was stirred at room temperature for 12 hours, and aqueous 1N hydrochloric acid solution was added to the reaction mixture at room temperature. The mixture was extracted with ethyl acetate, the organic layer was dried and concentrated under reduced pressure, and the obtained unpurified thiocarboxylic acid was dissolved in methylene chloride (2.5 ml). Trifluoroacetic acid (2.5 ml) was added to the reaction mixture at room temperature, and the mixture was stirred at room temperature for 30 minutes and concentrated under reduced pressure. The resulting residue was subjected three times to azeotropic distillation with toluene, and the mixture was concentrated under reduced pressure. The residue was purified by silica gel column chromatography (hexane:ethyl acetate=2:1) to obtain the diastereomer A of the captioned compound (43.0 mg, yield: 21%) as colorless oily matter and the diastereomer B thereof (7.0 mg, yield: 4%) as colorless oily matter.

Diastereomer A

$^1$HNMR(CDCl$_3$) δ :1.14(3H,d,J=6.7 Hz),1.31(3H,d,J=6.7 Hz),3.61–3.71 (1H,m),3.81(1H, dd,J=0.7,4.6 Hz),7.31–7.60 (8H,m),7.91(1H,dd,J=2.7,7.9 Hz) FAB-MS(m/e):324[M+H]$^+$

Diastereomer B

$^1$HNMR(CDCl$_3$) δ :0.85(3H,d,J=6.6 Hz), 1.05(3H,d,J=6.6 Hz), 1.51–1.62(1H,m),4.53(1H, d, J=10.3 Hz),7.14–7.17 (1H,m),7.30–7.98(8H,m) FAB-MS(m/e):324[M+H]$^+$

In the same manner as in Example 4002, compounds of Examples 4007, 4011, 4024, 4061, 4063, 4073, 4074, 4079, 4087, 4092, 4113, 4410, 4419 and 4424 corresponding to the compound numbers of the compounds of the general formula [I-4] in the aforementioned compound lists were obtained. Physical constants of these compounds are shown below.

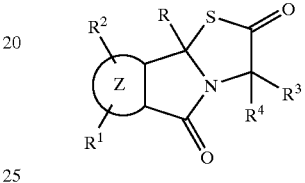

[I-4]

Example 4007

R[1]:H;R[2]:H;R[3]:i-Pr;R[4]:H;Z:Ph;R:4-HO-Ph

$^1$HNMR(CDCl$_3$) δ :0.85(3H,d,J=6.6 Hz),1.07(3H,d,J=6.7 Hz),1.52–1.64(1H,m),4.50(1H,d,J=10.4 Hz),5.11(1H, brs),6.79(2H,d,J=8.8 Hz),7.15–7.17(1H,m),7.32(2H,d, J=8.8 Hz),7.51–7.57(2H,m),7.94–7.97(1H,m) FAB-MS(m/e):340[M+H]$^+$

Example 4011

R[1]:H;R[2]:H;R[3]:i-Pr;R[4]:H;Z:Ph;R:4-MeO-Ph

$^1$HNMR(CDCl$_3$) δ :0.85(3H,d,J=6.1 Hz),1.07(3H,d,J=6.7 Hz),1.52–1.64(1H,m),3.81(3H, s),4.50(1H,d,J=10.4 Hz), 6.85(2H,d,J=9.0 Hz),7.14–7.17(1H,m),7.36(2H,d,J=90 Hz), 7.51–7.57(2H,m),7.94–7.97(1H,m) FAB-MS(m/e):354[M+H]$^+$

Example 4024

R[1]:H;R[2] :H;R[3]:i-Pr;R[4]:H;Z:Ph;R:4-n-PrNHCOCH$_2$O-Ph

$^1$HNMR(CDCl$_3$) δ :0.84(3H,d,J=6.6 Hz),0.91 (3H,t,J=7.4 Hz),1.07(3H,d,J=6.7 Hz),1.50–1.62(3H,m),3.31(2H,q,J=7.0 Hz),4.48(2H,s),4.51(1H,d,J=10.4 Hz),6.54(1H,brs),6.89 (2H,d,J=9.0 Hz),7.13–7.16(1H,m),7.41(2H,d,J=9.0 Hz), 7.52–7.59(2H,m),7.95–7.98(1H,m) FAB-MS(m/e):439[M+H]$^+$

Example 4061

R[1]:H;R[2]:H;R[3]:i-Pr;R[4]:H;Z:Ph;R:4-HO-3-I-Ph

$^1$HNMR(CDCl$_3$) δ :0.89(3H,d,J=6.6 Hz),1.08(3H,d,J=6.8 Hz),1.52–1.64(1H,m),4.50(1H,d,J=10.4 Hz),5.70(1H,brs), 6.94(1H,d,J=8.6 Hz),7.14–7.19(1H,m),7.30(1H,dd,J=2.4, 8.6 Hz),7.53–7.62(2H,m),7.77(1H,d,J=2.4 Hz),7.95–7.98 (1H,m) FAB-MS(m/e):466[M+H]$^+$

Example 4063

R[1]:H;R[2]:H;R[3]:i-Pr;R[4]:H;Z:Ph;R:3-I-4-MeO-Ph

$^1$HNMR(CDCl$_3$) δ :0.89(3H,d,J=6.6 Hz),1.08(3H,d,J=6.9 Hz),1.52–1.64(1H,m),3.88(3H,s),4.51(1H,d,J=10.4 Hz), 6.76(1H,d,J=8.6 Hz),7.16–7.18(1H,m),7.43(1H,dd,J=2.5, 8.6 Hz),7.55–7.59(2H,m),7.81(1H,d,J=2.5 Hz),7.95–7.98 (1H,m) FAB-MS(m/e):480[M+H]$^+$

Example 4073

R$^1$:H;R$^2$:H;R$^3$:i-Pr;R$^4$:H;Z:Ph; R:4-EtNHCOCH$_2$O-3-I-Ph $^1$HNMR(CDCl$_3$) δ :0.89(3H,d,J=6.6 Hz),1.08(3H,d,J=6.6 Hz),1.23(3H,t,J=7.2 Hz),1.50–1.58(1H,m),3.38–3.47(2H, m),4.45(2H,s),4.52(1H,d,J=10.7 Hz),6.73(1H,d,J=8.5 Hz), 6.86(1,brs),7.14–7.26(1H,m),7.47(1H,dd,J=2.2,8.5 Hz), 7.56–7.59(2H,m),7.84(1H,d, J=2.2 Hz),7.96–7.99(1H,m) FAB-MS(m/e):551[M+H]$^+$ Example 4074

R$^1$:H;R$^2$:H;R$^3$:i-Pr;R$^4$:H;Z:Ph; R:3-I-4-n-PrNHCOCH$_2$O-Ph $^1$HNMR(CDCl$_3$) δ :0.89(3H,d,J=6.6 Hz),0.98(3H,t,J=7.4 Hz),1.08(3H,d,J=6.6 Hz),1.50–1.65(3H,m),3.36(2H,q,J=7.0 Hz),4.51 (2H,s),4.52(1H,d,J=10.4 Hz),6.74(1H,d,J=8.6 Hz), 6.91 (1H,brs),7.14–7.17(1H,m),7.48(1H,dd,J=2.4,8.6 Hz), 7.56–7.60(2H,m),7.85(1H,d, J=2.4 Hz),7.96–7.99(1H,m) FAB-MS(m/e):565[M+H]$^+$ Example 4079

R$^1$:H;R$^2$:H;R$^3$:i-Pr;R$^4$:H;Z:Ph; R:4-t-BuO$_2$CCH$_2$O-3-I-Ph $^1$HNMR(CDCl$_3$) δ :0.88(3H,d,J=6.6 Hz),1.07(3H,d,J=6.6 Hz),1.46(9H,s),1.52–1.64(1H, m),4.50(1H,d,J=10.5 Hz), 4.57(2H,s),6.62(1H,d,J=8.7 Hz),7.15–7.18(1H,m),7.40(1H, dd, J=2.4,8.7 Hz),7.55–7.59(2H,m),7.84(1H,d,J=2.4 Hz), 7.95–7.98(1H,m) FAB-MS(m/e):580[M+H]$^+$

Example 4087

R$^1$:H;R$^2$:H;R$^3$:i-Pr;R$^4$:H;Z:Ph; R:4-HO2CCH$_2$O-3-I-Ph $^1$HNMR(CDCl$_3$) δ :0.88(3H,d,J=6.0 Hz),1.07(3H,d,J=6.6 Hz),1.50–1.58(1H,m),4.51(1H, d,J=10.6 Hz),4.73(2H,s), 5.93(1H,brs),6.69(1H,d,J=8.5 Hz),7.16–7.19(1H,m),7.42 (1H,dd, J=2.2,8.5 Hz),7.54–7.61 (2H,m),7.85(1H,d,J=2.2 Hz),7.96–7.99(1H,m) FAB-MS(m/e):524[M+H]$^+$ Example 4092

R$^1$:H;R$^2$:H;R$^1$:i-Pr;R$^4$:H;Z:Ph; R:3-Cl-4-n-PrNHCOCH$_2$O-Ph $^1$HNMR(CDCl$_3$) δ :0.88(3H,d,J=6.6 Hz),0.95(3H,t,J=7.4 Hz),1.08(3H,d,J=6.7 Hz),1.50–1.65(3H,m),3.34(2H,q,J=6.9 Hz),4.52(1H,d,J=10.3 Hz),4.53(2H,s),6.78(1H,brs),6.88 (1H,d,J=8.6 Hz),7.14–7.17(1H,m),7.39(1H,dd,J=2.4,8.6 Hz),7.50(1H,d,J=2.4 Hz),7.56–7.62(2H,m),7.96–7.99(1H, m) FAB-MS(m/e):473[M+H]$^+$ Example 4113

R$^1$:H;Re:H;R$^3$:i-Pr;R$^4$:H;Z:Ph;R:3,5-I$_{2-4}$-HO-Ph $^1$HNMR(CDCl$_3$) δ :0.93(3H,d,J=6.6 Hz),1.10(3H,d,J=6.6 Hz),1.52–1.64(1H,m),4.51(1H,d, J=10.6 Hz),7.18–7.21(1H, m),7.57–7.62(2H,m),7.75(2H,s),7.96–7.99(1H,m) FAB-MS (m/e):592[M+H]$^+$

Example 4410

R$^1$:H;R$^2$:H;R$^3$:i-Pr;R$^4$:H;Z:4,5-pyridazinyl;R:4-n-PrNHCOCH$_2$O-Ph

FAB-MS(m/e):441[M+H]$^+$

Example 4419

R$^1$:H;R$^2$:H;R$^3$:i-Pr;R$^4$:H;Z:Ph; R:4-n-PrNHCOCH$_2$O-pyrazin-2-yl)

FAB-MS(m/e):441[M+H]$^+$

Example 4424

R$^1$:H;R$^2$:H;R$^3$:i-Pr;R$^4$:H;Z:Ph;R:3-Cl-4-HO-Ph $^1$HNMR(CDCl$_3$) δ :0.88(3H,d,J=6.6 Hz),1.08(3H,d,J=6.6 Hz),1.52–1.64(1H,m),4.51 (1H,d,J=10.3 Hz),5.72(1H,brs), 6.98(1H,d,J=8.6 Hz),7.16–7.19(1H,m),7.24(1H,dd,J=2.2, 8.6 Hz),7.47(1H,d,J=2.2 Hz),7.56–7.59(2H,m),7.95–7.98 (1H,m) FAB-MS(m/e):374[M+H]$^+$ Pharmaceutical Preparation Example 1

Compound of Example 1002 (45 parts), heavy magnesium oxide (15 parts) and lactose (75 parts) are uniformly mixed to form powdery or finely granular powder of 350 μm or less. This powder is put in capsule vessels to obtain capsules.

Pharmaceutical Preparation Example 2

Compound of Example 3011 (45 parts), starch (15 parts), lactose (16 parts). crystalline cellulose (21 parts), polyvinyl alcohol (3 parts) and distilled water (30 parts) are uniformly mixed, disrupted and granulated, dried, and then sieved to obtain granules of 141 to 177 μm.

Pharmaceutical Preparation Example 3

After granules are obtained in the same manner as in Pharmaceutical preparation example 2, calcium stearate (4 parts) is added to these granules (96 parts), and the mixture is compression molded to obtain tablets of diameter 10 mm.

Pharmaceutical Preparation Example 4

After granules are obtained in the same manner as in Pharmaceutical preparation example 2, crystalline cellulose (10 parts) and calcium stearate (3 parts) are added to these granules (90 parts), the mixture is compression molded to obtain tablets of diameter 8 mm, and a suspension obtained by mixing syrup gelatin and precipitated calcium carbonate is added to these tablets to obtain sugar-coated tablets.

Industrial Applicability

The compounds of the invention show an activity to bring about high GLP-1 concentration in the blood, and can be used as agents for treating diabetes, prophylactic agents for chronic complications of diabetes or drugs against obesity.

What is claimed is:

1. A compound represented by the general formula [I] or a pharmaceutically acceptable salt thereof;

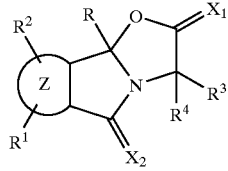

[I]

wherein,

R represents (1) an aryl group, (2) a mono- to tricyclic $C_7$–$C_{15}$ aromatic carbocyclic group selected from the group consisting of acenaplithylenyl, adamantyl, anthryl, indenyl, norbornyl and phenanthryl, (3) a 5- or 6-membered heterocyclic group selected from the group consisting of isoxazolyl, isothiazolyl, imidazolyl, oxazolyl, oxadiazolyl, thiazolyl, thiadiazolyl, thienyl, triazinyl, triazolyl, pyridyl, pyrazinyl, pyrimidinyl, pyridazinyl, pyrazolyl, pyrrolyl, pyranyl, furyl, furazanyl, imidazolidinyl, imidazolinyl, tetrahydrofuranyl, pyrazolidinyl, pyrazolinyl, piperazinyl, piperidinyl, pyrrolidinyl, pyrrolinyl and morpholino (hereinafter, "isoxazolyl, . . . and morpholino" is referred to as a series of groups A), or (4) a mono- to tricyclic aromatic heterocyclic group having per one ring 1 to 5 hetero atoms selected from the group consisting of nitrogen atoms, oxygen atoms and sulfur atoms, selected from the group consisting of acridinyl, isoquinolyl, isoindolyl, indazolyl, indolyl, indolizinyl, ethylenedioxyphenyl, carbazolyl, quinazolinyl, quinoxalinyl, quinolidinyl, quinolyl, cumaronyl, chromenyl, phenanthridinyl, phenanthrolinyl, dibenzofuranyl, dibenzothiophenyl, cinnolinyl, thionaplithenyl, naphthyridinyl, phenazinyl, phenoxazinyl, phenothiazinyl, phthalazinyl, pteridinyl, purinyl, benzimidazolyl, benzoxazolyl, benzothiazolyl, benzotriazolyl, benzofuranyl and methylenedioxyphenyl (hereinafter, "acridinyl, . . . and methylenedioxyphenyl" is referred to as a series of groups B), each of the above-mentioned groups (1) to (4) may optionally have one or more substituents selected from the group consisting of (5) substituents selected from the group consisting of azido, amino, carbamoyl, carbamoylamino, carbamoyloxy, carboxyl, cyano, sulfamoyl, sulfo, nitro, halogen, hydroxy, formyl, formylamino, cyclic saturated $C_3$–$C_9$ aliphatic groups, cyclic unsaturated $C_3$–$C_9$ aliphatic groups, aralkyl, N-aralkylamino, N,N-diaralkylamino, aralkyloxy, aralkylcarbonyl, N-aralkylcarbamoyl, aryl, N-arylamino, N,N-diarylamino, aryloxy, arylsulfonyl, arylsulfonyloxy, N-arylsulfonylamino, N-arylsulfonylamino $C_1$–$C_{10}$ alkylamino, N-arylsulfonylamino $C_1$–$C_{10}$ alkylcarbamoyl, N-arylsulfonylamino $C_1$–$C_6$ alkoxycarbonyl, arylsulfamoyl, arylsulfamoyloxy, N-arylsulfamoyl $C_1$–$C_{10}$ alkylcarbamoyl, arylsulfamoyl $C_1$–$C_6$ alkoxycarbonyl, N-arylcarbamoyl, aroyl, aroxy, N-(N-aroylamino) $C_1$–$C_{10}$ alkylcarbamoyl, N-aroylamino $C_1$–$C_{10}$ alkoxycarbonyl, $C_2$–$C_6$ alkanoyl, N—$C_2$–$C_6$ alkanoylamino, N,N-di-$C_2$–$C_6$ alkanoylamino, N—$C_1$–$C_6$ alkylamino, N,N-di-$C_1$–$C_6$ alkylamino, N—$C_1$–$C_{10}$ alkylcarbamoyl, N—$C_1$–$C_{10}$ alkylthiocarbamoyl, N,N-di-$C_1$–$C_{10}$ alkylcarbamoyl, N,N-di-$C_1$–$C_{10}$ alkylthiocarbamoyl, N—$C_2$–$C_6$ alkenylcarbamoyl, N,N-di-$C_2$–$C_6$ alkenylcarbamoyl, N-amino $C_1$–$C_{10}$ alkylcarbamoyl, N—$C_1$–$C_6$ alkoxy $C_1$–$C_{10}$ alkylcarbamoyl, N—$C_1$–$C_6$ alkoxycarbonyl $C_1$–$C_{10}$ alkylcarbamoyl, N—$C_1$–$C_6$ alkoxycarbonylamino $C_1$–$C_{10}$ alkylcarbamoyl, N—$C_1$–$C_6$ alkoxycarbonylamino $C_1$–$C_6$ alkoxycarbonyl, $C_1$–$C_6$ alkylthio, N—$C_1$–$C_6$ alkylsulfamoyl, N,N-di-$C_1$–$C_6$ alkylsulfamoyl, $C_1$–$C_6$ alkylsulfinyl, $C_1$–$C_6$ alkylsulfonyl, N—$C_1$–$C_6$ alkylsulfonylamino, $C_1$–$C_6$ alkoxy, $C_1$–$C_6$ alkoxycarbonyl, amino $C_1$–$C_6$ alkoxycarbonyl, N—$C_3$–$C_6$ cycloalkylamino, N,N-di-$C_3$–$C_6$ cycloalkylamino, $C_3$–$C_6$ cycloalkyloxy, N—$C_3$–$C_6$ cycloalkylcarbamoyl and N,N-di-$C_3$–$C_6$ cycloalkylcarbamoyl, (6) 5- or 6-membered heterocyclic groups selected from the group consisting of the above-mentioned series of groups A, (7) monocyclic to tricyclic aromatic heterocyclic groups having per one ring 1 to 5 hetero atoms selected from the group consisting of nitrogen atoms, oxygen atoms and sulfur atoms, selected from the group consisting of the above-mentioned series of groups B, (8) substituents selected from the group consisting of N—$C_1$–$C_{10}$ alkylcarbamoyl groups, N—$C_1$–$C_{10}$ alkylthiocarbamoyl groups, thiocarbonyl groups and carbonyl groups, each substituted with the above-mentioned heterocyclic group or the above-mentioned aromatic heterocyclic group, and (9) substituents selected from the group consisting of straight-chain or branched and saturated or unsaturated $C_1$–$C_9$ aliphatic groups, $C_1$–$C_6$ alkoxy groups, $C_1$–$C_6$ alkylthio groups and N—$C_1$–$C_6$ alkylamino groups, each of which groups may be substituted with a group selected from the group consisting of the substituents mentioned in the above item (8), (hereinafter, the above-mentioned groups (5) to (9) are referred to as series of groups C), $R^1$ and $R^2$ are the same or different, and represent (1) groups selected from the group consisting of hydrogen, azido, amino, carbamoyl, carbamoylamino, carbamoyloxy, carboxyl, cyano, sulfamoyl, sulfo, nitro, halogen, hydroxy, formyl, formylamino, cyclic saturated $C_3$–$C_9$ aliphatic groups, cyclic unsaturated $C_3$–$C_9$ aliphatic groups, aralkyl, N-aralkylamino, aralkyloxy, aralkylcarbonyl, aryl, N-arylamino, aryloxy, arylsulfonyl, N-arylsulfonylamino, N-arylsulfonylamino $C_1$–$C_{10}$ alkylanilno, N-arylsulfonylamino $C_1$–$C_{10}$ alkylcarbamoyl, N-arylsulfonylamino $C_1$–$C_6$ alkoxycarbonyl, $C_2$–$C_6$ alkanoyl, N—$C_2$–$C_6$ alkanoylamino, aroyl, N-aroylamino, N-aroyl $C_1$–$C_{10}$ alkylamino, N-aroyl $C_1$–$C_{10}$ alkylcarbamoyl, N—$C_1$–$C_6$ alkylamino, N,N-di-$C_1$–$C_6$ alkylamino, N—$C_1$–$C_{10}$ alkylcarbamoyl, N,N-di-$C_1$–$C_{10}$ alkylcarbamoyl, N—$C_1$–$C_6$ alkylsulfamoyl, $C_1$–$C_6$ alkylsulfinyl, $C_1$–$C_6$ alkylsulfonyl, N—$C_1$–$C_6$ alkylsulfonylamino, $C_1$–$C_6$ alkylthio, $C_1$–$C_6$ alkoxy, $C_1$–$C_6$ alkoxycarbonyl, N—$C_3$–$C_6$ cycloalkylamino, $C_3$–$C_6$ cycloalkyloxy and N—$C_3$–$C_6$ cycloalkylcarbamoyl (hereinafter, "hydrogen, . . . and N—$C_3$–$C_6$ cycloalkylcarbamoyl" is referred to as a series of groups D), or (2) straight-chain or branched and saturated or unsaturated $C_1$–$C_9$ aliphatic groups, N—$C_1$–$C_6$ alkylamino groups, $C_1$–$C_6$ alkylthio groups or $C_1$–$C_6$ alkoxy groups, each of which groups may optionally be substituted with a group selected from the group consisting of the series of groups D but excluding hydrogen, $R^3$ and $R^4$ are the same or different, and represent (1) groups selected from the group consisting of hydrogen, azido, amidino, amino, carbamoyl, carbamoylamino, carbamoyloxy, carboxyl, guanidino, cyano, sulfamoyl, sulfo, nitro, halogen, hydroxy, formyl, formylamino, cyclic saturated $C_3$–$C_9$ aliphatic groups, cyclic unsaturated $C_3$–$C_9$ aliphatic groups, $C_2$–$C_6$ alkanoyl, N—$C_2$–$C_6$ alkanoylamino, N—$C_1$–$C_6$ alkylamino, N,N-di-$C_1$–$C_6$ alkylamino, N—$C_1$–$C_{10}$ alkylcarbamoyl, N,N-di-$C_1$–$C_{10}$ alkylcarbamoyl, $C_1$–$C_6$ alkylthio, N—$C_1$–$C_6$ alkylsulfamoyl, $C_1$–$C_6$ alkylsulfinyl, $C_1$–$C_6$ alkylsulfonyl, N—$C_1$–$C_6$ alkylsulfonylamino, $C_1$–$C_6$ alkoxy, $C_1$–$C_6$ alkoxycarbonyl, N—$C_3$–$C_6$ cycloalkylamino, $C_3$–$C_6$ cycloalkyloxy and N—$C_3$–$C_6$ cycloalkylcarbamoyl (hererinafter, "hydrogen, . . . and N—$C_3$–$C_6$ cycloalkylcarbamoyl" is referred to as a series of groups E), (2) straight-chain or branched and saturated or unsaturated $C_1$–$C_9$ aliphatic groups optionally substituted with a group selected from the group consisting of the series of groups E but excluding hydrogen and provided the case is excluded where both of $R^3$ and $R^4$ are unsubstituted ethyl groups, or (3)

(3-1) aryl groups, (3-2) monocyclic to tricyclic $C_7$–$C_{15}$ aromatic carbocyclic groups selected from the group consisting of acenaphthylenyl, adamantyl, anthryl, indenyl, norbornyl and phenanthryl, (3-3) 5- or 6-membered heterocyclic groups selected from the group consisting of the aforementioned series of groups A, (3-4) monocyclic to tricyclic aromatic heterocyclic groups having per one ring 1 to 5 hetero atoms selected from the group consisting of nitrogen atoms, oxygen atoms and sulfur atoms, selected from the group consisting of the aforementioned series of groups B, or (3-5) straight-chain or branched and saturated or unsaturated $C_1$–$C_9$ aliphatic groups optionally substituted with the above-mentioned aryl group, the above-mentioned aromatic carbocyclic group, the above-mentioned heterocyclic group or the above-mentioned aromatic heterocyclic group, each of the above-mentioned groups (3-1) to (3-5) being optionally substituted with one or more substituents selected from the group consisting of the aforementioned series of group C, or (4) $R^3$ and $R^4$ combine together to form a straight-chain or branched and saturated or unsaturated $C_1$–$C_9$ aliphatic group, a 5- or 6-membered saturated carbocyclic group, or a 5- or 6-membered unsaturated carbocyclic group, $X_1$ represents an oxygen atom, a sulfur atom or a group $NR^5$ (wherein $R^5$ represents a group selected from the group consisting of hydrogen, halogen, hydroxy, N—$C_1$–$C_6$ alkylsulfonylamino, $C_1$–$C_6$ alkoxy, $C_1$–$C_6$ alkoxycarbonyl, $C_2$–$C_6$ alkanoyl, carbamoyl and N—$C_1$–$C_{10}$ alkylcarbamoyl; or a straight-chain or branched and saturated or unsaturated $C_1$–$C_9$ aliphatic group optionally substituted with a group selected from the group consisting of halogen, hydroxy, N—$C_1$–$C_6$ alkylsulfonylamino, $C_1$–$C_6$ alkoxy, $C_1$–$C_6$ alkoxycarbonyl, $C_2$–$C_6$ alkanoyl, carbamoyl and N—$C_1$–$C_{10}$ alkylcarbamoyl), $X_2$ represents an oxygen atom or a sulfur atom, and Z represents a condensed aryl.

2. The compound represented by the general formula [I-a] or pharmaceutically acceptable salt thereof, according to claim 1;

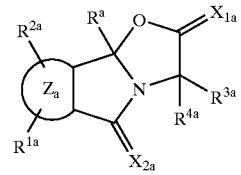

[I-a]

wherein, $R^a$ represents (1) an aryl group, (2) a mono- to tricyclic $C_7$–$C_{15}$ aromatic carbocyclic group selected from the group consisting of adamantyl, anthryl, indenyl, norbornyl and phenanthryl, (3) a 5- or 6-membered heterocyclic group selected from the group consisting of isoxazolyl, isothiazolyl, imidazolyl, oxazolyl, oxadiazolyl, thiazolyl, thiadiazolyl, thienyl, triazolyl, pyridyl, pyrazinyl, pyrimidinyl, pyridazinyl, pyrazolyl, pyrrolyl, pyranyl, furyl, imidazolidinyl, imidazolinyl, tetrahydrofuranyl, pyrazolidinyl, pyrazolinyl, piperazinyl, piperidinyl, pyrrolidinyl, pyrrolinyl and morpholino (hereinafter, "isoxazolyl, . . . and morpholino" is referred to as series of groups A'), or (4) a mono- to tricyclic aromatic heterocyclic group having per one ring 1 to 5 hetero atoms selected from the group consisting of nitrogen atoms, oxygen atoms and sulfur atoms, selected from the group consisting of isoquinolyl, isoindolyl, indazolyl, indolyl, ethylenedioxyphenyl, carbazolyl, quinazolinyl, quinoxalinyl, quinolidinyl, quinolyl, cumaronyl, chromenyl, phenanthridinyl, phenanthrolinyl, dibenzofuranyl, dibenzothiophenyl, cinnolinyl, thionaphthenyl, naphthyridinyl, phenazinyl, phenoxazinyl, benzimidazolyl, benzoxazolyl, benzothiazolyl, benzotriazolyl, benzofuranyl and methylenedioxyphenyl (hereinafter, "isoquinolyl, . . . and methylenedioxyphenyl" is referred to as series of groups B'), each of the above-mentioned groups (1) to (4) being optionally substituted with one or more substituents selected from the group consisting of (5) substituents selected from the group consisting of amino, carbamoyl, carbamoylamino, carbamoyloxy, carboxyl, nitro, halogen, hydroxy, cyclic saturated $C_3$–$C_9$ aliphatic groups, cyclic unsaturated $C_3$–$C_9$ aliphatic groups, aralkyl, N-aralkylamino, aralkyloxy, aralkylcarbonyl, N-aralkylcarbamoyl, aryl, N-arylamino, aryloxy, arylsulfonyl, arylsulfonyloxy, N-arylsulfonylamino, N-arylsulfonylamino $C_1$–$C_{10}$ alkylamino, N-arylsulfonylamino $C_1$–$C_{10}$ alkylcarbamoyl, N-arylsulfonylamino $C_1$–$C_6$ alkoxycarbonyl, arylsulfamoyl, arylsulfamoyloxy, N-arylsulfamoyl $C_1$–$C_{10}$ alkylcarbamoyl, arylsulfamoyl $C_1$–$C_6$ alkoxycarbonyl, N-arylcarbamoyl, aroyl, aroxy, N-(N-aroylamino) $C_1$–$C_{10}$ alkylcarbamoyl, N-aroylamino $C_1$–$C_{10}$ alkoxycarbonyl, $C_2$–$C_6$ alkanoyl, N—$C_2$–$C_6$ alkanoylamino, N—$C_1$–$C_6$ alkylanilno, N,N-di-$C_1$–$C_6$ alkylamino, N—$C_1$–$C_{10}$ alkylcarbamoyl, N—$C_1$–$C_{10}$ alkylthiocarbamoyl, N,N-di-$C_1$–$C_{10}$ alkylcarbamoyl, N,N-di-$C_1$–$C_{10}$ alkylthiocarbamoyl, N—$C_2$–$C_6$ alkenylcarbamoyl, N,N-di-$C_2$–$C_6$ alkenylcarbamoyl, N-amino $C_1$–$C_{10}$ alkylcarbamoyl, N—$C_1$–$C_6$ alkoxy $C_1$–$C_{10}$ alkylcarbamoyl, N—$C_1$–$C_6$ alkoxycarbonyl $C_1$–$C_{10}$ alkylcarbamoyl, N—$C_1$–$C_6$ alkoxycarbonylamino $C_1$–$C_{10}$ alkylcarbamoyl, N—$C_1$–$C_6$ alkoxycarbonylamino $C_1$–$C_6$ alkoxycarbonyl, $C_1$–$C_6$ alkylthio, $C_1$–$C_6$ alkylsulfinyl, $C_1$–$C_6$ alkylsulfonyl, N—$C_1$–$C_6$ alkylsulfonylamino, $C_1$–$C_6$ alkoxy, $C_1$–$C_6$ alkoxycarbonyl, amino $C_1$–$C_6$ alkoxycarbonyl, $C_3$–$C_6$ cycloalkylamino, N,N-di-$C_3$–$C_6$ cycloalkylamino, $C_3$–$C_6$ cycloalkyloxy, N—$C_3$–$C_6$ cycloalkylcarbamoyl and N,N-di-$C_3$–$C_6$ cycloalkylcarbamoyl, (6) 5- or 6-membered heterocyclic groups selected from the group consisting of the aforementioned series of groups A', (7) monocyclic to tricyclic aromatic heterocyclic groups having per one ring 1 to 5 hetero atoms selected from the group consisting of nitrogen atoms, oxygen atoms and sulfur atoms, selected from the group consisting of the aforementioned series of groups B', (8) substituents selected from the group consisting of N—$C_1$–$C_{10}$ alkylcarbamoyl groups, N—$C_1$–$C_{10}$ alkylthiocarbamoyl groups, thiocarbonyl groups and carbonyl groups, each substituted with the above-mentioned heterocyclic group or the above-mentioned aromatic heterocyclic group, and (9) substituents selected from the group consisting of straight-chain or branched and saturated or unsaturated $C_1$–$C_9$ aliphatic groups, $C_1$–$C_6$ alkoxy groups and $C_1$–$C_6$ alkylthio groups, each of which groups may be substituted with a group selected from the group consisting of the substituents mentioned in the above item (8), (hereinafter, the above-mentioned groups (5) to (9) are referred to as series of groups C'), $R^{1a}$ and $R^{2a}$ are the same or different, and represent (1) groups selected from the group consisting of hydrogen, amino, carboxyl, cyano, sulfamoyl, sulfo, nitro, halogen, hydroxy, formyl, cyclic saturated $C_3$–$C_9$ aliphatic groups, cyclic unsaturated $C_3$–$C_9$ aliphatic groups, aralkyl, aryl, N-arylamino, aryloxy, $C_2$–$C_6$ alkanoyl, N—$C_2$–$C_6$ alkanoylamino, aroyl, N—$C_1$–$C_6$ alkylamino, N,N-di-$C_1$–$C_6$ alkylamino, N—$C_1$–$C_{10}$ alkylcarbamoyl, N—$C_1$–$C_6$ alkylsulfamoyl, $C_1$–$C_6$ alkylsulfinyl, $C_1$–$C_6$ alkylsulfonyl, N—$C_1$–$C_6$ alkylsulfonylamino, $C_1$–$C_6$ alkoxy, $C_1$–$C_6$ alkoxycarbonyl, N—$C_3$–$C_6$ cycloalkylamino, $C_3$–$C_6$ cycloalkyloxy and N—$C_3$–$C_6$ cycloalkylcarbamoyl (hereinafter, "hydrogen, ... and N—$C_3$–$C_6$ cycloalkylcarbamoyl" is referred to as a series of groups D'); or (2) straight-chain or branched and saturated or unsaturated $C_1$–$C_9$ aliphatic groups or $C_1$–$C_6$ alkoxy groups, each of which may optionally be substituted with a group selected from the group consisting of the series of groups D' but excluding hydrogen, $R^{3a}$ and $R^{4a}$ are the same or different, and represent (1) groups selected from the group consisting of hydrogen, azido, amidino, amino, carbamoyl, carbamoylamino, carbamoyloxy, carboxyl, guanidino, cyano, sulfamoyl, sulfo, nitro, halogen, hydroxy, formyl, formylamino, cyclic saturated $C_3$–$C_9$ aliphatic groups, cyclic unsaturated $C_3$–$C_9$ aliphatic groups, $C_2$–$C_6$ alkanoyl, N—$C_1$–$C_6$ alkylamino, N—$C_1$–$C_{10}$ alkylcarbamoyl, $C_1$–$C_6$ alkylthio, N—$C_1$–$C_6$ alkylsulfamoyl, $C_1$–$C_6$ alkylsulfinyl, $C_1$–$C_6$ alkylsulfonyl, N—$C_1$–$C_6$ alkylsulfonylamino, $C_1$–$C_6$ alkoxy, $C_1$–$C_6$ alkoxycarbonyl and N—$C_3$–$C_6$ cycloalkylamino (hereinafter, "hydrogen, . . . and N—$C_3$–$C_6$ cycloalkylamino" is referred to as a series of groups E'), (2) straight-chain or branched and saturated or unsaturated $C_1$–$C_9$ aliphatic groups optionally substituted with a group selected from the group consisting of the series of groups E' but excluding hydrogen, or (3)

(3-1) aryl groups, (3-2) monocyclic to tricyclic $C_7$–$C_{15}$ aromatic carbocyclic groups selected from the group consisting of adamantyl, anthryl, indenyl, norbornyl and phenanthryl, (3-3) 5- or 6-membered heterocyclic groups selected from the group consisting of the aforementioned series of groups A', (3-4) monocyclic to tricyclic aromatic heterocyclic groups having per one ring 1 to 5 hetero atoms selected from the group consisting of nitrogen atoms, oxygen atoms and sulfur atoms, selected from the group consisting of the aforementioned series of groups B', or (3-5) straight-chain or branched and saturated or unsaturated $C_1$–$C_9$ aliphatic groups optionally substituted with the above-mentioned aryl group, the above-mentioned aromatic carbocyclic group, the above-mentioned heterocyclic group or the above-mentioned aromatic heterocyclic group, each of the above-mentioned groups (3-1) to (3-5) being optionally substituted with one or more substituents selected from the group consisting of the aforementioned series of groups C', or (4) $R^{3a}$ $R^{4a}$ combine together to form a straight-chain or branched and saturated or unsaturated $C_1$–$C_9$ aliphatic group, a 5- or 6-membered saturated carbocyclic group, or a 5- or 6-membered unsaturated carbocyclic group, $X_{1a}$ represents an oxygen atom, a sulfur atom or a group $NR^{5a}$ (wherein $R^{5a}$ represents a group selected from the group consisting of hydrogen, halogen, hydroxy, N—$C_1$–$C_6$ alkylsulfonylamino, $C_1$–$C_6$ alkoxy, $C_1$–$C_6$ alkoxycarbonyl, $C_2$–$C_6$ alkanoyl, carbamoyl and N—$C_1$–$C_{10}$ alkylcarbamoyl; or a straight-chain or branched and saturated or unsaturated $C_1$–$C_9$ aliphatic group optionally substituted with a group selected from the group consisting of halogen, hydroxy, N—$C_1$–$C_6$ alkylsulfonylamino, $C_1$–$C_6$ alkoxy, $C_1$–$C_6$ alkoxycarbonyl, $C_2$–$C_6$ alkanoyl, carbamoyl and N—$C_1$–$C_{10}$ alkylcarbamoyl), $X_{2a}$ represents an oxygen atom or a sulfur atom, and $Z_a$ represents a condensed aryl group.

3. The compound represented by the general formula [I-b] or pharmaceutically acceptable salt thereof, according to claim 1;

[I-b]

wherein, $R^b$ represents (1) an aryl group;

(2) a mono- to tricyclic $C_7$–$C_{15}$ aromatic carbocyclic group selected from the group consisting of anthryl and phenanthryl;

(3) a 5- or 6-membered heterocyclic group selected from the group consisting of thienyl, pyridyl, pyrazinyl, pyrimidinyl, furyl, tetrahydrofuranyl and morpholino; or (4) a mono- to tricyclic aromatic heterocyclic group having per one ring 1 to 5 hetero atoms selected from the group consisting of nitrogen atoms, oxygen atoms and sulfur atoms, selected from the group consisting of ethylenedioxyphenyl, dibenzofuranyl, dibenzothiophenyl and methylenedioxyphenyl, each of the above-mentioned groups (1) to (4) being optionally substituted with one or more substituents selected from the group consisting of (5) substituents selected from the group consisting of amino, carbamoyl, carboxyl, nitro, halogen, hydroxy, aralkylcarbonyl, N-aralkylcarbamoyl, aryl, aroyl, $C_2$–$C_6$ alkanoyl, N—$C_1$–$C_6$ alkylamino, N—$C_1$–$C_{10}$ alkylcarbamoyl, N—$C_1$–$C_{10}$ alkylthiocarbamoyl, N,N-di-$C_1$–$C_{10}$ alkylcarbamoyl, N,N-di-$C_1$–$C_{10}$ alkylthiocarbamoyl, N—$C_2$–$C_6$ alkenylcarbamoyl, N,N-di-$C_2$–$C_6$ alkenylcarbamoyl, N-amino $C_1$–$C_{10}$ alkylcarbamoyl, N—$C_1$–$C_6$ alkoxy $C_1$–$C_{10}$ alkylcarbamoyl, N—$C_1$–$C_6$ alkoxycarbonyl $C_1$–$C_{10}$ alkylcarbamoyl, $C_1$–$C_6$ alkoxy, amino $C_1$–$C_6$ alkoxycarbonyl, N—$C_3$–$C_6$ cycloalkylamino, N,N-di-$C_3$–$C_6$ cycloalkylamino, $C_3$–$C_6$ cycloalkyloxy, N—$C_3$–$C_6$ cycloalkylcarbamoyl and N,N-di-$C_3$–$C_6$ cycloalkylcarbamoyl, (6) 5- or 6-membered heterocyclic groups selected from the group consisting of thienyl, pyridyl, pyrazinyl, pyrimidinyl, furyl, tetrahydrofuranyl and morpholino, (7) monocyclic to tricyclic aromatic heterocyclic groups having per one ring 1 to 5 hetero atoms selected from the group consisting of nitrogen atoms, oxygen atoms and sulfur atoms, selected from the group consisting of ethylenedioxyphenyl, dibenzofuranyl, dibenzothiophenyl and methylenedioxyphenyl, (8) substituents selected from the group consisting of N—$C_1$–$C_{10}$ alkylcarbamoyl groups, N—$C_1$–$C_{10}$ alkylthiocarbamoyl groups, thiocarbonyl groups and carbonyl groups, each substituted with the above-mentioned heterocyclic group or the above-mentioned aromatic heterocyclic group, and (9) substituents selected from the group consisting of straight-chain or branched and saturated or unsaturated $C_1$–$C_9$ aliphatic groups and $C_1$–$C_6$ alkoxy groups, each of which groups may optionally be substituted with a group selected from the group consisting of the substituents mentioned in the above item (8), (hereinafter, the above-mentioned groups (5) to (9) are referred to as series of groups C"), $R^{1b}$ and $R^{2b}$ are the same or different, and represent (1) groups selected from the group consisting of hydrogen, amino, nitro, halogen, hydroxy, aryl, N-arylamino, N—$C_1$–$C_6$ alkylamino, N,N-di-$C_1$–$C_6$ alkylamino, N—$C_1$–$C_{10}$ alkylcarbamoyl, $C_1$–$C_6$ alkoxy, $C_1$–$C_6$ alkoxycarbonyl and N—$C_3$–$C_6$ cycloalkylamino (hereinafter, "hydrogen, . . . and N—$C_3$–$C_6$ cycloalkylamino" is referred to as a series of groups D"), or (2) straight-chain or branched and saturated or unsaturated $C_1$–$C_9$ aliphatic groups or $C_1$–$C_6$ alkoxy groups, each of which may optionally be substituted with a group selected from the group consisting of the series of groups D" but excluding hydrogen, $R^{3b}$ and $R^{4b}$ are the same or different, and represent (1) groups selected from the group consisting of hydrogen, azido, amidino, amino, carbamoyl, carboxyl, guanidino, cyano, sulfamoyl, sulfo, nitro, halogen, hydroxy, formyl, cyclic saturated $C_3$–$C_9$ aliphatic groups, cyclic unsaturated $C_3$–$C_9$ aliphatic groups, N—$C_1$–$C_6$ alkylamino, N—$C_1$–$C_{10}$ alkylcarbamoyl, $C_1$–$C_6$ alkylthio, $C_1$–$C_6$ alkoxy and $C_1$–$C_6$ alkoxycarbonyl (hereinafter, "hydrogen, . . . and $C_1$–$C_6$ alkoxylcarbonyl" is referred to as a series of groups E"), (2) straight-chain or branched and saturated or unsaturated $C_1$–$C_9$ aliphatic groups optionally substituted with a group selected from the group consisting of the series of groups E" but excluding hydrogen, or (3)

(3-1) aryl groups, (3-2) monocyclic to tricyclic $C_7$–$C_{15}$ aromatic carbocyclic groups selected from the group consisting of anthryl and phenanthryl, (3-3) 5- or 6-membered heterocyclic groups selected from the group consisting of thienyl, pyridyl, pyrazinyl, pyrimidinyl, furyl, tetrahydrofuranyl and morpholino, (3-4) monocyclic to tricyclic aromatic heterocyclic groups having per one ring 1 to 5 hetero atoms selected from the group consisting of nitrogen atoms, oxygen atoms and sulfur atoms, selected from the group consisting of ethylenedioxyphenyl, dibenzofuranyl, dibenzothiophenyl and methylenedioxyphenyl, or (3-5) straight-chain or branched and saturated or unsaturated $C_1$–$C_9$ aliphatic groups optionally substituted with the above-mentioned aryl group, the above-mentioned aromatic carbocyclic group, the above-mentioned heterocyclic group or the above-mentioned aromatic heterocyclic group, each of the above-mentioned groups (3-1) to (3-5) being optionally substituted with one or more substituents selected from the group consisting of the aforementioned series of groups C", or (4) $R^{3b}$ and $R^{4b}$ combine together to form a straight-chain unsaturated $C_2$–$C_9$ aliphatic group or a 5- or 6-membered saturated carbocyclic group, $X_{1b}$ represents an oxygen atom or a group $NR^{5b}$ (wherein $R^{5b}$ represents a group selected from the group consisting of hydrogen, hydroxy, $C_1$–$C_6$ alkoxy, $C_1$–$C_6$ alkoxycarbonyl and N—$C_1$–$C_{10}$ alkylcarbamoyl; or a straight-chain or branched and saturated or unsaturated $C_1$–$C_9$ aliphatic group optionally substituted with a group selected from the group consisting of hydroxy, $C_1$–$C_6$ alkoxy, $C_1$–$C_6$ alkoxycarbonyl and N—$C_1$–$C_{10}$ alkylcarbamoyl), $X_{2b}$ represents an oxygen atom or a sulfur atom, and $Z_b$ represents a condensed aryl.

4. The compound represented by the general formula [I-c] or pharmaceutically acceptable salt thereof, according to claim 1;

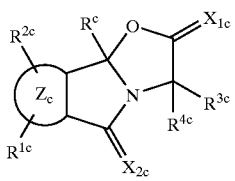

wherein,
R$^c$ represents an aryl group, a mono- to tricyclic C$_7$–C$_{15}$ aromatic carbocyclic group (excluding an aryl group), a 5- or 6-membered heterocyclic group, or a mono- to tricyclic aromatic heterocyclic group having per one ring 1 to 5 hetero atoms selected from the group consisting of nitrogen atoms, oxygen atoms and sulfur atoms (excluding a 5- or 6-membered heterocyclic group), R$^{1c}$ and R$^{2c}$ are the same or different, and represent (1) groups selected from the group consisting of hydrogen, azido, amino, carbamoyl, carbamoylamino, carbamoyloxy, carboxyl, cyano, sulfamoyl, sulfo, nitro, halogen, hydroxy, formyl, formylamino, cyclic saturated or unsaturated C$_3$–C$_9$ aliphatic groups, aralkyl, N-aralkylamino, aralkyloxy, aralkylcarbonyl, aryl, N-arylamino, aryloxy, arylsulfonyl, N-arylsulfonylamino, N-arylsulfonylamino C$_1$–C$_6$ alkylamino, N-arylsulfonylamino C$_1$–C$_{10}$ alkylcarbamoyl, arylsulfonylamino C$_1$–C$_6$ alkoxycarbonyl, C$_2$–C$_6$ alkanoyl, N—C$_2$–C$_6$ alkanoylamino, aroyl, N-aroylamino, N-aroyl C$_1$–C$_6$ alkylamino, N-aroyl C$_1$–C$_{10}$ alkylcarbamoyl, N—C$_1$–C$_6$ alkylamino, N,N-di-C$_1$–C$_6$ alkylamino, N—C$_1$–C$_{10}$ alkylcarbamoyl, N,N-di-C$_1$–C$_{10}$ alkylcarbamoyl, N—C$_1$–C$_6$ alkylsulfamoyl, C$_1$–C$_6$ alkylsulfinyl, C$_1$–C$_6$ alkylsulfonyl, C$_1$–C$_6$ alkylthio, C$_1$–C$_6$ alkoxy, C$_1$–C$_6$ alkoxycarbonyl, N—C$_3$–C$_6$ cycloalkylamino, C$_3$–C$_6$ cycloalkyloxy and N—C$_3$–C$_6$ cycloalkylcarbamoyl (hereinafter, "hydrogen, ... and N—C$_3$–C$_6$ cycloalkylcarbamoyl" is referred to as a series of groups D'''), or (2) straight-chain or branched and saturated or unsaturated C$_1$–C$_9$ aliphatic groups, N—C$_1$–C$_6$ alkylamino groups, C$_1$–C$_6$ alkylthio groups, or C$_1$–C$_6$ alkoxy groups, each of which groups may optionally be substituted with a group selected from the group consisting of the series of groups D''' but excluding hydrogen, R$^{3c}$ and R$^{4c}$ are the same or different, and represent (1) groups selected from the group consisting of hydrogen, azido, amidino, amino, carbamoyl, carbamoylamino, carbamoyloxy, carboxyl, guanidino, cyano, sulfamoyl, sulfo, nitro, halogen, hydroxy, formyl, formylamino, cyclic saturated C$_3$–C$_9$ aliphatic groups, cyclic unsaturated C$_3$–C$_9$ aliphatic groups, C$_2$–C$_6$ alkanoyl, N—C$_2$–C$_6$ alkanoylamino, N—C$_1$–C$_6$ alkylamino, N,N-di-C$_1$–C$_6$ alkylamino, N—C$_1$–C$_{10}$ alkylcarbamoyl, N,N-di-C$_1$–C$_{10}$ alkylcarbamoyl, C$_1$–C$_6$ alkylthio, N—C$_1$–C$_6$ alkylsulfamoyl, C$_1$–C$_6$ alkylsulfinyl, C$_1$–C$_6$ alkylsulfonyl, C$_1$–C$_6$ alkoxy, C$_1$–C$_6$ alkoxycarbonyl, N—C$_3$–C$_6$ cycloalkylamino, C$_3$–C$_6$ cycloalkyloxy and N—C$_3$–C$_6$ cycloalkylcarbamoyl (hereinafter, "hydrogen, ... and N—C$_3$–C$_6$ cycloalkylcarbamoyl" is referred to as a series of groups E'''), (2) straight-chain or branched and saturated or unsaturated C$_1$–C$_9$ aliphatic groups optionally substituted with a group selected from the group consisting of the series of groups E''' but excluding hydrogen, (3)

(3-1) aryl groups, (3-2) monocyclic to tricyclic C$_7$–C$_{15}$ aromatic carbocyclic groups (excluding aryl groups), (3-3) 5- or 6-membered heterocyclic groups, (3-4) monocyclic to tricyclic aromatic heterocyclic groups having per one ring 1 to 5 hetero atoms selected from the group consisting of nitrogen atoms, oxygen atoms and sulfur atoms (excluding 5- or 6-membered heterocyclic groups), or (3-5) straight-chain or branched and saturated or unsaturated C$_1$–C$_9$ aliphatic groups optionally substituted with the above-mentioned aryl group, aromatic carbocyclic group, heterocyclic group or aromatic heterocyclic group, each of the groups (3-1) to (3-5) being optionally substituted with substituent(s), or (4) R$^{3c}$ and R$^{4c}$ combine together to form a straight-chain or branched unsaturated C$_1$–C$_9$ aliphatic group, or a 5- or 6-membered saturated or unsaturated carbocyclic group, X$_{1c}$ and X$_{2c}$ are the same or different, and represent oxygen atoms or sulfur atoms, and Z$_c$ represents a condensed aryl group.

5. A process for preparing a compound represented by the general formula [I]

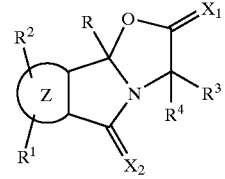

wherein, R, R$^1$, R$^2$, R$^3$, R$^4$, R$^6$, R$^7$, X$_1$, X$_2$ and Z are as defined in claim 1, or pharmaceutically acceptable salt thereof according to claim 1, which comprises reacting a carboxylic acid or thiocarboxylic acid represented by the general formula [II]

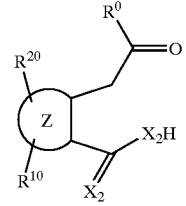

wherein,
R$^0$ represents (1) an aryl group, (2) a mono- to tricyclic C$_7$–C$_{15}$ aromatic carbocyclic group selected from the group consisting of acenaphthylenyl, adamantyl, anthryl, indenyl, norbornyl and phenanthryl, (3) a 5- or 6-membered heterocyclic group selected from the group consisting of the series of groups A defined in claim 1, or (4) a mono- to tricyclic aromatic heterocyclic group having per one ring 1 to 5 hetero atoms selected from the group consisting of nitrogen atoms, oxygen atoms and sulfur atoms, selected from the group consisting of the series of groups B defined in claim 1, each of the above-mentioned groups (1) to (4) being optionally substituted with one or more substituents selected from the group consisting of the series of groups C defined in claim 1 provided that amino, carboxyl, hydroxyl, N-amino $C_1$–$C_{10}$ alkylcarbamoyl and amino $C_1$–$C_6$ alkoxycarbonyl may optionally be protected, $R^{10}$ and $R^{20}$ are the same or different, and represent (1) groups selected from the group consisting of the series of groups D defined in claim 1 provided that amino, carboxyl and hydroxyl may optionally be protected, or (2) straight-chain or branched and saturated or unsaturated $C_1$–$C_9$ aliphatic groups, N—$C_1$–$C_6$ alkylamino groups, $C_1$–$C_6$ alkylthio groups, or $C_1$–$C_6$ alkoxy groups, each of which groups may optionally be substituted with a group selected from the group consisting of the series of groups D provided that hydrogen is excluded and amino, carboxyl and hydroxyl may optionally be protected, and $X_2$ and Z are as defined in claim 1, with an amine derivative represented by the general formula [III]

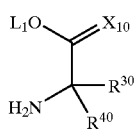

[III]

wherein, $R^{30}$ and $R^{40}$ are the same or different, and represent (1) groups selected from the group consisting of the series of groups E as defined in claim 1 provided that amino, carboxyl and hydroxyl may optionally be protected, (2) straight-chain or branched and saturated or unsaturated $C_1$–$C_9$ aliphatic groups optionally substituted with a group selected from the group consisting of the above-mentioned series of groups E provided that hydrogen is excluded and amino, carboxyl and hydroxyl may optionally be protected but excluding the case where both $R^3$ and $R^4$ are unsubstituted ethyl groups, or (3)

(3-1) aryl groups, (3-2) monocyclic to tricyclic $C_7$–$C_{15}$ aromatic carbocyclic groups selected from the group consisting of acenaphthylenyl, adamantyl, anthryl, indenyl, norbornyl and phenanthryl, (3-3) 5- or 6-membered heterocyclic groups selected from the group consisting of the aforementioned series of groups A, (3-4) monocyclic to tricyclic aromatic heterocyclic groups having per one ring 1 to 5 hetero atoms selected from the group consisting of nitrogen atoms, oxygen atoms and sulfur atoms, selected from the group consisting of the aforementioned series of groups B, or (3-5) straight-chain or branched and saturated or unsaturated $C_1$–$C_9$ aliphatic groups optionally substituted with the above-mentioned aryl group, the above-mentioned aromatic carbocyclic group, the above-mentioned heterocyclic group or the above-mentioned aromatic heterocyclic group, each of the above-mentioned groups (3-1) to (3-5) being optionally substituted with one or more substituents selected from the group consisting of the aforementioned series of groups C provided that amino, carboxyl, hydroxyl, N-amino $C_1$–$C_{10}$ alkylcarbamoyl and amino $C_1$–$C_6$ alkoxycarbonyl may optionally be protected, or (4) $R^{30}$ and $R^{40}$ combine together to form a straight-chain or branched and saturated or unsaturated $C_1$–$C_9$ aliphatic group, a 5- or 6-membered saturated carbocyclic group, or a 5- or 6-membered unsaturated carbocyclic group, $L_1$ represents a hydrogen atom, a protective group for carboxyl groups, or a resin carrier of carboxyl groups in solid synthesis of peptides, and $X_{10}$ represents an oxygen atom, a sulfur atom or a group $NR^{50}$ (wherein $R^{50}$ represents a group selected from the group consisting of hydrogen, a protective group for amino groups, halogen, optionally protected hydroxy, N—$C_1$–$C_6$ alkylsulfonylamino, $C_1$–$C_6$ alkoxy, $C_1$–$C_6$ alkoxycarbonyl, $C_2$–$C_6$ alkanoyl, carbamoyl and N—$C_1$–$C_{10}$ alkylcarbamoyl; or a straight-chain or branched and saturated or unsaturated $C_1$–$C_9$ aliphatic group optionally substituted with a group selected from the group consisting of a protective group for amino groups, halogen, optionally protected hydroxy, N—$C_1$–$C_6$ alkylsulfonylamino, $C_1$–$C_6$ alkoxy, $C_1$–$C_6$ alkoxycarbonyl, $C_2$–$C_6$ alkanoyl, carbamoyl and N—$C_1$–$C_{10}$ alkylcarbamoyl), and removing the protective group for amino groups, the protective group for hydroxyl groups or the protective group for carboxyl groups, according to necessity, to form an equilibrium mixture of a compound represented by the general formula [IV']

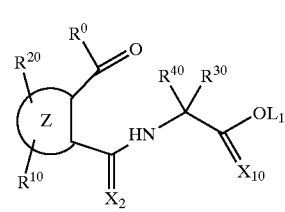

[IV']

wherein, $R^0$, $R^{10}$, $R^{20}$, $R^{30}$, $R^{40}$, $L_1$, $X_2$, $X_{10}$ and Z are as defined above, and a compound represented by the general formula [V']

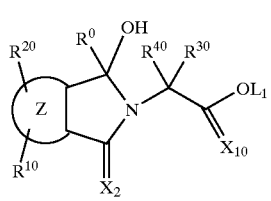

[V']

wherein, $R^0$, $R^{10}$, $R^{20}$, $R^{30}$, $R^{40}$, $L_1$, $X_2$, $X_{10}$ and Z are as defined above, and then reacting the equilibrium mixture with an acid in sented by the general formula [VIII']an inert organic solvent to form a compound repre-

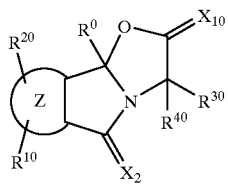

[VIII']

wherein, $R^0$, $R^{10}$, $R^{20}$, $R^{30}$, $R^{40}$, $X_2$, $X_{10}$ and Z are as defined above, and removing the protective groups, when exist.

6. A composition comprising, together with a carrier or diluent, a compound represented by the general formula [I] or a pharmaceutically acceptable salt thereof:

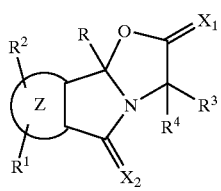

[I]

wherein,

R represents (1) an aryl group, (2) a mono- to tricyclic $C_7$–$C_{15}$ aromatic carbocyclic group selected from the group consisting of acenaphthylenyl, adamantyl, anthryl, indenyl, norbornyl and phenanthryl, (3) a 5- or 6-membered heterocyclic group selected from the group consisting of isoxazolyl, isothiazolyl, imidazolyl, oxazolyl, oxadiazolyl, thiazolyl, thiadiazolyl, thienyl, triazinyl, triazolyl, pyridyl, pyrazinyl, pyrimidinyl, pyridazinyl, pyrazolyl, pyrrolyl, pyranyl, furyl, furazanyl, imidazolidinyl, imidazolinyl, tetrahydrofuranyl, pyrazolidinyl, pyrazolinyl, piperazinyl, piperidinyl, pyrrolidinyl, pyrrolinyl and morpholino (hereinafter, "isoxazolyl, . . . and morpholino" is referred to as a series of groups A), or (4) a mono- to tricyclic aromatic heterocyclic group having per one ring 1 to 5 hetero atoms selected from the group consisting of nitrogen atoms, oxygen atoms and sulfur atoms, selected from the group consisting of acridinyl, isoquinolyl, isoindolyl, indazolyl, indolyl, indolizinyl, ethylenedioxyphenyl, carbazolyl, quinazolinyl, quinoxalinyl, quinolidinyl, quinolyl, cumaronyl, chromenyl, phenanthridinyl, phenanthrolinyl, dibenzofuranyl, dibenzothiophenyl, cinnolinyl, thionaphthenyl, naphthyridinyl, phenazinyl, phenoxazinyl, phenothiazinyl, phthalazinyl, pteridinyl, purinyl, benzimidazolyl, benzoxazolyl, benzothiazolyl, benzotriazolyl, benzofuranyl and methylenedioxyphenyl (hereinafter, "acridinyl, . . . and methylenedioxyphenyl" is referred to as a series of groups B), each of the above-mentioned groups (1) to (4) may optionally have one or more substituents selected from the group consisting of (5) substituents selected from the group consisting of azido, amino, carbamoyl, carbamoylamino, carbamoyloxy, carboxyl, cyano, sulfamoyl, sulfo, nitro, halogen, hydroxy, formyl, formylamino, cyclic saturated $C_3$–$C_9$ aliphatic groups, cyclic unsaturated $C_3$–$C_9$ aliphatic groups, aralkyl, N-aralkylamino, N,N-diaralkylamino, aralkyloxy, aralkylcarbonyl, N-aralkylcarbamoyl, aryl, N-arylamino, N,N-diarylamino, aryloxy, arylsulfonyl, arylsulfonyloxy, N-arylsulfonylamino, N-arylsulfonylanuno $C_1$–$C_{10}$ alkylamino, N-arylsulfonylamino $C_1$–$C_{10}$ alkylcarbamoyl, N-arylsulfonylamino $C_1$–$C_6$ alkoxycarbonyl, arylsulfamoyl, arylsulfamoyloxy, N-arylsulfamoyl $C_1$–$C_{10}$ alkylcarbamoyl, arylsulfamoyl $C_1$–$C_6$ alkoxycarbonyl, N-arylcarbamoyl, aroyl, aroxy, N-(N-aroylamino) $C_1$–$C_{10}$ alkylcarbamoyl, N-aroylamino $C_1$–$C_{10}$ alkoxycarbonyl, $C_2$–$C_6$ alkanoyl, N—$C_2$–$C_6$ alkanoylamino, N,N-di-$C_2$–$C_6$ alkanoylamino, N—$C_1$–$C_6$ alkylamino, N,N-di-$C_1$–$C_6$ alkylamino, N—$C_1$–$C_{10}$ alkylcarbamoyl, N—$C_1$–$C_{10}$ alkylthiocarbamoyl, N,N-di-$C_1$–$C_{10}$ alkylcarbamoyl, N,N-di-$C_1$–$C_{10}$ alkylthiocarbamoyl, N—$C_2$–$C_6$ alkenylcarbamoyl, N,N-di-$C_2$–$C_6$ alkenylcarbamoyl, N-amino $C_1$–$C_{10}$ alkylcarbamoyl, N—$C_1$–$C_6$ alkoxy $C_1$–$C_{10}$ alkylcarbamoyl, N—$C_1$–$C_6$ alkoxycarbonyl $C_1$–$C_{10}$ alkylcarbamoyl, N—$C_1$–$C_6$ alkoxycarbonylamino $C_1$–$C_{10}$ alkylcarbamoyl, N—$C_1$–$C_6$ alkoxycarbonylamino $C_1$–$C_6$ alkoxycarbonyl, $C_1$–$C_6$ alkylthio, N—$C_1$–$C_6$ alkylsulfamoyl, N,N-di-$C_1$–$C_6$ alkylsulfamoyl, $C_1$–$C_6$ alkylsulfinyl, $C_1$–$C_6$ alkylsulfonyl, N—$C_1$–$C_6$ alkylsulfonylamino, $C_1$–$C_6$ alkoxy, $C_1$–$C_6$ alkoxycarbonyl, amino $C_1$–$C_6$ alkoxycarbonyl, N—$C_3$–$C_6$ cycloalkylamino, N,N-di-$C_3$–$C_6$ cycloalkylamino, $C_3$–$C_6$ cycloalkyloxy, N—$C_3$–$C_6$ cycloalkylcarbamoyl and N,N-di-$C_3$–$C_6$ cycloalkylcarbamoyl, (6) 5- or 6-membered heterocyclic groups selected from the group consisting of the above-mentioned series of groups A, (7) monocyclic to tricyclic aromatic heterocyclic groups having per one ring 1 to 5 hetero atoms selected from the group consisting of nitrogen atoms, oxygen atoms and sulfur atoms, selected from the group consisting of the above-mentioned series of groups B, (8) substituents selected from the group consisting of N—$C_1$–$C_{10}$ alkylcarbamoyl groups, N—$C_1$–$C_{10}$ alkylthiocarbamoyl groups, thiocarbonyl groups and carbonyl groups, each substituted with the above-mentioned heterocyclic group or the above-mentioned aromatic heterocyclic group, and (9) substituents selected from the group consisting of straight-chain or branched and saturated or unsaturated $C_1$–$C_9$ aliphatic groups, $C_1$–$C_6$ alkoxy groups, $C_1$–$C_6$ alkylthio groups and N—$C_1$–$C_6$ alkylamino groups, each of which groups may be substituted with a group selected from the group consisting of the substituents mentioned in the above item (8), (hereinafter, the above-mentioned groups (5) to (9) are referred to as series of groups C), $R^1$ and $R^2$ are the same or different, and represent (1) groups selected from the group consisting of hydrogen, azido, amino, carbamoyl, carbamoylamino, carbamoyloxy, carboxyl, cyano, sulfamoyl, sulfo, intro, halogen, hydroxy, formyl, formylamino, cyclic saturated $C_3$–$C_9$ aliphatic groups, cyclic unsaturated $C_3$–$C_9$ aliphatic groups, aralkyl, N-aralkylamino, aralkyloxy, aralkylcarbonyl, aryl, N-arylamino, aryloxy, arylsulfonyl, N-arylsulfonylamino, N-arylsulfonylamino $C_1$–$C_{10}$ alkylamino, N-arylsulfonylamino $C_1$–$C_{10}$ alkylcarbamoyl, N-arylsulfonylamino $C_1$–$C_6$ alkoxycarbonyl, $C_2$–$C_6$ alkanoyl, N—$C_2$–$C_6$ alkanoylamino, aroyl, N-aroylamino, N-aroyl $C_1$–$C_{10}$ alkylamino, N-aroyl $C_1$–$C_{10}$ alkylcarbamoyl, N—$C_1$–$C_6$ alkylamino, N,N-di-$C_1$–$C_6$ alkylamino, N—$C_1$–$C_{10}$ alkylcarbamoyl, N,N-di-$C_1$–$C_{10}$ alkylcarbamoyl, N—$C_1$–$C_6$ alkylsulfamoyl, $C_1$–$C_6$ alkylsulfinyl, $C_1$–$C_6$ alkylsulfonyl, N—$C_1$–$C_6$ alkylsulfonylamino, $C_1$–$C_6$ alkylthio, $C_1$–$C_6$ alkoxy, $C_1$–$C_6$ alkoxycarbonyl, N—$C_3$–$C_6$ cycloalkylamino, $C_3$–$C_6$ cycloalkyloxy and N—$C_3$–$C_6$ cycloalkylcarbamoyl (hereinafter, "hydrogen, ... and N—$C_3$–$C_6$ cycloalkylcarbamoyl" is referred to as a series of groups D), or (2) straight-chain or branched and saturated or unsaturated $C_1$–$C_9$ aliphatic groups, N—$C_1$–$C_6$ alkylamino groups, $C_1$–$C_6$ alkylthio groups or $C_1$–$C_6$ alkoxy groups, each of which groups may optionally be substituted with a group selected from the group consisting of the series of groups D but excluding hydrogen, $R^3$ and $R^4$ are the same or different, and represent (1) groups selected from the group consisting of hydrogen, azido, amidino, amino, carbamoyl, carbamoylamino, carbamoyloxy, carboxyl, guanidino, cyano, sulfamoyl, sulfo, nitro, halogen, hydroxy, formyl, formylamino, cyclic saturated $C_3$–$C_9$ aliphatic groups, cyclic unsaturated $C_3$–$C_9$ aliphatic groups, $C_2$–$C_6$ alkanoyl, N—$C_2$–$C_6$ alkanoylamino, N—$C_1$–$C_6$ alkylamino, N,N-di-$C_1$–$C_6$ alkylamino, N—$C_1$–$C_{10}$ alkylcarbamoyl, N,N-di-$C_1$–$C_{10}$ alkylcarbamoyl, $C_1$–$C_6$ alkylthio, N—$C_1$–$C_6$ alkylsulfamoyl, $C_1$–$C_6$ alkylsulfinyl, $C_1$–$C_6$ alkylsulfonyl, N—$C_1$–$C_6$ alkylsulfonylamino, $C_1$–$C_6$ alkoxy, $C_1$–$C_6$ alkoxycarbonyl, N—$C_3$–$C_6$ cycloallcylamino, $C_3$–$C_6$ cycloalkyloxy and N—$C_3$–$C_6$ cycloalkylcarbamoyl (hereinafter, "hydrogen, ... and N—$C_3$–$C_6$ cycloalkylcarbamoyl " is referred to as a series of groups E), (2) straight-chain or branched and saturated or unsaturated $C_1$–$C_9$ aliphatic groups optionally substituted with a group selected from the group consisting of the series of groups E but excluding hydrogen, or (3)

(3-1) aryl groups, (3-2) monocyclic to tricyclic $C_7$–$C_{15}$ aromatic carbocyclic groups selected from the group consisting of acenaphthylenyl, adamantyl, anthryl, indenyl, norbornyl and phenanthryl, (3-3) 5- or 6-membered heterocyclic groups selected from the group consisting of the aforementioned series of groups A, (3-4) monocyclic to tricyclic aromatic heterocyclic groups having per one ring 1 to 5 hetero atoms selected from the group consisting of nitrogen atoms, oxygen atoms and sulfur atoms, selected from the group consisting of the aforementioned series of groups B, or (3-5) straight-chain or branched and saturated or unsaturated $C_1$–$C_9$ aliphatic groups optionally substituted with the above-mentioned aryl group, the above-mentioned aromatic carbocyclic group, the above-mentioned heterocyclic group or the above-mentioned aromatic heterocyclic group, each of the above-mentioned groups (3-1) to (3-5) being optionally substituted with one or more substituents selected from the group consisting of the aforementioned series of group C, or (4) $R^3$ and $R^4$ combine together to form a straight-chain or branched and saturated or unsaturated $C_1$–$C_9$ aliphatic group, a 5- or 6-membered saturated carbocyclic group, or a 5- or 6-membered unsaturated carbocyclic group, $X_1$ represents an oxygen atom, a sulfur atom or a group $NR^5$ (wherein $R^5$ represents a group selected from the group consisting of hydrogen, halogen, hydroxy, N—$C_1$–$C_6$ alkylsulfonylamino, $C_1$–$C_6$ alkoxy, $C_1$–$C_6$ alkoxycarbonyl, $C_2$–$C_6$ alkanoyl, carbamoyl and N—$C_1$–$C_{10}$ alkylcarbamoyl; or a straight-chain or branched and saturated or unsaturated $C_1$–$C_9$ aliphatic group optionally substituted with a group selected from the group consisting of halogen, hydroxy, N—$C_1$–$C_6$ alkylsulfonylamino, $C_1$–$C_6$ alkoxy, $C_1$–$C_6$ alkoxycarbonyl, $C_2$–$C_6$ alkanoyl, carbamoyl and N—$C_1$–$C_{10}$ alkylcarbamoyl), $X_2$ represents an oxygen atom or a sulfur atom, and Z represents a condensed aryl.

7. A composition for treating diabetes, a prophylactic agent for chronic complications of diabetes or a drug against obesity, comprising, together with a carrier or diluent a compound represented by the general formula [I] or a pharmaceutically acceptable salt thereof:

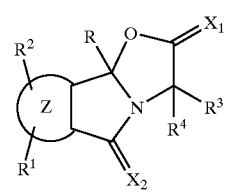

[I]

wherein,

R represents (1) an aryl group, (2) a mono- to tricyclic $C_7$–$C_{15}$ aromatic carbocyclic group selected from the group consisting of acenaphthylenyl, adamantyl, anthryl, indenyl, norbornyl and phenanthryl, (3) a 5- or 6-membered heterocyclic group selected from the group consisting of isoxazolyl, isothiazolyl, imidazolyl, oxazolyl, oxadiazolyl, thiazolyl, thiadiazolyl, thienyl, triazinyl, triazolyl, pyridyl, pyrazinyl, pyrimidinyl, pyridazinyl, pyrazolyl, pyrrolyl, pyranyl, furyl, furazanyl, imidazolidinyl, imidazolinyl, tetrahydrofuranyl, pyrazolidinyl, pyrazolinyl, piperazinyl, piperidinyl, pyrrolidinyl, pyrrolinyl and morpholino (hereinafter, "isoxazolyl, . . . and morpholino" is referred to as a series of groups A), or (4) a mono- to tricyclic aromatic heterocyclic group having per one ring 1 to 5 hetero atoms selected from the group consisting of nitrogen atoms, oxygen atoms and sulfur atoms, selected from the group consisting of acridinyl, isoquinolyl, isoindolyl, indazolyl, indolyl, indolizinyl, ethylenedioxyphenyl, carbazolyl, quinazolinyl, quinoxalinyl, quinolidinyl, quinolyl, cumaronyl, chromenyl, phenanthridinyl, phenanthrolinyl, dibenzofuranyl, dibenzothiophenyl, cinnolinyl, thionaphthenyl, naphthyridinyl, phenazinyl, phenoxazinyl, phenothiazinyl, phthalazinyl, pteridinyl, purinyl, benzimidazolyl, benzoxazolyl, benzothiazolyl, benzotriazolyl, benzofuranyl and methylenedioxyphenyl (hereinafter, "acridinyl, . . . and methylenedioxyphenyl" is referred to as a series of groups B), each of the above-mentioned groups (1) to (4) may optionally have one or more substituents selected from the group consisting of (5) substituents selected from the group consisting of azido, amino, carbamoyl, carbamoylamino, carbamoyloxy, carboxyl, cyano, sulfamoyl, sulfo, nitro, halogen, hydroxy, formyl, formylamino, cyclic saturated $C_3$–$C_9$ aliphatic groups, cyclic unsaturated $C_3$–$C_9$ aliphatic groups, aralkyl, N-aralkylamino, N,N-diaralkylamino, aralkyloxy, aralkylcarbonyl, N-aralkylcarbamoyl, aryl, N-arylamino, N,N-diarylamino, aryloxy, arylsulfonyl, arylsulfonyloxy, N-arylsulfonylamino, N-arylsulfonylamino $C_1$–$C_{10}$ alkylamino, N-arylsulfonylamino $C_1$–$C_{10}$ alkylcarbamoyl, N-arylsulfonylamino $C_1$–$C_6$ alkoxycarbonyl, arylsulfamoyl, arylsulfamoyloxy, N-arylsulfamoyl $C_1$–$C_{10}$ alkylcarbamoyl, arylsulfamoyl $C_1$–$C_6$ alkoxycarbonyl, N-arylcarbamoyl, aroyl, aroxy, N-(N-aroylamino) $C_1$–$C_{10}$ alkylcarbamoyl, N-aroylamino $C_1$–$C_{10}$ alkoxycarbonyl, $C_2$–$C_6$ alkanoyl, N—$C_2$–$C_6$ alkanoylamino, N,N-di-$C_2$–$C_6$ alkanoylamino, N—$C_1$–$C_6$ alkylamino, N,N-di-$C_1$–$C_6$ alkylamino, N—$C_1$–$C_{10}$ alkylcarbamoyl, N—$C_1$–$C_{10}$ alkylthiocarbamoyl, N,N-di-$C_1$–$C_{10}$ alkylcarbamoyl, N,N-di-$C_1$–$C_{10}$ alkylthiocarbamoyl, N—$C_2$–$C_6$ alkenylcarbamoyl, N,N-di-$C_2$–$C_6$ alkenylcarbamoyl, N-amino $C_1$–$C_{10}$ alkylcarbamoyl, N—$C_1$–$C_6$ alkoxy $C_1$–$C_{10}$ alkylcarbamoyl, N—$C_1$–$C_6$ alkoxycarbonyl $C_1$–$C_{10}$ alkylcarbamoyl, N—$C_1$–$C_6$ alkoxycarbonylamino $C_1$–$C_{10}$ alkylcarbamoyl, N—$C_1$–$C_6$ alkoxycarbonylamino $C_1$–$C_6$ alkoxycarbonyl, $C_1$–$C_6$ alkylthio, N—$C_1$–$C_6$ alkylsulfamoyl, N,N-di-$C_1$–$C_6$ alkylsulfamoyl, $C_1$–$C_6$ alkylsulfinyl, $C_1$–$C_6$ alkylsulfonyl, N—$C_1$–$C_6$ alkylsulfonylamino, $C_1$–$C_6$ alkoxy, $C_1$–$C_6$ alkoxycarbonyl, amino $C_1$–$C_6$ alkoxycarbonyl, N—$C_3$–$C_6$ cycloalkylamino, N,N-di-$C_3$–$C_6$ cycloalkylamino, $C_3$–$C_6$ cycloalkyloxy, N—$C_3$–$C_6$ cycloalkylcarbamoyl and N,N-di-$C_3$–$C_6$ cycloalkylcarbamoyl, (6) 5- or 6-membered heterocyclic groups selected from the group consisting of the above-mentioned series of groups A, (7) monocyclic to tricyclic aromatic heterocyclic groups having per one ring 1 to 5 hetero atoms selected from the group consisting of nitrogen atoms, oxygen atoms and sulfur atoms, selected from the group consisting of the above-mentioned series of groups B, (8) substituents selected from the group consisting of N—$C_1$–$C_{10}$ alkylcarbamoyl groups, N—$C_1$–$C_{10}$ alkylthiocarbamoyl groups, thiocarbonyl groups and carbonyl groups, each substituted with the above-mentioned heterocyclic group or the above-mentioned aromatic heterocyclic group, and (9) substituents selected from the group consisting of straight-chain or branched and saturated or unsaturated $C_1$–$C_9$ aliphatic groups, $C_1$–$C_6$ alkoxy groups, $C_1$–$C_6$ alkylthio groups and N—$C_1$–$C_6$ alkylamino groups, each of which groups may be substituted with a group selected from the group consisting of the substituents mentioned in the above item (8), (hereinafter, the above-mentioned groups (5) to (9) are referred to as series of groups C), $R^1$ and $R^2$ are the same or different, and represent (1) groups selected from the group consisting of hydrogen, azido, amino, carbamoyl, carbamoylamino, carbamoyloxy, carboxyl, cyano, sulfamoyl, sulfo, nitro, halogen, hydroxy, formyl, formylamino, cyclic saturated $C_3$–$C_9$ aliphatic groups, cyclic unsaturated $C_3$–$C_9$ aliphatic groups, aralkyl, N-aralkylamino, aralkyloxy, aralkylcarbonyl, aryl, N-arylamino, aryloxy, arylsulfonyl, N-arylsulfonylamino, N-arylsulfonylamino $C_1$–$C_{10}$ alkylamino, N-arylsulfonylamino $C_1$–$C_{10}$ alkylcarbamoyl, N-arylsulfonylamino $C_1$–$C_6$ alkoxycarbonyl, $C_2$–$C_6$ alkanoyl, N—$C_2$–$C_6$ alkanoylamino, aroyl, N-aroylamino, N-aroyl $C_1$–$C_{10}$ alkylamino, N-aroyl $C_1$–$C_{10}$ alkylcarbamoyl, N—$C_1$–$C_6$ alkylamino, N,N-di-$C_1$–$C_6$ alkylamino, N—$C_1$–$C_{10}$ alkylcarbamoyl, N,N-di-$C_1$–$C_{10}$ alkylcarbamoyl, N—$C_1$–$C_6$ alkylsulfamoyl, $C_1$–$C_6$ alkylsulfinyl, $C_1$–$C_6$ alkylsulfonyl, N—$C_1$–$C_6$ alkylsulfonylaxnino, $C_1$–$C_6$ alkylthio, $C_1$–$C_6$ alkoxy, $C_1$–$C_6$ alkoxycarbonyl, N—$C_3$–$C_6$ cycloalkylamino, $C_3$–$C_6$ cycloalkyloxy and N—$C_3$–$C_6$ cycloalkylcarbamoyl (hereinafter, "hydrogen, . . . and N—$C_3$–$C_6$ cycloalkylcarbamoyl" is referred to as a series of groups D), or (2) straight-chain or branched and saturated or unsaturated $C_1$–$C_9$ aliphatic groups, N—$C_1$–$C_6$ alkylamino groups, $C_1$–$C_6$ alkylthio groups or $C_1$–$C_6$ alkoxy groups, each of which groups may optionally be substituted with a group selected from the group consisting of the series of groups D but excluding hydrogen, $R^3$ and $R^4$ are the same or different, and represent (1) groups selected from the group consisting of hydrogen, azido, amino, amino, carbamoyl, carbamoylamino, carbamoyloxy, carboxyl, guanidino, cyano, sulfamoyl, sulfo, nitro, halogen, hydroxy, formyl, formylamino, cyclic saturated $C_3$–$C_9$ aliphatic groups, cyclic unsaturated $C_3$–$C_9$ aliphatic groups, $C_2$–$C_6$ alkanoyl, N—$C_2$–$C_6$ alkanoylamino, N—$C_1$–$C_6$ alkylamino, N,N-di-$C_1$–$C_6$ alkylamino, N—$C_1$–$C_{10}$ alkylcarbamoyl, N,N-di-$C_1$–$C_{10}$ alkylcarbamoyl, $C_1$–$C_6$ alkylthio, N—$C_1$–$C_6$ alkylsulfamoyl, $C_1$–$C_6$ alkylsulfinyl, $C_1$–$C_6$ alkylsulfonyl, N—$C_1$–$C_6$ alkylsulfonylamino, $C_1$–$C_6$ alkoxy, $C_1$–$C_6$ alkoxycarbonyl, N—$C_3$–$C_6$ cycloalkylamino, $C_3$–$C_6$ cycloalkyloxy and N—$C_3$–$C_6$ cycloallcylcarbamoyl (hererinafter, "hydrogen, . . . and N—$C_3$–$C_6$ cycloalkylcarbamoyl" is referred to as a series of groups E), (2) straight-chain or branched and saturated or unsaturated $C_1$–$C_9$ aliphatic groups optionally substituted with a group selected from the group consisting of the series of groups E but excluding hydrogen, or (3)

(3-1) aryl groups, (3-2) monocyclic to tricyclic $C_7$–$C_{15}$ aromatic carbocyclic groups selected from the group consisting of acenaphthylenyl, adamantyl, anthryl, indenyl, norbornyl and phenanthryl, (3-3) 5- or 6-membered heterocyclic groups selected from the group consisting of the aforementioned series of groups A, (3-4) monocyclic to tricyclic aromatic heterocyclic groups having per one ring 1 to 5 hetero atoms selected from the group consisting of nitrogen atoms, oxygen atoms and sulfur atoms, selected from the group consisting of the aforementioned series of groups B, or (3-5) straight-chain or branched and saturated or unsaturated $C_1$–$C_9$ aliphatic groups optionally substituted with the above-mentioned aryl group, the above-mentioned aromatic carbocyclic group, the above-mentioned heterocyclic group or the above-mentioned aromatic heterocyclic group, each of the above-mentioned groups (3-1) to (3-5) being optionally substituted with one or more substituents selected from the group consisting of the aforementioned series of group C, or (4) $R^3$ and $R^4$ combine together to form a straight-chain or branched and saturated or unsaturated $C_1$–$C_9$ aliphatic group, a 5- or 6-membered saturated carbocyclic group, or a 5- or 6-membered unsaturated carbocyclic group, $X_1$ represents an oxygen atom, a sulfur atom or a group $NR^5$ (wherein $R^5$ represents a group selected from the group consisting of hydrogen, halogen, hydroxy, N—$C_1$–$C_6$ alkylsulfonylamino, $C_1$–$C_6$ alkoxy, $C_1$–$C_6$ alkoxycarbonyl, $C_2$–$C_6$ alkanoyl, carbamoyl and N—$C_1$–$C_{10}$ alkylcarbamoyl; or a straight-chain or branched and saturated or unsaturated $C_1$–$C_9$ aliphatic group optionally substituted with a group selected from the group consisting of halogen, hydroxy, N—$C_1$–$C_6$ alkylsulfonylamino, $C_1$–$C_6$ alkoxy, $C_1$–$C_6$ alkoxycarbonyl, $C_2$–$C_6$ alkanoyl, carbamoyl and N—$C_1$–$C_{10}$ alkylcarbamoyl), $X_2$ represents an oxygen atom or a sulfur atom, and Z represents a condensed aryl.

* * * * *